US011453703B2

(12) United States Patent
Keen et al.

(10) Patent No.: US 11,453,703 B2
(45) Date of Patent: Sep. 27, 2022

(54) HETEROTANDEM BICYCLIC PEPTIDE COMPLEXES

(71) Applicant: BicycleTX Limited, Cambridge (GB)

(72) Inventors: Nicholas Keen, Carlisle, MA (US); Kevin McDonnell, Lexington, MA (US); Peter Park, Lincoln, MA (US); Punit Upadhyaya, Lexington, MA (US); Gemma Mudd, Cambridge (GB)

(73) Assignee: BICYCLETX LIMITED, Cambridge (GB)

( * ) Notice: Subject to any disclaimer, the term of this patent is extended or adjusted under 35 U.S.C. 154(b) by 0 days.

(21) Appl. No.: 16/372,692

(22) Filed: Apr. 2, 2019

(65) Prior Publication Data

US 2019/0307836 A1 Oct. 10, 2019
US 2021/0299210 A2 Sep. 30, 2021

(30) Foreign Application Priority Data

Apr. 4, 2018 (GB) .................................... 1805492
Dec. 21, 2018 (GB) .................................... 1820981

(51) Int. Cl.
*C07K 14/00* (2006.01)
*A61K 38/12* (2006.01)
*C07K 7/08* (2006.01)
*A61P 35/00* (2006.01)
*C07K 7/50* (2006.01)
*A61K 38/00* (2006.01)
*C07K 7/06* (2006.01)
*C07K 14/705* (2006.01)
*C07K 14/715* (2006.01)
*C07K 17/08* (2006.01)

(52) U.S. Cl.
CPC ............ *C07K 14/001* (2013.01); *A61K 38/12* (2013.01); *A61P 35/00* (2018.01); *C07K 7/06* (2013.01); *C07K 7/08* (2013.01); *C07K 7/50* (2013.01); *C07K 14/70503* (2013.01); *C07K 14/70578* (2013.01); *C07K 14/715* (2013.01); *A61K 38/00* (2013.01); *C07K 17/08* (2013.01)

(58) Field of Classification Search
CPC ......... A61K 38/00; A61K 38/12; A61P 35/00; C07K 14/001; C07K 14/70503; C07K 14/70578; C07K 14/715; C07K 17/08; C07K 7/06; C07K 7/08
See application file for complete search history.

(56) References Cited

U.S. PATENT DOCUMENTS

| 10,875,894 | B2 * | 12/2020 | Chen ....................... A61K 47/60 |
| 2014/0249292 | A1 * | 9/2014 | Tite .......................... C07K 2/00 |
| | | | 530/300 |
| 2019/0184025 | A1 | 6/2019 | Chen et al. |
| 2019/0263866 | A1 | 8/2019 | Chen et al. |
| 2020/0255477 | A1 | 8/2020 | Chen et al. |
| 2020/0338203 | A1 | 10/2020 | Chen et al. |
| 2021/0040154 | A1 | 2/2021 | Mudd et al. |
| 2021/0069287 | A1 | 3/2021 | Mudd et al. |
| 2021/0101933 | A1 | 4/2021 | Chen et al. |
| 2021/0101937 | A1 | 4/2021 | Mudd et al. |
| 2021/0261620 | A1 | 8/2021 | Teufel et al. |

FOREIGN PATENT DOCUMENTS

| WO | WO2010089115 | | 8/2010 |
| WO | WO2016067035 | | 5/2016 |
| WO | WO2017/182672 | * | 10/2017 |
| WO | WO2017173408 | | 10/2017 |
| WO | WO2019025811 | | 2/2019 |
| WO | WO-2019/122860 A1 | | 6/2019 |
| WO | WO-2019/122861 A1 | | 6/2019 |
| WO | WO-2019/122863 A1 | | 6/2019 |
| WO | WO-2019/162682 A1 | | 8/2019 |
| WO | WO-2019/243313 A1 | | 12/2019 |
| WO | WO-2020/201753 A1 | | 10/2020 |
| WO | WO-2021/019243 A1 | | 2/2021 |
| WO | WO-2021/064428 A1 | | 4/2021 |
| WO | WO-2021/105694 A1 | | 6/2021 |

OTHER PUBLICATIONS

Gfeller et al. ('Current tools for predicting cancer-specific T cell immunity' Oncoimmunology 2016 v5(7) pp. 1-9) (Year: 2016).*
Liu et al. ('Abstract 3642: Tumor-antigen expression-dependent activation of the CD137 costimulatory pathway by bispecific DART proteins' American Association for Cancer Research v77(13) supplement Jul. 2017, pp. 1-4) (Year: 2017).*
Bicycle Therapeutics, Press Release—MarketWatch.com, Apr. 2018.
Rhodes et al., Chemistry—A European Journal, vol. 23, No. 52, Sep. 2017, pp. 12690-12703.
International Search Report and Written Opinion for PCT/GB2019/050951.

* cited by examiner

*Primary Examiner* — Fred H Reynolds
*Assistant Examiner* — Joseph Fischer
(74) *Attorney, Agent, or Firm* — Dechert LLP; Andrea L. C. Reid; Gang Wang

(57) ABSTRACT

The present invention relates to heterotandem bicyclic peptide complexes which comprise a first peptide ligand, which binds to a component present on an immune cell, conjugated via a linker to a second peptide ligand, which binds to a component present on a cancer cell. The invention also relates to the use of said heterotandem bicyclic peptide complexes in preventing, suppressing or treating cancer.

17 Claims, 73 Drawing Sheets

Specification includes a Sequence Listing.

BCY00010568

BCY00010000

BCY00010567

BCY00010578

BCY00011373

BCY00011375

US 11,453,703 B2

HETEROTANDEM BICYCLIC PEPTIDE COMPLEXES

FIELD OF THE INVENTION

The present invention relates to heterotandem bicyclic peptide complexes which comprise a first peptide ligand, which binds to a component present on an immune cell, conjugated via a linker to a second peptide ligand, which binds to a component present on a cancer cell. The invention also relates to the use of said heterotandem bicyclic peptide complexes in preventing, suppressing or treating cancer.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 $Å^2$; Wu et al. (2007), Science 330, 1066-71), a cyclic peptide with the Arg-Gly-Asp motif binding to integrin αVb3 (355 $Å^2$) (Xiong et al. (2002), Science 296 (5565), 151-5) or the cyclic peptide inhibitor upain-1 binding to urokinase-type plasminogen activator (603 $Å^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a heterotandem bicyclic peptide complex comprising:
(a) a first peptide ligand which binds to a component present on an immune cell; conjugated via a linker to
(b) a second peptide ligand which binds to a component present on a cancer cell; wherein each of said peptide ligands comprise a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

According to a further aspect of the invention, there is provided a pharmaceutical composition comprising a heterotandem bicyclic peptide complex as defined herein in combination with one or more pharmaceutically acceptable excipients.

According to a further aspect of the invention, there is provided a heterotandem bicyclic peptide complex as defined herein for use in preventing, suppressing or treating cancer.

DETAILED DESCRIPTION OF THE INVENTION

Figure 1:
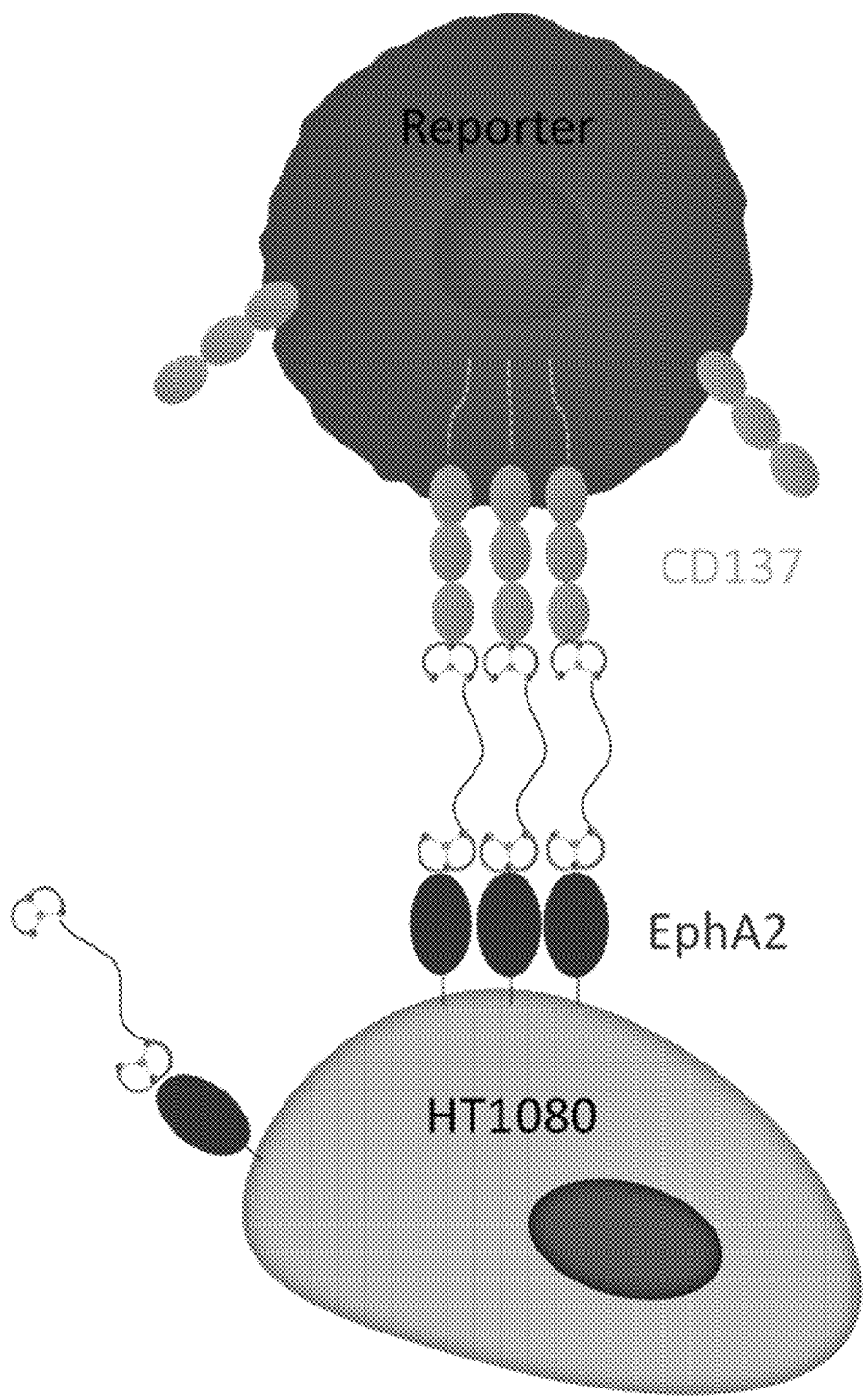
FIG. 1: Schematic representation of a heterotandem bicyclic peptide complex comprising an EphA2 and CD137 peptide ligand binding to both an immune cell and a cancer cell.

According to a first aspect of the invention, there is provided a heterotandem bicyclic peptide complex comprising:
(a) a first peptide ligand which binds to a component present on an immune cell; conjugated via a linker to
(b) a second peptide ligand which binds to a component present on a cancer cell; wherein each of said peptide ligands comprise a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

First Peptide Ligands

References herein to the term "immune cell" includes any cell within the immune system. Suitable examples include white blood cells, such as lymphocytes (e.g. T lymphocytes or T cells, B cells or natural killer cells). In one embodiment, the T cell is CD8 or CD4. In a further embodiment, the T cell is CD8. Other examples of immune cells include dendritic cells, follicular dendritic cells and granulocytes.

In one embodiment, the component present on an immune cell is CD137.

CD137 is a member of the tumour necrosis factor (TNF) receptor family. Its alternative names are tumour necrosis factor receptor superfamily member 9 (TNFRSF9), 4-IBB and induced by lymphocyte activation (ILA). CD137 can be expressed by activated T cells, but to a larger extent on CD8+ than on CD4+ T cells. In addition, CD137 expression is found on dendritic cells, follicular dendritic cells, natural killer cells, granulocytes and cells of blood vessel walls at sites of inflammation. One characterized activity of CD137 is its costimulatory activity for activated T cells. Crosslinking of CD137 enhances T cell proliferation, IL-2 secretion, survival and cytolytic activity. Further, it can enhance immune activity to eliminate tumours in mice.

CD137 is a T-cell costimulatory receptor induced on TCR activation (Nam et al., Curr. Cancer Drug Targets, 5:357-363 (2005); Waits et al., Annu. Rev, Immunol., 23:23-68 (2005)). In addition to its expression on activated CD4+ and CD8+ T cells, CD137 is also expressed on CD4+CD25+ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al. Annu. Rev. Immunol, 23:23-68 (2005)). On interaction with its ligand, CD137 leads to increased TCR-induced T-cell proliferation, cytokine production, functional maturation, and prolonged CD8+ T-cell survival (Nam et al, Curr. Cancer Drug Targets, 5:357-363 (2005), Watts et d-I., Annu. Rev. Immunol, 23:23-68 (2005)).

Signalling through CD137 by either CD137L or agonistic monoclonal antibodies (mAbs) against CD137 leads to increased TCR-induced T cell proliferation, cytokine production and functional maturation, and prolonged CD8+ T cell survival. These effects result from: (1) the activation of the NF-κB, c-Jun NH2-terminal kinase/stress-activated protein kinase (JNK/SAPK), and p38 mitogen-activated protein kinase (MAPK) signalling pathways, and (2) the control of anti-apoptotic and cell cycle-related gene expression.

Experiments performed in both CD137 and CD137L-deficient mice have additionally demonstrated the importance of CD137 costimulation in the generation of a fully competent T cell response.

IL-2 and IL-15 activated NK cells express CD137, and ligation of CD137 by agonistic mAbs stimulates NK cell proliferation and IFN-γ secretion, but not their cytolytic activity.

Furthermore, CD137-stimulated NK cells promote the expansion of activated T cells in vitro.

In accordance with their costimulatory function, agonist mAbs against CD137 have been shown to promote rejection of cardiac and skin allografts, eradicate established tumours, broaden primary antiviral CD8+ T cell responses, and increase T cell cytolytic potential. These studies support the view that CD137 signalling promotes T cell function which may enhance immunity against tumours and infection.

In one embodiment, the first peptide ligand comprises a CD137 binding bicyclic peptide ligand.

Suitable examples of CD137 binding bicyclic peptide ligands are disclosed in GB Patent Application Nos. 1712589.9 and 1802934.8, the peptides of which are incorporated herein by reference.

In one embodiment, the CD137 binding bicyclic peptide ligand comprises an amino acid sequence:

$C_i$IEEGQYC$_{ii}$FADPY[Nle]C$_{iii}$; (SEQ ID NO: 1)

$C_i$[tBuAla]PE[D-Ala]PYC$_{ii}$FADPY[Nle]C$_{iii}$; (SEQ ID NO: 3)

$C_i$IEEGQYC$_{ii}$F[D-Ala]DPY[Nle]C$_{iii}$; (SEQ ID NO: 4)

$C_i$[tBuAla]PK[D-Ala]PYC$_{ii}$FADPY[Nle]C$_{iii}$; (SEQ ID NO: 5)

$C_i$[tBuAla]PE[D-Lys]PYC$_{ii}$FADPY[Nle]C$_{iii}$; (SEQ ID NO: 6)

$C_i$[tBuAla]P[K(PYA)][D-Ala]PYC$_{ii}$FADPY[Nle]C$_{iii}$; (SEQ ID NO: 7)

$C_i$[tBuAla]PE[D-Lys(PYA)]PYC$_{ii}$FADPY[Nle]C$_{iii}$; (SEQ ID NO: 8)

$C_i$IEE[D-Lys(PYA)]QYC$_{ii}$FADPY(Nle)C$_{iii}$; and (SEQ ID NO: 9)

[dC$_i$][dI][dE][dE][K(PYA)][dQ][dY][dC$_{ii}$][dF][dA] [dD][dP][dY][dNle][dC$_{iii}$]; (SEQ ID NO: 10)

wherein $C_i$, $C_{ii}$ and $C_{iii}$ represent first, second and third cysteine residues, respectively, Nle represents norleucine, tBuAla represents t-butyl-alanine, PYA represents 4-pentynoic acid, or a pharmaceutically acceptable salt thereof.

In one particular embodiment which may be mentioned, the CD137 binding bicyclic peptide ligand comprises an amino acid sequence:

$C_i$IEEGQYC$_{ii}$FADPY[Nle]C$_{iii}$; (SEQ ID NO: 1)

wherein $C_i$, $C_{ii}$ and $C_{iii}$ represent first, second and third cysteine residues, respectively, Nle represents norleucine, or a pharmaceutically acceptable salt thereof.

In a further embodiment, the CD137 binding bicyclic peptide ligand comprises N- and C-terminal modifications and comprises:
Ac-A-(SEQ ID NO: 1)-Dap (hereinafter referred to as BCY7732);
Ac-A-(SEQ ID NO: 1)-Dap(PYA) (hereinafter referred to as BCY7741);
Ac-(SEQ ID NO: 3)-Dap (hereinafter referred to as BCY9172);
Ac-(SEQ ID NO: 3)-Dap(PYA) (hereinafter referred to as BCY11014);
Ac-A-(SEQ ID NO: 4)-Dap (hereinafter referred to as BCY8045);
Ac-(SEQ ID NO: 5)-A (hereinafter referred to as BCY8919);
Ac-(SEQ ID NO: 6)-A (hereinafter referred to as BCY8920);
Ac-(SEQ ID NO: 7)-A (hereinafter referred to as BCY8927);
Ac-(SEQ ID NO: 8)-A (hereinafter referred to as BCY8928);
Ac-A-(SEQ ID NO: 9)-A (hereinafter referred to as BCY7744); and
Ac-[dA]-(SEQ ID NO: 10)-[dA]-NH$_2$ (hereinafter referred to as BCY11506);

wherein Ac represents an acetyl group, Dap represents diaminopropionic acid and PYA represents 4-pentynoic acid, or a pharmaceutically acceptable salt thereof.

In a further embodiment which may be mentioned, the CD137 binding bicyclic peptide ligand comprises N- and C-terminal modifications and comprises:
Ac-A-(SEQ ID NO: 1)-Dap (hereinafter referred to as BCY7732);

wherein Ac represents an acetyl group and Dap represents diaminopropionic acid, or a pharmaceutically acceptable salt thereof.

Second Peptide Ligands

References herein to the term "cancer cell" includes any cell which is known to be involved in cancer. Cancer cells are created when the genes responsible for regulating cell division are damaged. Carcinogenesis is caused by mutation and epimutation of the genetic material of normal cells, which upsets the normal balance between proliferation and cell death. This results in uncontrolled cell division and the evolution of those cells by natural selection in the body. The uncontrolled and often rapid proliferation of cells can lead to benign or malignant tumours (cancer). Benign tumors do not spread to other parts of the body or invade other tissues. Malignant tumors can invade other organs, spread to distant locations (metastasis) and become life-threatening.

In one embodiment, the cancer cell is selected from an HT1080, SC-OV-3, PC3, H1376, NCI-H292, LnCap, MC38, 4T1-D02 and RKO tumor cell.

In one embodiment, the component present on a cancer cell is EphA2.

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov et al. (2004) Dev Cell 7, 465-80). Functional and biochemical Eph responses occur at higher ligand oligomerization states (Stein et al. (1998) Genes Dev 12, 667-678).

Among other patterning functions, various Ephs and ephrins have been shown to play a role in vascular development. Knockout of EphB4 and ephrin-B2 results in a lack of the ability to remodel capillary beds into blood vessels (Poliakov et al., supra) and embryonic lethality. Persistent expression of some Eph receptors and ephrins has also been observed in newly-formed, adult micro-vessels (Brantley-Sieders et al. (2004) Curr Pharm Des 10, 3431-42; Adams (2003) J Anat 202, 105-12).

The de-regulated re-emergence of some ephrins and their receptors in adults also has been observed to contribute to tumor invasion, metastasis and neo-angiogenesis (Nakamoto et al. (2002) Microsc Res Tech 59, 58-67; Brantley-Sieders et al., supra). Furthermore, some Eph family members have been found to be over-expressed on tumor cells from a variety of human tumors (Brantley-Sieders et al., supra); Marme (2002) Ann Hematol 81 Suppl 2, S66; Booth et al. (2002) Nat Med 8, 1360-1).

EPH receptor A2 (ephrin type-A receptor 2) is a protein that in humans is encoded by the EPHA2 gene.

EphA2 is upregulated in multiple cancers in man, often correlating with disease progression, metastasis and poor prognosis e.g.: breast (Zelinski et al (2001) Cancer Res. 61, 2301-2306; Zhuang et al (2010) Cancer Res. 70, 299-308; Brantley-Sieders et al (2011) PLoS One 6, e24426), lung (Brannan et al (2009) Cancer Prev Res (Phila) 2, 1039-1049; Kinch et al (2003) Clin Cancer Res. 9, 613-618; Guo et al (2013) J Thorac Oncol. 8, 301-308), gastric (Nakamura et al (2005) Cancer Sci. 96, 42-47; Yuan et al (2009) Dig Dis Sci 54, 2410-2417), pancreatic (Mudali et al (2006) Clin Exp Metastasis 23, 357-365), prostate (Walker-Daniels et al (1999) Prostate 41, 275-280), liver (Yang et al (2009) Hepatol Res. 39, 1169-1177) and glioblastoma (Wykosky et al (2005) Mol Cancer Res. 3, 541-551; Li et al (2010) Tumour Biol. 31, 477-488).

The full role of EphA2 in cancer progression is still not defined although there is evidence for interaction at numerous stages of cancer progression including tumour cell growth, survival, invasion and angiogenesis. Downregulation of EphA2 expression suppresses tumour cancer cell propagation (Binda et al (2012) Cancer Cell 22, 765-780), whilst EphA2 blockade inhibits VEGF induced cell migration (Hess et al (2001) Cancer Res. 61, 3250-3255), sprouting and angiogenesis (Cheng et al (2002) Mol Cancer Res. 1, 2-11; Lin et al (2007) Cancer 109, 332-40) and metastatic progression (Brantley-Sieders et al (2005) FASEB J. 19, 1884-1886).

An antibody drug conjugate to EphA2 has been shown to significantly diminish tumour growth in rat and mouse xenograft models (Jackson et al (2008) Cancer Research 68, 9367-9374) and a similar approach has been tried in man although treatment had to be discontinued for treatment related adverse events (Annunziata et al (2013) Invest New drugs 31, 77-84).

In one embodiment, the second peptide ligand comprises an EphA2 binding bicyclic peptide ligand.

Suitable examples of EphA2 binding bicyclic peptide ligands are disclosed in GB Patent Application Nos. 1721259.8 and 1804102.0, the peptides of which are incorporated herein by reference.

In one embodiment, the EphA2 binding bicyclic peptide ligand comprises an amino acid sequence:

(SEQ ID NO: 2)
$C_i$[HyP]LVNPLC$_{ii}$LHP[dD]W[HArg]C$_{iii}$;
and (SEQ ID NO: 11)
$C_i$LWDPTPC$_{ii}$ANLHL[HArg]C$_{iii}$;

wherein $C_i$, $C_{ii}$ and $C_{iii}$ represent first, second and third cysteine residues, respectively, HyP represents hydroxyproline, dD represents aspartic acid in D-configuration and HArg represents homoarginine, or a pharmaceutically acceptable salt thereof.

In one embodiment which may be mentioned, the EphA2 binding bicyclic peptide ligand comprises an amino acid sequence:

(SEQ ID NO: 2)
$C_i$[HyP]LVNPLC$_{ii}$LHP[dD]W[HArg]C$_{iii}$;

wherein $C_i$, $C_{ii}$ and $C_{iii}$ represent first, second and third cysteine residues, respectively, HyP represents hydroxyproline, dD represents aspartic acid in D-configuration and HArg represents homoarginine, or a pharmaceutically acceptable salt thereof.

In a further embodiment, the EphA2 binding bicyclic peptide ligand comprises N-terminal modifications and comprises:

A-HArg-D-(SEQ ID NO: 2) (hereinafter referred to as BCY9594);

[B-Ala][Sar$_{10}$]-A-[HArg]-D-(SEQ ID NO: 2) (hereinafter referred to as BCY6099);

[PYA][B-Ala]-[Sar$_{10}$]-A-[HArg]-D-(SEQ ID NO: 2) (hereinafter referred to as BCY6169); and

[PYA]B-Ala)-[Sar$_{10}$]-VGP-(SEQ ID NO: 11) (hereinafter referred to as BCY8941);

wherein HArg represents homoarginine, PYA represents 4-pentynoic acid, Sar$_{10}$ represents 10 sarcosine units, B-Ala represents beta-alanine, or a pharmaceutically acceptable salt thereof.

In a further embodiment which may be mentioned, the EphA2 binding bicyclic peptide ligand comprises N-terminal modifications and comprises:

A-HArg-D-(SEQ ID NO: 2) (hereinafter referred to as BCY9594).

wherein HArg represents homoarginine, or a pharmaceutically acceptable salt thereof.

In an alternative embodiment, the component present on a cancer cell is PD-L1.

Programmed cell death 1 ligand 1 (PD-L1) is a 290 amino acid type I transmembrane protein encoded by the CD274 gene on mouse chromosome 19 and human chromosome 9. PD-L1 expression is involved in evasion of immune responses involved in chronic infection, e.g., chronic viral infection (including, for example, HIV, HBV, HCV and HTLV, among others), chronic bacterial infection (including, for example, *Helicobacter pylori*, among others), and chronic parasitic infection (including, for example, *Schistosoma mansoni*). PD-L1 expression has been detected in a number of tissues and cell types including T-cells, B-cells, macrophages, dendritic cells, and nonhaematopoietic cells including endothelial cells, hepatocytes, muscle cells, and placenta.

PD-L1 expression is also involved in suppression of anti-tumour immune activity. Tumours express antigens that can be recognised by host T-cells, but immunologic clearance of tumours is rare. Part of this failure is due to immune suppression by the tumour microenvironment. PD-L1 expression on many tumours is a component of this suppressive milieu and acts in concert with other immunosuppressive signals. PD-L1 expression has been shown in situ on a wide variety of solid tumours including breast, lung, colon, ovarian, melanoma, bladder, liver, salivary, stomach, gliomas, thyroid, thymic epithelial, head, and neck (Brown J A et al. 2003 Immunol. 170:1257-66; Dong H et al. 2002 Nat. Med. 8:793-800; Hamanishi J, et al. 2007 Proc. Natl. Acad. Sci. USA 104:3360-65; Strome S E et al. 2003 Cancer Res. 63:6501-5; Inman B A et al. 2007 Cancer 109:1499-505; Konishi J et al. 2004 Clin. Cancer Res. 10:5094-100; Nakanishi J et al. 2007 Cancer Immunol. Immunother. 56:1173-82; Nomi T et al. 2007 Clin. Cancer Res. 13:2151-57; Thompson R H et al. 2004 Proc. Natl. Acad. Sci. USA 101: 17174-79; Wu C et al. 2006 Acta Histochem. 108:19-24). In addition, the expression of the receptor for PD-L1, Programmed cell death protein 1 (also known as PD-1 and CD279) is upregulated on tumour infiltrating lymphocytes, and this also contributes to tumour immunosuppression (Blank C et al. 2003 Immunol. 171:4574-81). Most importantly, studies relating PD-L1 expression on tumours to disease outcome show that PD-L1 expression strongly correlates with unfavourable prognosis in kidney, ovarian, bladder, breast, gastric, and pancreatic cancer (Hamanishi J et al. 2007 Proc. Natl. Acad. Sci. USA 104:3360-65; Inman B A et al. 2007 Cancer 109:1499-505; Konishi J et al. 2004 Clin. Cancer Res. 10:5094-100; Nakanishi J et al. 2007 Cancer Immunol. Immunother. 56:1173-82; Nomi T et al. 2007 Clin. Cancer Res. 13:2151-57; Thompson R H et al. 2004 Proc. Natl. Acad. Sci. USA 101:17174-79; Wu C et al. 2006 Acta Histochem. 108:19-24). In addition, these studies suggest that higher levels of PD-L1 expression on tumours may facilitate advancement of tumour stage and invasion into deeper tissue structures.

The PD-1 pathway can also play a role in haematologic malignancies. PD-L1 is expressed on multiple myeloma cells but not on normal plasma cells (Liu J et al. 2007 Blood 110:296-304). PD-L1 is expressed on some primary T-cell lymphomas, particularly anaplastic large cell T lymphomas (Brown J A et al, 2003 Immunol. 170:1257-66). PD-1 is highly expressed on the T-cells of angioimmunoblastic lymphomas, and PD-L1 is expressed on the associated follicular dendritic cell network (Dorfman D M et al. 2006 Am. J. Surg. Pathol. 30:802-10). In nodular lymphocyte-predominant Hodgkin lymphoma, the T-cells associated with lymphocytic or histiocytic (L&H) cells express PD-1. Microarray analysis using a readout of genes induced by PD-1 ligation suggests that tumour-associated T-cells are responding to PD-1 signals in situ in Hodgkin lymphoma (Chemnitz J M et al. 2007 Blood 110:3226-33). PD-1 and PD-L1 are expressed on CD4 T-cells in HTLV-1-mediated adult T-cell leukaemia and lymphoma (Shimauchi T et al. 2007 Int. J. Cancer 121: 2585-90). These tumour cells are hyporesponsive to TCR signals.

Studies in animal models demonstrate that PD-L1 on tumours inhibits T-cell activation and lysis of tumour cells and in some cases leads to increased tumour-specific T-cell death (Dong H et al. 2002 Nat. Med. 8:793-800; Hirano F et al. 2005 Cancer Res. 65:1089-96). Tumour-associated APCs can also utilise the PD-1:PD-L1 pathway to control antitumour T-cell responses. PD-L1 expression on a population of tumour-associated myeloid DCs is upregulated by tumour environmental factors (Curiel T J et al. 2003 Nat. Med. 9:562-67). Plasmacytoid dendritic cells (DCs) in the tumour-draining lymph node of B16 melanoma express IDO, which strongly activates the suppressive activity of regulatory T-cells. The suppressive activity of IDO-treated regulatory T-cells required cell contact with IDO-expressing DCs (Sharma M D et al. 2007 Clin. Invest. 117:2570-82).

In one embodiment, the second peptide ligand comprises a PD-L1 binding bicyclic peptide ligand.

Suitable examples of PD-L1 binding bicyclic peptide ligands are disclosed in GB Patent Application Nos. 1820956.9 and 1820969.2, the peptides of which are incorporated herein by reference.

In one embodiment, the PD-L1 binding bicyclic peptide ligand comprises an amino acid sequence selected from:

$C_i$[HArg]DWC$_{ii}$HWTFSHGHPC$_{iii}$; (SEQ ID NO: 12)

$C_i$SAGWLTMC$_{ii}$QKLHLC$_{iii}$; (SEQ ID NO: 13)
and $C_i$SAGWLTMC$_{ii}$Q[K(PYA)]LHLC$_{iii}$; (SEQ ID NO: 14)

wherein $C_i$, $C_{ii}$ and $C_{iii}$ represent first, second and third cysteine residues, respectively, HArg represents homoarginine and PYA represents 4-pentynoic acid, or a pharmaceutically acceptable salt thereof.

In a further embodiment, the PD-L1 binding bicyclic peptide ligand comprises N-terminal and/or C-terminal modifications and comprises:

[PYA]B-Ala)-[Sar$_{10}$]-(SEQ ID NO: 12) (hereinafter referred to as BCY8938);

[PYA][B-Ala]-[Sar$_{10}$]-SDK-(SEQ ID NO: 13) (hereinafter referred to as BCY10043);

NH$_2$-SDK-(SEQ ID NO: 13)-[Sar$_{10}$]-[K(PYA)] (hereinafter referred to as BCY10044);

NH$_2$-SDK-(SEQ ID NO: 14) (hereinafter referred to as BCY10045); and

Ac-SDK-(SEQ ID NO: 14)-PSH (hereinafter referred to as BCY10861);

wherein PYA represents 4-pentynoic acid, B-Ala represents beta-alanine, Sar$_{10}$ represents 10 sarcosine units, or a pharmaceutically acceptable salt thereof.

In an alternative embodiment, the component present on a cancer cell is Nectin-4.

Nectin-4 is a surface molecule that belongs to the nectin family of proteins, which comprises 4 members. Nectins are cell adhesion molecules that play a key role in various biological processes such as polarity, proliferation, differentiation and migration, for epithelial, endothelial, immune and neuronal cells, during development and adult life. They are involved in several pathological processes in humans. They are the main receptors for poliovirus, herpes simplex virus and measles virus. Mutations in the genes encoding Nectin-1 (PVRL1) or Nectin-4 (PVRL4) cause ectodermal dysplasia syndromes associated with other abnormalities. Nectin-4 is expressed during foetal development. In adult tissues its expression is more restricted than that of other members of the family. Nectin-4 is a tumour-associated antigen in 50%, 49% and 86% of breast, ovarian and lung carcinomas, respectively, mostly on tumours of bad prognosis. Its expression is not detected in the corresponding normal tissues. In breast tumours, Nectin-4 is expressed mainly in triple-negative and ERBB2+ carcinomas. In the serum of patients with these cancers, the detection of soluble forms of Nectin-4 is associated with a poor prognosis. Levels of serum Nectin-4 increase during metastatic progression and decrease after treatment. These results suggest that Nectin-4 could be a reliable target for the treatment of cancer. Accordingly, several anti-Nectin-4 antibodies have been described in the prior art. In particular, Enfortumab Vedotin (ASG-22ME) is an antibody-drug conjugate (ADC) targeting Nectin-4 and is currently clinically investigated for the treatment of patients suffering from solid tumours.

In one embodiment, the second peptide ligand comprises a Nectin-4 binding bicyclic peptide ligand.

Suitable examples of Nectin-4 binding bicyclic peptide ligands are disclosed in GB Patent Application Nos 1810250.9, 1815684.4 and 1818499.4, the peptides of which are incorporated herein by reference.

In one embodiment, the Nectin-4 binding bicyclic peptide ligand comprises an amino acid sequence selected from:

$C_iP[1Nal][dD]C_{ii}M[HArg]DWSTP[HyP]WC_{iii}$ (SEQ ID NO: 15; hereinafter referred to as BCY8116);

$C_iP[1Nal][dD]C_{ii}M[HArg]D[dW]STP[HyP][dW]C_{iii}$ (SEQ ID NO: 16; hereinafter referred to as BCY11415); and $C_iP[1Nal][dK](Sar_{10}-(B-Ala))C_{ii}M[HArg]DWSTP[HyP]WC_{iii}$ (SEQ ID NO: 17);

$C_iPFGC_{ii}M[HArg]DWSTP[HyP]WC_{iii}$ (SEQ ID NO: 18; hereinafter referred to as BCY11414);

wherein $C_i$, $C_{ii}$ and $C_{iii}$ represent first, second and third cysteine residues, respectively, 1Nal represents 1-naphthylalanine, HArg represents homoarginine, HyP represents hydroxyproline, $Sar_{10}$ represents 10 sarcosine units, B-Ala represents beta-alanine, or a pharmaceutically acceptable salt thereof.

In a further embodiment, the Nectin-4 binding bicyclic peptide ligand optionally comprises N-terminal modifications and comprises:

SEQ ID NO: 15 (hereinafter referred to as BCY8116);
[PYA]-[B-Ala]-[$Sar_{10}$]-(SEQ ID NO: 15) (hereinafter referred to as BCY8846);
SEQ ID NO: 16 (hereinafter referred to as BCY11415);
[PYA]-[B-Ala]-[$Sar_{10}$]-(SEQ ID NO: 16) (hereinafter referred to as BCY11942);
Ac-(SEQ ID NO: 17) (hereinafter referred to as BCY8831); and
SEQ ID NO: 18 (hereinafter referred to as BCY11414);

wherein PYA represents 4-pentynoic acid, B-Ala represents beta-alanine, $Sar_{10}$ represents 10 sarcosine units, or a pharmaceutically acceptable salt thereof.

In an alternative embodiment, the component present on a cancer cell is prostate-specific membrane antigen (PSMA).

Prostate-specific membrane antigen (PSMA) (also known as Glutamate carboxypeptidase II (GCPII), N-acetyl-L-aspartyl-L-glutamate peptidase I (NAALADase I) and NAAG peptidase) is an enzyme that in humans is encoded by the FOLH1 (folate hydrolase 1) gene. Human GCPII contains 750 amino acids and weighs approximately 84 kDa.

Human PSMA is highly expressed in the prostate, roughly a hundred times greater than in most other tissues. In some prostate cancers, PSMA is the second-most upregulated gene product, with an 8- to 12-fold increase over levels in noncancerous prostate cells. Because of this high expression, PSMA is being developed as potential biomarker for therapy and imaging of some cancers. In human prostate cancer, the higher expressing tumors are associated with quicker time to progression and a greater percentage of patients suffering relapse.

In one embodiment, the second peptide ligand comprises a PSMA binding bicyclic peptide ligand.

Suitable examples of PSMA binding bicyclic peptide ligands are disclosed in GB Patent Application Nos 1810318.4, 1810325.9 and 1820325.7, the peptides of which are incorporated herein by reference.

Linkers

It will be appreciated that the first peptide ligand may be conjugated to the second peptide ligand via any suitable linker. Typically the design of said linker will be such that the two Bicyclic peptides are presented in such a manner that they can bind unencumbered to their respective targets either alone or while simultaneously binding to both target receptors. Additionally, the linker should permit binding to both targets simultaneously while maintaining an appropriate distance between the target cells that would lead to the desired functional outcome. The properties of the linker may be modulated to increase length, rigidity or solubility to optimise the desired functional outcome. The linker may also be designed to permit the attachment of more than one Bicycle to the same target. Increasing the valency of either binding peptide may serve to increase the affinity of the heterotandem for the target cells or may help to induce oligomerisation of one or both of the target receptors.

In one embodiment, the linker is selected from the following sequences: $-CH_2-$, $-PEG_5-$, $-PEG_{10}-$, $-PEG_{12}-$, $-PEG_{23}-$, $-PEG_{24}-$, $-PEG_{15}-Sar_5-$, $-PEG_{10}-Sar_{10}-$, $-PEG_5-Sar_{15}-$, $-PEG_5-Sar_5-$, $-B-Ala-Sar_{20}-$, $-B-Ala-Sar_{10}-PEG_{10}-$, $-B-Ala-Sar_5-PEG_{15}-$ and $-B-Ala-Sar_5-PEG_5-$.

Structural representations of suitable linkers are detailed below:

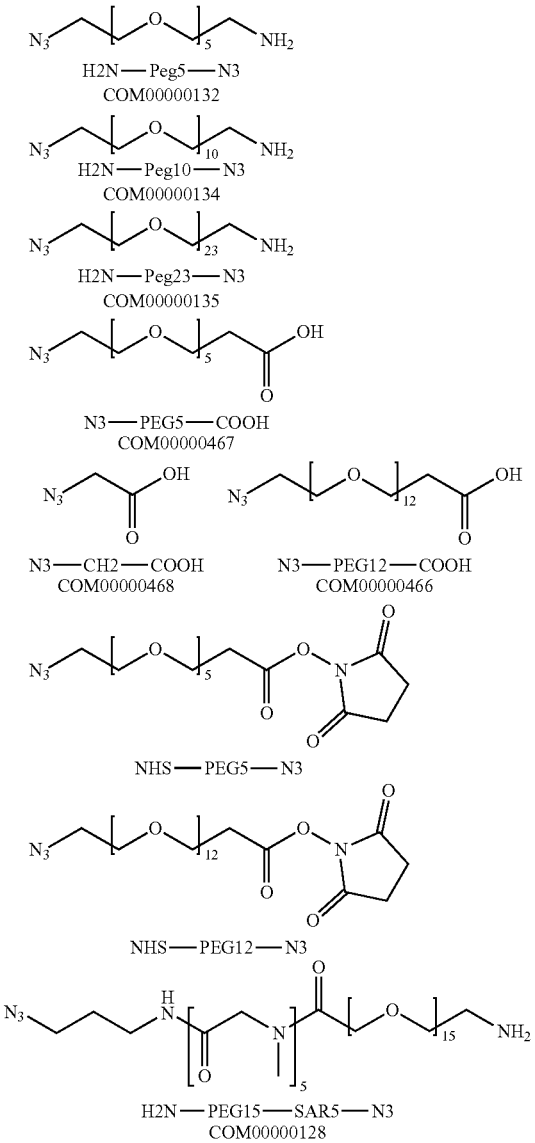

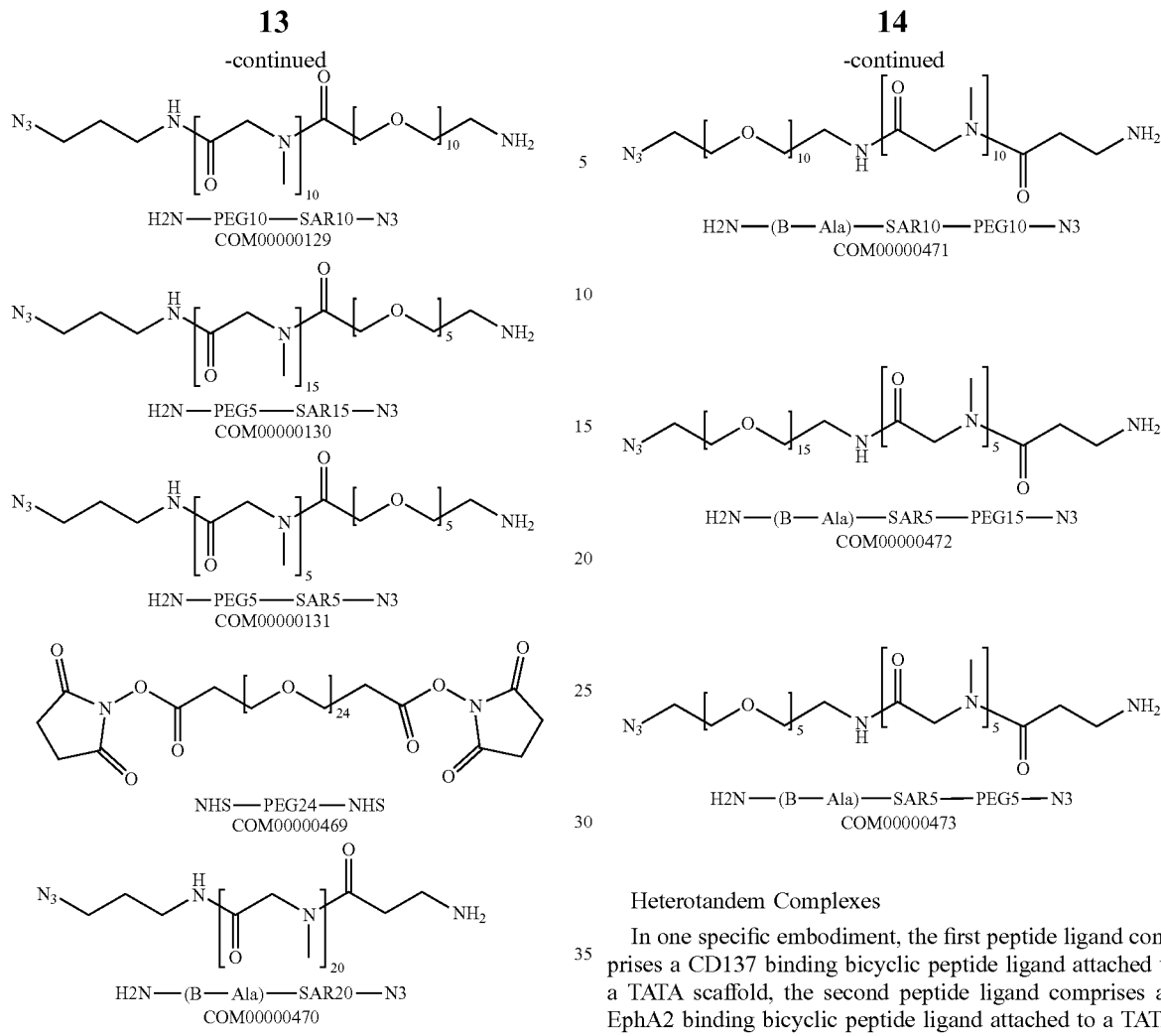

Heterotandem Complexes

In one specific embodiment, the first peptide ligand comprises a CD137 binding bicyclic peptide ligand attached to a TATA scaffold, the second peptide ligand comprises an EphA2 binding bicyclic peptide ligand attached to a TATA scaffold and said heterotandem complex is selected from:

| Complex No. | EphA2 BCY No. | Attachment Point | Linker | CD137 BCY No. | Attachment Point |
|---|---|---|---|---|---|
| BCY9173 | BCY6169 | N-terminal PYA | -PEG$_{12}$- | BCY9172 | C-terminal Dap |
| BCY7985 | BCY6169 | N-terminal PYA | -PEG$_{12}$- | BCY7732 | C-terminal Dap |
| BCY8942 | BCY6169 | N-terminal PYA | -PEG$_{12}$- | BCY8045 | C-terminal Dap |
| BCY8943 | BCY8941 | N-terminal PYA | -PEG$_{12}$- | BCY7732 | C-terminal Dap |
| BCY9647 | BCY6099 | N-terminus | -PEG$_{10}$- | BCY7741 | C-terminal Dap(PYA) |
| BCY9648 | BCY6099 | N-terminus | -PEG$_{23}$- | BCY7741 | C-terminal Dap(PYA) |
| BCY9655 | BCY6099 | N-terminus | -PEG$_{15}$- | BCY7741 | C-terminal Dap(PYA) |
| BCY9656 | BCY6099 | N-terminus | -PEG$_{10}$-Sar$_{5}$- | BCY7741 | C-terminal Dap(PYA) |
| BCY9657 | BCY6099 | N-terminus | -PEG$_{5}$-Sar$_{10}$- | BCY7741 | C-terminal Dap(PYA) |
| BCY9658 | BCY6099 | N-terminus | -PEG$_{5}$-Sar$_{15}$- | BCY7741 | C-terminal Dap(PYA) |
| BCY9659 | BCY6099 | N-terminus | -PEG$_{5}$-Sar$_{5}$- | BCY7741 | C-terminal Dap(PYA) |
| BCY9758 | BCY6099 | N-terminus | -PEG$_{24}$- | BCY7732 | C-terminal Dap |
| BCY10568 | BCY6169 | N-terminal PYA | -PEG$_{12}$- | BCY8919 | Lys3 |
| BCY10570 | BCY6169 | N-terminal PYA | -PEG$_{12}$- | BCY8920 | dLys4 |
| BCY10574 | BCY9594 | N-terminus | -PEG$_{5}$- | BCY8927 | Lys (PYA)3 |
| BCY10575 | BCY9594 | N-terminus | -PEG$_{5}$- | BCY8928 | dLys (PYA)4 |
| BCY10576 | BCY9594 | N-terminus | -PEG$_{5}$- | BCY11014 | C-terminal Dap(PYA) |
| BCY10577 | BCY6169 | N-terminus | —CH$_{2}$— | BCY9172 | C-terminal Dap |

Figure 2:
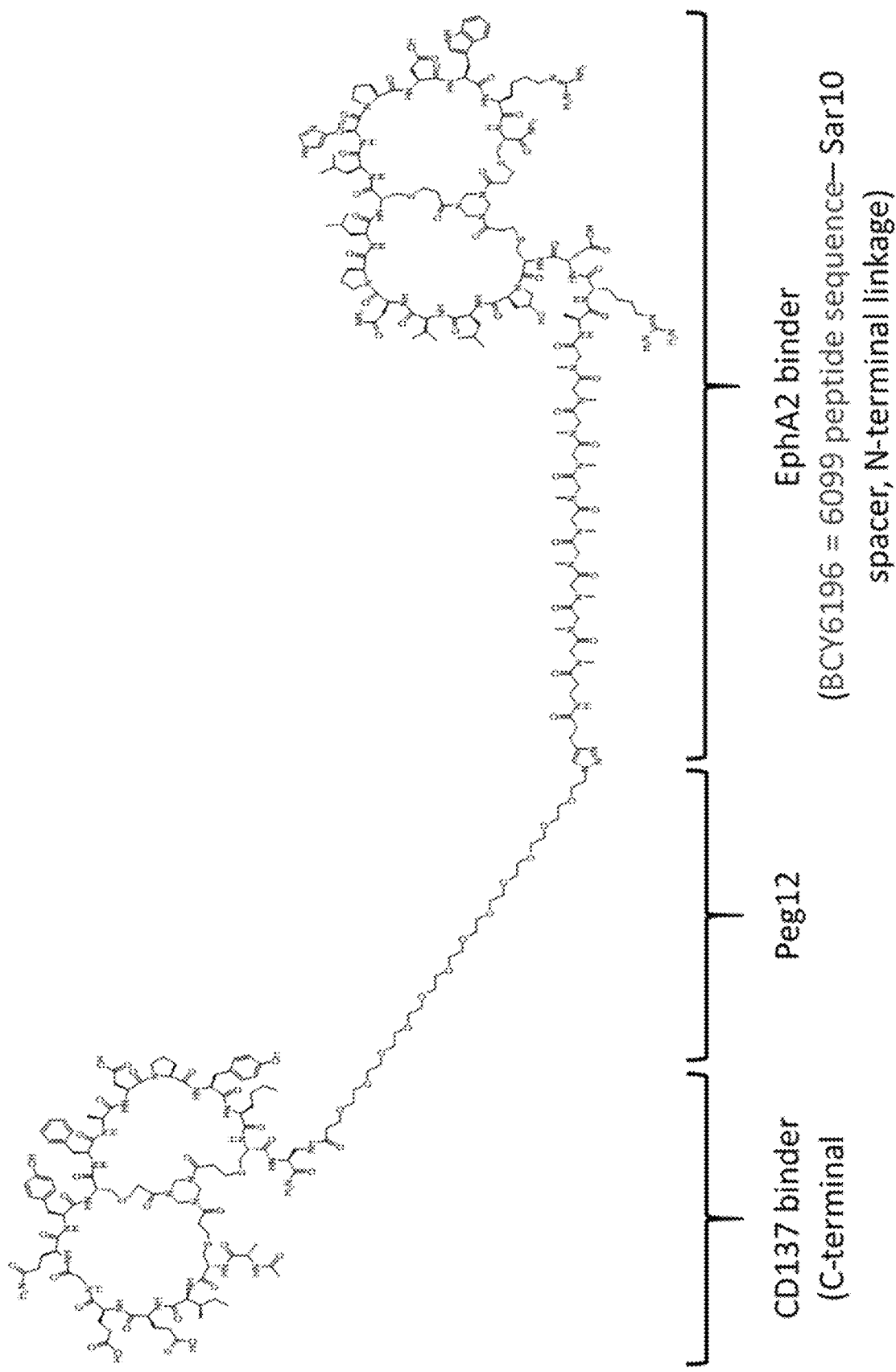
FIG. 2: Structure and composition of the EphA2-CD137 heterotandem bicyclic peptide complex BCY7985.

The heterotandem bicyclic peptide complex BCY7985 consists of a CD137-specific peptide BCY7859 linked to the N-terminal PYA group of an EphA2-specific peptide BCY6169 via PEG$_{12}$ (shown pictorially in FIG. 2).

Figure 3:
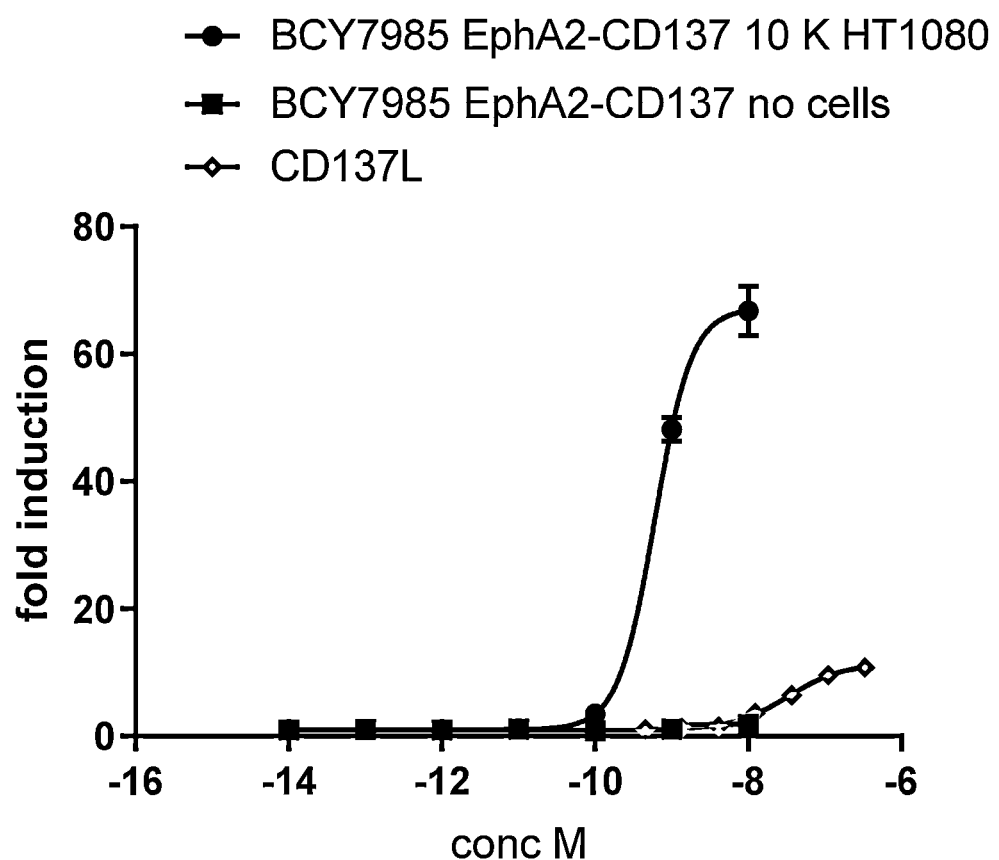
FIG. 3: Analysis of the EphA2-CD137 heterotandem bicyclic peptide complex BCY7985 in the Promega CD137 luciferase reporter assay (CS196008) in the presence of EphA2-expressing HT1080 cells.

CD137 is a homotrimeric protein and the natural ligand CD137L exists as a homotrimer either expressed on immune cells or secreted. The biology of CD137 is highly dependent on multimerization to induce CD137 activity in immune cells. One way to generate CD137 multimerization is through cellular cross-linking of the CD137 specific agonist through interaction with a specific receptor present on another cell.

herein in FIG. 3 wherein it can be seen that BCY7985 showed strong induction of CD137 cell activity in the Promega CD137 luciferase reporter assay (CS196008) in the presence of EphA2-expressing HT1080 cells.

In one alternative specific embodiment, the first peptide ligand comprises a CD137 binding bicyclic peptide ligand attached to a TATA scaffold, the second peptide ligand comprises a Nectin-4 binding bicyclic peptide ligand attached to a TATA scaffold and said heterotandem complex is selected from:

| Complex No. | Nectin-4 BCY No. | Attachment Point | Linker | CD137 BCY No. | Attachment Point |
|---|---|---|---|---|---|
| BCY8854 | BCY8846 | N-terminal PYA | -PEG$_{12}$- | BCY7732 | C-terminal Dap |
| BCY9350 | BCY11942 | N-terminal PYA | -PEG$_{12}$- | BCY7732 | C-terminal Dap |
| BCY9351 | BCY8846 | N-terminal PYA | -PEG$_{12}$- | BCY8045 | C-terminal Dap |
| BCY9399 | BCY8116 | N-terminus | -PEG$_{10}$- | BCY7741 | C-terminal Dap(PYA) |
| BCY9400 | BCY8116 | N-terminus | -PEG$_{23}$- | BCY7741 | C-terminal Dap(PYA) |
| BCY9401 | BCY8116 | N-terminus | -B-Ala-Sar$_{20}$- | BCY7741 | C-terminal Dap(PYA) |
| BCY9403 | BCY8116 | N-terminus | -B-Ala-Sar$_{10}$-PEG$_{10}$- | BCY7741 | C-terminal Dap(PYA) |
| BCY9405 | BCY8116 | N-terminus | -B-Ala-Sar$_5$-PEG$_{15}$- | BCY7741 | C-terminal Dap(PYA) |
| BCY9406 | BCY8116 | N-terminus | -B-Ala-Sar$_5$-PEG$_5$- | BCY7741 | C-terminal Dap(PYA) |
| BCY9407 | BCY8116 | N-terminus | -PEG$_{15}$-Sar$_5$- | BCY7741 | C-terminal Dap(PYA) |
| BCY9408 | BCY8116 | N-terminus | -PEG$_{10}$-Sar$_{10}$- | BCY7741 | C-terminal Dap(PYA) |
| BCY9409 | BCY8116 | N-terminus | -PEG$_5$-Sar$_{15}$- | BCY7741 | C-terminal Dap(PYA) |
| BCY9410 | BCY8116 | N-terminus | -PEG$_5$-Sar$_5$- | BCY7741 | C-terminal Dap(PYA) |
| BCY9411 | BCY8116 | N-terminus | -PEG$_5$- | BCY7741 | C-terminal Dap(PYA) |
| BCY9759 | BCY8116 | N-terminus | -PEG$_{24}$- | BCY7732 | C-terminal Dap |
| BCY10000 | BCY8846 | N-terminal PYA | -PEG$_{12}$- | BCY9172 | C-terminal Dap |
| BCY10567 | BCY8846 | N-terminal PYA | -PEG$_{12}$- | BCY8919 | Lys3 |
| BCY10569 | BCY8846 | N-terminal PYA | -PEG$_{12}$- | BCY8920 | dLys4 |
| BCY10571 | BCY8116 | N-terminus | -PEG$_5$- | BCY8927 | Lys(PYA)3 |
| BCY10572 | BCY8116 | N-terminus | -PEG$_5$- | BCY8928 | dLys (PYA)4 |
| BCY10573 | BCY8116 | N-terminus | -PEG$_5$- | BCY11014 | C-terminal Dap(PYA) |
| BCY10578 | BCY8846 | N-terminal PYA | —CH$_2$— | BCY9172 | C-terminal Dap |
| BCY10917 | BCY8831 | dLys(Sar$_{10}$)-(B-Ala))4 | -PEG$_{12}$- | BCY11014 | C-terminal Dap(PYA) |
| BCY11020 | BCY8831 | dLys(Sar$_{10}$)-(B-Ala))4 | -PEG$_5$- | BCY11014 | C-terminal Dap(PYA) |
| BCY11373 | BCY8116 | N-terminus | —CH$_2$— | BCY8927 | Lys(PYA)3 |
| BCY11374 | BCY8116 | N-terminus | —CH$_2$— | BCY8928 | dLys (PYA)4 |
| BCY11375 | BCY8116 | N-terminus | —CH$_2$— | BCY11014 | C-terminal Dap(PYA) |
| BCY11616 | BCY8116 | N-terminus | -PEG$_5$- | BCY7744 | dLys (PYA)4 |
| BCY11617 | BCY8116 | N-terminus | -PEG$_5$- | BCY11506 | Lys(PYA)4 |
| BCY11857 | BCY11414 | N-terminus | -PEG$_5$- | BCY7744 | dLys (PYA)4 |
| BCY11858 | BCY11414 | N-terminus | -PEG$_5$- | BCY8928 | dLys (PYA)4 |
| BCY11859 | BCY11415 | N-terminus | -PEG$_5$- | BCY8928 | dLys (PYA)4 |

EphA2 is highly expressed on tumour cells and oligomerization of this receptor tyrosine kinase by Ephrin-A ligands drives its activation. Without being bound by theory, the inventors believe that a EphA2-CD137 heterotandem consisting of one EphA2-specific peptide coupled to one CD137-specific peptide acts to cross-link CD137. The implication is that CD137 would be multimerized and activated in the presence of EphA2 on cells such as tumour cells. This would drive CD137 immune cell activation in the local tumour environment (FIG. 1).

This hypothesis was tested in the CD137 cellular activity reporter assay described herein and the results are shown Without being bound by theory, the inventors believe that a Nectin-4-CD137 heterotandem consisting of one Nectin-4-specific peptide coupled to one CD137-specific peptide acts to cross-link CD137 in the same manner as described hereinbefore for EphA2.

In one embodiment, the Nectin-4-CD137 heterotandem is other than any one or more of: BCY11857, BCY11858 and/or BCY11859.

In one alternative specific embodiment, the first peptide ligand comprises a CD137 binding bicyclic peptide ligand attached to a TATA scaffold, the second peptide ligand comprises a PD-L1 binding bicyclic peptide ligand attached to a TATA scaffold and said heterotandem complex is selected from:

| Complex No. | PD-L1 BCY No. | Attachment Point | Linker | CD137 BCY No. | Attachment Point |
|---|---|---|---|---|---|
| BCY8939 | BCY8938 | N-terminal PYA | -PEG$_{12}$- | BCY7732 | C-terminal Dap |
| BCY10580 | BCY10043 | N-terminal PYA | -PEG$_{12}$- | BCY9172 | C-terminal Dap |
| BCY10581 | BCY10044 | C-terminal Lys(PYA) | -PEG$_{12}$- | BCY9172 | C-terminal Dap |
| BCY10582 | BCY10045 | Lys(PYA)9 | -PEG$_{12}$- | BCY9172 | C-terminal Dap |
| BCY11017 | BCY10861 | Lys(PYA)9 | -PEG$_{12}$- | BCY8919 | Lys3 |
| BCY11018 | BCY10861 | Lys(PYA)9 | -PEG$_{12}$- | BCY8920 | dLys4 |
| BCY11019 | BCY10861 | Lys(PYA)9 | -PEG$_{12}$- | BCY9172 | C-terminal Dap |
| BCY11376 | BCY10861 | Lys(PYA)9 | —CH$_2$— | BCY8919 | Lys3 |
| BCY11377 | BCY10861 | Lys(PYA)9 | —CH$_2$— | BCY8920 | dLys4 |
| BCY11378 | BCY10861 | Lys(PYA)9 | —CH$_2$— | BCY9172 | C-terminal Dap |
| BCY11379 | BCY10861 | Lys(PYA)9 | -PEG$_5$- | BCY8919 | Lys3 |
| BCY11380 | BCY10861 | Lys(PYA)9 | -PEG$_5$- | BCY8920 | dLys4 |
| BCY11381 | BCY10861 | Lys(PYA)9 | -PEG$_5$- | BCY9172 | C-terminal Dap |

Without being bound by theory, the inventors believe that a PD-L1-CD137 heterotandem consisting of one PD-L1-specific peptide coupled to one CD137-specific peptide acts to cross-link CD137 in the same manner as described hereinbefore for EphA2.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

Nomenclature

Numbering

When referring to amino acid residue positions within compounds of the invention, cysteine residues ($C_i$, $C_{ii}$ and $C_{iii}$) are omitted from the numbering as they are invariant, therefore, the numbering of amino acid residues within SEQ ID NO: 1 is referred to as below:

(SEQ ID NO: 1)
$C_i$-I$_1$-E$_2$-E$_3$-G$_4$-Q$_5$-Y$_6$-$C_{ii}$-F$_7$-A$_8$-D$_9$-P$_{10}$-Y$_{11}$-[Nle]$_{12}$-

$C_{iii}$.

For the purpose of this description, all bicyclic peptides are assumed to be cyclised with TBMB (1,3,5-tris(bromomethyl)benzene) or 1,1',1"-(1,3,5-triazinane-1,3,5-triyl)triprop-2-en-1-one (TATA) and yielding a tri-substituted structure. Cyclisation with TBMB and TATA occurs on $C_i$, $C_{ii}$ and $C_{iii}$.

Molecular Format

N- or C-terminal extensions to the bicycle core sequence are added to the left or right side of the sequence, separated by a hyphen. For example, an N-terminal βAla-Sar10-Ala tail would be denoted as:

βAla-Sar10-A-(SEQ ID NO: X).

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa).

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the invention contain an amine function, these may form quaternary ammonium salts, for example by reaction with an alkylating agent according to methods well known to the skilled person. Such quaternary ammonium compounds are within the scope of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}$H (D) and $^{3}$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the Nectin-4 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment, the molecular scaffold may be a macromolecule. In one embodiment, the molecular scaffold is a macromolecule composed of amino acids, nucleotides or carbohydrates.

In one embodiment, the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of hexahydro-1,3,5-triazine, especially 1,3, 5-Triacryloylhexahydro-1,3,5-triazine ('TATA'), or a derivative thereof.

In one embodiment, the molecular scaffold is 2,4,6-tris (bromomethyl)mesitylene. This molecule is similar to 1,3, 5-tris(bromomethyl)benzene (TBMB) but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene (the scaffold reactive group exemplified by TBMB) or iodoacetamide. Other scaffold reactive groups that are used to selectively couple compounds to cysteines in proteins are maleimides, αβ unsaturated carbonyl containing compounds and α-halomethylcarbonyl containing compounds. Examples of maleimides which may be used as molecular scaffolds in the invention include: tris-(2-maleimidoethyl)amine, tris-(2-maleimidoethyl)benzene, tris-(maleimido)benzene. An example of an αβ unsaturated carbonyl containing compound is 1,1',1"-(1,3,5-triazinane-1,3,5-triyl)triprop-2-en-1-one (TATA) (Angewandte Chemie, International Edition (2014), 53(6), 1602-1606). An example of an α-halomethylcarbonyl containing compound is N,N',N"-(benzene-1,3,5-triyl)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TBMB) could be added during the chemical synthesis of the first peptide so as to react with the three cysteine groups; a further cysteine or thiol could then be appended to the N- or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

According to a further aspect of the invention, there is provided a heterotandem bicyclic peptide complex as defined herein for use in preventing, suppressing or treating cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Example 1: Synthesis of Linkers

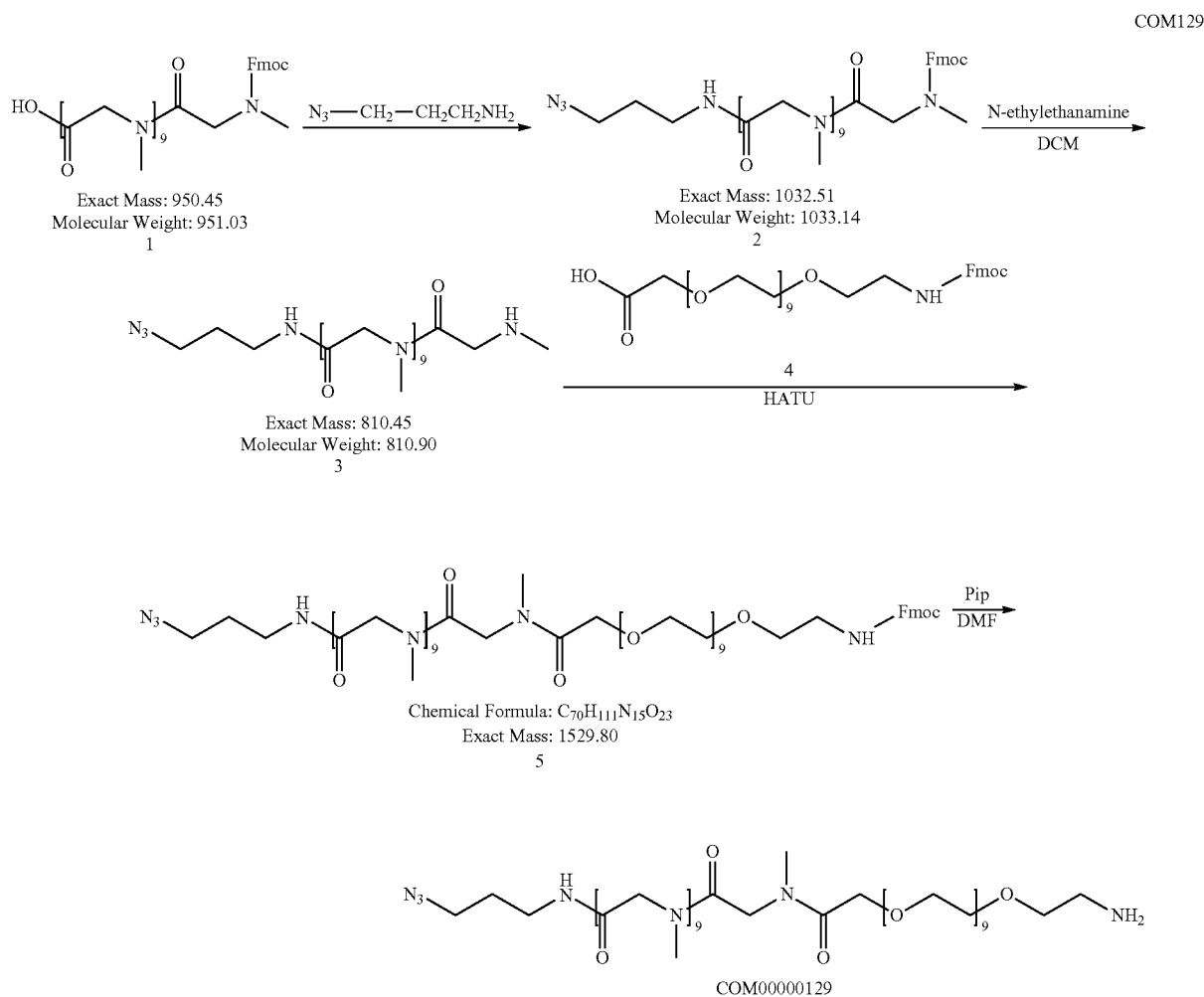

A mixture of compound 1 (700.0 mg, 1.18 mmol, 1.0 eq), 3-azidopropan-1-amine (117.66 mg, 1.18 mmol, 1.0 eq), EDCI (270.4 mg, 1.41 mmol, 1.2 eq), HOBt (190.6 mg, 1.41 mmol, 1.2 eq) was dissolved in DCM (20 mL, pre-degassed and purged with $N_2$ for 3 times), and then the mixture was stirred at 20-25° C. for 1 hr under $N_2$ atmosphere. LC-MS showed compound 1 was consumed completely and one main peak with desired m/z (calculated MW: 677.33, observed m/z: 678.2 ([M+H]$^+$)) was detected. The solvent was evaporated to produce compound 2 (600 mg, crude) was obtained as a white solid.

A mixture of compound 2 (600.0 mg, 885.3 μmol, 1.0 eq), N-ethylethanamine (1.29 g, 15.19 mmol, 1.50 mL, 17.2 eq) was dissolved in DCM (3 mL, pre-degassed and purged with $N_2$ for 3 times), and then the mixture was stirred at 25-30° C. for 2 hr under $N_2$ atmosphere. LC-MS showed compound 2 was consumed completely and one main peak with desired m/z (calculated MW: 455.51, observed m/z: 456.3 ([M+H]$^+$)) was detected. The solvent was evaporated to produce compound 3 (400 mg, crude) was obtained as colorless oil.

A mixture of compound 3 (150.0 mg, 329.3 μmol, 1.0 eq), compound 4 (320.1 mg, 329.3 μmol, 1.0 eq), HATU (125.2 mg, 329.3 μmol, 1.0 eq), DIEA (42.6 mg, 329.3 μmol, 57.4 μL, 1.0 eq) was dissolved in DMF (2 mL, pre-degassed and purged with $N_2$ for 3 times), and then the mixture was stirred at 25-30° C. for 2 under $N_2$ atmosphere. LC-MS showed compound 3 was consumed completely and one main peak with desired m/z (calculated MW: 1408.76, observed m/z: 705.3 ([M/2+H]$^+$)) was detected. The solvent was evaporated to produce compound 5 (400 mg, crude) was obtained as yellow oil.

Compound 5 (400 mg, 283.77 μmol, 1.0 eq) was dissolved in DMF (4 mL, pre-degassed and purged with $N_2$ for 3 times), following by addition of piperidine (862.2 mg, 10.13 mmol, 1 mL, 35.7 eq), and then the mixture was stirred at 25-30° C. for 15 min under $N_2$ atmosphere. LC-MS showed compound 5 was consumed completely and one main peak with desired m/z (calculated MW: 1187.37, observed m/z: 594.4 ([M/2+H$^+$], 1187.4 ([M+H]$^+$)) was detected. The solvent was evaporated to produce COM128 (250 mg, crude) was obtained as colorless oil.

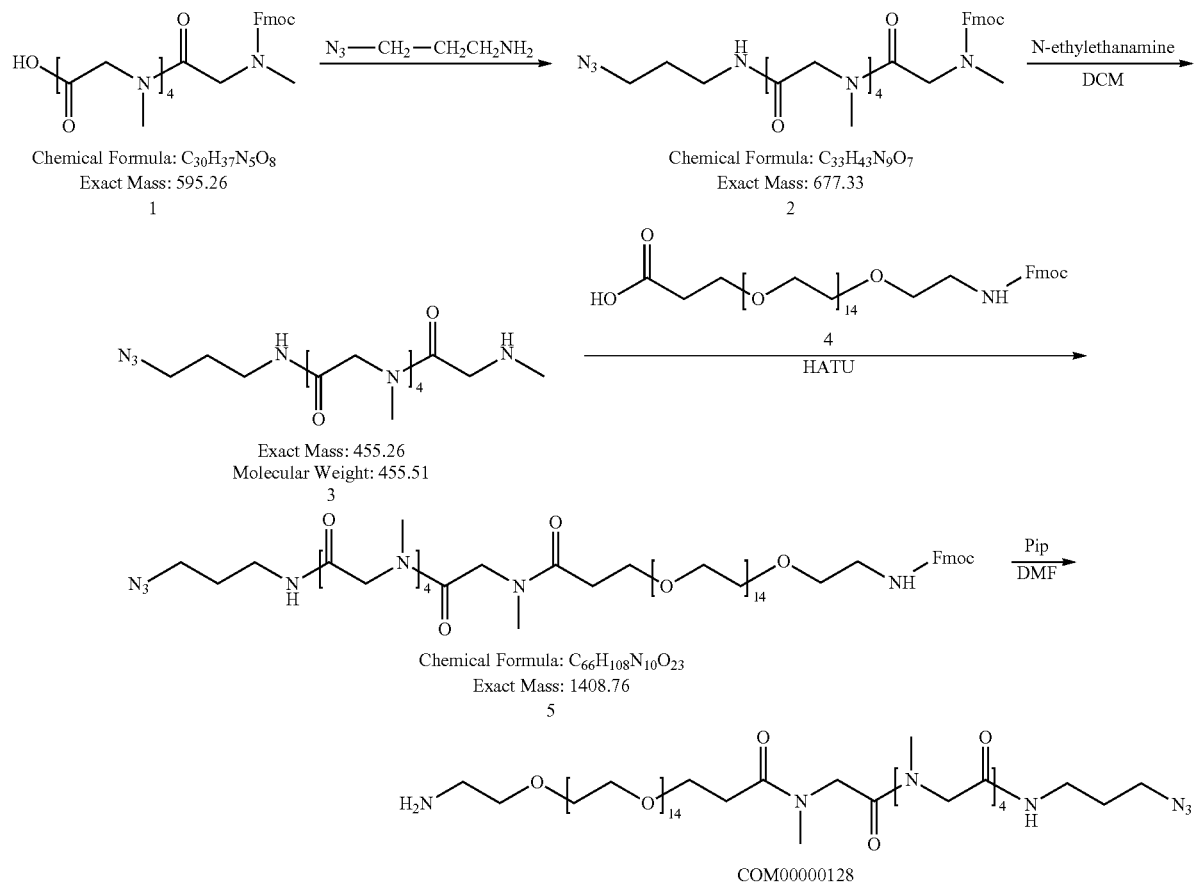

A mixture of compound 1 (1.4 g, 1.47 mmol, 1.0 eq), 3-azidopropan-1-amine (162.1 mg, 1.62 mmol, 1.1 eq), EDCI (338.6 mg, 1.77 mmol, 1.2 eq), HOBt (238.7 mg, 1.77 mmol, 1.2 eq) was dissolved in DCM (5 mL, pre-degassed and purged with $N_2$ for 3 times), and then the mixture was stirred at 20-25° C. for 1 hr under $N_2$ atmosphere. LC-MS showed compound 1 was consumed completely and one main peak with desired m/z (calculated MW: 1033.14, observed m/z: 1033.2 ([M+H]$^+$)) was detected. The reaction mixture was treated with a few drops of 1 M HCl, and the organic layer was evaporated under reduced pressure to remove solvent. Compound 2 (1.1 g, crude) was obtained as yellow oil.

A mixture of compound 2 (1.1 g, 1.06 mmol, 1 eq), N-ethylethanamine (3.89 g, 53.24 mmol, 5.48 mL, 50 eq) was dissolved in DCM (5 mL, pre-degassed and purged with $N_2$ for 3 times), and then the mixture was stirred at 20-25° C. for 1 hr under $N_2$ atmosphere. LC-MS showed compound 2 was consumed completely and one main peak with desired m/z (calculated MW: 810.90, observed m/z: 810.9 ([M+H]$^+$)) was detected. The reaction mixture was evaporated under reduced pressure and compound 3 (810 mg, crude) was obtained as a white solid.

A mixture of compound 3 (810.0 mg, 998.9 µmol, 1.0 eq), compound 4 (810.7 mg, 1.10 mmol, 1.1 eq), HATU (455.8 mg, 1.20 mmol, 1.2 eq), DIEA (258.2 mg, 2.00 mmol, 348.0 µL, 2.0 eq) was dissolved in DMF (2 mL, pre-degassed and purged with $N_2$ for 3 times), and then the mixture was stirred at 25-30° C. for 2 under $N_2$ atmosphere. LC-MS showed compound 3 was consumed completely and one main peak with desired m/z (calculated MW: 1530.72, observed m/z: 765.5 ([M/2+H]$^+$)) was detected. The reaction mixture was treated with a few drops of 1 M HCl, and the organic layer was collected and evaporated under reduced pressure to remove solvent. Compound 5 (1.1 g, crude) was obtained as a yellow solid.

Compound 5 (1 g, 653.29 µmol, 1 eq) was dissolved in DCM (10 mL, pre-degassed and purged with $N_2$ for 3 times), following by addition of piperidine (2.39 g, 32.66 mmol, 3.36 mL, 50 eq), and then the mixture was stirred at 25-30° C. for 2 hr under $N_2$ atmosphere. LC-MS showed Compound 5 was consumed completely and one main peak with desired m/z (calculated MW: 1308.47, observed m/z: 1308.4 ([M+H]$^+$)) was detected. The residue was purified by prep-HPLC (TFA condition: Phase A: 0.075% TFA in $H_2O$, phase B: MeCN, Column: Luna 200*25 mm 10 um, C18, 110 A and Gemin150*30 mm, C18, 5 um, 110 A, connection, 50° C.). COM129 (700 mg, 463.72 µmol, 70.98% yield) was obtained as a yellow solid.

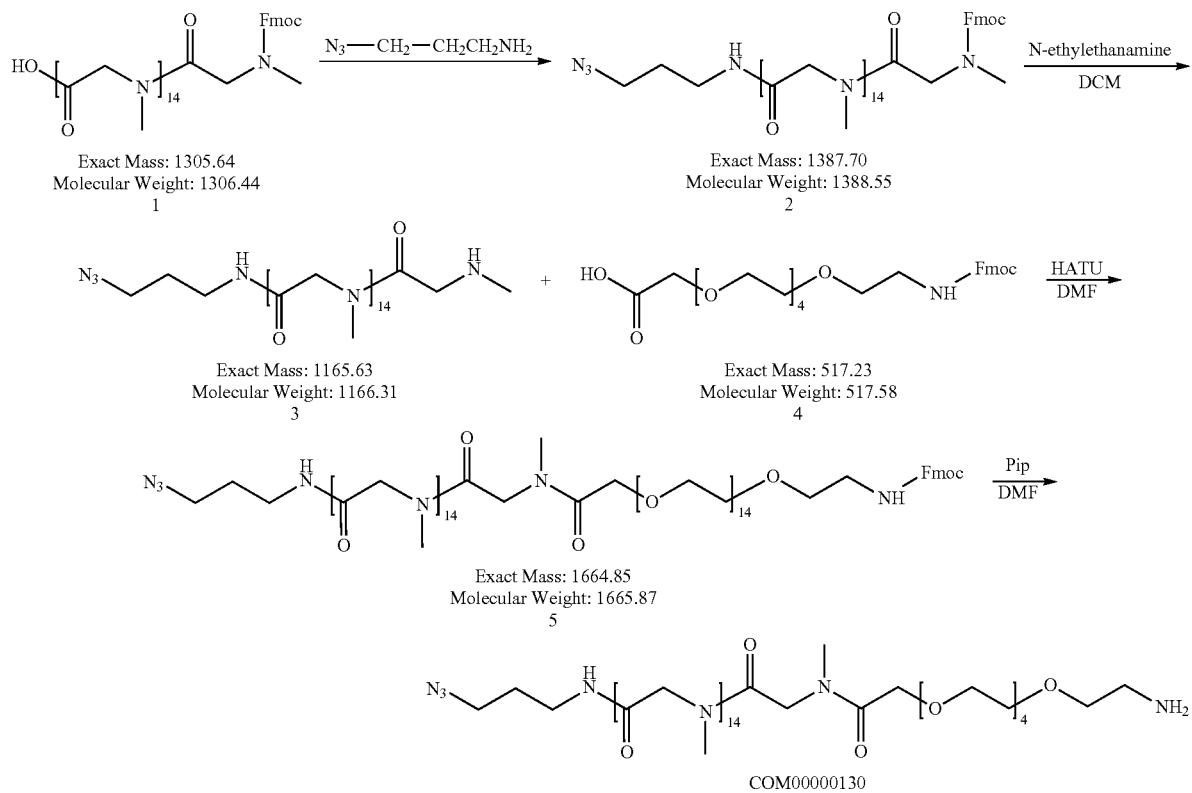

A mixture of Compound 1 (291 mg, 222.75 μmol, 1.0 eq), 3-azidopropan-1-amine (24.53 mg, 245.02 μmol, 1.1 eq), EDCI (51.24 mg, 267.30 μmol, 1.2 eq), HOBt (36.12 mg, 267.30 μmol, 1.2 eq) was dissolved in DCM (3 mL, pre-degassed and purged with $N_2$ for 3 times), and then the mixture was stirred at 20-25° C. for 1 hr under $N_2$ atmosphere. LC-MS showed Compound 1 was consumed completely and one main peak with desired m/z (MW: 1388.53, observed m/z: 694.7 ($[M/2+H]^+$)) was detected. The residue was purified by prep-HPLC (neutral condition). Compound 2 (200 mg, 144.04 μmol, 64.66% yield) was obtained as a white solid.

A mixture of Compound 2 (200 mg, 144.04 μmol, 1.0 eq), N-ethylethanamine (210.7 mg, 2.88 mmol, 297 μL, 20.0 eq) was dissolved in DCM (3 mL, pre-degassed and purged with $N_2$ for 3 times), and then the mixture was stirred at 20-25° C. for 1 hr under $N_2$ atmosphere. LC-MS showed Compound 2 was consumed completely and one main peak with desired m/z (MW: 1166.29, observed m/z: 1166.3 ($[M+H]^+$)) was detected. The reaction mixture was evaporated and Compound 3 (150 mg, crude) was obtained as yellow oil.

A mixture of compound 3 (150 mg, 128.61 μmol, 1.0 eq), compound 4 (75 mg, 144.91 μmol, 1.13 eq), HATU (58.7 mg, 154.34 μmol, 1.2 eq) and DIEA (33.24 mg, 257.23 μmol, 44.80 μL, 2.0 eq) was dissolved in DMF (5 mL, pre-degassed and purged with $N_2$ for 3 times), and then the mixture was stirred at 20-25° C. for 2 hr under $N_2$ atmosphere. LC-MS showed compound 3 was consumed completely and one main peak with desired m/z (MW: 1665.84, observed m/z: 833.2 ($[M/2+H]^+$)) was detected. The solvent was removed under reduced pressure and compound 5 (300 mg, crude) was obtained as yellow oil.

To crude compound 5 (300 mg, dissolved in 10 mL DMF) was added piperidine (2 mL), and the mixture was stirred at 30° C. for 2 hr. LCMS indicated one main peak with desired m/z (MW: 1443.60 observed m/z: 722.7 ($[M/2+H]^+$)) was detected. The residue was purified by prep-HPLC (neutral condition). COM130 (140 mg, 58.19 μmol, 32.31% yield, 60% purity) was obtained as a white solid.

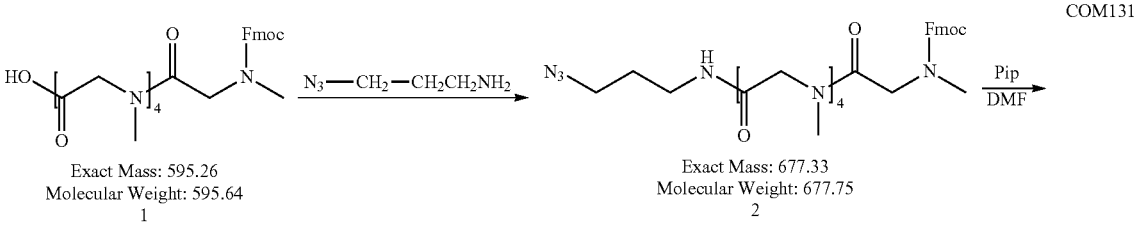

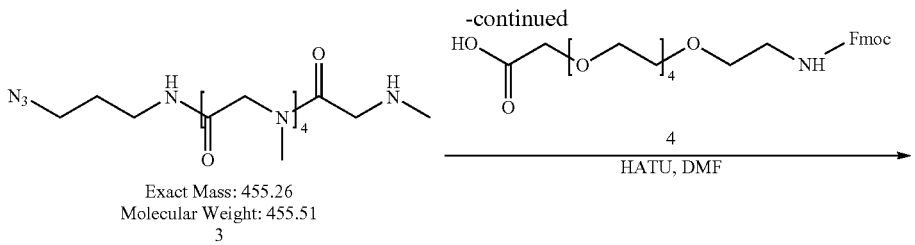

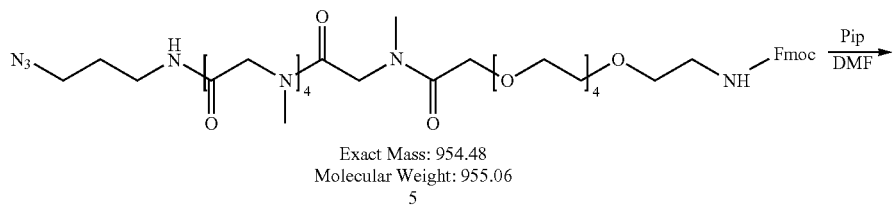

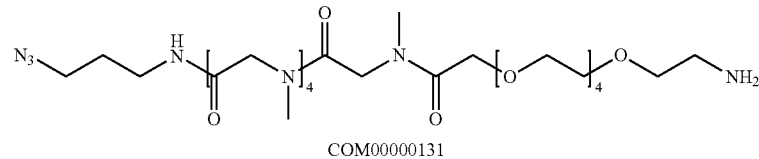

A mixture of compound 1 (700.0 mg, 1.18 mmol, 1.0 eq), 3-azidopropan-1-amine (117.7 mg, 1.18 mmol, 1.0 eq), HOBt (190.6 mg, 1.41 mmol, 1.2 eq), EDCI (270.4 mg, 1.41 mmol, 1.2 eq) was dissolved in DCM (20 mL, pre-degassed and purged with $N_2$ for 3 times), and then the mixture was stirred at 25-30° C. for 2 hr under $N_2$ atmosphere. LC-MS showed compound 1 was consumed completely and one main peak with desired m/z (calculated MW: 677.75, observed m/z: 678.2 ([M+H]$^+$)) was detected. The reaction mixture was treatment with a few drops of 1 M HCl, and the organic layer was collected and evaporated under reduced pressure. Compound 2 (600.0 mg, crude) was obtained as a white solid.

Compound 2 (600.0 mg, 885.2 μmol, 1.0 eq) was dissolved in DMF (3 mL, pre-degassed and purged with $N_2$ for 3 times), and then piperidine (1.29 g, 15.19 mmol, 1.50 mL, 17.2 eq) was added and the mixture was stirred at 25-30° C. for 2 hr under $N_2$ atmosphere. LC-MS showed compound 2 was consumed completely and one main peak with desired m/z (calculated MW: 455.51 observed m/z: 456.3 ([M+H]$^+$)) was detected. The reaction mixture was purified by prep-HPLC (TFA condition), and compound 3 (400.0 mg, 879.1 μmol) was obtained as colorless oil.

A mixture of compound 3 (250.0 mg, 548.83 μmol, 1.0 eq), compound 4 (284.1 mg, 548.83 μmol, 1 eq), HATU (229.6 mg, 603.72 μmol, 1.1 eq), DIEA (141.9 mg, 1.10 mmol, 191.19 μL, 2.0 eq) in DCM (20 mL, pre-degassed and purged with $N_2$ for 3 times), and then the mixture was stirred at 25-30° C. for 2 hr under $N_2$ atmosphere. LC-MS showed compound 3 was consumed completely and one main peak with desired m/z (calculated MW: 955.06, observed m/z: 955.6 ([M+H]$^+$)) was detected. The residue was purified by prep-HPLC (TFA condition). Compound 5 (400.0 mg, 419.1 μmol) was obtained as a white solid A mixture of Compound 5 (400.0 mg, 418.82 μmol, 1.0 eq) was dissolved in DMF (4 mL, pre-degassed and purged with $N_2$ for 3 times), and then piperidine (862.2 mg, 10.13 mmol, 1 mL, 24.2 eq) was added and the mixture was stirred at 25-30° C. for 2 hr under $N_2$ atmosphere. LC-MS showed Compound 5 was consumed completely and one main peak with desired m/z (MW: 732.83 observed m/z: 733.3 ([M+H]$^+$)) was detected. The residue was purified by prep-HPLC (TFA condition). COM131 (200 mg, 272.9 μmol) was obtained as colorless oil.

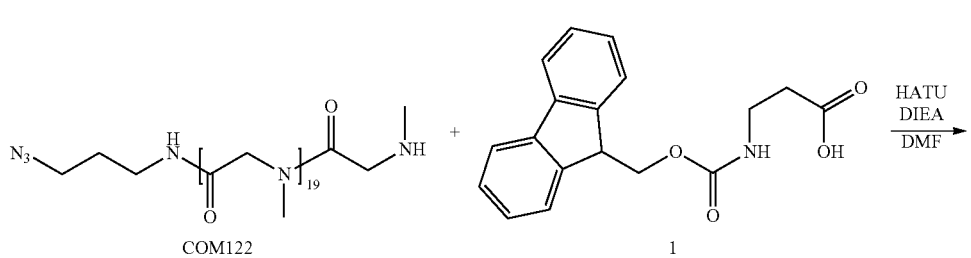

-continued

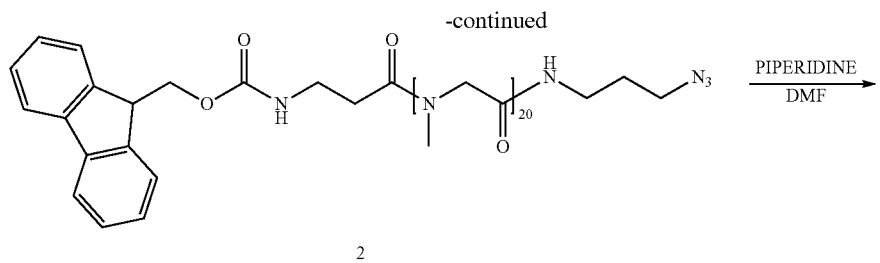

2

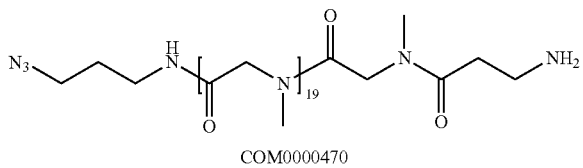

COM0000470

To a solution of COM122 (228 mg, 149.83 μmol, 1.0 eq), Compound 1 (51.31 mg, 164.82 μmol, 1.1 eq) in DMF (6 mL) was added HATU (85.40 mg, 224.75 μmol, 1.5 eq) and DIEA (19.37 mg, 149.83 μmol, 26.10 μL, 1.0 eq). The mixture was stirred at 25-30° C. for 2 hr. LC-MS showed Compound 1 was consumed completely and one main peak with desired m/z (MW: 1814.99, observed m/z: 908.2 ([M/2+H]$^+$)) was detected. The reaction mixture was concentrated under reduced pressure to remove solvent to give a residue. The residue was purified by prep-HPLC (neutral condition). Compound 2 (54 mg, 29.75 μmol, 19.86% yield) was obtained as a white solid.

To a solution of Compound 2 (54 mg, 29.8 μmol, 1.0 eq) in DMF (2 mL) was added piperidine (61 mg, 715 μmol, 71 μL, 24.0 eq). The mixture was stirred at 25-30° C. for 2 hr. LC-MS showed Compound 2 was consumed completely and one main peak with desired m/z (MW: 1592.75 observed m/z: 796.27 ([M/2+H]$^+$)) was detected. The reaction mixture was concentrated under reduced pressure to remove solvent to give a residue. The residue was purified by prep-HPLC (TFA condition). COM470 (40 mg, 25.11 μmol, 84.41% yield) was obtained as a white solid.

COM471

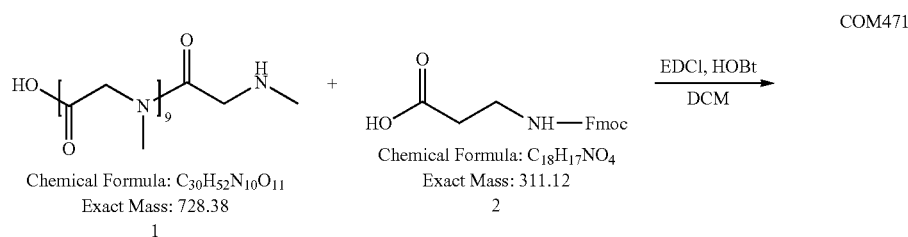

Chemical Formula: $C_{30}H_{52}N_{10}O_{11}$
Exact Mass: 728.38
1

Chemical Formula: $C_{18}H_{17}NO_4$
Exact Mass: 311.12
2

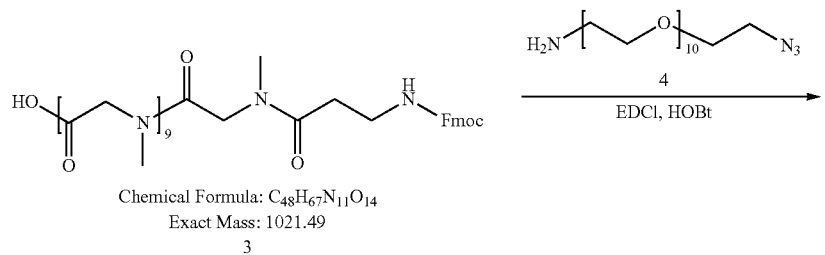

Chemical Formula: $C_{48}H_{67}N_{11}O_{14}$
Exact Mass: 1021.49
3

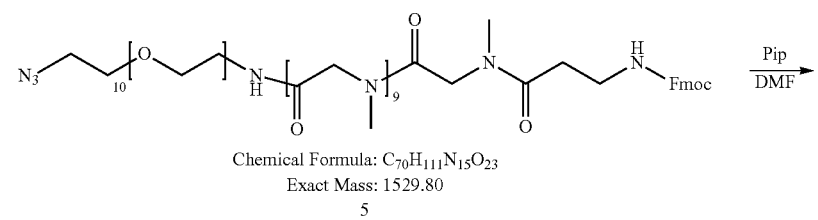

Chemical Formula: $C_{70}H_{111}N_{15}O_{23}$
Exact Mass: 1529.80
5

-continued

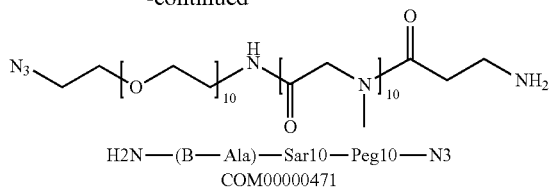

H2N—(B—Ala)—Sar10—Peg10—N3
COM00000471

A mixture of compound 1 (900 mg, 1.23 mmol, 1.0 eq) and compound 2 (1.0 g, 3.21 mmol, 2.6 eq) was dissolved in DCM (20 mL), following by addition of (284.0 mg, 1.48 mmol, 1.2 eq), HOBt (200.2 mg, 1.48 mmol, 1.2 eq). The mixture was stirred at 25° C. for 2 hr. LC-MS showed compound 1 was consumed completely and one peak with desired m/z (calculated MW: 1021.49, observed m/z: 1022.2 ([M+H]$^+$)) was detected. The reaction mixture was concentrated under reduced pressure to remove solvent. The residue was purified by prep-HPLC (TFA condition). Compound 3 (0.900 g, 880.53 μmol, 71.30% yield) was obtained as a white solid.

A mixture of compound 3 (500.0 mg, 489.19 μmol, 1.0 eq), compound 4 (257.6 mg, 489.19 μmol, 1.0 eq) was dissolved in DCM (5 mL), following by addition of HOBt (132.2 mg, 978.37 μmol, 2.0 eq), EDCI (187.6 mg, 978.37 μmol, 2.0 eq). The mixture was stirred at 25-30° C. for 2 hrs. LC-MS showed compound 3 was consumed completely and one main peak with desired m/z (MW: 1529.80 observed m/z: 765.9 ([M/2+H]$^+$) was detected. The reaction mixture was concentrated under reduced pressure to remove solvent to give a residue. The residue was purified by prep-HPLC (neutral condition). Compound 3 (420 mg, 246.94 μmol, 50.48% yield) was obtained as colorless oil.

Compound 5 (420 mg, 274.38 μmol, 1.0 eq) was dissolved in DMF (4 mL), following by addition of piperidine (865.2 mg, 10.16 mmol, 1 mL, 37 eq). The mixture was stirred at 25-30° C. for 2 hr. LC-MS showed compound 5 was consumed completely and one main peak with desired m/z (calculated MW: 1308.48, observed m/z: 654.8 ([M/2+H]$^+$) was detected. The crude product was purified by prep-HPLC (TFA condition). COM471 (386 mg, 265.50 μmol, 96.76% yield) was obtained as colorless oil.

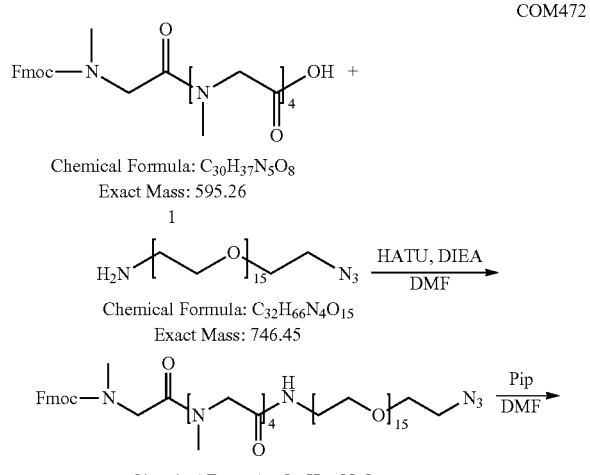

-continued

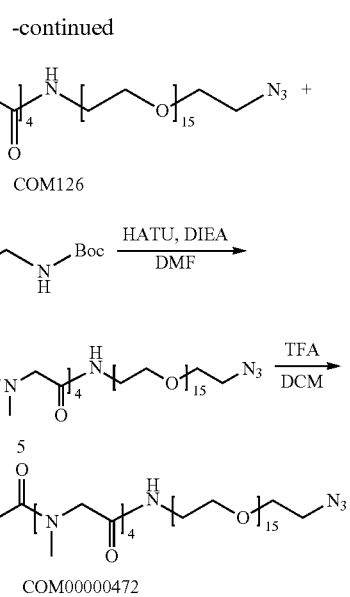

A mixture of compound 1 (0.5 g, 839.43 μmol, 1.0 eq), compound 2 (627.0 mg, 839.43 μmol, 1.0 eq) and DIEA (217.0 mg, 1.68 mmol, 292.4 μL, 2.0 eq) was dissolved in DMF (2 mL), then HATU (319.2 mg, 839.4 μmol, 1.0 eq) was added to the mixture. The mixture was then stirred at 25° C. for 30 min. TLC (DCM: CH$_3$OH=10:1, R$_f$=0.24) showed compound 1 was consumed completely and one new spot formed. The solvent was evaporated to produce compound 3 (0.45 g, 339.75 μmol, 40.47% yield, crude) as colorless oil, which was used in next step without further purification.

Compound 3 (450.0 mg, 339.75 μmol, 1.0 eq) was dissolved in DMF (8 mL), following by addition of piperidine (2 mL). The mixture was stirred for 15 mins at 25° C. LC-MS showed compound 3 was consumed completely and one main peak with desired (calculated MW: 1102.27, observed m/z: 552.1 ([M/2+H]$^+$)) was detected. The residue was purified by prep-HPLC (TFA condition). Compound 3 (370.0 mg, 335.67 μmol, 98.80% yield) was obtained as colorless oil.

To a solution of COM126 (60 mg, 54.45 μmol, 1.0 eq), compound 4 (15.5 mg, 81.68 μmol, 1.5 eq) in DMF (5 mL) was added HATU (31 mg, 81.68 μmol, 1.5 eq) and DIEA (10.5 mg, 61.68 μmol, 15 μL, 1.5 eq). The mixture was stirred at 30° C. for 2 hr. LC-MS showed COM126 was consumed completely and one main peak with desired was detected. The mixture was evaporated to remove solvent, and compound 5 (30 mg, crude) was obtained as colorless oil, which was used in next step without further purification.

Compound 5 (30 mg, 23.57 μmol, 1.0 eq) was dissolved DCM (4.5 mL), and then TFA (0.5 mL) was added and the mixture was stirred at 25-30° C. for 2 hr. LC-MS showed compound 5 was consumed completely and one main peak with desired was detected. The residue was purified by prep-HPLC (TFA condition). COM472 (10 mg, 8.52 μmol) was obtained as white solid.

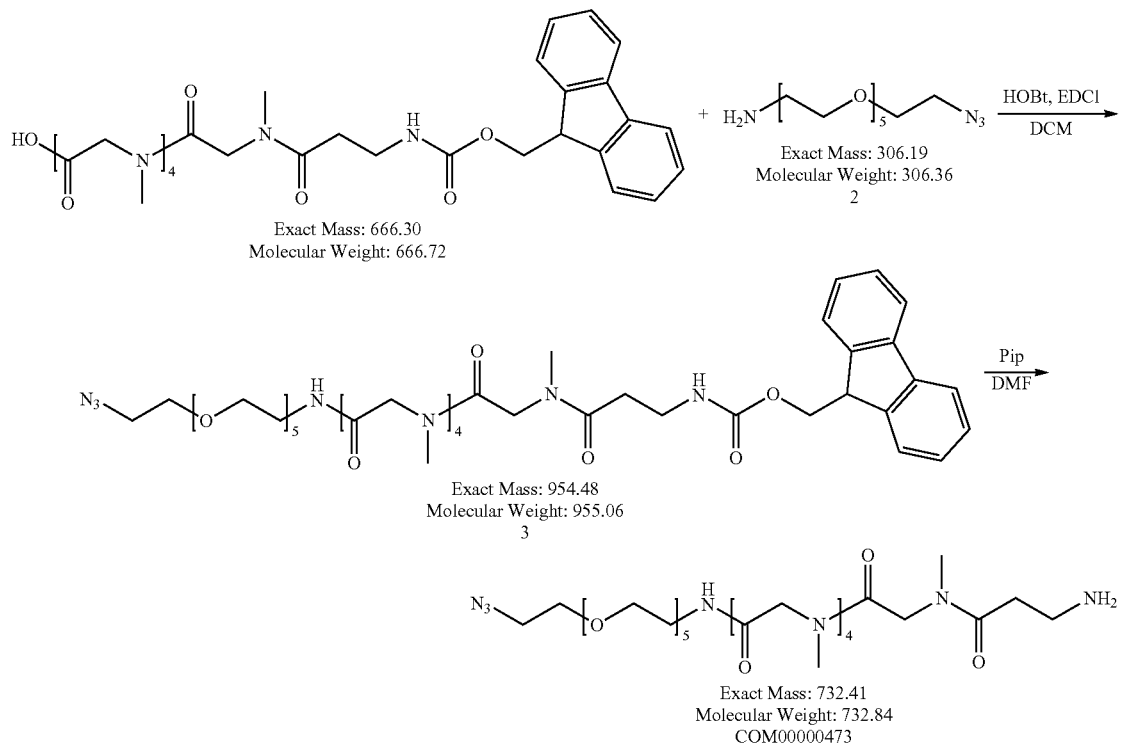

A mixture of compound 1 (300 mg, 449.96 µmol, 1.0 eq), compound 2 (138 mg, 449.96 µmol, 1.0 eq), HOBt (122 mg, 899.93 µmol, 2.0 eq), EDCI (173 mg, 899.93 µmol, 2.0 eq) was dissolved in DCM (10 mL, pre-degassed and purged with $N_2$ for 3 times), and then the mixture was stirred at 20-25° C. for 1 hr under $N_2$ atmosphere. LC-MS showed compound 1 was consumed completely and one main peak with desired (MW: 955.06, observed m/z: 955.3 ([M+H]$^+$)) was detected. The reaction mixture was concentrated under reduced pressure to remove solvent. The mixture was evaporated under reduced pressure and compound 3 (300 mg, crude) was obtained as yellow oil.

Compound 3 (300 mg, 314.12 µmol, 1.0 eq) was dissolved in DMF (4 mL), and then piperidine (1 mL) was added and the mixture was stirred at 20-25° C. for 1 hr. LC-MS showed compound 3 was consumed completely and one main peak with desired m/z (MW: 732.83 observed m/z: 733.2 ([M+H]$^+$)) was detected. The residue was purified by prep-HPLC (neutral condition). COM473 (160 mg, 218.33 µmol, 69.51% yield) was obtained as a colorless oil.

Example 2: Synthesis of EphA2/CD137 Binding Heterotandem Bicyclic Peptides BCY9173

Procedure for Preparation of BCY9172-PEG12-N$_3$

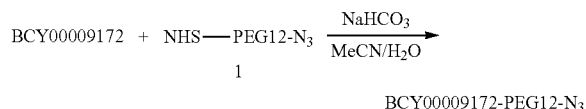

BCY9172 (520 mg, 248.16 µmol, 1 eq) and compound 1 (370 mg, 499.47 µmol, 2.01 eq), were dissolved in in DMF (5 mL) was added DIEA (48.11 mg, 372.24 µmol, 64.84 µL, 1.5 eq) and then the mixture was stirred at 30° C. for 12 hr. LC-MS showed BCY9172 was consumed completely and one main peak with desired m/z (calculated MW: 2721.12 observed m/z: 1360.9 ([M/2+H]$^+$)) was detected. The reaction mixture was purified by prep-HPLC (TFA condition) and compound 2 (284 mg, 101.10 µmol, 40.74% yield, 96.87% purity) was obtained as a white solid.

BCY00009172-PEG12-N$_3$ + 2

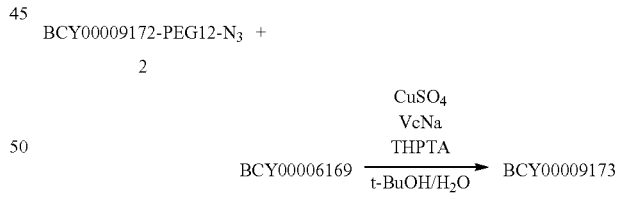

Procedure for Preparation of BCY9173

This reaction was performed in two independent containers in parallel. For one container, Compound 2 (100 mg, 36.75 µmol, 1.0 eq) and BCY6169 (120 mg, 36.78 µmol, 1.0 eq) were first dissolved in 10 mL of t-BuOH/H$_2$O (1:1), and then CuSO$_4$ (0.4 M, 91.9 µL, 1.0 eq), VcNa (0.4 M, 183.8 µL, 2.0 eq) and THPTA (0.4 M, 91.9 µL, 1.0 eq) was added. Finally 1 M NH$_4$HCO$_3$ was added to adjust pH to 8. All solvents here were degassed and purged with $N_2$ for 3 times. The reaction mixture was stirred at 40° C. for 16 hr under $N_2$ atmosphere. LC-MS showed compound 2 was consumed completely and one main peak with desired m/z (calculated MW: 5983.85 observed m/z: 997.6600 ([M/6+H]$^+$) and 1197.2300 ([M/5+H]$^+$)). The reaction mixture was purified by prep-HPLC (TFA condition) and BCY9173 (218 mg, 34.97 μmol, 47.58% yield, 96% purity) was obtained as a white solid.

BCY7985
General Procedure for Preparation of BCY7859

To a solution of N3-PEG12-COOH (250 mg, 388 μmol) and HOSu (67.0 mg, 583 μmol) in DMA (4.5 mL) and DCM (1.5 mL) was added EDCI (89.3 mg, 466 μmol) with stirring at 20° C. for 16 hr. To another 50 mL of round flask containing a mixture of BCY7732 (855 mg, 388 μmol) in 5 mL of DMA was added DIEA (186 mg, 1.44 mmol, 250 μL) with stirring for 10 min. Then the initial reaction mixture was added to the flask with further stirring at 20° C. for additional 5 hr. LC-MS (ES8396-307-P1B1) showed BCY7732 was consumed completely and one main peak with desired mass was detected. The resulting reaction mixture was purified directly by prep-HPLC (TFA condition) to give compound BCY7859 (621 mg, 200 μmol, 51.6% yield, TFA salt) as a white solid.

General Procedure for Preparation of BCY6169

To a solution of BCY6099 (300 mg, 94.3 μmol) in DMA (2 mL) was added DIEA (36.6 mg, 283 μmol, 49.3 μL) with stirring for 10 min. After, PYA-NHS (36.8 mg, 189 μmol) was added with further stirring at 20° C. for additional 15 hr. LC-MS showed BCY6099 was consumed completely and one main peak with desired mass was detected. The reaction mixture was purified by prep-HPLC (neutral condition) to give compound BCY6169 (299 mg, 86.2 μmol, 91.5% yield) as a white solid.

General Procedure for Preparation of BCY7985

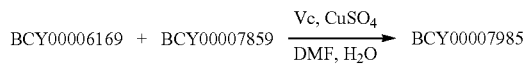

To a solution of BCY7859 (220 mg, 77.8 μmol) and BCY6169 (251 mg, 77.1 μmol) in DMF (5 mL) purged by nitrogen for 2 hr was added aqueous ascorbic acid solution (0.8 M, 963 μL) followed by adding aqueous CuSO4 (0.8 M, 289 μL) under nitrogen atmosphere. Then the mixture was stirred at 20° C. for 2 hr. LC-MS showed BCY6169 was consumed completely and one main peak with desired mass was detected. The reaction mixture was directly purified by prep-HPLC (TFA condition) to give compound BCY7985 (283 mg, 43.4 μmol, 56.3% yield, TFA) as a white solid.

BCY8942
General Procedure for Preparation of BCY8940

To a solution of N3-PEG12-COOH (120 mg, 186 μmol, 1.0 eq) in DMA (3 mL) and DCM (1 mL) was added HOSu (32.2 mg, 280 μmol, 1.5 eq) with stirring. Then EDCI (42.9 mg, 224 μmol, 1.2 eq) was added to the mixture with further stirring for additional 7 hr at 20° C. LCMS showed the activated ester was formed completely. To another flask with BCY8045 (410 mg, 186 μmol, 1.0 eq) in DMA (3 mL) was added DIEA (120 mg, 932 μmol, 162 μL, 5.0 eq) with stirring, then the activated ester was added and the mixture was stirred for 18 hr at 20° C. LC-MS showed one main peak with desired m/z was detected. The reaction mixture was concentrated in vacuum to remove the DCM. The resulting mixture was purified by prep-HPLC (TFA condition) to give BCY8940 (190 mg, 67.2 μmol, 36.1% yield) as a white solid.

General Procedure for Preparation of BCY8942

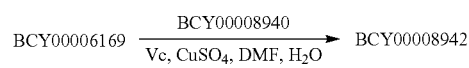

To a solution of BCY8940 (28.6 mg, 10.1 μmol, 1.1 eq) and BCY6169 (30.0 mg, 9.19 μmol, 1.0 eq) in DMF (2.0 mL) was added (2R)-2-[(1S)-1,2-dihydroxyethyl]-3, 4-dihydroxy-2H-furan-5-one (1.0 M, 92.0 μL) and CuSO4 (1.0 M, 27.6 μL) with stirring under nitrogen atmosphere for 2 hr at 20° C. LC-MS showed BCY6169 was consumed completely and one main peak with desired m/z (calculated MW: 6089.91 observed m/z: 1218.4 ([M/5+H]$^+$), 1016.0 ([M/6+H]$^+$), 870.7 ([M/7+H]$^+$) was detected. The reaction mixture was purified by prep-HPLC (TFA condition) to give compound BCY8942 (15.4 mg, 2.46 μmol, 26.8% yield, 97.3% purity) as a white solid.

BCY8943
General Procedure for Preparation of BCY8941

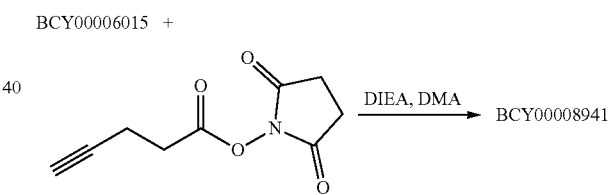

To a solution of BCY6015 (a peptide identical to BCY8941 except for the absence of a PYA moiety; 100 mg, 32.9 μmol) in DMA (2 mL) was added DIEA (12.8 mg, 98.7 μmol, 17.2 μL) with stirring for 10 min. Then (2,5-dioxopyrrolidin-1-yl) pent-4-ynoate (12.8 mg, 65.8 μmol) was added to the mixture, following with further stirring at 20° C. for 16 hr. LC-MS showed compound 1 was consumed completely and one main peak with desired m/z (calculated MW: 3119.60, observed m/z: 1040.5 ([M/3+H]$^+$) was detected. The mixture was purified by prep-HPLC (neutral condition) to give compound BCY8941 (90.0 mg, 28.9 μmol, 87.7% yield) as a white solid.

General Procedure for Preparation of BCY8943

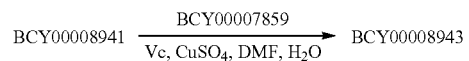

To a solution of BCY7859 (which may be prepared as described in BCY7985; 40.0 mg, 14.2 μmol) and BCY8941 (42.0 mg, 13.5 μmol) in DMSO (2 mL, pre-purged by nitrogen for 1 hr) was added (2R)-2-[(1S)-1,2-dihydroxy-ethyl]-3,4-dihydroxy-2H-furan-5-one (1.0 M, 270 μL) and CuSO₄ (1.0 M, 80.9 μL). The mixture was purged with nitrogen for 3 times and stirred at 15° C. for 2 hr. LC-MS showed BCY8941 was consumed completely and one main peak with desired m/z (calculated MW: 5946.77, observed m/z: 1190.2 ([M/5+H]⁺), 991.5 ([M/6+H]⁺), 849.9 ([M/7+H]⁺) was detected. The reaction mixture was purified by prep-HPLC (A: 0.075% TFA in H₂O, B: ACN) to give compound BCY8943 (11.5 mg, 1.90 μmol, 14.1% yield, 98.1% purity) as a white solid.

BCY9647

Procedure for Preparation of Compound 2

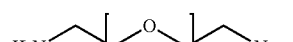

Exact Mass: 526.32139
Molecular Weight: 526.62144

COM00000134

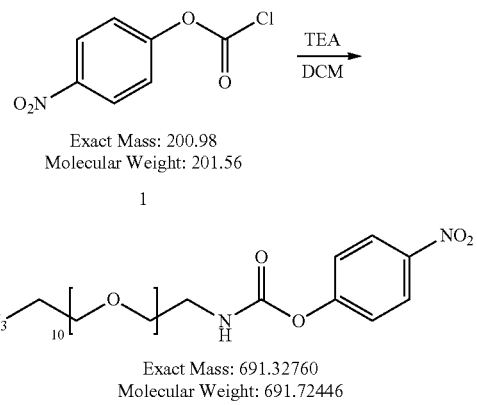

Exact Mass: 200.98
Molecular Weight: 201.56

1

Exact Mass: 691.32760
Molecular Weight: 691.72446

2

To a solution of COM134 (30.0 mg, 57.0 μmol, 1.0 eq), compound 1 (17.2 mg, 85.3 μmol, 1.5 eq) in DCM (0.5 mL) was added TEA (8.65 mg, 11.9 μL, 1.5 eq). The mixture was stirred at 25° C. for 1 hr. LC-MS showed COM134 was consumed completely and one main peak with desired mass (calculated MW: 691.72, observed m/z: 692.3 ([M+H]⁺) and 709.3 ([M+NH4]⁺)) was detected. The reaction mixture was concentrated under reduced pressure, and then lyophilized to produce crude compound 2 (30.5 mg, crude) as a white Procedure for Preparation of Compound 3

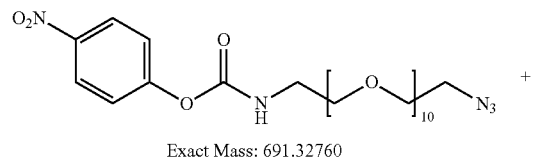

Exact Mass: 691.32760
Molecular Weight: 691.72446

2

BCY00006099
Exact Mass: 3180.55
Molecular Weight: 3182.66

→ DIEA / DMF

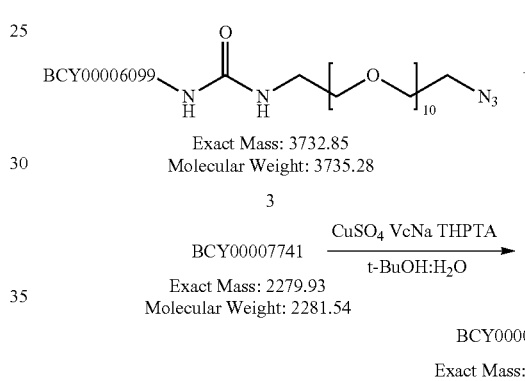

Exact Mass: 3732.85
Molecular Weight: 3735.28

3

To a solution of compound 2 (10 mg, 1.0 eq) in DMF (1 mL) was added BCY6099 (46 mg, 1.0 eq) and DIEA (5.61 mg, 7.55 μL, 3.0 eq). The mixture was stirred at 30° C. for 2 hr. LC-MS showed compound 2 was consumed completely and one main peak with desired m/z (calculated MW: 3735.28 observed m/z: 1245.9 ([M/3+H]⁺) and 934.5 ([M/4+H]⁺)) was detected. The reaction mixture was filtered and concentrated under reduced pressure to give a residue. The crude product was purified by reversed-phase HPLC (TFA condition). Compound 3 (34 mg, 62.96% yield, 100% purity) was obtained as a white solid.

Procedure for Preparation of BCY9647

BCY00006099—NH—C(O)—NH—[CH₂CH₂O]₁₀—N₃ +

Exact Mass: 3732.85
Molecular Weight: 3735.28

3

BCY00007741  → CuSO₄ VcNa THPTA / t-BuOH:H₂O

Exact Mass: 2279.93
Molecular Weight: 2281.54

BCY00009647
Exact Mass: 6012.79
Molecular Weight: 6016.82

A mixture of Compound 3 (34 mg, 9.10 μmol, 1.0 eq), BCY7741 (23 mg, 10.08 μmol, 1.11 eq), and THPTA (0.4 M, 11.4 μL, 0.5 eq) was dissolved in t-BuOH/H₂O (1:1, 2 mL, pre-degassed and purged with N₂ for 3 times), and then CuSO₄ (0.4 M, 11.4 μL, 0.5 eq) and VcNa (0.4 M, 22.8 μL, 1 eq) were added under N₂. The pH of this solution was adjusted to 8 by dropwise addition of 0.2 M NH₄HCO₃ (in 1:1 t-BuOH/H₂O), and the solution turned to light yellow. The reaction mixture was stirred at 25-30° C. for 12 hr under N₂ atmosphere. LC-MS showed compound 3 was consumed completely and one main peak with desired m/z (calculated MW: 6016.82, observed m/z: 1204.1 ([M/5+H]⁺), 1003.5 ([M/6+H]⁺), 860.3 ([M/7+H]⁺)). The reaction mixture was directly purified by prep-HPLC (TFA condition). BCY9647 (31.2 mg, 54.67% yield, 95.96% purity) was obtained as a white solid.

BCY9648

Procedure for Preparation of Compound 2

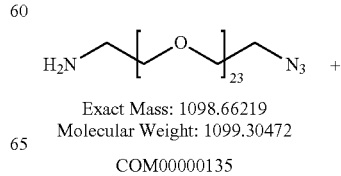

Exact Mass: 1098.66219
Molecular Weight: 1099.30472

COM00000135

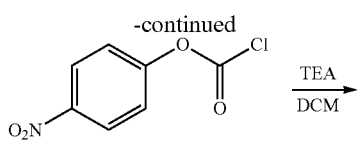

Exact Mass: 200.98
Molecular Weight: 201.56

1

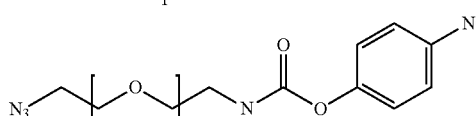

Exact Mass: 1263.66839
Molecular Weight: 1264.40774

2

To a solution of COM135 (30 mg, 27.29 μmol, 1.0 eq), compound 1 (8.25 mg, 40.94 μmol, 1.5 eq) in DCM (0.5 mL) was added TEA (4.14 mg, 40.94 μmol, 5.70 μL, 1.5 eq). The mixture was stirred at 25~30° C. for 1 hr. LC-MS showed COM135 was consumed completely and one main peak with desired mass [calculated MW: 1264.41, observed m/z: 1281.4 ([M+NH₄]⁺), 649.8 ([M/2+H]⁺)] was detected. The reaction mixture was concentrated under reduced pressure to remove solvent to give a residue. The residue was purified by prep-HPLC (TFA condition) to give compound 2 (18 mg, 14.2 μmol, 52.14% yield).

Procedure for Preparation of Compound 3

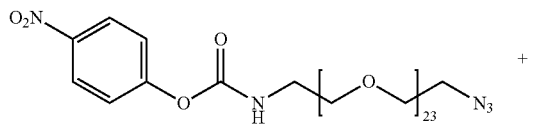

To a solution of compound 3 (9 mg, 7.12 μmol, 1 eq) in DMF (1 mL) was added BCY6099 (23 mg, 7.23 μmol, 1.02 eq) and DIEA (2.76 mg, 21.35 μmol, 3.72 μL, 3.0 eq). The mixture was stirred at 30° C. for 2 hr. LC-MS showed compound 2 was consumed completely and one main peak with desired m/z (calculated MW: 4307.96 observed m/z: 1436.9 ([M/3+H]⁺), 1077.9 ([M/4+H]⁺), 862.5 ([M/5+H]⁺)) was detected. The reaction mixture was filtered and concentrated under reduced pressure to give a residue. The crude product was purified by reversed-phase HPLC (TFA condition). Compound 3 (14.6 mg, 47.61% yield, 100% purity) was obtained as a white solid.

Procedure for Preparation of BCY9648

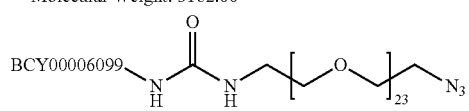

Exact Mass: 4305.19
Molecular Weight: 4307.96

3

BCY00007741         CuSO4 VcNa THPTA
                    ——————————————→
Exact Mass: 2279.93      t-BuOH:H2O
Molecular Weight: 2281.54

BCY00009648

Exact Mass: 6585.13
Molecular Weight: 6589.50

A mixture of compound 3 (14.6 mg, 3.39 μmol, 1 eq), BCY7741 (8.5 mg, 3.73 μmol, 1.1 eq) and THPTA (0.4 M, 4.3 μL, 0.5 eq) was dissolved in t-BuOH/H₂O (1:1, 2 mL, pre-degassed and purged with N₂ for 3 times), and then CuSO₄ (0.4 M, 4.3 μL, 0.5 eq) and VcNa (0.4 M, 8.6 μL, 1.0 eq) were added under N₂. The pH of this solution was adjusted to 8 by dropwise addition of 0.2 M NH₄HCO₃ (in 1:1 t-BuOH/H₂O), and the solution turned to light yellow. The reaction mixture was stirred at 25-30° C. for 12 hr under N₂ atmosphere. LC-MS showed compound 3 was consumed completely and one main peak with desired m/z (MW: 6589.50 observed m/z: 1098.8 ([M/6+H]⁺), 942.1 ([M/7+H]⁺), 824.6 ([M/8+H]⁺)). The reaction mixture was directly purified by prep-HPLC (TFA condition). BCY9648 (14.7 mg, 63.34% yield, 96.22% purity) was obtained as a white solid.

BCY9655

Procedure for Preparation of Compound 2

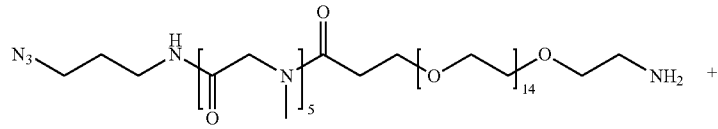

Exact Mass: 1186.69
Molecular Weight: 1187.38

COM00000128

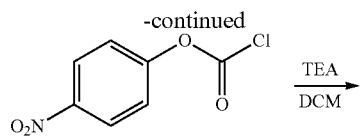

Exact Mass: 200.98
Molecular Weight: 201.56

1

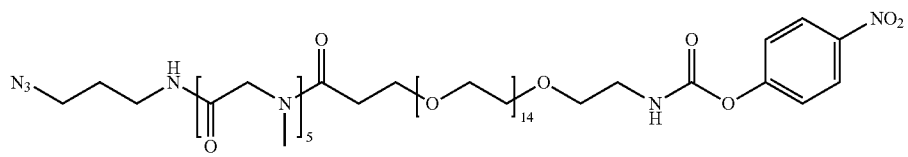

Exact Mass: 1351.70
Molecular Weight: 1352.48

2

To a solution of COM128 (120 mg, 101.06 μmol, 1.0 eq), compound 1 (25 mg, 124.03 μmol, 1.25 eq) in DCM (0.5 mL) was added TEA (15.34 mg, 151.59 μmol, 21.10 μL, 1.5 eq). The mixture was stirred at 25° C. for 1 hr. LC-MS showed one new peak with desired m/z (calculated MW: 1352.48, observed m/z: 676.8 ([M/2+H]$^+$), 1369.3 ([M+NH4]$^+$)) was detected. The reaction mixture was concentrated under reduced pressure to remove solvent to give a residue. The residue was purified by prep-HPLC (neutral condition). Compound 2 (14 mg, 8.99 μmol, 8.90% yield, 86.86% purity) was obtained as colorless oil.

Procedure for Preparation of Compound 3

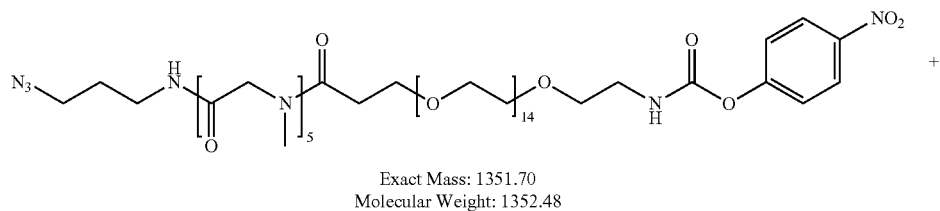

Exact Mass: 1351.70
Molecular Weight: 1352.48

2

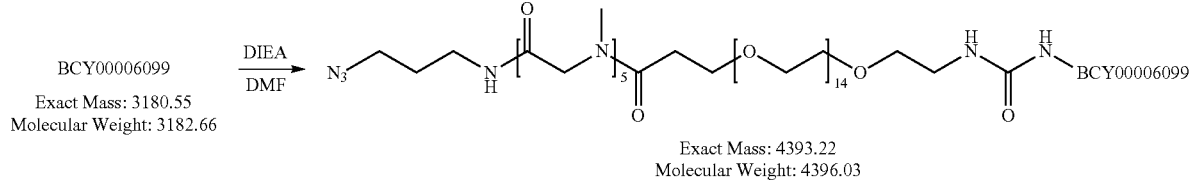

BCY00006099
Exact Mass: 3180.55
Molecular Weight: 3182.66

Exact Mass: 4393.22
Molecular Weight: 4396.03

3

To a solution of compound 2 (7 mg, 5.18 μmol, 1.0 eq) and BCY6099 (16 mg, 5.03 μmol, 1.0 eq) in DMF (2 mL) was added DIEA (2.01 mg, 15.53 μmol, 2.70 μL). The mixture was stirred at 30° C. for 2 hrs. LC-MS showed compound 2 was consumed completely and one main peak with desired m/z (calculated MW: 4396.02, observed m/z: 879.8 ([M/5+H]$^+$) and 1099.8 ([M/4+H]$^+$)) was detected. The reaction mixture was filtered and concentrated under reduced pressure to give a residue. The crude product was purified by reversed-phase HPLC (0.1% TFA condition). Compound 3 (11.8 mg, 48.29% yield, 93.11% purity) was obtained as a white solid.

Procedure for Preparation of BCY9655

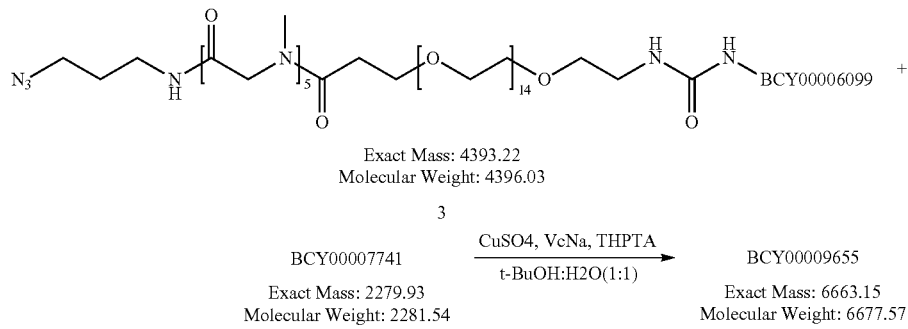

Exact Mass: 4393.22
Molecular Weight: 4396.03

3

BCY00007741 →[CuSO4, VcNa, THPTA][t-BuOH:H2O(1:1)] BCY00009655

Exact Mass: 2279.93
Molecular Weight: 2281.54

Exact Mass: 6663.15
Molecular Weight: 6677.57

A mixture of Compound 3 (11.8 mg, 2.69 μmol, 1.0 eq), BCY7741 (7.0 mg, 3.07 μmol, 1.14 eq), and THPTA (0.4 M, 6.8 μL, 1 eq) was dissolved in t-BuOH/H$_2$O (1:1, 2 mL, pre-degassed and purged with N$_2$ for 3 times), and then CuSO$_4$ (0.4 M, 6.8 μL, 1.0 eq) and VcNa (0.4 M, 13.6 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed compound 3 was consumed completely and one main peak with desired m/z (calculated MW: 6677.57, observed m/z: 1113.7 ([M/6+H]$^+$), 954.7 ([M/7+H]$^+$)). The reaction mixture was directly purified by prep-HPLC (TFA condition). BCY9655 (1.9 mg, 0.26 μmol, 9.65% yield, 91.15% purity) was obtained as a white solid.

BCY9656
Procedure for Preparation of Compound 2

To a solution of COM129 (30.0 mg, 22.93 μmol, 1.0 eq), compound 1 (6.9 mg, 34.39 μmol, 1.5 eq) in DCM (3 mL) was added TEA (3.5 mg, 34.39 μmol, 4.8 μL, 1.5 eq). The mixture was degassed and purged with N$_2$ for 3 times, and then the mixture was stirred at 25° C. for 1 hr under N$_2$ atmosphere. LC-MS showed COM129 was consumed completely and one main peak with desired m/z (calculated MW: 1473.58, observed m/z: 737.3 ([M/2+H]$^+$)) was detected. The reaction mixture was concentrated under reduced pressure to remove solvent to give a residue. The residue was purified by prep-HPLC (neutral condition) to produce Compound 2 (12.3 mg, 8.35 μmol, 36.41% yield) as a white solid.

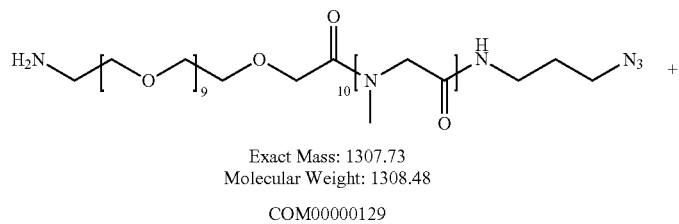

Exact Mass: 1307.73
Molecular Weight: 1308.48

COM00000129

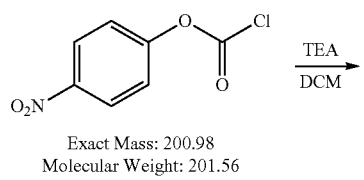

Exact Mass: 200.98
Molecular Weight: 201.56

1

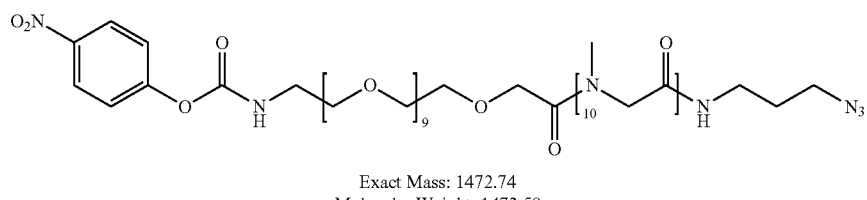

Exact Mass: 1472.74
Molecular Weight: 1473.58

2

Procedure for Preparation of Compound 3

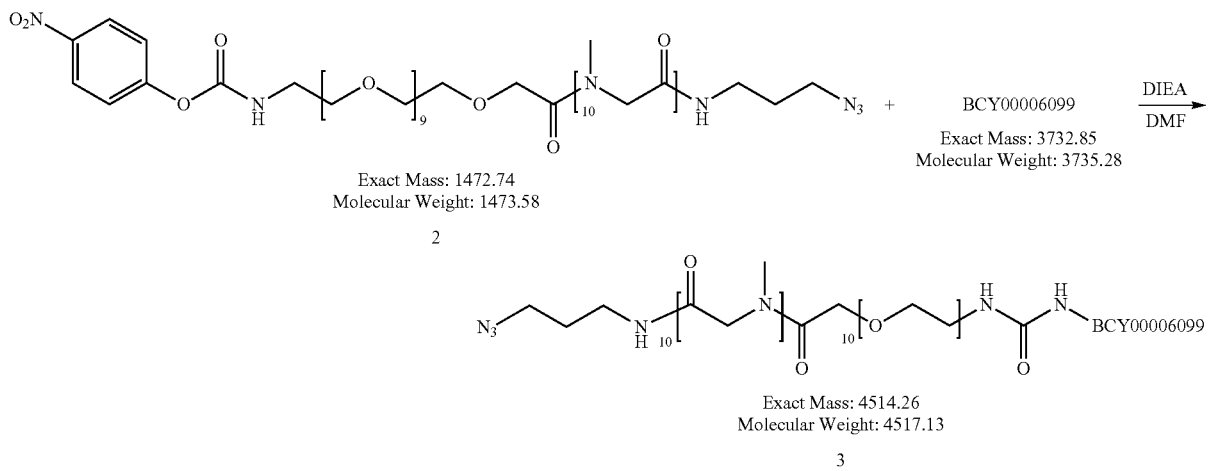

To a solution of compound 2 (9.26 mg, 6.28 µmol, 1.0 eq) and BCY6099 (10 mg, 3.14 µmol, 0.5 eq) in DMF (3 mL) was added TEA (0.7 mg, 6.93 µmol, 1 µL, 1.1 eq). The mixture was degassed and purged with $N_2$ for 3 times, and then the mixture was stirred at 25-30° C. for 1 hr under $N_2$ atmosphere. LC-MS showed compound 2 was consumed completely and one main peak with desired m/z (calculated MW: 4517.12, observed m/z: 1129.8 ($[M/4+H]^+$), 904.1 ($[M/5+H]^+$), 753.7 ($[M/6+H]^+$)) was detected. The reaction mixture was filtered and concentrated under reduced pressure to give a residue. The crude product was purified by reversed-phase HPLC (TFA condition). Compound 3 (12 mg, 72.36% yield, 85.58% purity) was obtained as a white solid.

Procedure for Preparation of BCY9656

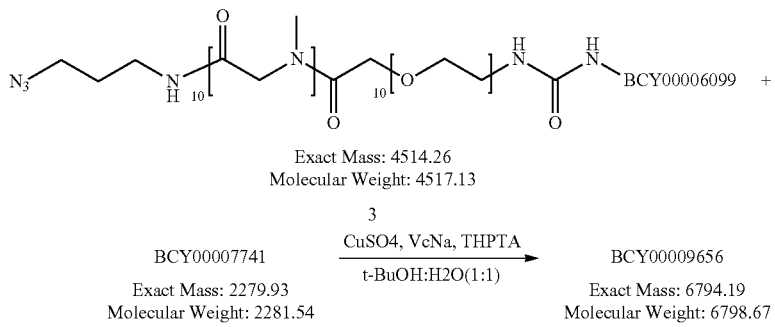

A mixture of Compound 3 (11 mg, 2.44 µmol, 1.0 eq), BCY7741 (6.0 mg, 2.63 µmol, 1.08 eq), and THPTA (0.4 M, 6.1 µL, 1.0 eq) was dissolved in t-BuOH/$H_2O$ (1:1, 2 mL, pre-degassed and purged with $N_2$ for 3 times), and then $CuSO_4$ (0.4 M, 6.1 µL, 1.0 eq) and VcNa (0.4 M, 12.2 µL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z (calculated MW: 6798.66, observed m/z: 1133.8 ($[M/6+H]^+$), 971.9 ($[M/7+H]^+$), 850.7 ($[M/8+H]^+$)) was detected. The reaction mixture was directly purified by prep-HPLC (TFA condition). BCY9656 (6.8 mg, 37.36% yield, 90.97% purity) was obtained as a white solid.

BCY9657
Procedure for Preparation of Compound 2

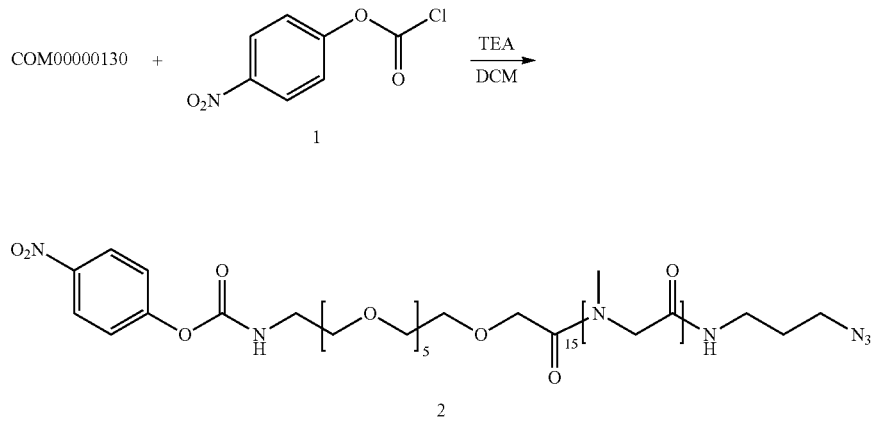

To a solution of COM130 (30.0 mg, 20.78 μmol, 1.0 eq), compound 1 (6.3 mg, 31.17 μmol, 1.5 eq) in DCM (3 mL) was added TEA (3.2 mg, 31.17 μmol, 4.4 μL, 1.5 eq). The mixture was stirred at 25-30° C. for 1 hr. LC-MS showed COM130 was consumed completely and one main peak with desired m/z (calculated MW: 1608.7, observed m/z: 804.8 ([M/2+H]$^+$)) was detected. The reaction mixture was concentrated under reduced pressure and lyophilized to produce compound 2 (7.9 mg, crude) as a white solid.

Procedure for Preparation of Compound 3

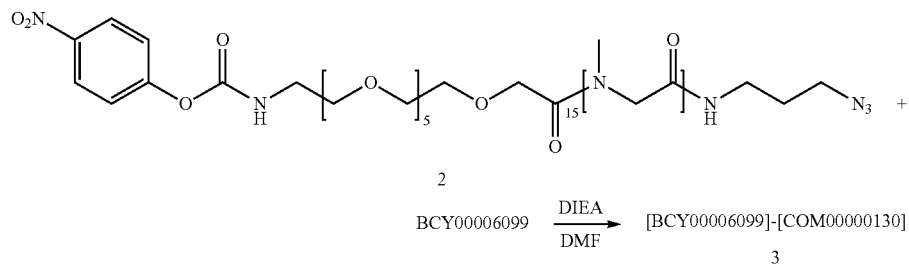

To a solution of compound 2 (7.9 mg, 4.91 μmol, 1.0 eq) and BCY6099 (16 mg, 5.03 μmol, 1.02 eq) in DMF (1 mL) was added DIEA (1.9 mg, 14.73 μmol, 2.6 μL, 3.0 eq). The mixture was stirred at 30° C. for 2 hrs. LC-MS showed compound 2 was consumed completely and one main peak with desired m/z (calculated MW: 4652.25, observed m/z: 1551.3 ([M/3+H]$^+$), 1163.6 ([M/4]$^+$), 931.1 ([M/5+H]$^+$), 776.1 ([M/6+H]$^+$)) was detected. The reaction mixture was filtered and concentrated under reduced pressure to give a residue. The crude product was purified by reversed-phase HPLC (TFA condition). Compound 3 (13.3 mg, 2.86 μmol, 53.22% yield, 91.42% purity) was obtained as a white solid.

Procedure for Preparation of BCY9657

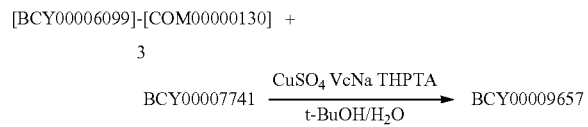

A mixture of Compound 3 (13.3 mg, 2.86 μmol, 1.0 eq), BCY7741 (7.0 mg, 3.07 μmol, 1.03 eq), and THPTA (0.4 M, 7.5 μL, 1.0 eq) was dissolved in t-BuOH/H$_2$O (1:1, 2 mL, pre-degassed and purged with N$_2$ for 3 times), and then CuSO$_4$ (0.4 M, 7.5 μL, 1 eq) and VcNa (0.4 M, 15 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 6933.78, observed m/z: 1156.7 ([M/6+H]$^+$), 991.4 ([M/7+H]$^+$), 867.4 ([M/8+H]$^+$)] was detected. The reaction mixture was directly purified by prep-HPLC (TFA condition). BCY9657 (8.4 mg, 40.21% yield, 94.9% purity) was obtained as a white solid.

BCY9658
Procedure for Preparation of Compound 2

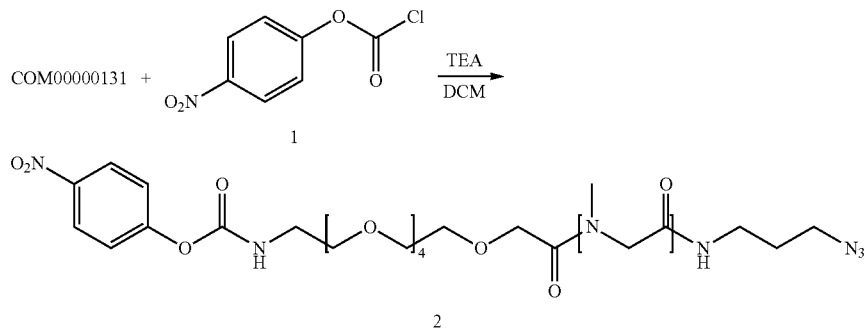

To a solution of COM131 (167.0 mg, 227.89 μmol, 1.0 eq), compound 1 (55.0 mg, 272.87 μmol, 1.2 eq) in DCM (5 mL) was added TEA (36.4 mg, 359.23 μmol, 50.0 μL, 1.6 eq). The mixture was stirred at 25-30° C. for 1 hr. LC-MS showed one main peak with desired m/z (MW: 897.93 observed 920.3 ([M+Na]$^+$) was detected. The reaction mixture was concentrated under reduced pressure to remove solvent to give a residue. The residue was purified by prep-HPLC (TFA condition). Compound 2 (35 mg, 33.74 μmol, 14.81% yield, 86.56% purity) was obtained as colorless oil.

Procedure for Preparation of Compound 3

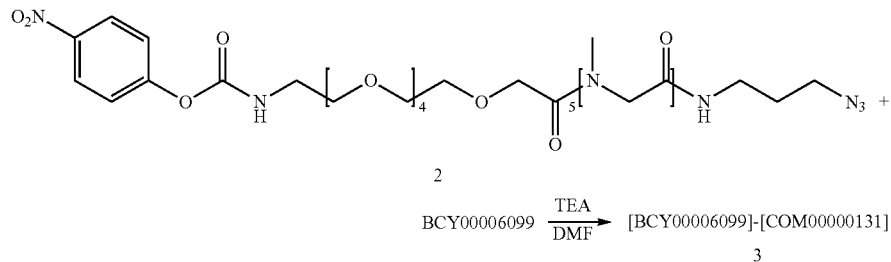

To a solution of compound 2 (15 mg, 16.71 μmol, 1.0 eq) and BCY6099 (53 mg, 16.65 μmol, 1.0 eq) in DMF (2 mL) was added DIEA (6.48 mg, 65.05 μmol, 50.1 μL, 4.0 eq). The mixture was stirred at 30° C. for 2 hrs. LC-MS showed compound 2 was consumed completely and one main peak with desired m/z (MW: 3941.47 observed m/z: 986.0 ([M/4+H]$^+$)) was detected. The reaction mixture was filtered and concentrated under reduced pressure to give a residue. The crude product was purified by reversed-phase HPLC (TFA condition). [BCY6099]-[COM131] (5 mg, 50.48% yield, 94.96% purity) was obtained as a white solid.

Procedure for Preparation of BCY9658

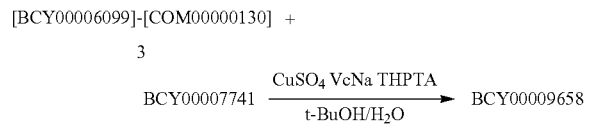

A mixture of Compound 3 (35 mg, 8.88 μmol, 1.0 eq), BCY7741 (21 mg, 9.20 μmol, 1.03 eq), and THPTA (0.4 M, 22.2 μL, 1.0 eq) was dissolved in t-BuOH/H$_2$O (1:1, 2 mL, pre-degassed and purged with N$_2$ for 3 times), and then CuSO$_4$ (0.4 M, 22.2 μL, 1.0 eq) and VcNa (0.4 M, 44.4 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 6223.01 observed m/z: 1038.0 ([M/6+H]$^+$) and 889.8 ([M/8+H]$^+$)] was detected. The reaction mixture was directly purified by prep-HPLC (TFA condition). BCY9658 (13.2 mg, 21.54% yield, 90.16% purity) was obtained as a white solid.

BCY9659
Procedure for Preparation of Compound 2

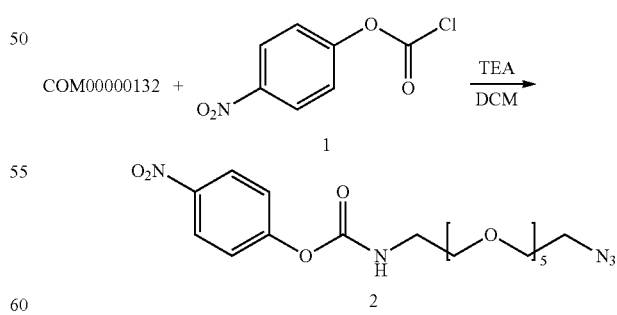

To a solution of COM132 (20.0 mg, 65.28 μmol, 1.0 eq), compound 1 (15.8 mg, 78.34 μmol, 1.2 eq) in DCM (5 mL) was added TEA (36.4 mg, 359.23 μmol, 50 μL, 5.5 eq). The mixture was stirred at 25° C. for 1 hr. LC-MS one main peak with desired m/z (MW: 471.46, observed m/z: 489.2 ([M+

NH$_4$]$^+$)) was detected. The reaction mixture was concentrated under reduced pressure to give compound 2 (26 mg, crude) colorless oil.

Procedure for Preparation of Compound 3

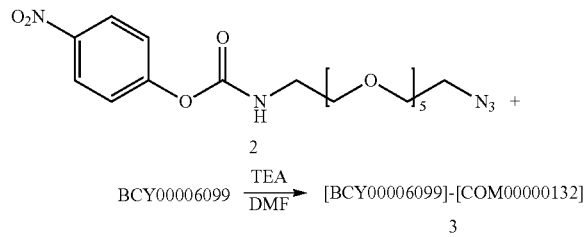

To a solution of compound 2 (15.0 mg, 4.71 μmol, 1.0 eq) and BCY6099 (3.33 mg, 7.07 μmol, 1.5 eq) in DMF (3 mL) was added TEA (0.7 mg, 6.93 μmol, 1 μL, 1.5 eq). The mixture was stirred at 30° C. for 2 hrs. LC-MS showed compound 2 was consumed completely and one main peak with desired m/z (MW: 3515.01, observed m/z: 1172.1 ([M/3+H]$^+$) 879.5 ([M/4+H]$^+$)) was detected. The reaction mixture was filtered and concentrated under reduced pressure to give a residue. The crude product was purified by reversed-phase HPLC (TFA condition). Compound 3 (12.7 mg, 3.26 μmol, 69.23% yield, 90.3% purity) was obtained as a white solid.

Procedure for Preparation of BCY9659

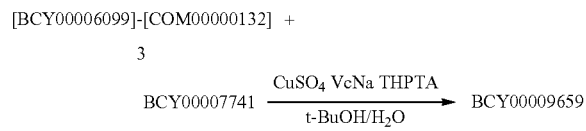

A mixture of Compound 3 (12.7 mg, 2.89 μmol, 1.0 eq), BCY7741 (6.80 mg, 2.98 μmol, 1.03 eq), and THPTA (1.3 mg, 2.99 μmol, 1.03 eq) was dissolved in t-BuOH/H$_2$O (1:1, 2 mL, pre-degassed and purged with N$_2$ for 3 times), and then CuSO$_4$ (0.4 M, 7.3 μL, 1.0 eq) and VcNa (0.4 M, 14.6 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 5796.54 observed m/z: 1159.8 ([M/5+H]) 966.7 ([M/6+H]$^+$)] was detected. The reaction mixture was directly purified by prep-HPLC (TFA condition). BCY9659 (6.2 mg, 1.06 μmol, 36.58% yield, 98.86% purity) was obtained as a white solid.

BCY9758

Procedure for Preparation of Compound 2

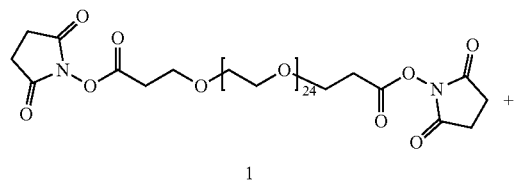

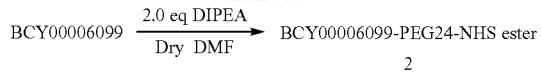

To a solution of compound 1 (5.0 mg, 3.54 μmol, 1.0 eq), BCY6099 (11.3 mg, 3.54 μmol, 1.0 eq) in DMF (3 mL) was added DIEA (0.9 mg, 7.07 μmol, 1.2 μL, 2.0 eq). The mixture was stirred at 25-30° C. for 20 min. LC-MS showed one peak with desired m/z (MW: 4481.11, observed m/z: 1101.3 ([M/4+H]$^+$)) was detected. The reaction mixture was filtered and concentrated under reduced pressure and lyophilized to give compound 2 (15 mg, crude) as a white solid.

Procedure for Preparation of BCY9758

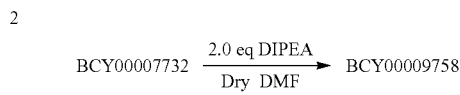

To a solution of compound 2 (15 mg, 3.35 μmol, 1.0 eq) and BCY7732 (14.74 mg, 6.69 μmol, 2.0 eq) in DMF (3 mL) was added DIEA (0.9 mg, 7.07 μmol, 1.2 μL, 2.1 eq). The mixture was stirred at 25-30° C. for 2 hrs. LC-MS showed compound 2 was consumed completely and one main peak with desired m/z (MW: 6567.48, observed m/z: 1095.1 ([M/6+H]), 938.8 ([M/7+H]$^+$)) was detected. The reaction mixture was filtered and concentrated under reduced pressure to give a residue. The crude product was purified by reversed-phase HPLC (TFA condition). BCY9758 (5.8 mg, 24.26% yield, 91.97% purity) was obtained as a white solid.

BCY10568

Procedure for Preparation of BCY8919-PEG12-N$_3$

BCY00008919 + NHS—PEG12-N$_3$ $\xrightarrow{\text{DIEA}}$ BCY00008919-PEG12-N$_3$
$\qquad\qquad\qquad$ 1 $\qquad\qquad\qquad$ DMSO $\qquad\qquad\qquad$ 2

BCY8919 (80.0 mg, 38.47 μmol, 1.0 eq) and compound 1 (29.6 mg, 40.01 μmol, 1.04 eq) were dissolved in DMSO (1 mL). The solution was then added with DIPEA (7.46 mg, 55.71 μmol, 10.0 μl, 1.5 eq), and then the mixture was stirred at 25-30° C. for 2 hr. LC-MS showed majority of BCY8919 was consumed and one main peak with desired m/z (calculated MW: 2705.16, observed m/z: 1353.1 ([M/2+H]$^+$)) was detected. The reaction mixture was purified by prep-HPLC (TFA condition) and compound 2 (18.6 mg, 6.86 μmol, 17.83% yield, 99.76% purity) was obtained as a white solid.

Procedure for Preparation of BCY10568

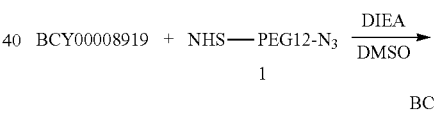

Compound 2 (9.0 mg, 3.33 μmol, 1.0 eq) and BCY6169 (11.0 mg, 3.36 μmol, 1.01 eq) were first dissolved in 2 mL of t-BuOH/H$_2$O (1:1), and then CuSO$_4$ (0.4 M, 8.3 μL, 1.0 eq), VcNa (1.4 mg, 7.06 μmol, 2.1 eq) and THPTA (1.4 mg, 3.22 μmol, 1.0 eq) were added. Finally 0.4 M NH$_4$HCO$_3$ was added to adjust pH to 8. All solvents here were degassed and purged with N$_2$ for 3 times. The reaction mixture was stirred at 30° C. for 16 hr under N$_2$ atmosphere. LC-MS showed compound 2 was consumed completely and one main peak with desired m/z (calculated MW: 5967.90, observed m/z: 995.00 ([M/5+H]$^+$) and 1194.70 ([M/6+H]$^+$)). The reaction mixture was purified by prep-HPLC (TFA condition) and BCY10568 (13.4 mg, 2.16 μmol, 69.44% yield, 96.3% purity) was obtained as a white solid.

BCY10570

Procedure for Preparation of BCY8920-PEG12-N$_3$

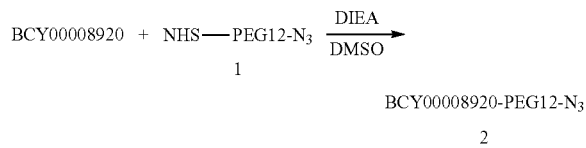

To a solution of BCY8920 (37 mg, 17.31 μmol, 1.0 eq) and compound 1 (15 mg, 20.25 μmol, 1.2 eq) in DMSO (2 mL) was added DIEA (3.36 mg, 25.96 μmol, 4.5 μL, 1.5 eq). The mixture was stirred at 30° C. for 12 hr. LC-MS showed BCY8920 was consumed completely and one main peak with desired m/z (calculated MW: 2763.2, observed m/z: 689.07 ([M/4−H$^+$])) was detected. The reaction mixture was concentrated under reduced pressure to remove solvent and produced a residue. The residue was then purified by prep-HPLC (neutral condition). Compound 2 (22.8 mg, 8.15 μmol, 47.09% yield, 98.78% purity) was obtained as a white solid.

Procedure for Preparation of BCY10570

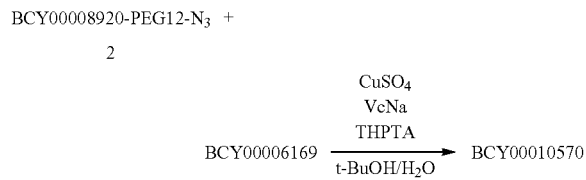

Compound 2 (6 mg, 2.17 μmol, 1.0 eq) and BCY6169 (7.08 mg, 2.17 μmol, 1.0 eq) were first dissolved in 2 mL of t-BuOH/H$_2$O (1:1), and then CuSO$_4$ (0.4 M, 5.4 μL, 1.0 eq), VcNa (0.4 M, 10.8 μL, 2.0 eq) and THPTA (0.4 M, 5.4 μL, 1.0 eq) was added. Finally 0.2 M NH$_4$HCO$_3$ was added to adjust pH to 8. All solvents here were degassed and purged with N$_2$ for 3 times. The reaction mixture was stirred at 30° C. for 4 hr under N$_2$ atmosphere. LC-MS showed compound 2 was consumed completely and one main peak with desired m/z (MS: 6025.93, observed m/z: 1004.56 ([M/6]+H$^+$) and 861.48 ([M/7+H$^+$])) was detected. The reaction mixture was filtered and concentrated under reduced pressure to give a residue. The crude product was purified by prep-HPLC (TFA condition). BCY10570 (7.2 mg, 1.17 μmol, 53.90% yield, 97.95% purity) was obtained as a white solid.

BCY10574

Procedure for Preparation of Compound 2

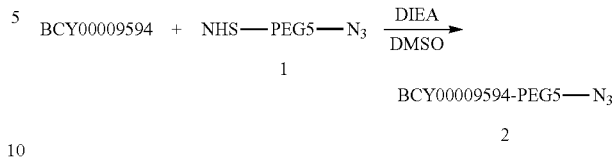

To a solution of BCY9594 (65 mg, 27.07 μmol, 1 eq), Compound 1 (12.00 mg, 27.75 μmol, 1.02 eq) in DMSO (1 mL) was added DIEA (5.25 mg, 40.61 μmol, 7.07 μL, 1.5 eq). The mixture was stirred at 25-30° C. for 2 hr. LC-MS showed BCY9594 was consumed completely and one main peak with desired m/z (calculated MW: 2718.13, observed m/z: 906.04 ([M/3+H]$^+$), 1359.07 ([M/2+H]$^+$)) was detected. The reaction mixture was concentrated under reduced pressure to remove solvent to give a residue. The residue was purified by prep-HPLC (TFA condition). Compound 2 (42.6 mg, 15.67 μmol, 57.89% yield, 100% purity) was obtained as a white solid.

Procedure for Preparation of BCY10574

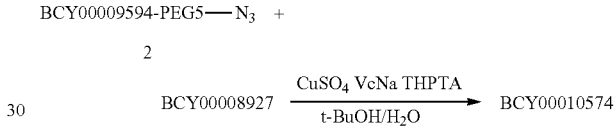

A mixture of Compound 2 (20 mg, 7.36 μmol, 1.0 eq), BCY8927 (17 mg, 7.87 μmol, 1.07 eq), and THPTA (0.4 M, 18.4 μL, 1.0 eq) was dissolved in t-BuOH/H$_2$O (1:1, 2 mL, pre-degassed and purged with N$_2$ for 3 times), and then CuSO$_4$ (0.4 M, 18.4 μL, 1.0 eq) and VcNa (0.4 M, 36.8 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 2 was consumed completely and one main peak with desired m/z (calculated MW: 4877.68, observed m/z: 1219.42 ([M/4+H]$^+$) and 975.54 ([M/5+H]$^+$)) was detected. The reaction mixture was directly purified by prep-HPLC (TFA condition). BCY10574 (17.6 mg, 3.41 μmol, 46.29% yield, 94.40% purity) was obtained as a white solid.

BCY10575

Procedure for Preparation of Compound 2

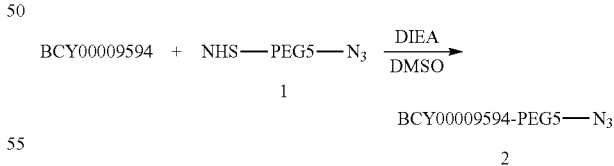

To a solution of BCY9594 (65 mg, 27.07 μmol, 1 eq), Compound 1 (12.0 mg, 27.75 μmol, 1.02 eq) in DMSO (1 mL) was added DIEA (5.25 mg, 40.61 μmol, 7.07 μL, 1.5 eq). The mixture was stirred at 25-30° C. for 2 hr. LC-MS showed Compound 1 was consumed completely and one main peak with desired m/z [calculated MW: 2718.13 observed m/z: 906.04 ([M/3+H]$^+$) and 1359.07 ([M/2+H]$^+$)] was detected. The reaction mixture was concentrated under reduced pressure to remove solvent to give a residue. The residue was purified by prep-HPLC (TFA condition). Compound 2 (42.6 mg, 15.67 μmol, 57.89% yield, 100% purity) was obtained as a white solid.

Procedure for Preparation of BCY10575

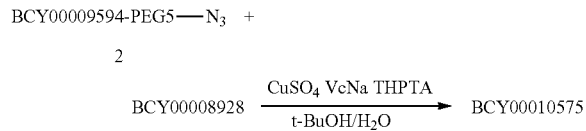

A mixture of Compound 2 (20 mg, 7.36 μmol, 1.0 eq), BCY8928 (17 mg, 7.67 μmol, 1.04 eq), and THPTA (0.4 M, 18.4 μL, 1.0 eq) was dissolved in t-BuOH/H$_2$O (1:1, 2 mL, pre-degassed and purged with N$_2$ for 3 times), and then CuSO$_4$ (0.4 M, 18.4 μL, 1.0 eq) and VcNa (0.4 M, 36.8 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 2 was consumed completely and one main peak with desired m/z [calculated MW: 4935.71, observed m/z: 1234.59 ([M/4+H]$^+$) and 987.71 ([M/5+H]$^+$)] was detected. The reaction mixture was directly purified by prep-HPLC (TFA condition). BCY10575 (12 mg, 2.37 μmol, 32.27% yield, 97.67% purity) was obtained as a white solid.

BCY10576

Procedure for Preparation of Compound 2

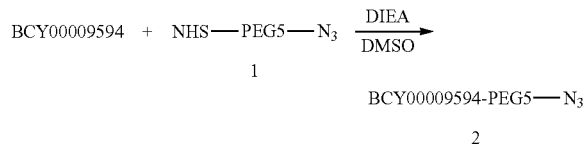

To a solution of BCY9594 (30.0 mg, 12.50 μmol, 1.0 eq), Compound 1 (5.54 mg, 12.81 μmol, 1.02 eq) in DMSO (1 mL) was added DIEA (2.42 mg, 18.74 μmol, 3.3 μL, 1.5 eq). The mixture was stirred at 25-30° C. for 2 hr. LC-MS showed Compound 1 was consumed completely and one main peak with desired m/z [calculated MW: 2718.13, observed m/z: 906.45 ([M/3+H]$^+$) and 1359.50 ([M/2+H]$^+$)] was detected. The reaction mixture was concentrated under reduced pressure to remove solvent to give a residue. The residue was purified by prep-HPLC (TFA condition). Compound 2 (16 mg, 5.80 μmol, 46.42% yield, 98.54% purity) was obtained as a white solid.

Procedure for Preparation of BCY10576

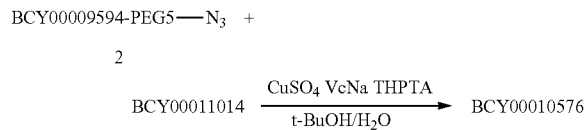

A mixture of compound 2 (17.0 mg, 6.25 μmol, 1.0 eq), BCY11014 (13.6 mg, 6.25 μmol, 1.0 eq), and THPTA (0.4 M, 1.8 μL, 2.0 eq) was dissolved in t-BuOH/H$_2$O (1:1, 2 mL, pre-degassed and purged with N$_2$ for 3 times), and then CuSO$_4$ (0.4 M, 15.6 μL, 1.0 eq) and VcNa (0.4 M, 1.84 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed majority of compound 2 was consumed and one main peak with desired m/z [calculated MW: 4893.63, observed m/z: 1224.7 ([M/4+H]$^+$) and 980.0 ([M/6+H]$^+$)] was detected. The reaction mixture was directly purified by prep-HPLC (TFA condition). BCY10576 (20.5 mg, 4.13 μmol, 66.02% yield, 98.57% purity) was obtained as a white solid.

BCY10577

Procedure for Preparation of Compound 2

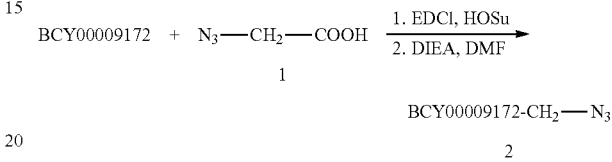

To a solution of compound 1 (5.0 mg, 49.5 μmol, 1.0 eq) in DMF (1 mL) was added EDCI (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then BCY9172 (53 mg, 25.29 μmol, 0.47 eq) and DIEA (3.27 mg, 25.29 μmol, 4.4 μL, 0.47 eq) were added to the reaction mixture. The mixture was stirred at 25-30° C. for 2 hr. LC-MS showed BCY9172 was consumed completely and one main peak with desired m/z (MW: 2178.46, observed m/z: 1089.5700 ([(M/2+H$^+$])) was detected. The reaction mixture was concentrated under reduced pressure to remove solvent and produced a residue. The residue was then purified by prep-HPLC (neutral condition). Compound 2 (30 mg, 13.77 μmol, 54.45% yield, 100% purity) was obtained as a white solid.

Procedure for Preparation of BCY10577

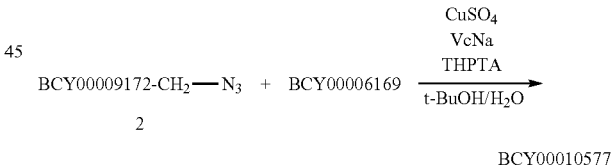

Compound 2 (20 mg, 9.18 μmol, 1.0 eq) and BCY6169 (32.95 mg, 10.10 μmol, 1.1 eq) were first dissolved in 2 mL of t-BuOH/H$_2$O (1:1), and then CuSO$_4$ (0.4 M, 23 μL, 1 eq), VcNa (0.4 M, 46 μL, 2.0 eq) and THPTA (0.4 M, 23 μL, 1.0 eq) was added. Finally 1 M NH$_4$HCO$_3$ was added to adjust pH to 8. All solvents here were degassed and purged with N$_2$ for 3 times. The reaction mixture was stirred at 30° C. for 4 hr under N$_2$ atmosphere. LC-MS showed compound 2 was consumed completely and one main peak with desired m/z (calculated MW: 5441.20, observed m/z: 1361.8 ([M/4+H]$^+$)) was detected. The reaction mixture was filtered and concentrated under reduced pressure to give a residue. The crude product was purified by prep-HPLC (TFA condition). BCY10577 (16.2 mg, 2.98 μmol, 32.43% yield) was obtained as a white solid.

Example 3: Synthesis of Nectin-4/CD137 Binding Heterotandem Bicyclic Peptides BCY8854
General Procedure for Preparation of BCY8846

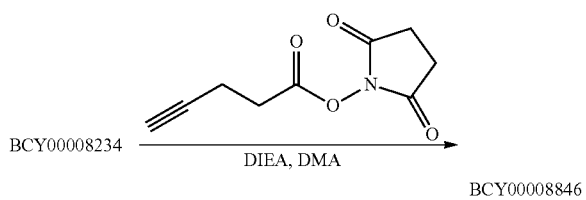

To a solution of BCY8234 (a peptide identical to BCY8846 except for the absence of a PYA moiety; 300 mg, 102 µmol, 1.0 eq) in DMA (3 mL) was added DIEA (52.5 mg, 406 µmol, 70.8 µL, 4.0 eq) with stirring for 10 min. Then (2,5-dioxopyrrolidin-1-yl) pent-4-ynoate (25.8 mg, 132 µmol, 1.3 eq) was added thereto and the mixture was further stirred at 20° C. for additional 16 hr. LC-MS showed BCY8234 was consumed completely and one main peak with desired m/z (calculated MW: 3034.43, observed m/z: 1011.8 ([M/3+H]$^+$), 1517.0 ([M/2+H]$^+$)) was detected. The reaction mixture was purified by prep-HPLC (neutral condition) to give compound BCY8846 (290 mg, 95.6 µmol, 94.1% yield) as a white solid.

General Procedure for Preparation of BCY8854

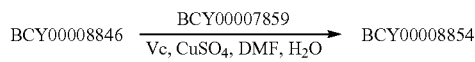

To a solution of BCY8846 (234 mg, 77.1 µmol, 1.0 eq) in DMF (5 mL) was added BCY7859 (which may be prepared as described in BCY7985; 220 mg, 77.8 µmol, 1.0 eq), followed by addition (2R)-2-[(1S)-1,2-dihydroxyethyl]-3,4-dihydroxy-2H-furan-5-one (0.80 M, 963 µL, 1.0 eq) and CuSO$_4$ (0.80 M, 289 µL, 0.3 eq). The mixture was stirred at 20° C. for 2 hr. LC-MS showed BCY8846 was consumed completely and one main peak with desired m/z (Calculated MW: 5861.59, observed m/z: 837.9 ([M/7+H]$^+$), 977.6 ([M/6+H]$^+$), 1173.3 ([M/5+H]$^+$)) was detected. The reaction mixture was purified by prep-HPLC (A: 0.075% TFA in H$_2$O, B: ACN) to give compound BCY8854 (292 mg, 46.8 µmol, 60.8% yield, 95.9% purity, TFA) as a white solid.

BCY9350
General Procedure for Preparation of BCY8782-PYA

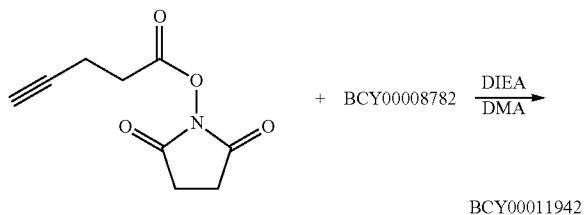

To a solution of BCY8782 (a peptide identical to BCY11942 except for the absence of a PYA moiety; 20.0 mg, 6.77 µmol, 1.0 eq) in DMA (1 mL) was added DIEA (4.37 mg, 33.9 µmol, 5.90 µL, 5.0 eq) and (2,5-dioxopyrrolidin-1-yl) pent-4-ynoate (2.64 mg, 13.5 µmol, 2.0 eq) with stirring for 12 hr at 25° C. LC-MS showed BCY8782 was consumed completely and one main peak with desired m/z (calculated MW: 3034.43, observed m/z: 1012.1 [M/3+H]$^+$) was detected. The reaction mixture was purified by prep-HPLC (neutral condition) to give BCY11942 (20.0 mg, 6.00 µmol, 88.6% yield, 91.0% purity) as a white solid.

General Procedure for Preparation of BCY9350

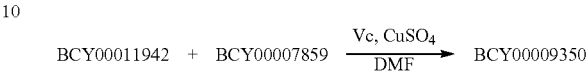

To a solution of BCY11942 (20 mg, 6.59 µmol, 1.0 eq) and BCY7859 (which may be prepared as described in BCY7985; 20.5 mg, 7.25 µmol, 1.1 eq) in DMF (1 mL) was added (2R)-2-[(1S)-1,2-dihydroxyethyl]-3, 4-dihydroxy-2H-furan-5-one (0.4 M, 330 µL, 20.0 eq) and CuSO$_4$ (0.4 M, 98.9 µL, 6.0 eq) were added to the mixture. The mixture was stirred at 25° C. for 2 hr. LC-MS showed BCY8782-PYA was consumed completely and one main peak with desired m/z (calculated MW: 5861.59, observed m/z: 1173.3 [M/5+H]$^+$) was detected. The reaction mixture was purified by prep-HPLC (A: 0.075% TFA in H$_2$O, B: ACN) to give BCY9350 (14.5 mg, 2.40 µmol, 36.5% yield, 97.2% purity) as a white solid.

BCY9351
General Procedure for Preparation of BCY9351

To a solution of BCY8940 (which may be prepared as described in BCY8942; 9.4 mg, 3.33 µmol, 1.01 eq) and BCY8846 (10.0 mg, 3.30 µmol, 1.0 eq) in DMF (1 mL) was added Vc (0.4 M, 165 µL, 20.0 eq) and CuSO$_4$ (0.4 M, 49.4 µL, 6.0 eq) under nitrogen atmosphere. The mixture was stirred at 25° C. for 1 hr. LC-MS showed BCY8940 was consumed completely and one main peak with desired m/z (calculated MW: 5861.59, observed m/z: 975.4 [M/6+H]$^+$, 1172.3 [M/5+H]$^+$) was detected. The reaction mixture was purified by prep-HPLC (A: 0.075% TFA in H$_2$O, B: ACN) to give BCY9351 (5.30 mg, 0.904 µmol, 26.3% yield, 96.0% purity) as a white solid.

BCY9399
Procedure for Preparation of Compound 2

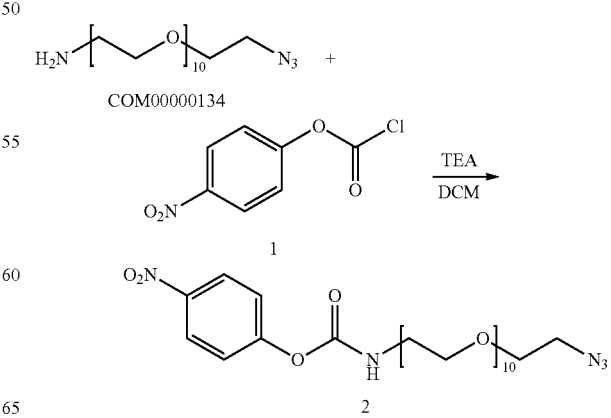

To a solution of COM134 (30 mg, 56.97 μmol), Compound 1 (17.22 mg, 85.45 μmol) in DCM (0.5 mL) was added TEA (8.65 mg, 85.45 μmol, 11.9 μL). The mixture was stirred at 25° C. for 1 hr. LC-MS showed COM134 was consumed completely and one main peak with desired m/z (calculated MW: 691.72, observed m/z: 692.3 ([M+H]$^+$) and 709.3 ([M+NH4]$^+$)) was detected. The reaction mixture was concentrated under reduced pressure to remove solvent to give a residue. The residue was purified by prep-HPLC (neutral condition). Compound 2 (30.5 mg) was obtained as a colorless oil.

Procedure for Preparation of Compound 3

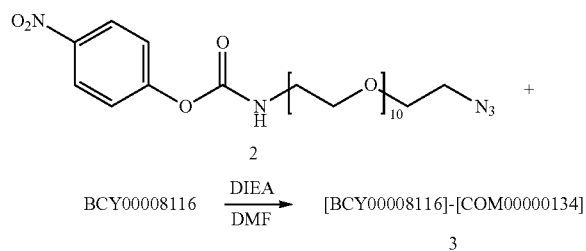

To a solution of Compound 2 (15 mg, 21.68 μmol) and BCY8116 (47 mg, 21.68 μmol) in DMF (1 mL) was added DIEA (8.41 mg, 65.05 μmol, 11.33 μL). The mixture was stirred at 30° C. for 2 hrs. LC-MS showed Compound 2 was consumed completely and one main peak with desired m/z (MW: 2725.1 observed m/z: 1362.7 ([M/2+H]$^+$), 909.0 ([M/3+H]$^+$)) was detected. The reaction mixture was filtered and concentrated under reduced pressure to give a residue. The crude product was purified by reversed-phase HPLC (TFA condition). Compound 3 (20 mg, 33.41% yield, 98.71% purity) was obtained as a white solid.

Procedure for Preparation of BCY9399

[BCY00008116]-[COM00000134]  +

3

BCY00007741  →(CuSO₄ VcNa THPTA / t-BuOH/H₂O)→  BCY00009399

A mixture of Compound 3 (20.0 mg, 5.35 μmol, 1.0 eq), BCY7741 (13.0 mg, 5.70 μmol, 1.01 eq), and THPTA (0.4 M, 13.4 μL, 1.0 eq) was dissolved in t-BuOH/H₂O (1:1, 2 mL, pre-degassed and purged with N₂ for 3 times), and then CuSO₄ (0.4 M, 13.4 μL, 1.0 eq) and VcNa (0.4 M, 26.8 μL, 2.0 eq) were added under N₂. The pH of this solution was adjusted to 8 by dropwise addition of 0.2 M NH₄HCO₃ (in 1:1 t-BuOH/H₂O), and the solution turned to light yellow. The reaction mixture was stirred at 25-30° C. for 12 hr under N₂ atmosphere. LC-MS showed Compound 3 was consumed completely and one main peak with desired m/z [MW: 5006.64 observed m/z: 834.9 ([M/6+H]$^+$), 1002.3 ([M/5+H]$^+$), 1252.4 ([M/4+H]$^+$)] was detected. The reaction mixture was directly purified by prep-HPLC (TFA condition). BCY9399 (9.1 mg, 27.20% yield, 96.29% purity) was obtained as a white solid.

BCY9400
Procedure for Preparation of Compound 2

COM00000135 + [structure 1: 4-nitrophenyl chloroformate] →(TEA / DCM)→ [structure 2]

To a solution of COM135 (which may be prepared as described in BCY9648; 30.0 mg, 27.29 μmol), Compound 1 (8.3 mg, 40.94 μmol) in DCM (2 mL) was added TEA (4.14 mg, 40.94 μmol, 5.7 μL). Then the reaction mixture was stirred at 25-30° C. for 1 hr. LC-MS showed COM135 was consumed completely and one main peak with desired m/z (calculated MW: 1264.40, observed m/z: 1281.4 ([M+NH4]$^+$)) was detected. The reaction mixture was concentrated under reduced pressure to remove solvent to give a residue. The residue was purified by prep-HPLC (neutral condition) to give compound 2 (18 mg) as a white solid.

Procedure for Preparation of Compound 3

[structure 2 with PEG23 azide] + BCY00008116 →(TEA / DMF)→ [BCY00008116]-[COM00000135]

3

To a solution of Compound 2 (15.5 mg, 7.12 μmol) and BCY8116 (9 mg, 7.12 μmol) in DMF (2 mL) was added DIEA (1.4 mg, 10.68 μmol, 1.9 μL). The mixture was stirred at 30° C. for 2 hrs. LC-MS showed Compound 2 was consumed completely and one main peak with desired m/z (MW: 3297.78, observed m/z: 1099.7 ([M/3+H]$^+$)) was detected. The reaction mixture was filtered and concentrated under reduced pressure to give a residue. The crude product was purified by reversed-phase HPLC (TFA condition). Compound 3 (19.5 mg, 5.91 μmol, 33.41% yield, 83.07% purity) was obtained as a white solid.

Procedure for Preparation of BCY9400

[BCY00008116]-[COM00000135]  +

3

BCY00007741  →(CuSO₄ VcNa THPTA / t-BuOH/H₂O)→  BCY00009400

A mixture of Compound 3 (19.5 mg, 5.91 μmol), BCY7741 (14 mg, 6.14 μmol, 1.01 eq), and THPTA (0.4 M, 15 μL, 1 eq) was dissolved in t-BuOH/H₂O (1:1, 2 mL, pre-degassed and purged with N₂ for 3 times), and then CuSO₄ (0.4 M, 15 μL, 1 eq) and VcNa (0.4 M, 30 μL, 2 eq) were added under N₂. The pH of this solution was adjusted to 8 by dropwise addition of 0.2 M NH₄HCO₃ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 5579.31 observed m/z: 930.5 ([M/6+H]$^+$), 1116.6 ([M/5+H]$^+$)] was detected. The reaction mixture was directly purified by prep-HPLC (TFA condition). BCY9400 (13.9 mg, 2.33 μmol, 27.20% yield, 93.56% purity) was obtained as a white solid.

BCY9401

Procedure for Preparation of Compound 3 fied by prep-HPLC (neutral condition). Compound 4 (10 mg, 2.43 μmol, 21.33% yield, 92% purity) was obtained as colorless oil.

Procedure for Preparation of BCY9401

[BCY00008116]-[COM00000122] +

4

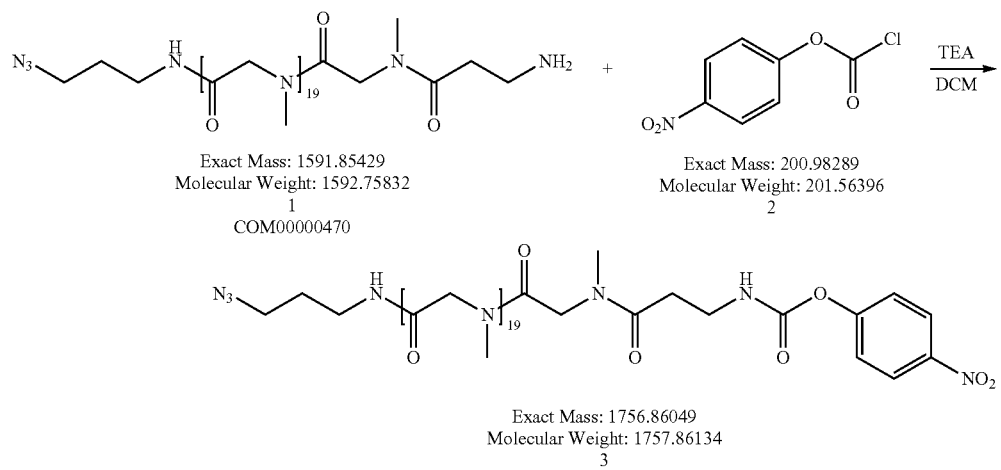

Exact Mass: 1591.85429
Molecular Weight: 1592.75832
1
COM00000470

Exact Mass: 200.98289
Molecular Weight: 201.56396
2

Exact Mass: 1756.86049
Molecular Weight: 1757.86134
3

To a solution of Compound 1 (50.0 mg, 31.39 μmol, 1 eq), Compound 2 (6.6 mg, 32.96 μmol, 1.05 eq) in DCM (2 mL) was added TEA (4.8 mg, 47.09 μmol, 6.6 μL, 1.5 eq). The mixture was stirred at 25-30° C. for 2 hr. LC-MS showed Compound 1 was consumed completely and one main peak with desired m/z (MW: 1757.86 observed m/z: 879.10 ([M/2+H]$^+$)) was detected. The reaction mixture was concentrated under reduced pressure to remove solvent to give a residue. The residue was purified by prep-HPLC (TFA condition). Compound 3 (0.02 g, 6.56 μmol, 20.91% yield, 57.7% purity) was obtained as a white solid.

Procedure for Preparation of Compound 4

-continued

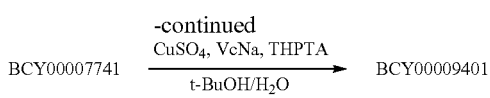

A mixture of Compound 4 (10 mg, 2.43 μmol, 0.9 eq), BCY7741 (6.32 mg, 2.77 μmol, 1.0 eq) and THPTA (0.4 M, 6.7 μL, 1.0 eq) was dissolved in t-BuOH/H$_2$O (1:1, 2 mL, pre-degassed and purged with N$_2$ for 3 times), and then CuSO$_4$ (0.4 M, 6.7 μL, 1.0 eq) and VcNa (0.4 M, 13.4 μL, 2.0 eq) were added under N$_2$. The pH of this solution was adjusted to 8 by dropwise addition of 0.2 M NH$_4$HCO$_3$ (in

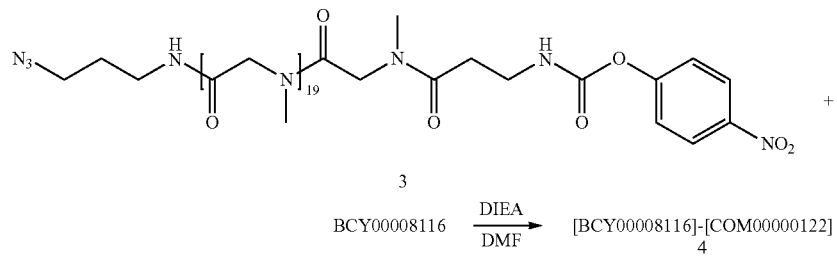

To a solution of Compound 3 (20 mg, 11.38 μmol, 1 eq), BCY8116 (25 mg, 11.51 μmol, 1.01 eq) in DMF (4 mL) was added DIEA (2.2 mg, 17.07 μmol, 2.97 μL, 1.5 eq). The mixture was stirred at 25-30° C. for 12 hr. LC-MS showed Compound 3 was consumed completely and one main peak with desired m/z (MW: 3791.23, observed m/z: 1263.2 ([M/3+H]$^+$)) was detected. The reaction was directly puri- 1:1 t-BuOH/H$_2$O), and the solution turned to light yellow. The reaction mixture was stirred at 25-30° C. for 12 hr under N$_2$ atmosphere. LC-MS showed Compound 4 was consumed completely and one main peak with desired m/z [MW: MW: 6072.77, observed m/z: 1012.00 ([M/6+H]$^+$)] was detected. The reaction mixture was directly purified by prep-HPLC (TFA condition). BCY9401 (8.4 mg, 1.56 μmol, 59.31% yield, 95.52% purity) was obtained as a white solid.

BCY9403
Procedure for Preparation of Compound 2

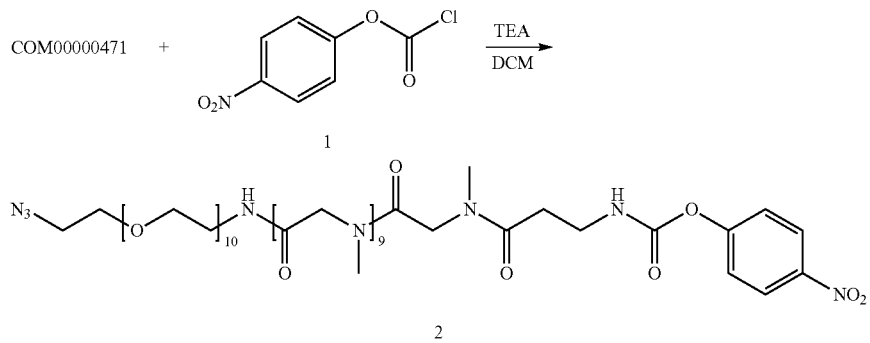

To a solution of COM471 (100.0 mg, 76.42 μmol, 1.0 eq), 4-nitrophenylchloroformate (16.2 mg, 80.25 μmol, 1.05 eq) in DCM (10 mL) was added TEA (11.6 mg, 114.64 μmol, 16.0 μL, 1.5 eq). The mixture was stirred at 25-30° C. for 2 hr. LC-MS showed COM471 was consumed completely and one main peak with desired m/z (MW: 1473.58, observed m/z: 736.83 ([M/2+H]$^+$)) was detected. The reaction mixture was concentrated under reduced pressure to remove solvent to give a residue. The residue was purified by prep-HPLC (TFA condition). Compound 2 (62.8 mg, 42.67 μmol, 55.84% yield, 48.37% purity) was obtained as a white oil.

Procedure for Preparation of Compound 3

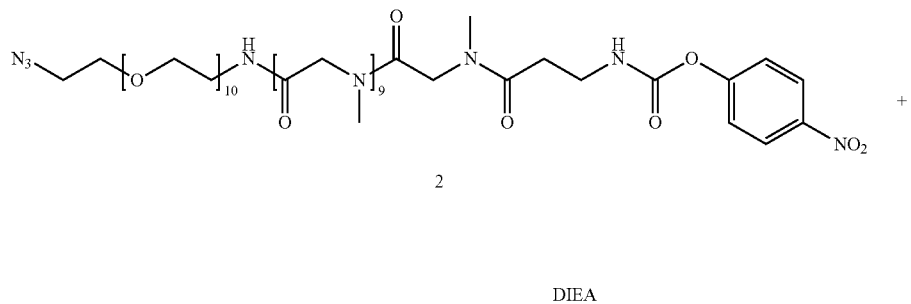

To a solution of Compound 2 (44 mg, 29.46 μmol, 1.0 eq), BCY8116 (63 mg, 29.18 μmol, 1.0 eq) in DMF (2 mL) was added DIEA (5.66 mg, 43.77 μmol, 7.62 μL, 1.5 eq). The mixture was stirred at 40° C. for 12 hr. LC-MS showed Compound 2 was consumed completely and one main peak with desired m/z (MW: 3506.95, observed m/z: 1168.58 ([M/3+H]$^+$)) was detected. The residue was purified by prep-HPLC (TFA condition). Compound 3 (20 mg, 5.42 μmol, 18.57% yield, 95.04% purity) was obtained as a white solid.

Procedure for Preparation of BCY9403

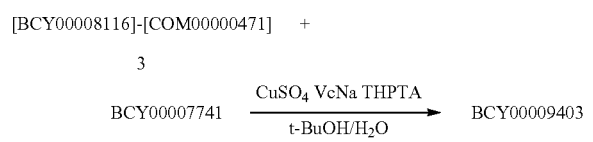

A mixture of Compound 3 (10.0 mg, 2.71 μmol, 1.0 eq), BCY7741 (6.83 mg, 2.99 μmol, 1.1 eq), and THPTA (0.4 M, 7 μL, 1.0 eq) was dissolved in t-BuOH/H$_2$O (1:1, 2 mL, pre-degassed and purged with N$_2$ for 3 times), and then CuSO$_4$ (0.4 M, 7 μL, 1.0 eq) and VcNa (0.4 M, 14 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 5788.49, observed m/z: 1157.00 ([M/5+H]$^+$) and 964.60 ([M/6+H]$^+$)] was detected. The reaction mixture was directly purified by prep-HPLC (TFA condition). BCY9403 (2.1 mg, 0.34 μmol, 11.93% yield, 93.80% purity) was obtained as a white solid.

BCY9405
Procedure for Preparation of Compound 2

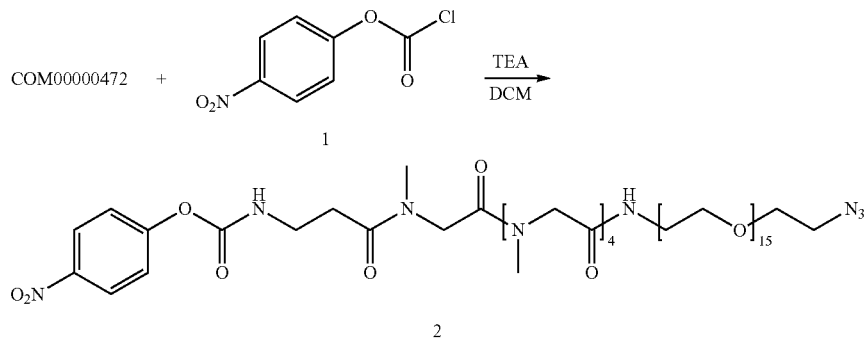

To a solution of COM472 (44.7 mg, 38.1 μmol), Compound 1 (9.2 mg, 45.72 μmol) in DCM (4 mL) was added TEA (5.8 mg, 57.14 μmol, 8 μL). The mixture was stirred at 25° C. for 2 hr. LC-MS showed COM472 was consumed completely and one main peak with desired m/z (MW: 1338.45, observed m/z: 686.23 ([M/2+NH4]$^+$)) was detected. The reaction mixture was concentrated under reduced pressure to remove solvent to give a residue. The residue was purified by prep-HPLC (neutral condition). Compound 2 (20 mg, 14.94 μmol, 39.2% yield) was obtained as colorless oil.

Procedure for Preparation of Compound 3

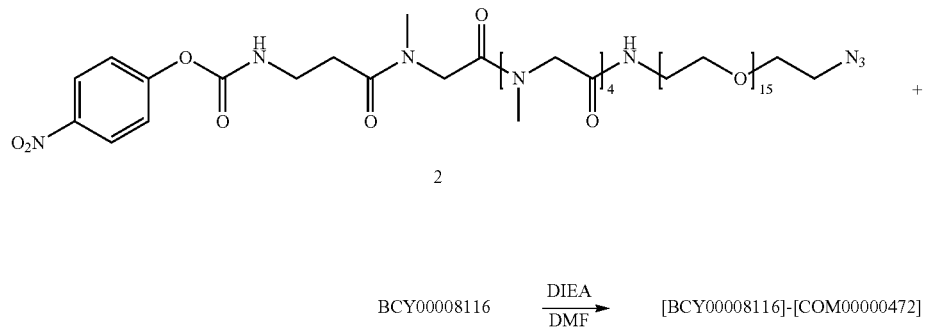

To a solution of Compound 2 (20 mg, 14.94 μmol) and BCY8116 (38.96 mg, 17.93 μmol) in DMF (4 mL) was added DIEA (1.9 mg, 14.94 μmol, 2.6 μL). The mixture was stirred at 30° C. for 2 hrs. LC-MS showed Compound 2 was consumed completely and one main peak with desired m/z (MW: 3371.82, observed m/z: 1123.94 ([M/3+H$^+$])) was detected. The reaction mixture was filtered and concentrated under reduced pressure to give a residue. The crude product was purified by reversed-phase HPLC (TFA condition). Compound 3 (10 mg, 99.07% yield, 19.66 purity) was obtained as a white solid.

Procedure for Preparation of BCY9405

[BCY00008116]-[COM00000472]  +
3

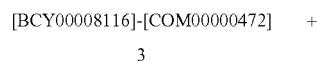

A mixture of Compound 3 (10.0 mg, 2.97 μmol, 1.0 eq), BCY7741 (7.4 mg, 3.26 μmol, 1.1 eq), and THPTA (1.3 mg, 2.97 μmol, 1.0 eq) was dissolved in t-BuOH/H$_2$O (1:1, 2 mL, pre-degassed and purged with N$_2$ for 3 times), and then CuSO$_4$ (0.4 M, 7.5 μL, 1.0 eq) and VcNa (0.4 M, 151 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 5653.36, observed m/z: 1130.47 ([M/5+H]$^+$)] was detected. The reaction mixture was directly purified by prep-HPLC (TFA condition). BCY9405 (7.8 mg, 46.08% yield, 97.8% purity) was obtained as a white solid.

BCY9406
Procedure for Preparation of Compound 2

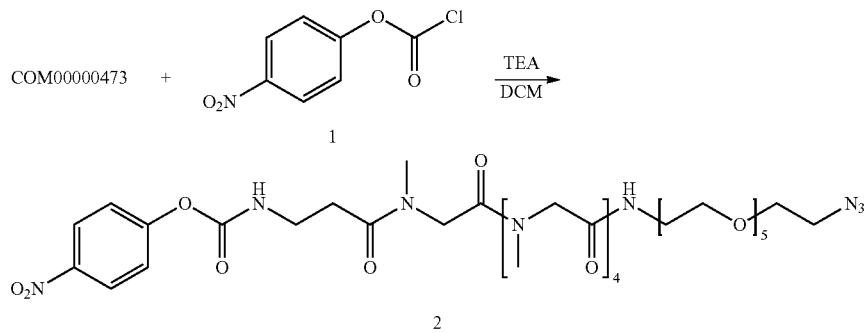

To a solution of COM473 (130.0 mg, 177.40 μmol, 1.0 eq), (4-nitrophenyl) carbonochloridate (36.4 mg, 180.59 μmol, 1.02 eq) in DCM (3 mL) was added TEA (27.0 mg, 266.09 μmol, 37 μL, 1.5 eq). The mixture was stirred at 35° C. for 2 hr. LC-MS showed COM473 was consumed completely and one main peak with desired m/z (MW: 897.93, observed m/z: 897.65 ([M+H]$^+$), 914.60 ([M+NH$_4$]$^+$)) was detected. The reaction mixture was concentrated under reduced pressure to remove solvent to give a residue. The residue was purified by prep-HPLC (TFA condition). Compound 2 (90 mg, 95.87 μmol, 54.04% yield, 95.65% purity) was obtained as colorless oil.

Procedure for Preparation of Compound 3

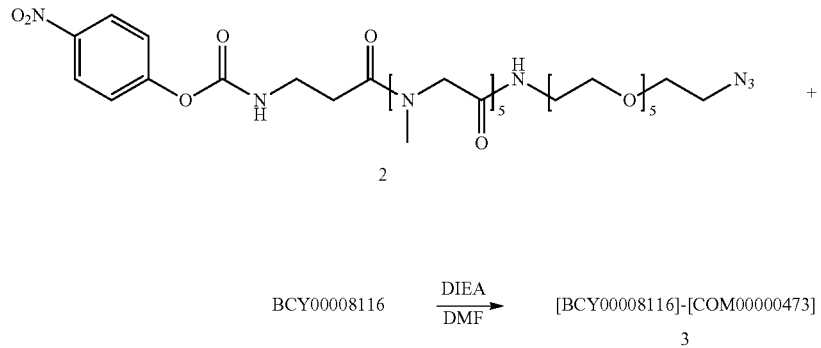

To a solution of Compound 2 (10 mg, 11.14 μmol, 1 eq), BCY8116 (25 mg, 11.51 μmol, 1.03 eq) in DMF (2 mL) was added DIEA (2.16 mg, 16.71 μmol, 2.91 μL, 1.5 eq). The mixture was stirred at 25-30° C. for 12 hr. LC-MS showed one main peak with desired m/z (MW: 2931.30, observed m/z: 977.00 ([M/3+H]$^+$)) was detected. The reaction mixture was filtered and concentrated under reduced pressure to give a residue. The crude product was purified by reversed-phase HPLC (FTA condition). Compound 3 (15 mg, 5.12 μmol, 45.79% yield, 99.66% purity) was obtained as a white solid.

Procedure for Preparation of BCY9406

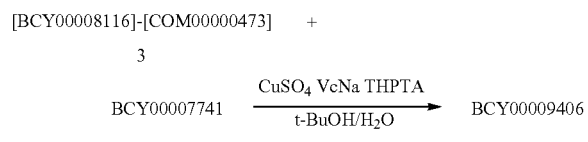

A mixture of Compound 3 (15 mg, 5.12 μmol, 1.0 eq), BCY7741 (12 mg, 5.26 μmol, 1.03 eq), and THPTA (0.4 M, 12.8 μL, 1.0 eq) was dissolved in t-BuOH/H$_2$O (1:1, 2 mL, pre-degassed and purged with N$_2$ for 3 times), and then CuSO$_4$ (0.4 M, 12.8 μL, 1.0 eq) and VcNa (0.4 M, 25.6 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 5212.84 observed m/z: 1042.74 ([M/4+H]$^+$)] was detected. The reaction mixture was directly purified by prep-HPLC (TFA condition). BCY9406 (14.4 mg, 2.57 μmol, 50.21% yield, 93.01% purity) was obtained as a white solid.

BCY9407
Procedure for Preparation of Compound 2

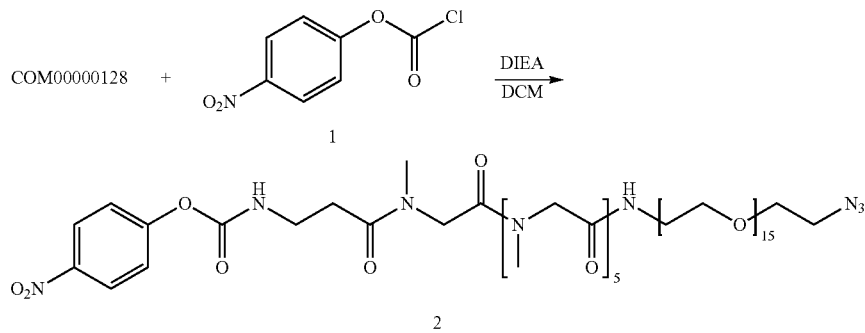

To a solution of COM128 (60 mg, 50.53 μmol, 1.0 eq), compound 1 (13 mg, 64.50 μmol, 1.28 eq), DIEA (9.80 mg, 75.80 μmol, 13.20 μL, 1.5 eq) in DCM (5 mL) was degassed and purged with $N_2$ for 3 times, and then the mixture was stirred at 25-30° C. for 1 hr under $N_2$ atmosphere. LC-MS showed COM128 was consumed completely and one main peak with desired m/z (calculated MW: 1352.48, observed m/z: 676.7 ([M/2+H]$^+$)) was detected. The reaction mixture was concentrated under reduced pressure to remove solvent to give a residue. The residue was purified by prep-HPLC (TFA condition). Compound 2 (12 mg, 8.87 μmol, 17.56% yield) was obtained as colorless oil.

Procedure for Preparation of [BCY8116]-[COM128]

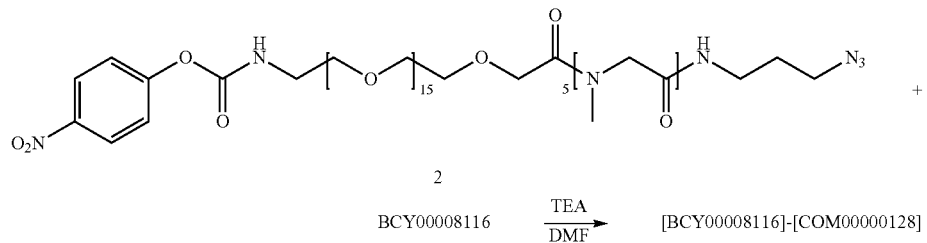

To a solution of compound 2 (7 mg, 5.18 μmol, 1.0 eq) and BCY8116 (11 mg, 5.06 μmol, 1.0 eq). DIEA (2.01 mg, 15.53 μmol, 2.70 μL, 3.0 eq) in DMF (3 mL) was degassed and purged with $N_2$ for 3 times, and then the mixture was stirred at 25-30° C. for 1 hr under $N_2$ atmosphere. LC-MS showed one main peak with desired m/z (calculated MW: 3385.85, observed m/z: 1129.3 ([M/3+H]$^+$)) was detected. The reaction mixture was filtered and concentrated under reduced pressure to give a residue. The crude product was purified by reversed-phase HPLC (TFA condition). [BCY8116]-[COM128] (15.6 mg, 4.46 μmol, 86.13% yield, 96.75% purity) was obtained as a white solid Procedure for Preparation of BCY9407

[BCY00008116]-[COM00000128] + BCY00007741 $\xrightarrow[\text{t-BuOH/H}_2\text{O}]{\text{CuSO}_4 \text{ VcNa THPTA}}$ BCY00009407

A mixture of [BCY8116]-[COM128] (15.6 mg, 4.61 μmol, 1.0 eq), BCY7741 (11 mg, 4.82 μmol, 1.05 eq), and THPTA (0.8 M, 5.8 μL, 1.0 eq) was dissolved in t-BuOH/$H_2O$ (1:1, 2 mL, pre-degassed and purged with $N_2$ for 3 times), and then CuSO$_4$ (0.4 M, 11.6 μL, 1.0 eq) and VcNa (0.4 M, 23.2 μL, 2.0 eq) were added under $N_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under $N_2$ atmosphere. LC-MS showed one peak with desired m/z (calculated MW: 5667.39, observed m/z: 945.6 ([M/6+H]$^+$) and 1134.2 ([M/5+H]$^+$)) was detected. The reaction mixture was directly purified by prep-HPLC (TFA condition). BCY9407 (1.3 mg, 0.23 μmol, 4.33% yield, 86.90% purity) was obtained as a white solid.

BCY9408
Procedure for Preparation of Compound 2

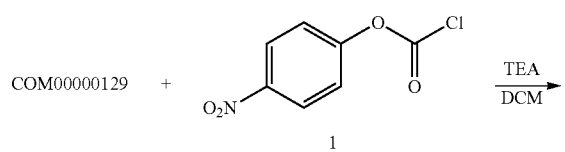

-continued

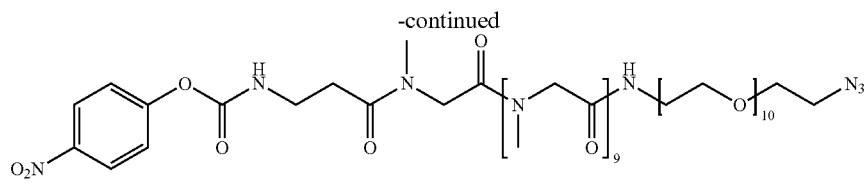

2

To a solution of COM129 (45.0 mg, 34.39 μmol, 1.0 eq), compound 1 (15.0 mg, 74.42 μmol, 2.1 eq) in DCM (5 mL) was added TEA (5.5 mg, 53.88 μmol, 7.5 μL, 1.5 eq), and then the mixture was stirred at 25-30° C. for 1 hr under $N_2$ atmosphere. LC-MS showed COM129 was consumed completely and one main peak with desired m/z (MW: 1473.58, observed m/z: 737.3 ($[M/2+H]^+$)) was detected. The reaction mixture was concentrated under reduced pressure to remove solvent to give a residue. The residue was purified by prep-HPLC (TFA condition). Compound 2 (9 mg, 6.11 μmol, 17.01% yield, 95.76% purity) was obtained as a white solid.

Procedure for Preparation of Compound 3

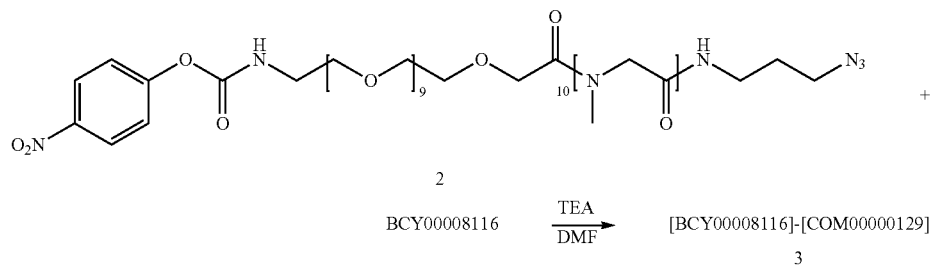

To a solution of compound 2 (9.0 mg, 6.11 μmol, 1.0 eq) and BCY8116 (13.3 mg, 6.11 μmol, 1.0 eq) in DMF (3 mL) was added DIEA (2.4 mg, 18.32 μmol, 3.2 μL, 3.0 eq). All solvents were degassed and purged with $N_2$ for 3 times, and then the mixture was stirred at 25-30° C. for 1 hr under $N_2$ atmosphere. LC-MS showed compound 2 was consumed completely and one main peak with desired m/z (MW: 3506.95, observed m/z: 877.4 ($[M/4+H]^+$) and m/z: 1169.6 ($[M/3+H]^+$)) was detected. The reaction mixture was filtered and concentrated under reduced pressure to give a residue. The crude product was purified by reversed-phase HPLC (TFA condition). Compound 3 (7.2 mg, 2.05 μmol, 31.93% yield, 95% purity) was obtained as a white solid.

Procedure for Preparation of BCY9408

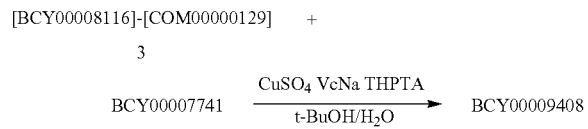

A mixture of Compound 3 (7.2 mg, 2.05 μmol, 1.0 eq), BCY7741 (5.0 mg, 2.19 μmol, 1.03 eq), and THPTA (0.4 M, 5.1 μL, 1.0 eq) was dissolved in t-BuOH/$H_2O$ (1:1, 2 mL, pre-degassed and purged with $N_2$ for 3 times), and then $CuSO_4$ (0.4 M, 5.1 μL, 1.0 eq) and VcNa (0.4 M, 10.2 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5788.49 observed m/z: 968.9 ($[M/6+H]^+$) and 1158.0 ($[M/5+H]^+$)] was detected. The reaction mixture was directly purified by prep-HPLC (TFA condition). BCY9408 (3.1 mg, 4.97e-1 μmol, 24.23% yield, 92.87% purity) was obtained as a white solid.

BCY9409

Procedure for Preparation of Compound 2

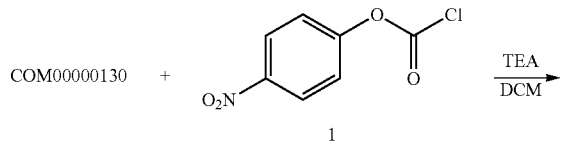

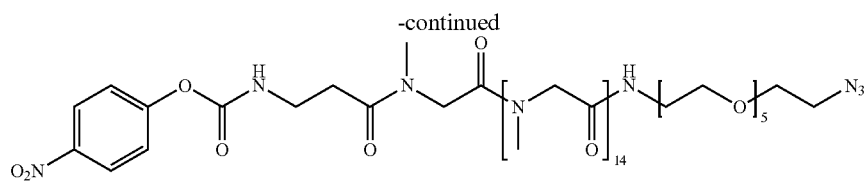

2

To a solution of compound 1 (30 mg, 20.78 μmol), COM130 (6.28 mg, 31.17 μmol) in DCM (3 mL) was added TEA (3.15 mg, 31.17 μmol, 4.34 μL, 1.5 eq). The mixture was stirred at 25-30° C. for 1 hr. LC-MS showed compound 1 was consumed completely and one main peak with desired m/z (MW: 1608.70 observed m/z: 804.8 ([M/2+H]$^+$) was detected. The reaction mixture was concentrated under reduced pressure and then lyophilized to give Compound 2 (10.2 mg, crude) as a white solid.

Procedure for Preparation of Compound 3

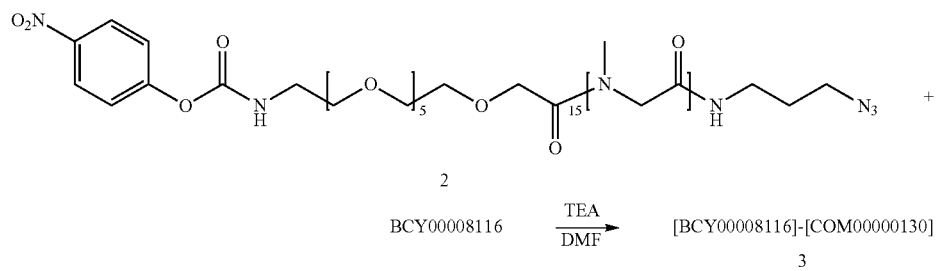

To a solution of compound 2 (10.2 mg, 6.34 μmol) and BCY8116 (13.50 mg, 6.22 μmol) in DMF (2 mL) was added DIEA (0.8 mg, 6.22 μmol, 1.1 μL, 1.0 eq). The mixture was stirred at 30° C. for 2 hr. LC-MS detected desired m/z (MW: 3642.08, observed m/z: 1214.4 ([M/3+H]$^+$). The reaction mixture was filtered and concentrated under reduced pressure to give a residue. The crude product was purified by reversed-phase HPLC (TFA condition). Compound 3 (15.0 mg, 4.12 μmol, 62.94% yield, 95% purity) was obtained as a white solid.

Procedure for Preparation of BCY9409

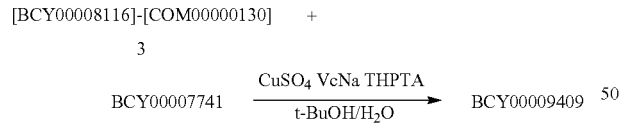

A mixture of Compound 3 (15 mg, 4.12 μmol, 1.0 eq), BCY7741 (10 mg, 4.38 μmol, 1.03 eq), and THPTA (0.4 M, 10.3 μL, 1.0 eq) was dissolved in t-BuOH/H$_2$O (1:1, 2 mL, pre-degassed and purged with N$_2$ for 3 times), and then CuSO$_4$ (0.4 M, 10.3 μL, 1.0 eq) and VcNa (0.4 M, 20.6 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 5923.61, observed m/z: 988.2 ([M/6+H]$^+$)] was detected. The reaction mixture was directly purified by prep-HPLC (TFA condition). BCY9409 (3.1 mg, 0.52 μmol, 12.62% yield, 90.89% purity) was obtained as a white solid.

BCY9410
Procedure for Preparation of Compound 2

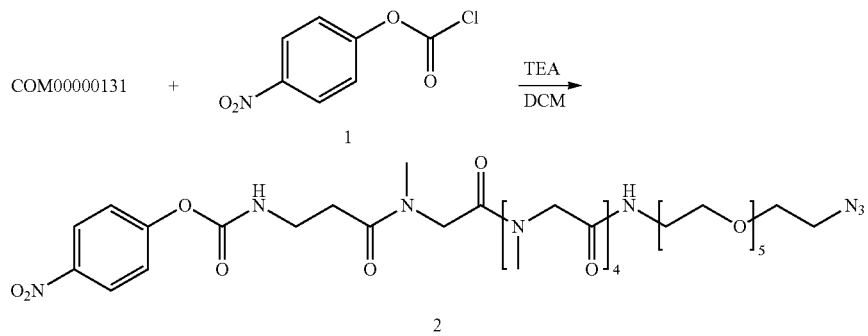

To a solution of COM131 (167.0 mg, 227.89 μmol, 1.0 eq), compound 1 (55.0 mg, 272.87 μmol, 1.2 eq) in DCM (5 mL) was added TEA (36.4 mg, 359.23 μmol, 50.0 μL, 1.6 eq). The mixture was stirred at 25-30° C. for 1 hr. LC-MS showed one main peak with desired m/z (MW: 897.93 observed 920.3 ([M+Na$^+$]) was detected. The reaction mixture was concentrated under reduced pressure to remove solvent to give a residue. The residue was purified by prep-HPLC (TFA condition). Compound 2 (35 mg, 33.74 μmol, 14.81% yield, 86.56% purity) was obtained as colorless oil.

Procedure for Preparation of Compound 3

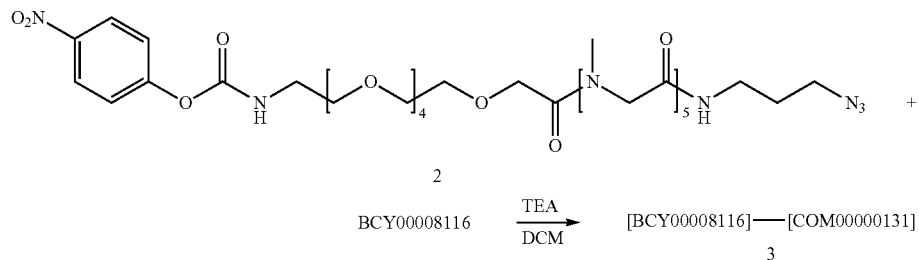

To a solution of compound 2 (20 mg, 22.27 μmol, 1.0 eq) and BCY8116 (48 mg, 22.09 μmol, 1.0 eq) in DMF (2 mL) was added DIEA (8.64 mg, 66.82 μmol, 11.64 μL, 3.0 eq). The mixture was stirred at 30° C. for 2 hr. LC-MS showed compound 3 was consumed completely and one main peak with desired m/z (MW: 2931.32, observed m/z: 977.7 ([M+H]$^+$)) was detected. The residue was purified by prep-HPLC (TFA condition). Compound 3 (40 mg, 13.08 μmol, 58.7% yield, 95.82% purity) was obtained as a white solid.

Procedure for Preparation of BCY9410

[BCY00008116]―[COM00000131] + BCY00007741 →(CuSO$_4$ VcNa THPTA / t-BuOH/H$_2$O)→ BCY00009410
3

A mixture of Compound 3 (40 mg, 13.08 μmol, 1.0 eq), BCY7741 (35 mg, 15.34 μmol, 1.17 eq), and THPTA (0.4 M, 34 μL, 1.0 eq) was dissolved in t-BuOH/H$_2$O (1:1, 2 mL, pre-degassed and purged with N$_2$ for 3 times), and then CuSO$_4$ (0.4 M, 34 μL, 1.0 eq) and VcNa (0.4 M, 68 μL, 2.0 eq) were added under N$_2$. The pH of this solution was adjusted to 8 by dropwise addition of 0.2 M NH$_4$HCO$_3$ (in 1:1 t-BuOH/H$_2$O) and the solution turned to light yellow. The reaction mixture was stirred at 25-30° C. for 12 hr under N$_2$ atmosphere. LC-MS showed Compound 3 was consumed completely and one main peak with desired m/z [MW: 5212.85, observed m/z: 1043.2 ([M/5+H]$^+$)] was detected. The reaction mixture was directly purified by prep-HPLC (TFA condition). BCY9410 (38.6 mg, 6.78 μmol, 49.71% yield, 91.6% purity) was obtained as a white solid.

BCY9411
Procedure for Preparation of Compound 2

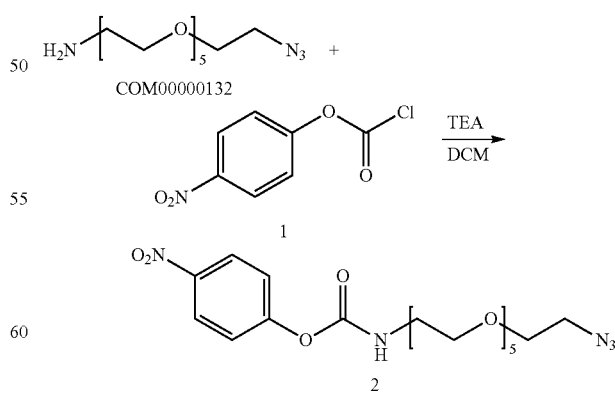

To a solution of COM132 (5 mg, 16.32 μmol, 1 eq), Compound 1 (4 mg, 19.85 μmol, 1.22 eq) in DCM (5 mL) was added TEA (2.8 mg, 24.48 μmol, 3.4 μL, 1.5 eq). The mixture was stirred at 25° C. for 1 hr. LC-MS showed one peak with desired m/z (calculated MW: 471.46, observed m/z: 489.2 ([M+NH4]$^+$)) was detected. The reaction mixture was concentrated under reduced pressure to remove solvent, and then lyophilized to give compound 2 (8 mg, crude) as a white solid.

Procedure for Preparation of Compound 3

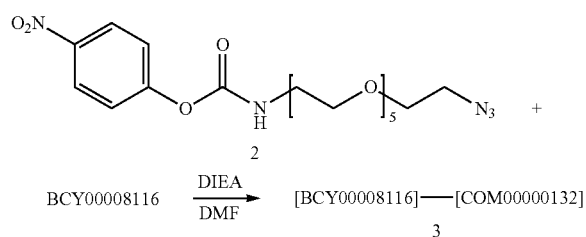

To a solution of Compound 2 (3.3 mg, 6.9 μmol, 1.5 eq) and BCY8116 (10.0 mg, 4.6 μmol, 1.0 eq) in DMF (5 mL) was added DIEA (0.7 mg, 6.90 μmol, 1 μL, 1.5 eq). The mixture was stirred at 30° C. for 2 hrs. LC-MS showed Compound 2 was consumed completely and one main peak with desired m/z (calculated MW: 2504.83, observed m/z: 1252.3 ([M/2+H]$^+$)) was detected. The reaction mixture was filtered and concentrated under reduced pressure to give a residue. The crude product was purified by reversed-phase HPLC (TFA condition). Compound 3 (4.2 mg, 1.51 μmol, 32.78% yield, 90% purity) was obtained as a white solid.

Procedure for Preparation of BCY9411

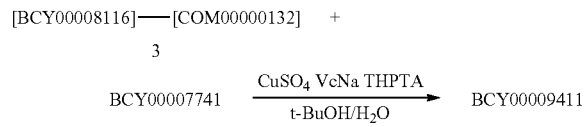

A mixture of Compound 3 (4.2 mg, 1.68 μmol, 1.0 eq), BCY7741 (4.0 mg, 1.75 μmol, 1.05 eq), and THPTA (0.04 M, 84 μL, 2.0 eq) was dissolved in t-BuOH/H$_2$O (1:1, 2 mL, pre-degassed and purged with N$_2$ for 3 times), and then CuSO$_4$ (0.04 M, 84 μL, 2.0 eq) and VcNa (0.04 M, 168 μL, 4.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 3 was consumed completely and one main peak with desired m/z [MW: 4786.37 observed m/z: 1596.2 ([M/3+H]$^+$), 1196.9 ([M/4+H]$^+$)] was detected. The reaction mixture was directly purified by prep-HPLC (TFA condition). BCY9411 (4.1 mg, 0.86 μmol, 50.20% yield, 98.26% purity) was obtained as a white solid.

BCY9759

Procedure for Preparation of Compound 2

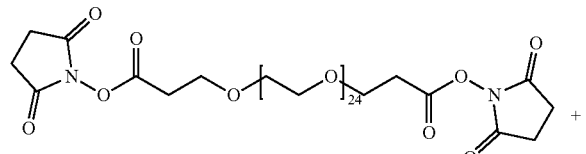

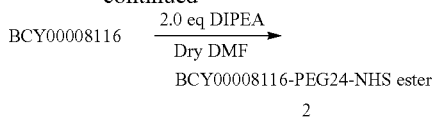

To a solution of compound 1 (5.0 mg, 3.54 μmol, 1.0 eq), BCY8116 (7.7 mg, 3.54 μmol, 1.0 eq) in DMF (3 mL) was added DIEA (0.9 mg, 7.07 μmol, 1.2 μL, 2.0 eq). The mixture was stirred at 0° C. for 20 min. LC-MS detected mass corresponding to compound 2 with NHS group falling off (calculated MW: 3470.95, hydrolyzed MW: 3373.81, observed m/z: 1125.0 ([M/3+H]$^+$)). The reaction mixture was filtered and concentrated under reduced pressure and lyophilized to give compound 2 (15 mg, crude) was obtained as a white solid.

Procedure for Preparation of BCY9759

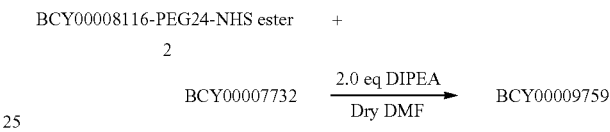

To a solution of compound 2 (20 mg, 5.76 μmol, 1.0 eq) and BCY7732 (12.7 mg, 5.76 μmol, 1.0 eq) in DMF (3 mL) was added DIEA (1.5 mg, 11.52 μmol, 2.0 μL, 2.0 eq). The mixture was stirred at 25~30° C. for 2 hrs. LC-MS showed compound 2 was consumed completely and one main peak with desired m/z (MW: 5557.3, observed m/z: 927.0 ([M/6+H]$^+$) and 1112.2 ([M/5+H]$^+$)) was detected. The reaction mixture was filtered and concentrated under reduced pressure to give a residue. The crude product was purified by reversed-phase HPLC (TFA condition). BCY9759 (2.3 mg, 6.92% yield, 96.29% purity) was obtained as a white solid.

BCY10000

Procedure for Preparation of BCY9172-PEG12-N$_3$

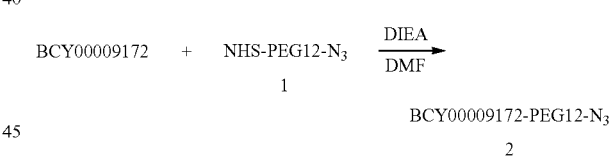

BCY9172 (520 mg, 248.16 μmol, 1.0 eq) and compound 1 (370 mg, 499.47 μmol, 2.01 eq) were dissolved in DMF (5 mL), then the mixture was added with DIEA (48.11 mg, 372.24 μmol, 64.84 μL, 1.5 eq) and stirred at 30° C. for 12 hr. LC-MS showed BCY9172 was consumed completely and one main peak with desired m/z (calculated MW: 2721.12, observed m/z: 1360.9 ([M/2+H]$^+$)) was detected. The reaction mixture was purified by prep-HPLC (TFA condition) and compound 2 (284 mg, 101.10 μmol, 40.74% yield, 96.87% purity) was obtained as a white solid.

Procedure for Preparation of BCY10000

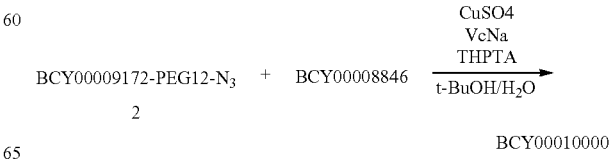

This reaction was performed in two independent containers in parallel. For one container, Compound 2 (142 mg, 52.18 μmol, 1.0 eq) and BCY8846 (157 mg, 51.74 μmol, 1.0 eq) were first dissolved in 10 mL of t-BuOH/H$_2$O (1:1), and then CuSO$_4$ (0.4 M, 130.5 μL, 1.0 eq), VcNa (0.4 M, 261.0 μL, 2.0 eq) and THPTA (0.4 M, 130.5 μL, 1.0 eq) were added. Finally 1 M NH$_4$HCO$_3$ was added to adjust pH to 8. All solvents here were degassed and purged with N$_2$ for 3 times. The reaction mixture was stirred at 30° C. for 12 hr under N$_2$ atmosphere. LC-MS showed compound 2 was consumed completely and one main peak with desired m/z (calculated MW: 5755.54, observed m/z: 959.60 ([M/6+H]$^+$) and 1151.55 ([M/5+H]$^+$)) was detected. The reaction mixture was purified by prep-HPLC (TFA condition) and BCY10000 (314.9 mg, 51.99 μmol, 49.82% yield, 95.03% purity) was obtained as a white solid.

BCY10567

Procedure for Preparation of BCY8919-PEG12-N$_3$

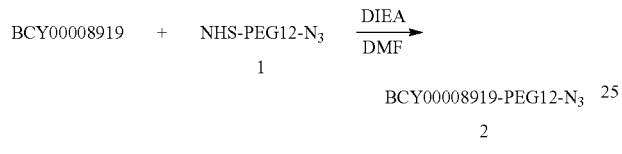

BCY8919 (60.0 mg, 28.85 μmol, 1.0 eq) and compound 1 (22.2 mg, 30.01 μmol, 1.04 eq) were dissolved in DMSO (1 mL). The solution was added with DIPEA (5.6 mg, 43.28 μmol, 7.6 μl, 1.5 eq), and then the mixture was stirred at 25-30° C. for 2 hr. LC-MS showed BCY8919 was consumed completely and one main peak with desired m/z (calculated MW: 2705.16, observed m/z: 1353.15 ([M/2+H]$^+$)) was detected. The reaction mixture was purified by prep-HPLC (TFA condition) and compound 2 (BCY8919-PEG12-N$_3$, 18.5 mg, 6.77 μmol, 23.47% yield, 99.04% purity) was obtained as a white solid.

Procedure for Preparation of BCY10567

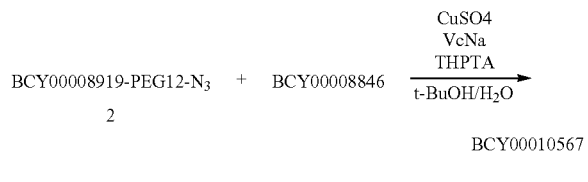

Note: This reaction has been performed twice, and the first one is described below.

Compound 2 (9.0 mg, 3.33 μmol, 1.0 eq) and BCY8846 (10.1 mg, 3.33 μmol, 1.0 eq) were first dissolved in 2 mL of t-BuOH/H$_2$O (1:1), and then CuSO$_4$ (0.4 M, 8.3 μL, 1.0 eq), VcN (1.3 mg, 6.56 μmol, 2.0 eq) and THPTA (1.4 mg, 3.22 μmol, 1.0 eq) were added. Finally 0.4 M NH$_4$HCO$_3$ was added to adjust pH to 8. All solvents here were degassed and purged with N2 for 3 times. The reaction mixture was stirred at 30° C. for 16 hr under N$_2$ atmosphere. LC-MS showed compound 2 was consumed completely and one main peak with desired m/z (calculated MW: 5739.58, observed m/z: 956.75 ([M/6+H]$^+$)). The reaction mixture was purified by prep-HPLC (TFA condition) and BCY10567 (6.85 mg, 1.18 μmol, 35.48% yield, 98.91% purity) was obtained as a white solid.

BCY10569

Procedure for Preparation of Compound 3

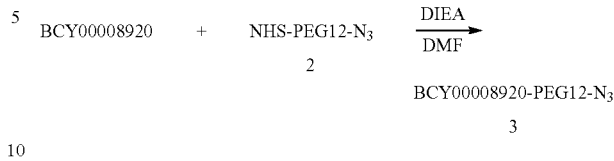

A mixture of compound BCY8920 (40.0 mg, 18.71 μmol, 1.0 eq.), compound 2 (16.0 mg, 21.6 μmol, 1.15 eq.) and DIEA (5.0 μL, 28.0 μmol, 1.5 eq.) was dissolved in DMF. The reaction mixture was stirred at 40° C. for 1 hr, till LC-MS showed one main peak with desired m/z (calculated MW: 2763.2, observed m/z: 912.17 ([(M−28)/2+H]$^+$) was detected. The reaction mixture was then concentrated under reduced pressure to remove solvent and produced a residue, following by purification by prep-HPLC (TFA condition). Compound 3 (23.4 mg, 8.47 μmol, 45.25% yield, 99.0% purity) was obtained as a white solid.

Procedure for Preparation of BCY10569

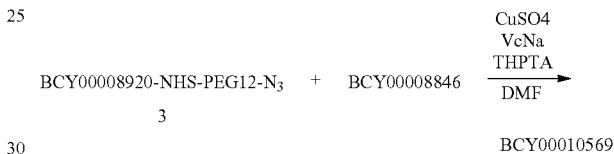

A mixture of compound 3 (5.0 mg, 1.81 μmol, 1.0 eq.), BCY8846 (5.8 mg, 1.9 μmol, 1.05 eq.), and THPTA (1.0 mg, 2.3 μmol, 1.3 eq.) was dissolved in t-BuOH/H$_2$O (1:1, 1 mL, pre-degassed and purged with N$_2$ for 3 times), and then CuSO$_4$ (0.4 M, 5.0 μL, 1.0 eq.) and VcNa (0.4 M, 5.0 μL, 1.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 2 hr under N$_2$ atmosphere. LC-MS showed compound 3 was consumed completely and one main peak with desired m/z (calculated MW: 5797.62, observed m/z: 1160.7 ([M/5+H]$^+$) was detected. The reaction mixture was filtered and concentrated under reduced pressure to give a residue. The crude product was purified by prep-HPLC (TFA condition), and BCY10569 (5.7 mg, 1.18 μmol, 52.25% yield, 96.16% purity) was obtained as a white solid.

BCY10571

Procedure for Preparation of BCY8116-PEG5-N$_3$

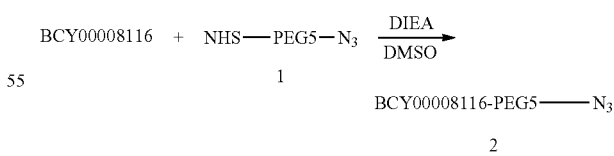

BCY8116 (60 mg, 27.62 μmol, 1.0 eq) and compound 1 (12.0 mg, 27.75 μmol, 1.0 eq) were first dissolved in DMSO (1 mL), then the mixture was added with DIEA (5.4 mg, 41.43 μmol, 7.22 μL, 1.5 eq). The mixture was stirred at 30° C. for 12 hr. LC-MS showed one main peak with desired m/z (MW: 2489.82. observed m/z: 1245.1700 ([M/2+H]$^+$)) was detected. The reaction mixture was concentrated under reduced pressure to remove solvent to give a residue. The residue was purified by prep-HPLC (TFA condition). Compound 2 (48 mg, 19.28 μmol, 69.80% yield, 100% purity) was obtained as a white solid.

Procedure for Preparation of BCY10571

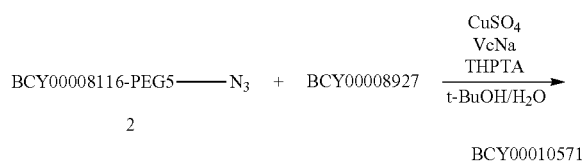

This reaction was performed in two independent containers in parallel. For one container, Compound 2 (10 mg, 4.02 μmol, 1.0 eq) and BCY8927 (9 mg, 4.17 μmol, 1.04 eq) were first dissolved in 2 mL of t-BuOH/H$_2$O (1:1), and then CuSO$_4$ (0.4 M, 10.0 μL, 1.0 eq), VcNa (0.4 M, 20.1 μL, 2.0 eq) and THPTA (0.4 M, 10.0 μL, 1 eq) were added. Finally 0.4 M NH$_4$HCO$_3$ was added to adjust pH to 8. All solvents here were degassed and purged with N$_2$ for 3 times. The reaction mixture was stirred at 30° C. for 4 hr under N$_2$ atmosphere. LC-MS showed compound 3 was consumed completely and one main peak with desired m/z (MW: 4649.36, observed m/z: 1162.57 ([M/4+H]$^+$), 1549.69 ([M/3+H]$^+$)) was detected. The residue was purified by prep-HPLC (TFA condition). BCY10571 (13 mg, 2.79 μmol, 34.88% yield, 96.48% purity) was obtained as a white solid.

BCY10572

Procedure for Preparation of BCY8116-PEG5-N$_3$

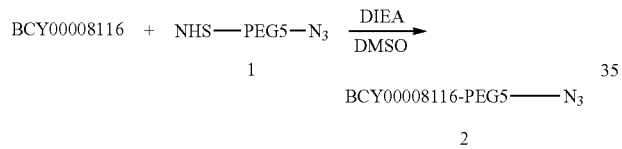

BCY8116 (60 mg, 27.62 μmol, 1.0 eq) and compound 1 (12.0 mg, 27.75 μmol, 1.0 eq) were first dissolved in DMSO (1 mL), then the mixture was added with DIEA (5.4 mg, 41.43 μmol, 7.22 μL, 1.5 eq). The mixture was stirred at 30° C. for 12 hr. LC-MS showed one main peak with desired m/z (MW: 2489.82. observed m/z: 1245.1700 ([M/2+H]$^+$)) was detected. The reaction mixture was concentrated under reduced pressure to remove solvent to give a residue. The residue was purified by prep-HPLC (TFA condition). Compound 2 (48 mg, 19.28 μmol, 69.80% yield, 100% purity) was obtained as a white solid.

Procedure for Preparation of BCY10572

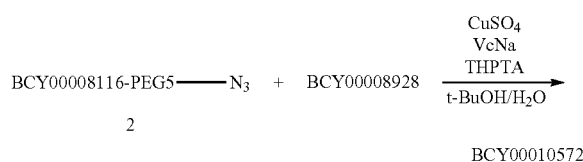

This reaction was performed in two independent containers in parallel. For one container, Compound 2 (10 mg, 4.02 μmol, 1.0 eq) and BCY8928 (9 mg, 4.06 μmol, 1.01 eq) were first dissolved in 2 mL of t-BuOH/H$_2$O (1:1), and then CuSO$_4$ (0.4 M, 10.1 μL, 1 eq), VcNa (0.4 M, 20.2 μL, 2.0 eq) and THPTA (0.4 M, 10.1 μL, 1.0 eq) was added. Finally 0.4 M NH$_4$HCO$_3$ was added to adjust pH to 8. All solvents here were degassed and purged with N$_2$ for 3 times. The reaction mixture was stirred at 30° C. for 4 hr under N$_2$ atmosphere. LC-MS showed compound 1 was consumed completely and one main peak with desired m/z (MW: 4707.40. observed m/z: 1568.29 ([M/3+H]$^+$) and 1176.83 ([M/4+H]$^+$)) was detected. The reaction mixture was concentrated under reduced pressure to remove solvent to give a residue. The residue was purified by prep-HPLC (TFA condition). BCY10572 (21 mg, 4.46 μmol, 55.7% yield, 97.51% purity) was obtained as a white solid.

BCY10573

Procedure for Preparation of Compound 2

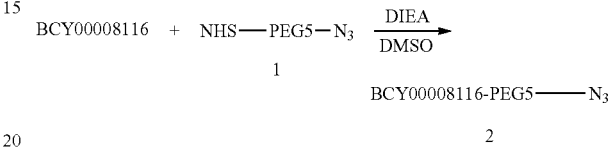

Toa solution of BCY8116 (35 mg, 16.11 μmol, 1 eq), Compound 1 (7.00 mg, 16.19 μmol, 1 eq) in DMSO (1 mL) was added DIEA (3.12 mg, 24.17 μmol, 4.21 μL, 1.5 eq). The mixture was stirred at 25-30° C. for 2 hr. LC-MS showed majority of BCY8116 was consumed and one main peak with desired m/z (calculated MW: 2489.82, observed m/z: 1245.37 ([M/2+H]$^+$) and 830.25 ([M/3+H]$^+$)) was detected. The reaction mixture was concentrated under reduced pressure to remove solvent to give a residue. The residue was purified by prep-HPLC (TFA condition). Compound 2 (26.8 mg, 10.76 μmol, 66.81% yield, 100% purity) was obtained as a white solid.

Procedure for Preparation of BCY10573

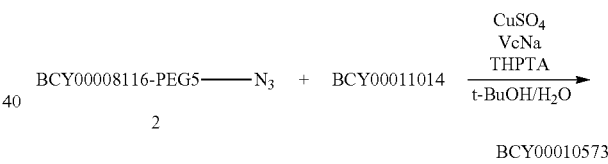

A mixture of Compound 2 (15 mg, 6.02 μmol, 1.0 eq), BCY11014 (13.50 mg, 6.21 μmol, 1.03 eq), and THPTA (0.4 M, 15.1 μL, 1.0 eq) was dissolved in t-BuOH/H$_2$O (1:1, 2 mL, pre-degassed and purged with N$_2$ for 3 times), and then CuSO$_4$ (0.4 M, 15.1 μL, 1.0 eq) and VcNa (0.4 M, 30.2 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 2 was consumed completely and one main peak with desired m/z [MW: 4665.32, observed m/z: 1167.50 ([M/4+H$^+$])] was detected. The reaction mixture was directly purified by prep-HPLC (TFA condition). BCY10573 (11.5 mg, 2.42 μmol, 40.14% yield, 98.11% purity) was obtained as a white solid.

BCY10578

Procedure for Preparation of Compound 2

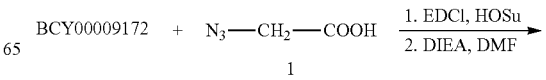

-continued

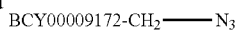

Compound 1 (5.0 mg, 49.5 μmol, 1.0 eq) was first activated by mixing with EDCI (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then compound BCY9172 (80.0 mg, 38.18 μmol, 0.8 eq.) and DIEA (6.3 mg, 8.5 μL, 49.5 μmol, 1.0 eq.) were added to this mixture, and stirred at 40° C. for 1 hr, till LC-MS showed one main peak with desired m/z (calculated MW: 2178.46, observed m/z: 1089.44 ([M/2+H]$^+$) was detected. The reaction mixture was then concentrated under reduced pressure to remove solvent and produced a residue, following by purification by prep-HPLC (TFA condition). Compound 2 (15 mg, 6.88 μmol, 18.66% yield, 73.3% purity) was obtained as a white solid.

Procedure for Preparation of BCY10578

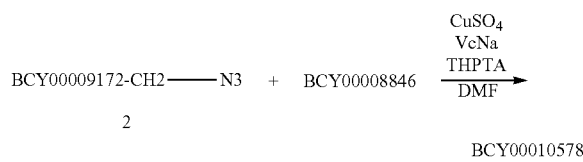

A mixture of compound 2 (9.8 mg, 4.5 μmol, 1.0 eq.), BCY8846 (14.0 mg, 4.6 μmol, 1.0 eq.), and THPTA (2.0 mg, 4.6 μmol 1.0 eq.) was dissolved in t-BuOH/H$_2$O (1:1, 1 mL, pre-degassed and purged with N$_2$ for 3 times), and then CuSO$_4$ (0.4 M, 12 μL, 1.0 eq.) and VcNa (0.4 M, 24 μL, 2.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 2 hr under N$_2$ atmosphere. LC-MS showed compound 2 was consumed completely and one main peak with desired m/z (calculated MW: 5212.88, observed m/z: 1304.2 ([M/4+H]$^+$)) was detected. The reaction mixture was filtered and concentrated under reduced pressure to give a residue. The crude product was purified by prep-HPLC (TFA condition), and BCY10578 (13.78 mg, 2.64 μmol, 58.66% yield, 96.23% purity) was obtained as a white solid.

BCY10917
Procedure for Preparation of BCY8831-PEG12-N$_3$

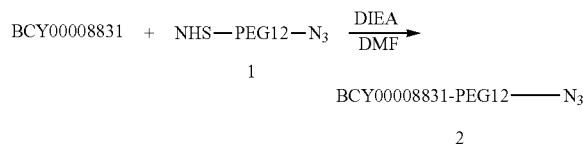

BCY8831 (40.0 mg, 13.29 μmol, 1.0 eq) and compound 1 (10.5 mg, 14.17 μmol, 1.07 eq) were dissolved in DMF (1 mL). The solution was added with DIPEA (2.6 mg, 20.09 μmol, 3.5 μL, 1.5 eq), and then the mixture was stirred at 30° C. for 16 hr. LC-MS showed BCY8831 was consumed completely and one main peak with desired m/z (calculated MW: 3635.16 observed m/z: 1212.0 ([M/3+H]$^+$)) was detected. The reaction mixture was purified by prep-HPLC (TFA condition) and compound 2 (22.0 mg, 5.83 μmol, 43.85% yield, 96.39% purity) was obtained as a white solid.

Procedure for Preparation of BCY10917

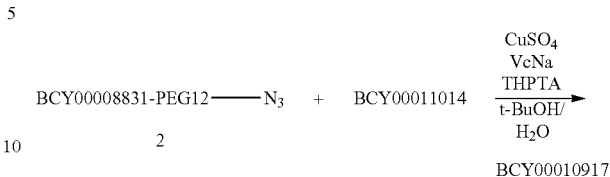

Note: Two batches were made, and the first one was written for final report.

Compound 2 (10.0 mg, 2.75 μmol, 1.0 eq) and BCY11014 (5.98 mg, 2.75 μmol, 1.0 eq), were first dissolved in 2 mL of t-BuOH/H$_2$O (1:1), and then CuSO$_4$ (0.4 M, 13.7 μL, 2.0 eq), VcNa (1.1 mg, 5.55 μmol, 2.0 eq) and THPTA (1.2 mg, 2.76 μmol, 1.0 eq) was added. Finally 1 M NH$_4$HCO$_3$ was added to adjust pH to 8. All solvents here were degassed and purged with N$_2$ for 3 times. The reaction mixture was stirred at 30° C. for 16 hr under N$_2$ atmosphere. LC-MS showed compound 2 was consumed completely and one main peak with desired m/z (calculated MW: 5810.66 observed m/z: 1163.0 ([M/5+H]$^+$)). The reaction mixture was purified by prep-HPLC (TFA condition) and BCY10917 (6.4 mg, 1.07 μmol, 39.03% yield, 97.49% purity) was obtained as a white solid.

BCY11020
Procedure for Preparation of BCY8831-PEG5-N$_3$

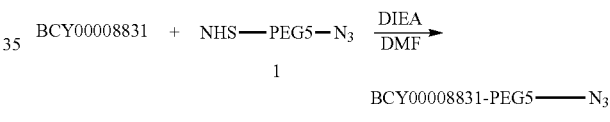

BCY8831 (25.0 mg, 8.31 μmol, 1.0 eq) and compound 1 (3.9 mg, 9.02 μmol, 1.09 eq), were dissolved in DMF (1 mL). The solution was added with DIPEA (1.6 mg, 12.46 μmol, 2.2 μl, 1.5 eq), and then the mixture was stirred at 35° C. for 2 hr. LC-MS showed BCY8831 was consumed completely and one main peak with desired m/z (calculated MW: 3326.79 observed m/z: 1109.66 ([M/3+H]$^+$)) was detected. The reaction mixture was purified by prep-HPLC (TFA condition) and compound 2 (7.3 mg, 2.09 μmol, 25.20% yield, 95.41% purity) was obtained as a white solid.

Procedure for Preparation of BCY11020

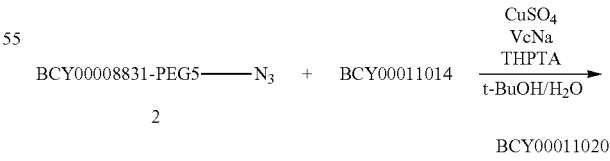

Compound 2 (7.3 mg, 2.19 μmol, 1.0 eq) and BCY11014 (4.8 mg, 2.19 μmol, 1.0 eq), were first dissolved in 2 mL of t-BuOH/H$_2$O (1:1), and then CuSO$_4$ (0.4 M, 5.5 μL, 1.0 eq), VcNa (1.0 mg, 5.05 μmol, 2.3 eq) and THPTA (1.0 mg, 2.30 μmol, 1.0 eq) was added. Finally 1 M NH$_4$HCO$_3$ was added to adjust pH to 8. All solvents here were degassed and purged with $N_2$ for 3 times. The reaction mixture was stirred at 30° C. for 12 hr under $N_2$ atmosphere. LC-MS showed compound 2 was consumed completely and one main peak with desired m/z (calculated MW: 5502.29, observed m/z: 1101.74 ($[M/5+H]^+$)) was detected. The reaction mixture was purified by prep-HPLC (TFA condition) and BCY11020 (3.3 mg, 0.577 µmol, 26.30% yield, 96.24% purity) was obtained as a white solid.

BCY11373

Procedure for Preparation of Compound 2

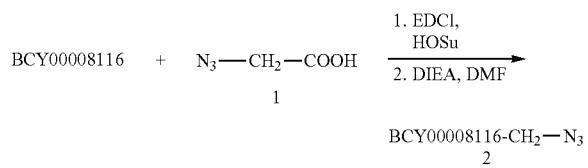

To a solution of compound 1 (5.0 mg, 49.5 µmol, 1.0 eq) in DMF (1 mL) was added EDCI (8.5 mg, 54.8 µmol, 1.1 eq) and HOSu (5.7 mg, 49.5 µmol, 1.0 eq). The mixture was stirred at 25-30° C. for 30 min. TLC indicated compound 1 was consumed completely and one new spot formed. Then 0.3 mL of this mixture was added with BCY8116 (30.0 mg, 13.81 µmol, 0.28 eq.) and DIEA (2.4 µL, 13.81 µmol, 0.28 eq.), and stirred at 25-30° C. for 2 hr. LC-MS showed BCY8116 was consumed completely and one main peak with desired m/z (calculated MW: 2255.53, observed m/z: 1128.34 ($[M/2+H]^+$) was detected. The reaction mixture was then concentrated under reduced pressure to remove solvent and produced a residue, following by purification by prep-HPLC (TFA condition). Compound 2 (21 mg, 8.9 µmol, 64.43% yield, 95.56% purity) was obtained as a white solid.

Procedure for Preparation of BCY11373

A mixture of compound 2 (5 mg, 2.22 µmol, 1.0 eq.), BCY8928 (4.79 mg, 2.22 µmol, 1.0 eq.), and THPTA (1.0 mg, 2.30 µmol, 1.0 eq.) was dissolved in t-BuOH/$H_2O$ (1:1, 1 mL, pre-degassed and purged with $N_2$ for 3 times), and then $CuSO_4$ (0.4 M, 5.6 µL, 1.0 eq.) and VcNa (0.4 M, 5.6 µL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 2 was consumed completely and one main peak with desired m/z (calculated MW: 4415.07, observed m/z: 1471.5 ($[M/3+H]^+$ and 1103.8 ($[M/4+H]^+$) was detected. The reaction mixture was filtered and concentrated under reduced pressure to give a residue. The crude product was purified by prep-HPLC (TFA condition), and BCY11373 (4.9 mg, 1.03 µmol, 46.26% yield, 92.4% purity) was obtained as a white solid.

BCY11374

Procedure for Preparation of BCY11374

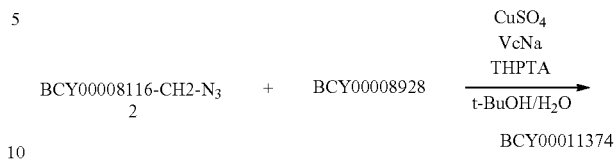

A mixture of compound 2 (which may be prepared as described in the procedure for preparing BCY11373; 5 mg, 2.22 µmol, 1.0 eq.), BCY8928 (4.9 mg, 2.22 µmol, 1.0 eq.), and THPTA (1.0 mg, 2.30 µmol, 1.0 eq.) was dissolved in t-BuOH/$H_2O$ (1:1, 1 mL, pre-degassed and purged with $N_2$ for 3 times), and then $CuSO_4$ (0.4 M, 5.6 µL, 1.0 eq.) and VcNa (0.4 M, 5.6 µL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 2 was consumed completely and one main peak with desired m/z (calculated MW: 4473.11, observed m/z: 1491.5 ($[M/3+H]^+$ and 1118.5 ($[M/4+H]^+$) was detected. The reaction mixture was filtered and concentrated under reduced pressure to give a residue. The crude product was purified by prep-HPLC (TFA condition), and BCY11374 (4.1 mg, 1.27 µmol, 38.04% yield, 92.0% purity) was obtained as a white solid.

BCY11375

Procedure for Preparation of BCY11375

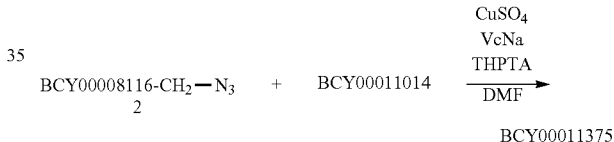

A mixture of compound 2 (which may be prepared as described in BCY11373; 5 mg, 2.22 µmol, 1.0 eq.), BCY11014 (4.8 mg, 2.22 µmol, 1.0 eq.), and THPTA (0.5 mg, 2.30 µmol, 1.0 eq.) was dissolved in t-BuOH/$H_2O$ (1:1, 1 mL, pre-degassed and purged with $N_2$ for 3 times), and then $CuSO_4$ (0.4 M, 5.6 µL, 1.0 eq.) and VcNa (0.4 M, 5.6 µL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS detected some desired m/z (calculated MW: 4431.03, observed m/z: 1107.59 ($[M/4+H]^+$ and 1477.90 ($[M/3+H]^+$). The reaction mixture was filtered and concentrated under reduced pressure to give a residue. The crude product was purified by prep-HPLC (TFA condition), and BCY11375 (6 mg, 1.31 µmol, 59.13% yield, 96.8% purity) was obtained as a white solid.

BCY11616

Procedure for Preparation of Compound 3

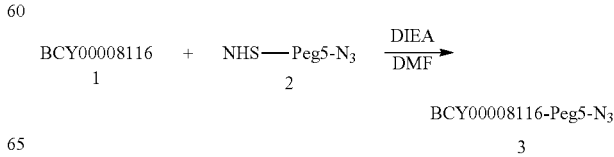

A mixture of compound BCY8116 (30.0 mg, 13.81 μmol, 1.0 eq.), compound 2 (6.0 mg, 13.88 μmol, 1.0 eq.) and DIEA (2.4 μL, 13.82 μmol, 1.0 eq.) was dissolved in DMF. The reaction mixture was stirred at 40° C. for 1 hr, till LC-MS showed compound 1 was consumed completely and one main peak with desired m/z (calculated MW: 2489.82, observed m/z: 1245.4 ([M/2+H]$^+$) was detected. The reaction mixture was then concentrated under reduced pressure to remove solvent and produced a residue, following by purification by prep-HPLC (TFA condition). Compound 3 (27 mg, 10.29 μmol, 74.52% yield, 94.9% purity) was obtained as a white solid.

Procedure for Preparation of BCY11616

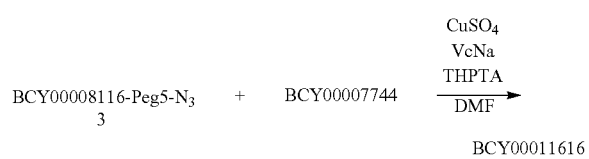

BCY00011616

A mixture of compound 3 (5 mg, 2.01 μmol, 1.0 eq.), BCY7744 (5.2 mg, 2.21 μmol, 1.1 eq.), and THPTA (1.0 mg, 2.30 μmol, 1.0 eq.) was dissolved in t-BuOH/H$_2$O (1:1, 1 mL, pre-degassed and purged with N$_2$ for 3 times), and then CuSO$_4$ (0.4 M, 5.0 μL, 1.0 eq.) and VcNa (0.4 M, 5.0 μL, 1.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 2 hr under N$_2$ atmosphere. LC-MS showed compound 3 was consumed completely and one main peak with desired m/z (calculated MW: 4827.46, observed m/z: 1207.12 ([M/4+H]$^+$) was detected. The reaction mixture was filtered and concentrated under reduced pressure to give a residue. The crude product was purified by prep-HPLC (TFA condition), and BCY11616 (4.7 mg, 1.0 μmol, 48.48% yield, 94.7% purity) was obtained as a white solid.

BCY11617
Procedure for Preparation of BCY11617

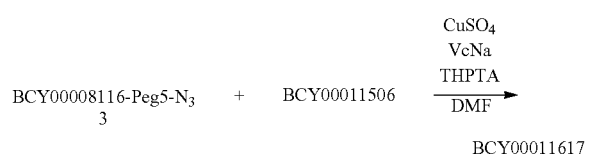

BCY00011617

A mixture of compound 3 (which may be prepared as described in the procedure for preparing BCY11616; 5 mg, 2.01 μmol, 1.0 eq.), BCY11506 (5.2 mg, 2.21 μmol, 1.1 eq.), and THPTA (1.0 mg, 2.30 μmol, 1.1 eq.) was dissolved in t-BuOH/H$_2$O (1:1, 1 mL, pre-degassed and purged with N$_2$ for 3 times), and then CuSO$_4$ (0.4 M, 5.0 μL, 1.0 eq.) and VcNa (0.4 M, 5.0 μL, 1.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 2 hr under N$_2$ atmosphere. LC-MS showed compound 3 was consumed completely and one main peak with desired m/z (calculated MW: 4828.45, observed m/z: 1206.97 ([M/4+H]$^+$) and 965.91 ([M/5+H]$^+$)) was detected. The reaction mixture was filtered and concentrated under reduced pressure to give a residue. The crude product was purified by prep-HPLC (TFA condition), and BCY11617 (3.2 mg, 0.63 μmol, 31.37% yield, 95.05% purity) was obtained as a white solid.

BCY11857
Procedure for Preparation of BCY11414-PEG5-N$_3$

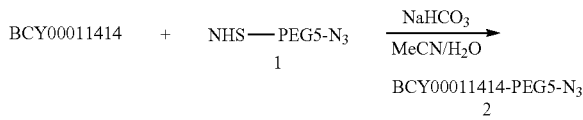

BCY11414 (60.0 mg, 29.06 μmol, 1.0 eq) and compound 1 (13.0 mg, 30.06 μmol, 1.03 eq) were dissolved in 2 mL of MeCN/H$_2$O (1:1). Adjust pH to 8 with NaHCO$_3$ (0.4 M), and then the mixture was stirred at 25-30° C. for 2 hr. LC-MS showed one main peak with desired m/z (calculated MW: 2381.72, observed m/z: 1191.07 ([M/2+H]$^+$)) was detected. The reaction mixture was purified by prep-HPLC (TFA condition) and compound 2 (38.0 mg, 15.9 μmol, 54.71% yield, 97.35% purity) was obtained as a white solid.

Procedure for Preparation of BCY11857

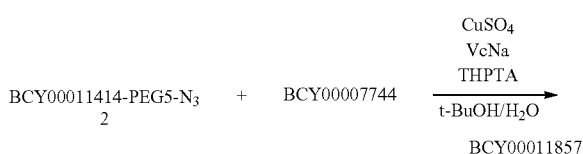

Compound 2 (10.0 mg, 4.20 μmol, 1.0 eq) and BCY7744 (11.5 mg, 4.92 μmol, 1.2 eq) were first dissolved in 2 mL of t-BuOH/H$_2$O (1:1), and then CuSO$_4$ (0.4 M, 11.0 μL, 1.0 eq), VcNa (2.0 mg, 10 μmol, 2.4 eq) and THPTA (2.0 mg, 4.6 μmol, 1.1 eq) were added. Finally 0.2 M NH$_4$HCO$_3$ was added to adjust pH to 8. All solvents here were degassed and purged with N2 for 3 times. The reaction mixture was stirred at 30° C. for 16 hr under N$_2$ atmosphere. LC-MS showed compound 2 was consumed completely and one main peak with desired m/z (calculated MW: 4719.37, observed m/z: 1180.24 ([M/4+H]$^+$)). The reaction mixture was purified by prep-HPLC (TFA condition) and BCY11857 (10.3 mg, 2.18 μmol, 51.90% yield, 96.02% purity) was obtained as a white solid.

BCY11858
Procedure for Preparation of BCY11414-PEG5-N$_3$

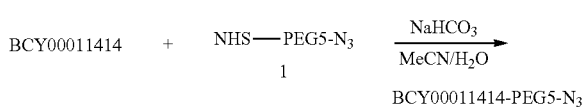

BCY11414 (60.0 mg, 29.06 μmol, 1.0 eq) and compound 1 (13.0 mg, 30.06 μmol, 1.03 eq), were dissolved in 2 mL of MeCN/H$_2$O (1:1). Adjust pH to 8 with NaHCO$_3$ (0.4 M), and then the mixture was stirred at 25-30° C. for 2 hr. LC-MS showed one main peak with desired m/z (calculated MW: 2381.72, observed m/z: 1191.07 ([M/2+H]$^+$)) was detected. The reaction mixture was purified by prep-HPLC (TFA condition) and compound 2 (38.0 mg, 15.9 μmol, 54.71% yield, 97.35% purity) was obtained as a white solid.

Procedure for Preparation of BCY11858

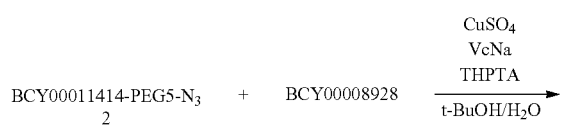

Compound 2 (20.0 mg, 8.40 μmol, 1.0 eq) and BCY8928 (22.0 mg, 9.92 μmol, 1.1 eq) were first dissolved in 2 mL of t-BuOH/H$_2$O (1:1), and then CuSO$_4$ (0.4 M, 21.0 μL, 1.0 eq), VcNa (4.0 mg, 20.19 μmol, 2.4 eq) and THPTA (4.0 mg, 9.20 μmol, 1.1 eq) were added. Finally 0.4 M NH$_4$HCO$_3$ was added to adjust pH to 8. All solvents here were degassed and purged with N$_2$ for 3 times. The reaction mixture was stirred at 30° C. for 16 hr under N$_2$ atmosphere. LC-MS showed compound 2 was consumed completely and one main peak with desired m/z (calculated MW: 4599.30, observed m/z: 920.38 ([M/5+H]$^+$), 1150.79 ([M/4+H]$^+$), 1533.35 ([M/3+H]$^+$)). The reaction mixture was purified by prep-HPLC (TFA condition) and BCY11858 (16.9 mg, 3.67 μmol, 43.43% yield, 99.25% purity) was obtained as a white solid.

BCY11859

Procedure for Preparation of BCY11415-PEG5-N$_3$

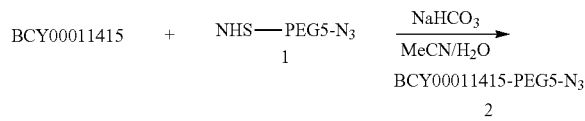

BCY11415 (30.0 mg, 13.81 μmol, 1.0 eq) and compound 1 (6.0 mg, 30.06 μmol, 1.0 eq), were dissolved in 2 mL of MeCN/H$_2$O (1:1). Adjust pH to 8 with NaHCO$_3$ (0.4 M), and then the mixture was stirred at 25-30° C. for 2 hr. LC-MS showed one main peak with desired m/z (calculated MW: 2489.82, observed m/z: 1245.18 ([M/2+H]$^+$)) was detected. The reaction mixture was purified by prep-HPLC (TFA condition) and compound 2 (24.0 mg, 9.63 μmol, 69.7% yield, 99.28% purity) was obtained as a white solid.

Procedure for Preparation of BCY11859

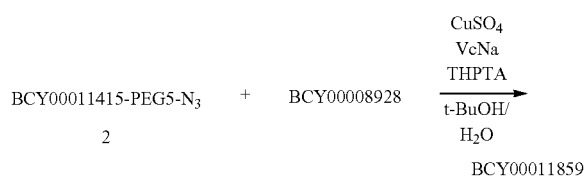

Compound 2 (20.0 mg, 8.03 μmol, 1.0 eq) and BCY8928 (21.0 mg, 9.47 μmol, 1.1 eq) were first dissolved in 2 mL of t-BuOH/H$_2$O (1:1), and then CuSO$_4$ (0.4 M, 21.0 μL, 1.0 eq), VcNa (4.0 mg, 2.5 eq) and THPTA (4.0 mg, 1.1 eq) was added. Finally 1 M NH$_4$HCO$_3$ was added to adjust pH to 8. All solvents here were degassed and purged with N$_2$ for 3 times. The reaction mixture was stirred at 30° C. for 16 hr under N$_2$ atmosphere. LC-MS showed compound 2 was consumed completely and one main peak with desired m/z (calculated MW: 4707.40, observed m/z: 941.7 ([M/5+H]$^+$), 1176.9 ([M/4+H]$^+$), 1569.6 ([M/3+H]$^+$)). The reaction mixture was purified by prep-HPLC (TFA condition) and BCY11859 (19.2 mg, 4.01 μmol, 49.87% yield, 98.22% purity) was obtained as a white solid.

Example 4: Synthesis of PD-L1/CD137 Binding Heterotandem Bicyclic Peptides

BCY8939

General Procedure for Preparation of BCY8939

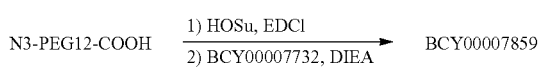

To a solution of N3-PEG12-COOH (250 mg, 388 μmol) and HOSu (67.0 mg, 583 μmol) in DMA (4.5 mL) and DCM (1.5 mL) was added EDCI (89.3 mg, 466 μmol) with stirring at 20° C. for 16 hr. LCMS showed the desired intermediate was formed completely. BCY7732 (854.97 mg, 388.37 μmol, 1 eq) and DIEA (186 mg, 1.44 mmol, 250 μL) were added to the mixture with further stirring at 20° C. for additional 5 hr. LC-MS showed BCY7732 was consumed completely and one main peak with desired mass was detected. The reaction mixture was purified by prep-HPLC (TFA condition) to give compound BCY7859 (621 mg, 200.58 μmol, 51.65% yield, 95% purity, TFA) as a white solid. Calculated MW: 2817.16, observed m/z: 942.7 [M/3+H]$^+$ General Procedure for Preparation of BCY8939

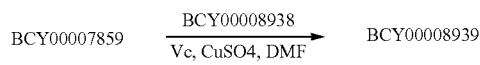

To a solution of BCY7859 (31.1 mg, 11.0 μmol) and BCY8938 (30.0 mg, 10.0 μmol) in DMF (2 mL) was added (2R)-2-[(1S)-1,2-dihydroxyethyl]-3,4-dihydroxyl-2H-furan-5-one (1 M, 100 μL) and CuSO$_4$ (1 M, 30.0 μL) with stirring under nitrogen atmosphere for 2 hr at 20° C. LC-MS showed BCY7859 was consumed completely and one main peak with desired mass was detected. The reaction mixture was purified by prep-HPLC (TFA condition) to give compound BCY8939 (16.1 mg, 2.72 μmol, 27.1% yield, 98.3% purity) as a white solid. Calculated MW: 5823.49, observed m/z: 1165.4 [M/5+H]$^+$, 971.0 [M/6+H]$^+$, 832.9[M/7+H]$^+$

BCY10580

Procedure for Preparation of BCY9172-PEG12-N$_3$

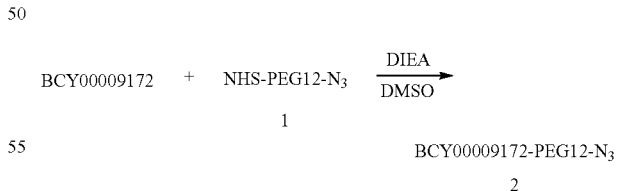

BCY9172 (100.0 mg, 47.72 μmol, 1 eq) and compound 1 (40.0 mg, 54.00 μmol, 1.13 eq) in DMSO (2 mL) was added DIEA (9.25 mg, 71.58 μmol, 12.47 μL, 1.5 eq). The mixture was stirred at 30° C. for 12 hr. LC-MS showed BCY9172 was consumed completely and one main peak with desired m/z (MW: 2721.12, observed m/z: 1361.07 ([(M/2+H$^+$])) was detected. The reaction mixture was concentrated under reduced pressure to remove solvent and produced a residue. The residue was then purified by prep-HPLC (neutral condition). Compound 2 (48 mg, 17.44 μmol, 45.68% yield, 98.87% purity) was obtained as a white solid.

Procedure for Preparation of BCY10580

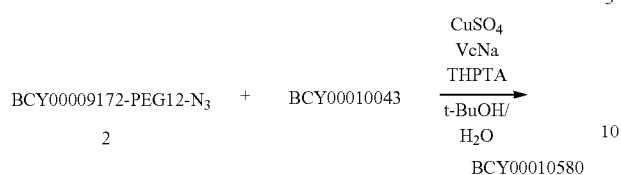

Compound 2 (20 mg, 7.35 μmol, 1.0 eq) and BCY10043 (23.1 mg, 7.35 μmol, 1.0 eq) were first dissolved in 2 mL of t-BuOH/H$_2$O (1:1), and then CuSO$_4$ (0.4 M, 18.4 μL, 1.0 eq), VcNa (0.4 M, 36.8 μL, 2.0 eq) and THPTA (0.4 M, 18.4 μL, 1.0 eq) were added. Finally 1 M NH$_4$HCO$_3$ was added to adjust pH to 8. All solvents here were degassed and purged with N$_2$ for 3 times. The reaction mixture was stirred at 30° C. for 4 hr under N$_2$ atmosphere. LC-MS showed compound 3 was consumed completely and one main peak with desired m/z (MW: 5855.74 observed m/z: 976.40 ([M/6+H]$^+$) and 1171.67 ([M/5+H]$^+$)) was detected. The residue was purified by prep-HPLC (TFA condition). BCY10580 (29 mg, 4.85 μmol, 65.95% yield, 97.879% purity) was obtained as a white solid.

BCY10581
Procedure for Preparation of BCY9172-PEG12-N$_3$

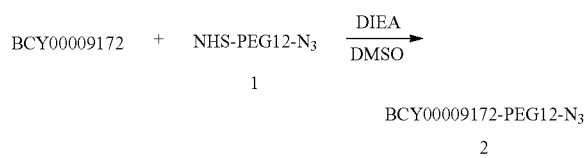

BCY9172 (100 mg, 47.72 μmol, 1 eq) and compound 1 (40.00 mg, 54.00 μmol, 1.13 eq) in DMSO (2 mL) was added DIEA (9.25 mg, 71.58 μmol, 12.47 μL, 1.5 eq). The mixture was stirred at 30° C. for 12 hr. LC-MS showed BCY9172 was consumed completely and one main peak with desired m/z (MW: 2721.12, observed m/z: 1361.07 ([(M/2+H$^+$])) was detected. The reaction mixture was concentrated under reduced pressure to remove solvent and produced a residue. The residue was then purified by prep-HPLC (neutral condition). Compound 2 (48 mg, 17.44 μmol, 45.68% yield, 98.87% purity) was obtained as a white solid.

Procedure for Preparation of BCY10581

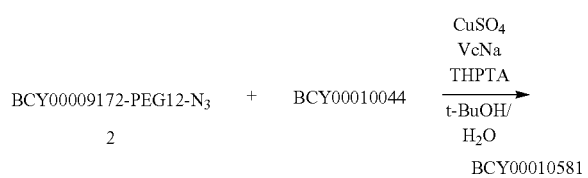

Compound 2 (12 mg, 4.41 μmol, 1 eq) and BCY10044 (14.08 mg, 4.41 μmol, 1 eq) were first dissolved in 2 mL of t-BuOH/H$_2$O (1:1), and then CuSO$_4$ (0.4 M, 11.02 μL, 1 eq), VcNa (0.4 M, 22.05 μL, 2 eq) and THPTA (0.4 M, 10.04 μL, 1 eq) was added. Finally 1 M NH$_4$HCO$_3$ was added to adjust pH to 8. All solvents here were degassed and purged with N$_2$ for 3 times. The reaction mixture was stirred at 30° C. for 4 hr under N$_2$ atmosphere. LC-MS showed compound 3 was consumed completely and one main peak with desired m/z (MW: 5912.84, observed m/z: 985.90 ([M/6+H]$^+$) and 1183.28 ([M/5+H]$^+$)) was detected. The residue was purified by prep-HPLC (TFA condition). BCY10581 (9.3 mg, 1.47 μmol, 33.36% yield, 93.541% purity) was obtained as a white solid.

BCY10582
Procedure for Preparation of Compound 2

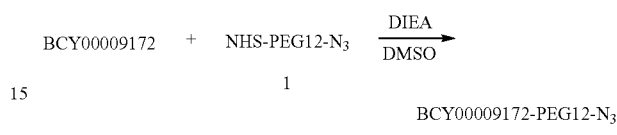

To a solution of BCY9172 (100.0 mg, 47.7 μmol, 1.0 eq), Compound 1 (40.0 mg, 54.0 μmol, 1.13 eq) in DMSO (2 mL) was added DIEA (9.2 mg, 71.6 μmol, 12.5 μL, 1.5 eq). The mixture was stirred at 30° C. for 12 hr. LC-MS showed BCY9172 was consumed completely and one main peak with desired m/z (calculated MW: 2721.12, observed m/z: 1361.07 ([M/2+H]$^+$)) was detected. The reaction mixture was concentrated under reduced pressure to remove solvent to give a residue. The residue was purified by prep-HPLC (TFA condition). Compound 2 (37 mg, 13.60 μmol, 28.49% yield) was obtained as a white solid.

Procedure for Preparation of BCY10582

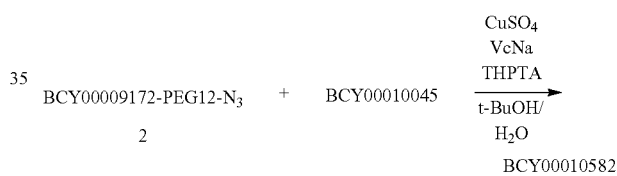

A mixture of Compound 2 (16.0 mg, 5.9 μmol, 1.0 eq), BCY10045 (14.0 mg, 6.0 μmol, 1.01 eq), and THPTA (0.4 M, 14.7 μL, 1.0 eq) was dissolved in t-BuOH/H$_2$O (1:1, 2 mL, pre-degassed and purged with N$_2$ for 3 times), and then CuSO$_4$ (0.4 M, 14.7 μL, 1.0 eq) and VcNa (0.4 M, 29.4 μL, 2.0 eq) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 25-30° C. for 12 hr under N$_2$ atmosphere. LC-MS showed Compound 2 was consumed completely and one main peak with desired m/z [calculated MW: 5073.89, observed m/z: 1015.24 ([M/5+H]$^+$) and 1268.97 ([M/4+H]$^+$) was detected. The reaction mixture was directly purified by prep-HPLC (TFA condition). BCY10582 (10 mg, 1.92 μmol, 32.58% yield, 97.21% purity) was obtained as a white solid.

BCY11017
Procedure for Preparation of BCY11017

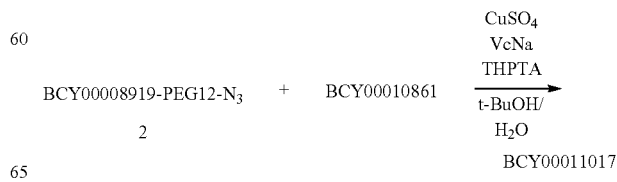

Compound 2 (which may be prepared as described in the procedure for preparing BCY10567; 7.0 mg, 2.59 μmol, 1.0 eq) and BCY10861 (7.03 mg, 2.59 μmol, 1.0 eq), were first dissolved in 2 mL of t-BuOH/H$_2$O (1:1), and then CuSO$_4$ (0.4 M, 13.0 μL, 2.0 eq), VcNa (1.0 mg, 5.03 μmol, 2.0 eq) and THPTA (1.1 mg, 2.53 μmol, 1.0 eq) were added. Finally 1 M NH$_4$HCO$_3$ was added to adjust pH to 8. All solvents here were degassed and purged with N$_2$ for 3 times. The reaction mixture was stirred at 35° C. for 16 hr under N$_2$ atmosphere. LC-MS showed compound 2 was consumed completely and one main peak with desired m/z (calculated MW: 5421.30, observed m/z: 1084.7 ([M/5+H]$^+$)). The reaction mixture was purified by prep-HPLC (TFA condition) and BCY11017 (6.6 mg, 1.17 μmol, 45.24% yield, 96.16% purity) was obtained as a white solid.

BCY11018
Procedure for Preparation of BCY11018

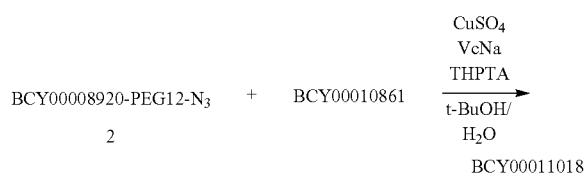

Compound 2 (which may be prepared as described in the procedure for preparing BCY10570; 6.0 mg, 2.17 μmol, 1.0 eq) and BCY10861 (5.9 mg, 2.17 μmol, 1.0 eq), were first dissolved in 2 mL of t-BuOH/H$_2$O (1:1), and then CuSO$_4$ (0.4 M, 11.0 μL, 2.0 eq), VcNa (1.0 mg, 2.3 eq) and THPTA (1.1 mg, 1.0 eq) was added. Finally 1 M NH$_4$HCO$_3$ was added to adjust pH to 8. All solvents here were degassed and purged with N$_2$ for 3 times. The reaction mixture was stirred at 35° C. for 16 hr under N$_2$ atmosphere. LC-MS showed compound 2 was consumed completely and one main peak with desired m/z (calculated MW: 5479.34, observed m/z: 1096.40 ([M/5+H]$^+$)). The reaction mixture was purified by prep-HPLC (TFA condition) and BCY11018 (2.3 mg, 0.40 μmol, 18.31% yield, 94.73% purity) was obtained as a white solid.

BCY11019
Procedure for Preparation of BCY11019

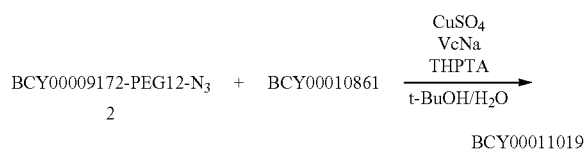

Compound 2 (which may be prepared as described in the procedure for preparing BCY10581; 8.0 mg, 2.94 μmol, 1.0 eq) and BCY10861 (8.0 mg, 2.95 μmol, 1.0 eq), were first dissolved in 2 mL of t-BuOH/H$_2$O (1:1), and then CuSO$_4$ (0.4 M, 14.7 μL, 2.0 eq), VcNa (1.2 mg, 6.05 μmol, 2.0 eq) and THPTA (1.3 mg, 2.99 μmol, 1.0 eq) was added. Finally 1 M NH$_4$HCO$_3$ was added to adjust pH to 8. All solvents here were degassed and purged with N$_2$ for 3 times. The reaction mixture was stirred at 35° C. for 16 hr under N$_2$ atmosphere. LC-MS showed compound 2 was consumed completely and one main peak with desired m/z (calculated MW: 5437.26, observed m/z: 1088.09 ([M/5+H]$^+$) and 1360.19 ([M/4+H]$^+$)). The reaction mixture was purified by prep-HPLC (TFA condition) and BCY11019 (7.6 mg, 1.36 μmol, 46.09% yield, 96.95% purity) was obtained as a white solid.

BCY11376
Procedure for Preparation of Compound 2

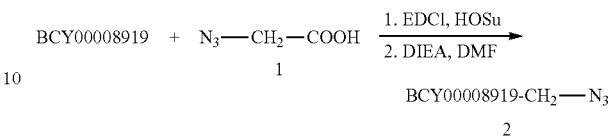

To a solution of compound 1 (5.0 mg, 49.5 μmol, 1.0 eq) in DMF (1 mL) was added EDCI (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then 0.2 mL of this mixture was added with BCY8919 (20.0 mg, 9.62 μmol) and DIEA (1.7 μL, 9.62 μmol). The mixture was stirred at 25-30° C. for 2 hr. LC-MS showed BCY8919 was consumed completely and one main peak with desired m/z (calculated MW: 2162.51, observed m/z: 1081.8 ([M/2+H]$^+$)) was detected. The reaction mixture was then concentrated under reduced pressure to remove solvent and produced a residue, following by purification by prep-HPLC (TFA condition). Compound 2 (12 mg, 5.55 μmol, 56.28% yield, 97.54% purity) was obtained as a white solid.

Procedure for Preparation of BCY11376

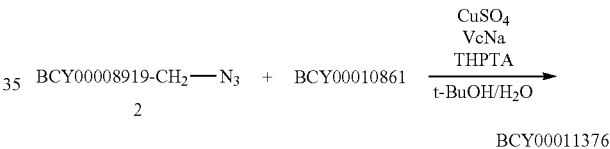

A mixture of compound 2 (3 mg, 1.39 μmol, 1.0 eq.), BCY10861 (3.8 mg, 1.40 μmol, 1.0 eq.), and THPTA (1.2 mg, 2.76 μmol, 2.0 eq.) was dissolved in t-BuOH/H$_2$O (1:1, 1 mL, pre-degassed and purged with N$_2$ for 3 times), and then CuSO$_4$ (0.4 M, 3.5 μL, 1.0 eq.) and VcNa (0.4 M, 3.5 μL, 1.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 2 hr under N$_2$ atmosphere. LC-MS showed BCY10861 was consumed completely and one main peak with desired m/z (calculated MW: 4878.64, observed m/z: 1220.8 ([M/4+H]$^+$) was detected. The reaction mixture was filtered and concentrated under reduced pressure to give a residue. The crude product was purified by prep-HPLC (TFA condition), and BCY11376 (1.9 mg, 1.0 μmol, 27.01% yield, 96.2% purity) was obtained as a white solid.

BCY11377
Procedure for Preparation of Compound 2

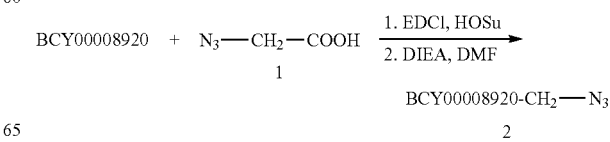

To a solution of compound 1 (5.0 mg, 49.5 μmol, 1.0 eq) in DMF (1 mL) was added EDCI (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then 0.2 mL of this mixture was added with BCY8920 (20.0 mg, 9.36 μmol) and DIEA (1.2 mg, 9.36 μmol). The mixture was stirred at 25-30° C. for 2 hr. LC-MS showed BCY8920 was consumed completely and one main peak with desired m/z (calculated MW: 2220.54, observed m/z: 1110.90 ([M/2+H]$^+$) was detected. The reaction mixture was then concentrated under reduced pressure to remove solvent and produced a residue, following by purification by prep-HPLC (TFA condition). Compound 2 (12 mg, 5.15 μmol, 56.28% yield, 95.3% purity) was obtained as a white solid.

Procedure for preparation of BCY11377

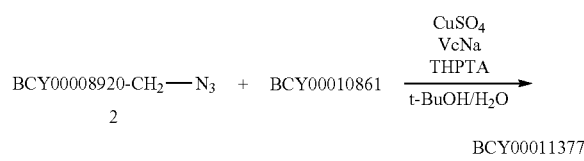

A mixture of compound 2 (3 mg, 1.35 μmol, 1.0 eq.), BCY10861 (3.8 mg, 1.35 μmol, 1.0 eq.), and THPTA (0.6 mg, 1.0 eq.) was dissolved in t-BuOH/H$_2$O (1:1, 1 mL, pre-degassed and purged with N$_2$ for 3 times), and then CuSO$_4$ (0.4 M, 3.4 μL, 1 eq.) and VcNa (0.4 M, 3.4 μL, 1 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 2 hr under N$_2$ atmosphere. LC-MS showed one main peak with desired m/z (calculated MW: 4936.68, observed m/z: 1234.9 ([M/4+H]$^+$) was detected. The reaction mixture was filtered and concentrated under reduced pressure to give a residue. The crude product was purified by prep-HPLC (TFA condition), and BCY11377 (3.5 mg, 0.66 μmol, 48.86% yield, 93.1% purity) was obtained as a white solid.

BCY11378

Procedure for Preparation of Compound 2

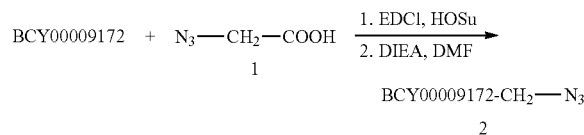

To a solution of compound 1 (5.0 mg, 49.5 μmol, 1.0 eq) in DMF (1 mL) was added EDCI (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then 0.2 mL of this mixture was added to BCY9172 (20.0 mg, 9.54 μmol) and DIEA (1.7 μL, 9.62 μmol). The mixture was stirred at 25-30° C. for 2 hr. LC-MS showed compound 1 was consumed completely and one main peak with desired m/z (calculated MW: 2176.49, observed m/z: 1090.0 ([M/2+H]$^+$) was detected. The reaction mixture was then concentrated under reduced pressure to remove solvent and produced a residue, following by purification by prep-HPLC (TFA condition). Compound 2 (20.2 mg, 7.48 μmol, 78.34% yield, 80.57% purity) was obtained as a white solid.

Procedure for Preparation of BCY11378

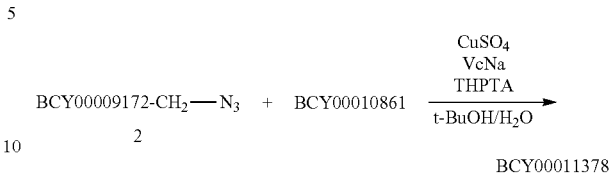

A mixture of compound 2 (5 mg, 2.30 μmol, 1.0 eq.), BCY10861 (6.24 mg, 2.30 μmol, 1.0 eq.), and THPTA (1.0 mg, 1.0 eq.) was dissolved in t-BuOH/H$_2$O (1:1, 1 mL, pre-degassed and purged with N$_2$ for 3 times), and then CuSO$_4$ (0.4 M, 5.8 μL, 1.0 eq.) and VcNa (0.4 M, 5.8 μL, 1.0 eq.) were added under N$_2$. The pH of this solution was adjusted to 8 by dropwise addition of 0.2 M NH$_4$HCO$_3$ (in 1:1 t-BuOH/H$_2$O), and the solution turned to light yellow. The reaction mixture was stirred at 40° C. for 2 hr under N$_2$ atmosphere. LC-MS showed compound 3 was consumed completely and one main peak with desired m/z (calculated MW: 4894.61, observed m/z: 1224.3 ([M/4+H]$^+$) was detected. The reaction mixture was filtered and concentrated under reduced pressure to give a residue. The crude product was purified by prep-HPLC (TFA condition), and BCY11378 (1.2 mg, 0.34 μmol, 10.07% yield, 94.3% purity) was obtained as a white solid.

BCY11379

Procedure for Preparation of BCY8919-PEG5-N$_3$

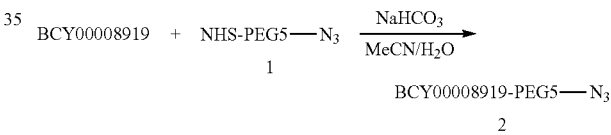

BCY8919 (30.0 mg, 14.43 μmol, 1.0 eq) and compound 1 (6.3 mg, 14.57 μmol, 1.01 eq), were dissolved in a mixture of MeCN (1 mL) and H$_2$O (1 mL). The solution was added with 1 M NaHCO$_3$ to adjust pH to 8, and then the mixture was stirred at 35° C. for 2 hr. LC-MS showed BCY8919 was consumed completely and one main peak with desired m/z (calculated MW: 2396.79, observed m/z: 1198.74 ([M/2+H]$^+$) and 799.50 ([M/4+H]$^+$)) was detected. The reaction mixture was purified by prep-HPLC (TFA condition) and compound 2 (20 mg, 8.07 μmol, 55.92% yield, 96.68% purity) was obtained as a white solid.

Procedure for Preparation of BCY11379

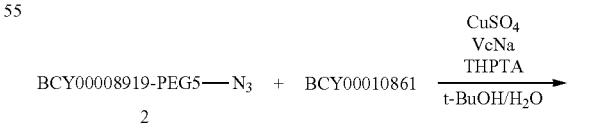

Compound 2 (3.0 mg, 1.25 μmol, 1.0 eq) and BCY10861 (3.4 mg, 1.25 μmol, 1.0 eq) were first dissolved in 2 mL of t-BuOH/H$_2$O (1:1), and then CuSO$_4$ (0.4 M, 7 μL, 2.24 eq), VcNa (1 mg, 5.04 μmol, 4.03 eq) and THPTA (1 mg, 2.30 μmol, 1.84 eq) was added. Finally 1 M NH$_4$HCO$_3$ was added to adjust pH to 8. All solvents here were degassed and purged with $N_2$ for 3 times. The reaction mixture was stirred at 25-30° C. for 16 hr under $N_2$ atmosphere. LC-MS showed compound 2 was consumed completely and one main peak with desired m/z (calculated MW: 5112.93 observed m/z: 1022.96 ($[M/5+H]^+$) and 1278.74 ($[M/4+H]^+$)). The reaction mixture was purified by prep-HPLC (TFA condition) and BCY11379 (3.4 mg, 0.615 µmol, 52.00% yield, 97.88% purity) was obtained as a white solid.

BCY11380

Procedure for Preparation of BCY8920-PEG5-$N_3$

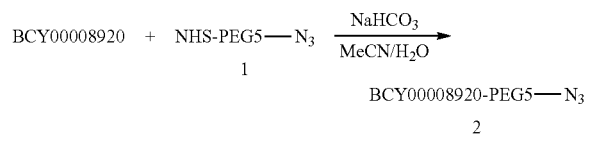

BCY8920 (30.0 mg, 14.04 µmol, 1.0 eq) and compound 1 (6.1 mg, 14.11 µmol, 1.01 eq), were dissolved in a mixture of MeCN (1 mL) and $H_2O$ (1 mL). The solution was added with 1 M $NaHCO_3$ to adjust pH to 8, and then the mixture was stirred at 35° C. for 2 hr. LC-MS showed BCY8920 was consumed completely and one main peak with desired m/z (calculated MW: 2454.83, observed m/z: 1227.63 ($[M/2+H]^+$) and 818.66 ($[M/3+H]^+$)) was detected. The reaction mixture was purified by prep-HPLC (TFA condition) and compound 2 (20 mg, 8.03 µmol, 57.21% yield, 98.56% purity) was obtained as a white solid.

Procedure for Preparation of BCY11380

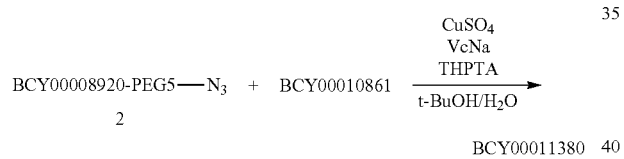

Compound 2 (3.5 mg, 1.43 µmol, 1.0 eq) and BCY10861 (3.9 mg, 1.44 µmol, 1.0 eq) were first dissolved in 2 mL of t-BuOH/$H_2O$ (1:1), and then $CuSO_4$ (0.4 M, 8 µL, 2.24 eq), VcNa (1 mg, 5.04 µmol, 3.52 eq) and THPTA (1 mg, 2.30 µmol, 1.61 eq) were added. Finally 1 M $NH_4HCO_3$ was added to adjust pH to 8. All solvents here were degassed and purged with $N_2$ for 3 times. The reaction mixture was stirred at 25-30° C. for 16 hr under $N_2$ atmosphere. LC-MS showed majority of compound 2 was consumed and one main peak with desired m/z (calculated MW: 5170.97, observed m/z: 1034.28 ($[M/5+H]^+$) and 1293.10 ($[M/4+H]^+$)). The reaction mixture was purified by prep-HPLC (TFA condition) and BCY11380 (1.6 mg, 0.296 µmol, 20.77% yield, 96.77% purity) was obtained as a white solid.

BCY11381

Procedure for Preparation of BCY8920-PEG5-$N_3$

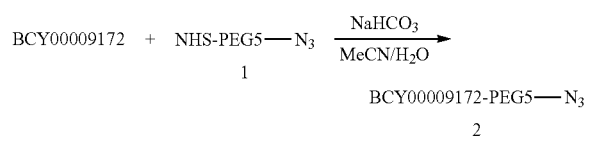

BCY9172 (30.0 mg, 14.32 µmol, 1.0 eq) and compound 1 (6.2 mg, 14.34 µmol, 1.0 eq), were dissolved in a mixture of MeCN (1 mL) and $H_2O$ (1 mL). The solution was added with 1 M $NaHCO_3$ to adjust pH to 8, and then the mixture was stirred at 35° C. for 2 hr. LC-MS showed BCY9172 was consumed completely and one main peak with desired m/z (calculated MW: 2412.75, observed m/z: 1206.72 ($[M/2+H]^+$)) was detected. The reaction mixture was purified by prep-HPLC (TFA condition) and compound 2 (15 mg, 6.14 µmol, 42.87% yield, 98.75% purity) was obtained as a white solid.

Procedure for Preparation of BCY11381

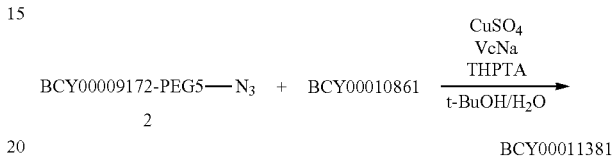

Compound 2 (3.0 mg, 1.24 µmol, 1.0 eq) and BCY10861 (3.4 mg, 1.25 µmol, 1.01 eq) were first dissolved in 2 mL of t-BuOH/$H_2O$ (1:1), and then $CuSO_4$ (0.4 M, 7 µL, 2.25 eq), VcNa (1 mg, 5.04 µmol, 4.06 eq) and THPTA (1 mg, 2.30 µmol, 1.85 eq) were added. Finally 1 M $NH_4HCO_3$ was added to adjust pH to 8. All solvents here were degassed and purged with $N_2$ for 3 times. The reaction mixture was stirred at 25-30° C. for 16 hr under $N_2$ atmosphere. LC-MS showed one peak with desired m/z (calculated MW: 5128.89, observed m/z: 1026.05 ($[M/5+H]^+$) and 1282.50 ($[M/4+H]^+$)). The reaction mixture was purified by prep-HPLC (TFA condition) and BCY11381 (1.6 mg, 0.295 µmol, 23.73% yield, 94.59% purity) was obtained as a white solid.

Example 5: Production of CD137 Monoclonal Antibody Agonist

The sequence of the CD137 monoclonal antibody agonist that was used for comparison to CD137 multimers in the experiments presented herein was disclosed in U.S. Pat. No. 7,288,638. The IgG4 isotype antibody was expressed using the ExpiCHO Expression System (Thermo Fisher Scientific) following transient transfection of the DNA expression construct. The antibody was purified by Protein A affinity chromatography and formulated in phosphate-buffered solution (PBS) pH 7.2. Purity analysis using HPLC-SEC (column GF-250, Agilent) indicated that the monomer rate of CD137 monoclonal antibody is approximately 95%. Binding activity analysis indicated that the CD137 monoclonal antibody with a concentration higher than 1 µg/ml can bind to CHO cells expressing CD137. Endotoxin analysis using the ToxinSensor™ Chromogenic LAL Endotoxin Assay Kit (Genscript) indicated that the CD137 monoclonal antibody preparation contained <7 EU/mg of endotoxin.

Biological Data

1. CD137 Biacore Experimental Description

Biacore experiments were performed to determine $k_a$ ($M^{-1}s^{-1}$), $k_d$ ($s^{-1}$), $K_D$ (nM) values of heterotandem peptides binding to human CD137 protein. Recombinant human CD137 (R&D systems) was resuspended in PBS and biotinylated using EZ-Link™ Sulfo-NHS-LC-LC-Biotin reagent (Thermo Fisher) as per the manufacturer's suggested protocol. The protein was desalted to remove uncoupled biotin using spin columns into PBS.

For analysis of peptide binding, a Biacore T200 or a Biacore 3000 instrument was used with a XanTec CMD500D chip. Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 µl/min. For capture of streptavidin, the protein was diluted to 0.2 mg/ml in 10 mM sodium acetate (pH 4.5) and captured by injecting 120 µl of onto the activated chip surface. Residual activated groups were blocked with a 7 min injection of 1 M ethanolamine (pH 8.5) and biotinylated CD137 captured to a level of 270-1500 RU. Buffer was changed to PBS/0.05% Tween 20 and a dilution series of the peptides was prepared in this buffer with a final DMSO concentration of 0.5%. The top peptide concentration was 500 nM with 6 further 2-fold or 3-fold dilutions. The SPR analysis was run at 25° C. at a flow rate of 90 µl/min with 60 seconds association and 900 seconds dissociation. After each cycle a regeneration step (10 µl of 10 mM glycine pH 2) was employed. Data were corrected for DMSO excluded volume effects as needed. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain heterotandem peptides were tested in this assay and the results are shown in Table 1 below

TABLE 1

CD137 Biacore Assay Data with Heterotandem Peptides

| Complex ID | SPR $(K_D)$(nM) |
|---|---|
| BCY9173 | 7.98 |
| BCY7985 | 143 |
| BCY8942 | 853 |
| BCY8943 | 156 |
| BCY9647 | 206 |
| BCY9648 | 202 |
| BCY9655 | 199 |
| BCY9656 | 159 |
| BCY9657 | 256 |
| BCY9658 | 152 |
| BCY9659 | 88.1 |
| BCY9758 | 189 |
| BCY8854 | 108 |
| BCY9350 | 69.4 |
| BCY9351 | 3640 |
| BCY9399 | 73 |
| BCY9400 | 53 |
| BCY9408 | 105 |
| BCY9409 | 97.7 |
| BCY9410 | 65.8 |
| BCY9411 | 71.1 |
| BCY9759 | 44.3 |
| BCY10000 | 6.19 |
| BCY10571 | 12.03 |
| BCY10572 | 5.00 |
| BCY10573 | 3.39 |

2. Nectin-4 Biacore Experimental Description

Biacore experiments were performed to determine $k_a$ ($M^{-1}s^{-1}$), $k_d$ ($s^{-1}$), $K_D$ (nM) values of heterotandem peptides binding to human Nectin-4 protein (obtained from Charles River). Human Nectin-4 (residues Gly32-Ser349; NCBI RefSeq: NP_112178.2) with a gp67 signal sequence and C-terminal FLAG tag was cloned into pFastbac-1 and baculovirus made using standard Bac-to-Bac™ protocols (Life Technologies). Sf21 cells at $1\times10^6$ ml$^{-1}$ in Excell-420 medium (Sigma) at 27° C. were infected at an MOI of 2 with a P1 virus stock and the supernatant harvested at 72 hours. The supernatant was batch bound for 1 hour at 4° C. with Anti-FLAG M2 affinity agarose resin (Sigma) washed in PBS and the resin subsequently transferred to a column and washed extensively with PBS. The protein was eluted with 100 µg/ml FLAG peptide. The eluted protein was concentrated to 2 ml and loaded onto an S-200 Superdex column (GE Healthcare) in PBS at 1 ml/min. 2 ml fractions were collected and the fractions containing Nectin-4 protein were concentrated to 16 mg/ml.

The protein was randomly biotinylated in PBS using EZ-Link™ Sulfo-NHS-LC-LC-Biotin reagent (Thermo Fisher) as per the manufacturer's suggested protocol. The protein was extensively desalted to remove uncoupled biotin using spin columns into PBS.

For analysis of peptide binding, a Biacore 3000 instrument was used with a CM5 chip (GE Healthcare). Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 minute injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 µl/min. For capture of streptavidin, the protein was diluted to 0.2 mg/ml in 10 mM sodium acetate (pH 4.5) and captured by injecting 120 µl of streptavidin onto the activated chip surface. Residual activated groups were blocked with a 7 minute injection of 1 M ethanolamine (pH 8.5) and biotinylated Nectin-4 captured to a level of 1,200-1,800 RU. Buffer was changed to PBS/0.05% Tween 20 and a dilution series of the peptides was prepared in this buffer with a final DMSO concentration of 0.5%. The top peptide concentration was 100 nM with 6 further 2-fold dilutions. The SPR analysis was run at 25° C. at a flow rate of 50 µl/min with 60 seconds association and dissociation between 400 and 1,200 seconds depending upon the individual peptide. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain heterotandem peptides of the invention were tested in the above mentioned Nectin-4 binding assays and the results are shown in Table 2 below:

TABLE 2

Nectin-4 Biacore Assay Data with Heterotandem Peptides

| Complex ID | SPR $K_D$(nM) |
|---|---|
| BCY8854 | 2.76 |
| BCY9350 | >200 nM |
| BCY9351 | 2.47 |
| BCY9399 | 1.67 |
| BCY9400 | 1.8 |
| BCY9408 | 1.57 |
| BCY9409 | 1.66 |
| BCY9410 | 1.49 |
| BCY9411 | 1.48 |
| BCY9759 | 2.14 |
| BCY10000 | 2.26 |

3. EphA2 Biacore Experimental Description

Biacore experiments were performed to determine $k_a$ ($M^{-1}s^{-1}$), $k_d$ ($s^{-1}$), $K_D$ (nM) values of heterotandem peptides binding to human EphA2 protein.

EphA2 were biotinylated with EZ-Link™ Sulfo-NHS-LC-Biotin for 1 hour in 4 mM sodium acetate, 100 mM NaCl, pH 5.4 with a 3× molar excess of biotin over protein. The degree of labelling was determined using a Fluorescence Biotin Quantification Kit (Thermo) after dialysis of the reaction mixture into PBS. For analysis of peptide binding, a Biacore T200 instrument was used with a XanTec CMD500D chip. Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 it/min. For capture of streptavidin, the protein was diluted to 0.2 mg/ml in 10 mM sodium acetate (pH 4.5) and captured by injecting 120 µl onto the activated chip surface. Residual activated groups were blocked with a 7 min injection of 1 M ethanolamine (pH 8.5):HBS-N (1:1). Buffer was changed to PBS/0.05% Tween 20 and biotinylated EphA2 was captured to a level of 500-1500 RU using a dilution of protein to 0.2 µM in buffer. A dilution series of the peptides was prepared in this buffer with a final DMSO concentration of 0.5% with a top peptide concentration was 50 or 100 nM and 6 further 2-fold dilutions. The SPR analysis was run at 25° C. at a flow rate of 90 µl/min with 60 seconds association and 900-1200 seconds dissociation. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain heterotandem peptides of the invention were tested in the EphA2 binding assays and the results are shown in Table 3 below:

TABLE 3

EphA2 Biacore Assay Data with Heterotandem Peptides

| Complex ID | SPR $K_D$(nM) |
|---|---|
| BCY9173 | 2.1 |
| BCY7985 | 2 |
| BCY8942 | 1.7 |
| BCY8943 | >200 nM |
| BCY9647 | 1.69 |
| BCY9648 | 1.75 |
| BCY9655 | 1.33 |
| BCY9656 | 0.75 |
| BCY9657 | 1.1 |
| BCY9658 | 1.9 |
| BCY9659 | 1.03 |
| BCY9758 | 1.5 |

4. CD137 Reporter Assay Co-Culture with Tumour Cells

Culture medium referred to as R1 media is prepared by adding 1% FBS to RPMI-1640 (component of Promega kit CS196005). Serial dilutions of test articles in R1 are prepared in a sterile 96 well-plate. Use 25 µl per well of test articles or R1 (as a background control) to designated wells in white cell culture plate. Tumour cells* are harvested and resuspended at a concentration of 400,000 cells/mL in R1 media. Twenty five (25) µL/well tumour cells are used in white cell culture plate. Jurkat cells (Promega kit CS196005, 0.5 mL) are thawed in the water bath and then added to 5 ml pre-warmed R1 medium. Twenty five (25) µL/well Jurkat cells are used in white cell culture plate. Incubate the cells and test articles for 6h at 37° C., 5% $CO_2$. At the end of 6 h, add 75 µl/well Bio-Glo™ (Promega) and incubate for 10 min before reading luminescence in a plate reader (Clariostar, BMG). The fold change relative to cells (Jurkat cells+ Cell line used in co-culture) is calculated and plotted in GraphPad Prism as log(agonist) vs response to determine EC50 (nM) and Fold Induction over background (Max)

The tumour cell type used in co-culture is dependent on the tumour target specific for heterotandem as is shown in Table 4 below:

TABLE 4

Cell Lines Used for each Tumour Target

| Tumour target | Cell line used in co-culture |
|---|---|
| EphA2 | A549, SC-OV-3, PC3, LNCaP |
| Nectin-4 | HT1376, NCI-H292 |
| PD-L1 | RKO |

Data is presented in FIG. 3 which shows that the EphA2-CD137 heterotandem BCY7985 showed strong induction of CD137 cell activity in the Promega CD137 luciferase reporter assay in the presence of EphA2-expressing HT1080 cells. There is no CD137 induction by the heterotandem in the absence of HT1080 cells.

Figure 4:
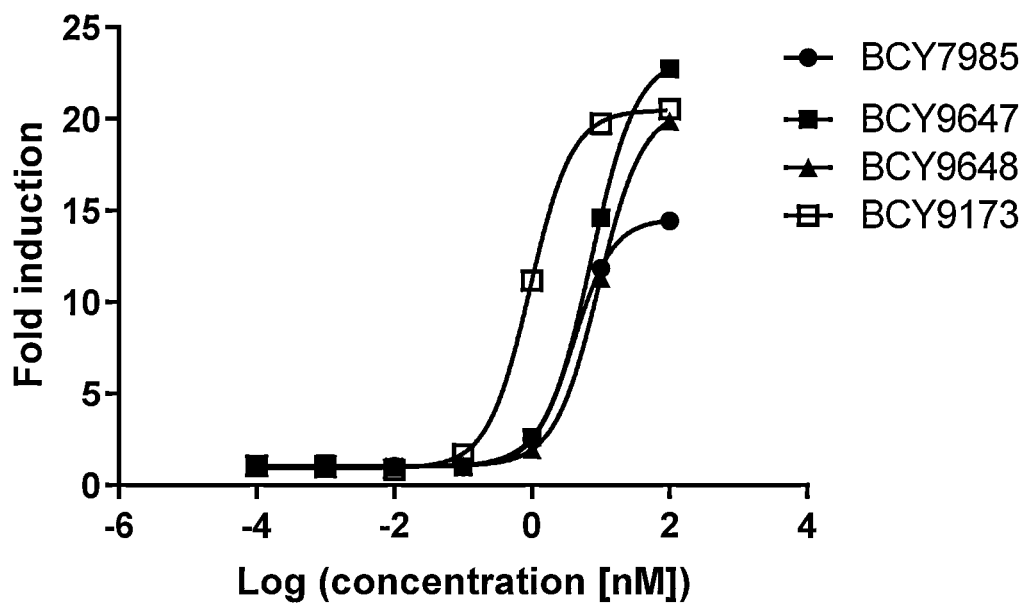
FIG. 4: EphA2/CD137 heterotandems are active in CD137 reporter assay and the fold induction of activation is dependent on tumour target expression level on the cell line used in co-culture.
Figure 4:
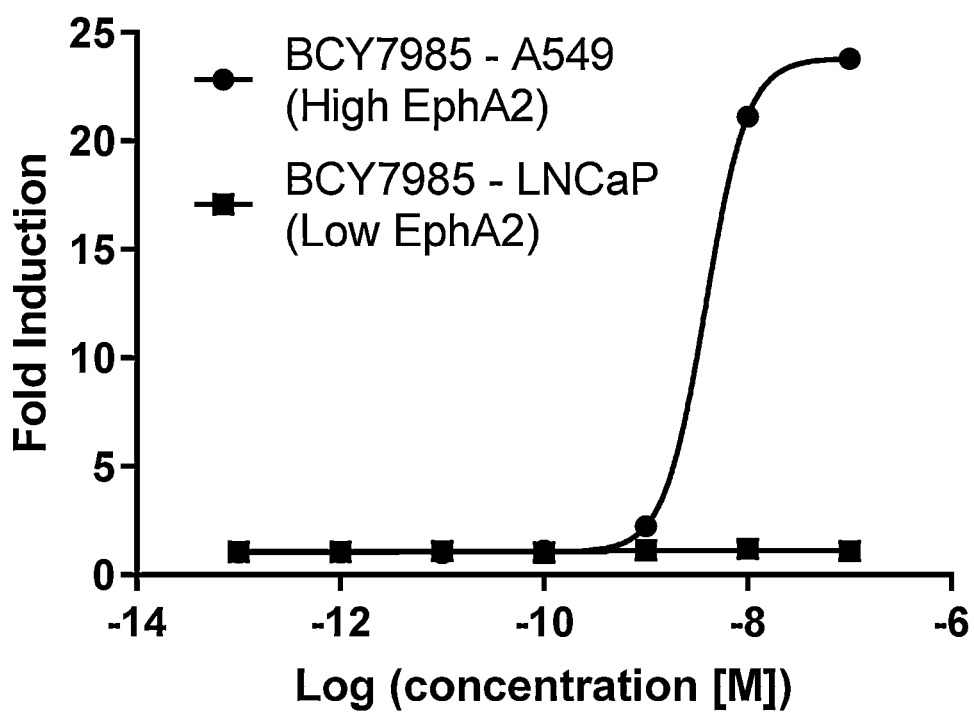

Data is presented in FIG. 4 which shows that EphA2/CD137 heterotandems induce strong CD137 activation in CD137 reporter assay and the fold induction of activation is dependent on tumour target expression level on the cell line (A549 and SC-OV-3:EphA2 High and LNCaP:EphA2 Low) used in co-culture.

Figure 6:
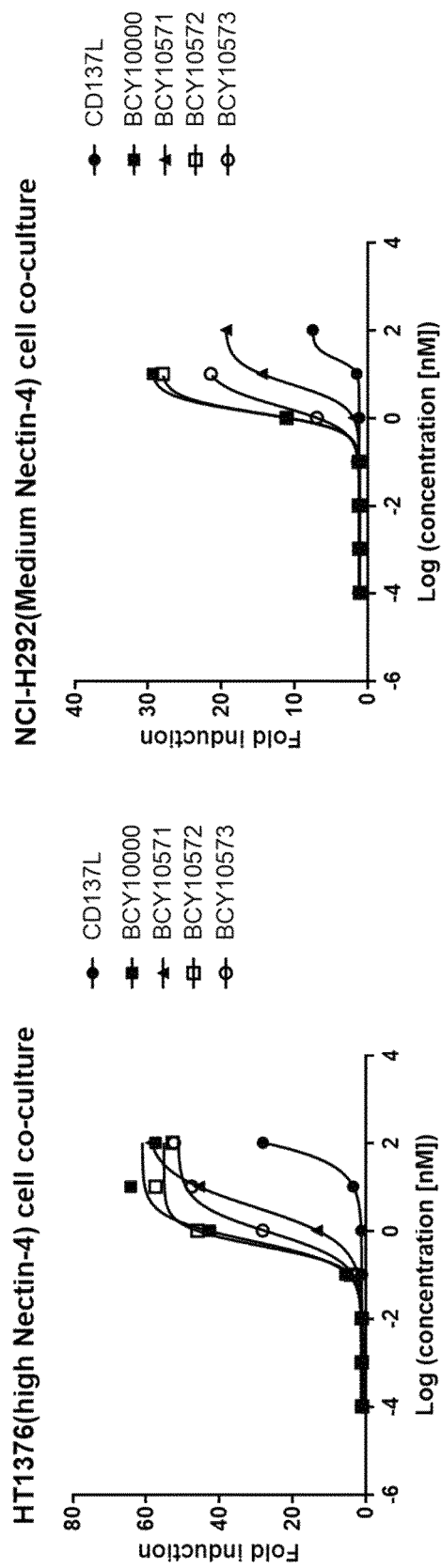
FIG. 6: Nectin-4/CD137 heterotandems are active in CD137 reporter assay and the fold induction of activation is dependent on tumour target expression level on the cell line (HT1376:Nectin-4 high and NCI-H292: Nectin-4 Medium) used in co-culture.

Data is presented in FIG. 6 which shows that Nectin-4/CD137 heterotandems induce strong CD137 activation in CD137 reporter assay and the fold induction of activation is dependent on tumour target expression level on the cell line (HT1376:Nectin-4 high and NCI-H292: Nectin-4 Medium) used in co-culture.

Figure 9:
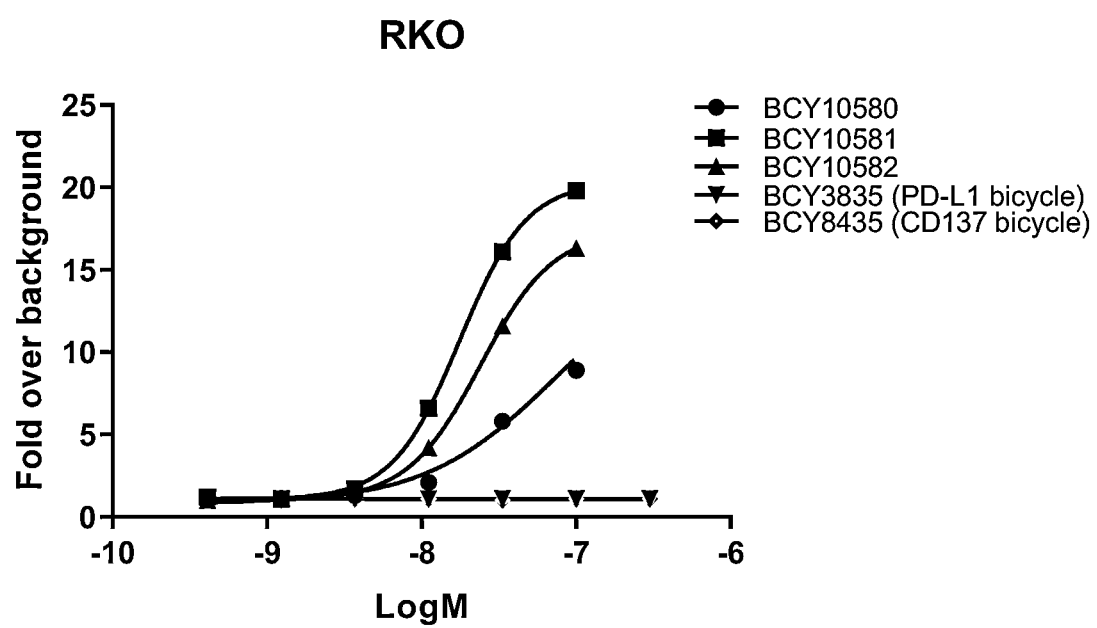
FIG. 9: PD-L1/CD137 heterotandems are active in CD137 reporter assay in presence of PD-L1 expressing cell line RKO.

Data is presented in FIG. 9 which shows that PD-L1/CD137 heterotandems induce strong activation of CD137 in the CD137 reporter assay in presence of PD-L1 expressing cell line. A summary of the EC50 (nM) and Fold Induction induced by heterotandem peptides in CD137 reporter assay in co-culture with different cells lines are reported in Table 5 below:

TABLE 5

Fold Induction induced by Heterotandem Peptides in CD137 Reporter Assay

| Complex ID | Tumour Target | Cell Line used in Coculture | EC50 (nM) | Fold Induction over Background |
|---|---|---|---|---|
| BCY9173 | EphA2 | SC-OV-3 | 0.94 | 21 |
| BCY7985 | EphA2 | SC-OV-3 | 4.0 | 15 |
| BCY8942 | EphA2 | PC3 | — | <2 fold induction at 100 nM |
| BCY8943 | EphA2 | PC3 | — | <2 fold induction at 100 nM |

TABLE 5-continued

Fold Induction induced by Heterotandem Peptides in CD137 Reporter Assay

| Complex ID | Tumour Target | Cell Line used in Coculture | EC50 (nM) | Fold Induction over Background |
|---|---|---|---|---|
| BCY9647 | EphA2 | SC-OV-3 | 7.2 | 24 |
| BCY9648 | EphA2 | SC-OV-3 | 9.3 | 20 |
| BCY9655 | EphA2 | SC-OV-3 | 4.1 | 6 |
| BCY9656 | EphA2 | SC-OV-3 | 1.1 | 3 |
| BCY9657 | EphA2 | SC-OV-3 | 9.0 | 26 |
| BCY9658 | EphA2 | SC-OV-3 | 6.2 | 11 |
| BCY9659 | EphA2 | SC-OV-3 | 9.9 | 7 |
| BCY9758 | EphA2 | SC-OV-3 | 1.2 | 7 |
| BCY10568 | EphA2 | PC3 | 0.25 | 32 |
| BCY10570 | EphA2 | PC3 | 0.41 | 38 |
| BCY10574 | EphA2 | PC3 | 1.0 | 32 |
| BCY10575 | EphA2 | PC3 | 0.62 | 38 |
| BCY10576 | EphA2 | PC3 | 0.51 | 38 |
| BCY10577 | EphA2 | PC3 | 0.28 | 37 |
| BCY8854 | Nectin4 | H1376 | 1.2 | 30 |
| BCY9350 | Nectin4 | H1376 | — | <2 fold induction at 100 nM |
| BCY9351 | Nectin4 | H1376 | — | <2 fold induction at 100 nM |
| BCY9399 | Nectin4 | H1376 | 11 | 13 |
| BCY9400 | Nectin4 | H1376 | 2.9 | 13 |
| BCY9401 | Nectin4 | H1376 | 18 | 70 |
| BCY9407 | Nectin4 | H1376 | 3.4 | 29 |
| BCY9408 | Nectin4 | H1376 | 1.1 | 20 |
| BCY9409 | Nectin4 | H1376 | 1.2 | 24 |
| BCY9410 | Nectin4 | H1376 | 1.3 | 24 |
| BCY9411 | Nectin4 | H1376 | 14 | 41 |
| BCY9759 | Nectin4 | H1376 | 2.7 | 15 |
| BCY10000 | Nectin4 | H1376 | 0.58 | 61 |
| BCY10567 | Nectin4 | H1376 | 1.7 | 45 |
| BCY10569 | Nectin4 | H1376 | 1.2 | 52 |
| BCY10571 | Nectin4 | H1376 | 3.5 | 60 |
| BCY10572 | Nectin4 | H1376 | 0.44 | 55 |
| BCY10573 | Nectin4 | H1376 | 0.90 | 55 |
| BCY10578 | Nectin4 | H1376 | 0.42 | 58 |
| BCY10917 | Nectin4 | H1376 | 0.27 | 54 |
| BCY11020 | Nectin4 | H1376 | 0.26 | 47 |
| BCY11373 | Nectin4 | H1376 | 0.16 | 74 |
| BCY11374 | Nectin4 | H1376 | 0.091 | 72 |
| BCY11375 | Nectin4 | H1376 | 0.23 | 72 |
| BCY8939 | mouse PD-L1 | MC38 | — | <2 fold induction at 100 nM |
| BCY10580 | PD-L1 | RKO | 28 | 3 |
| BCY10581 | PD-L1 | RKO | 18 | 6 |
| BCY10582 | PD-L1 | RKO | 28 | 4 |
| BCY11017 | PD-L1 | RKO | 66 | 4 |
| BCY11018 | PD-L1 | RKO | 27 | 7 |
| BCY11019 | PD-L1 | RKO | 18 | 6 |
| BCY11376 | PD-L1 | RKO | 127 | 9 |
| BCY11377 | PD-L1 | RKO | 40 | 6 |
| BCY11378 | PD-L1 | RKO | 80 | 3 |
| BCY11379 | PD-L1 | RKO | 68 | 6 |
| BCY11380 | PD-L1 | RKO | 34 | 7 |
| BCY11381 | PD-L1 | RKO | 105 | 7 |

5. Primary Human T Cells-A549 Co-Culture (Tumour Cell Killing)

PBMC were isolated from three healthy donors and added to Nuclight Red labelled tumour target cells (human lung carcinoma cells A549®, ATCC CLL-185™) at two defined ratios in the presence of anti-CD3 stimulation at two concentrations. Tumour cell: PBMC co-cultures were incubated with the lead bicycles at three concentrations. All test conditions were also plated onto tumour cells in the absence of stimulated PBMC in order to detect direct tumour cell cytotoxicity. Tumour killing was evaluated by counting viable Nuclight red positive tumour cells over time. In addition, a Caspase 3/7 dye was used to identify apoptotic tumour cells. Cultures were analysed using an IncuCyte S3 machine which allows real-time live cell fluorescence imaging. Co-cultures were imaged for 72 hours. Each condition was established in triplicate.

Figure 5:
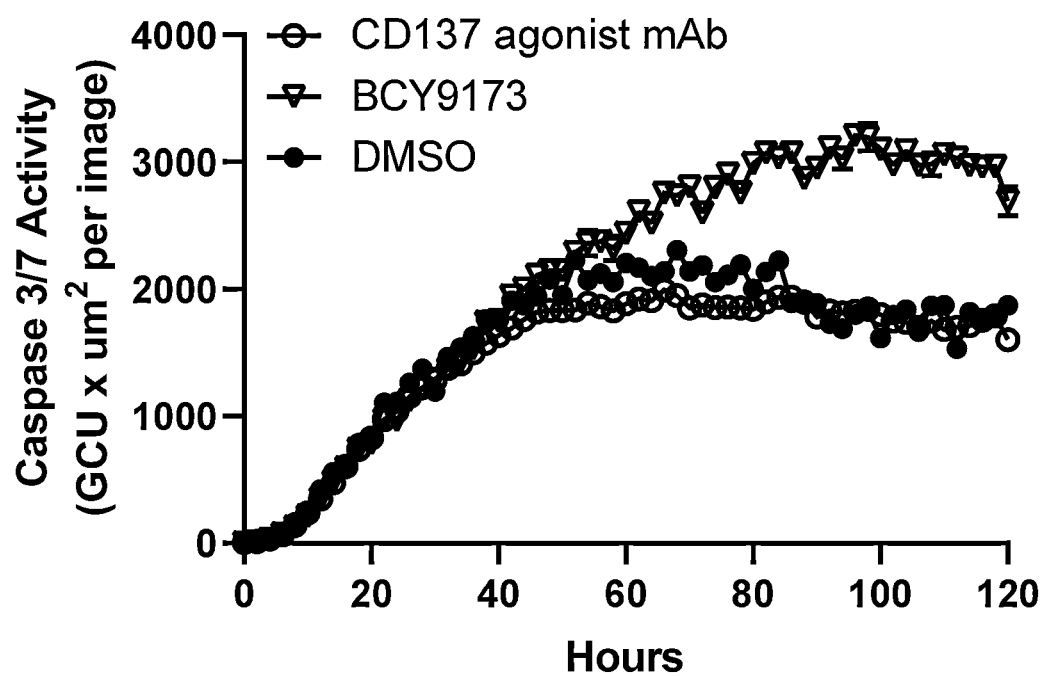
FIG. 5: EphA2/CD137 heterotandems induce tumour cell killing in primary human T-cell and cancer cell co-culture assay. Tumour cell killing is evaluated by counting viable Nuclight red positive tumour cells over time. A Caspase 3/7 dye is used to identify apoptotic tumour cells.

Data is presented in FIG. 5 which demonstrates that EphA2/CD137 heterotandems induce tumour cell killing in primary human T-cell and cancer cell co-culture assay. Anti-CD137 mAb agonist is used as a control.

6. Human PBMC-4T1 Co-Culture (Cytokine Release) Assay

Mouse mammary gland tumor cell line 4T1-1 (4T1-Parental) and murine Nectin-4 overexpressing 4T1 (4T1-D02) were cultured in RPMI1640 supplemented with 10% heat-inactivated Fetal Bovine Serum, 100 I.U/ml Penicillin and 100 I.U/Streptomycin, 20 mM HEPES, 1× Non-Essential Amino Acids, and 2 mM L-Glutamine (RPMI working medium). Frozen PBMCs from healthy human donors were thawed and washed one time in room temperature PBS, and then resuspended in RPMI working medium. For tumor cell and PBMC co-culture, 10000 PBMCs and 2000 tumor cells (5:1) were mixed and plated in each well of a 384 well plate. For stimulating human PBMCs, 125 ng/ml of soluble anti-CD3 mAb (clone OKT3) was added to the culture on day 0. Test, control compounds or vehicle controls were added to respective wells and brought the final volume per well to 100ul. Plates were incubated in a 37° C. cell culture incubator with 5% $CO_2$ for up to three days. Supernatants were collected 48 hours after stimulation, and human IL-2 and IFFγ were detected using HTRF assays. Raw data were analyzed using Excel or Prism software to generate standard curves to interpolate protein concentrations. Data represents one study with three different donor PBMC tested in experimental duplicates.

Figure 7:
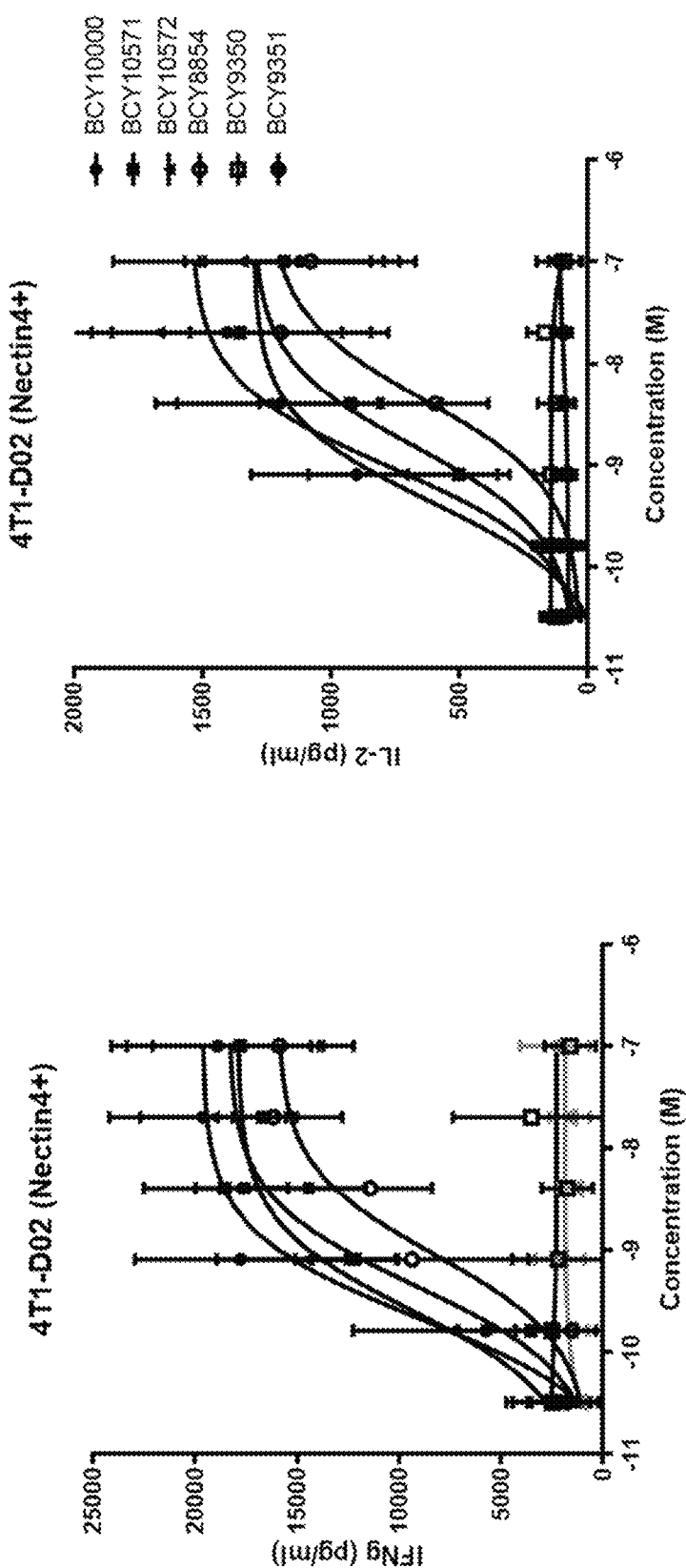
FIG. 7: Nectin-4/CD137 heterotandems induce IL-2 and IFN-γ cytokine secretion in a PBMC-4T1 co-culture assay. BCY9350 and BCY9351 are non-binding controls for Nectin-4 and CD137 respectively.

Data presented in FIG. 7 demonstrates that Nectin-4/CD137 heterotandems induce robust IL-2 and IFN-γ cytokine secretion in a PBMC-4T1 co-culture assay. BCY9350 and BCY9351 are non-binding controls for Nectin-4 and CD137 respectively.

A summary of the EC50 (nM) and maximum IFN-γ cytokine secretion (pg/ml) induced by selected Nectin-4/CD137 heterotandem peptides in Human PBMC-4T1 co-culture (cytokine release) assay is reported in Table 6 below:

TABLE 6

EC50 and maximum IFN-γ cytokine secretion induced by selected Nectin-4/CD137 heterotandem peptides in Human PBMC-4T1 co-culture (cytokine release) assay

| Complex ID | Cell line | EC50 (nM) | max IFN-γ (pg/ml) |
|---|---|---|---|
| BCY8854 | 4T1-D02(Nectin4+) | 0.89 | 15962 |
| BCY9350 | 4T1-D02(Nectin4+) | — | No Activity up to 1 µM |
| BCY9351 | 4T1-D02(Nectin4+) | — | No Activity up to 1 µM |
| BCY10000 | 4T1-D02(Nectin4+) | 0.21 | 19642 |
| BCY10571 | 4T1-D02(Nectin4+) | 0.44 | 18349 |
| BCY10572 | 4T1-D02(Nectin4+) | 0.25 | 17915 |

7. Ex Vivo Culture Protocol

Primary patient derived tumour cells from Discovery Life Sciences (DLS) are thawed gently in 10 mL pre-warmed wash medium spiked fresh with Benzonase. The 3D spheroid kit from Greiner (cat #655840) is used to maintain cells in culture for 2 days. Briefly, tumour cells are counted with trypan blue using a haemocytometer. The cells are centrifuged at 1500 rpm for 5 min to wash, and the pellet is resuspended in 100 µL per 1×10$^6$ cells N3D nanoshuttle. To make them magnetic, cells are spun down at 1500 rpm for 5 min and resuspended; this process is repeated for a total of 4 times. After the final spin, cells are resuspended in the appropriate amount of fresh Lung DTC medium (DLS) to give 50,000-100,000 cells per well in 100 µL/well. Greiner cell-repellent, 96-well plates (cat #655976) are used for this experiment.

If there are cell clumps or debris visible, sample is applied to a 70-100 µm filter before plating. At least 50,000 cells per sample are reserved for a Day 0 flow cytometry panel, these cells are stained, fixed, and stored at 4° C. for later flow analysis. Control/test compound dilutions are prepared in a separate plate at 2× in Lung DTC medium, and 100 µL/well of these 2× drug solutions are added to the wells as described by the plate map. The assay plate is then placed onto the 96-well magnetic spheroid drive in a humidified chamber at 37 C, 5% CO$_2$. At 24 h, the magnetic spheroid drive is removed. At 48 h, medium is collected for cytokine analysis and cells are collected for a Day 2 flow cytometry panel. Cytokines are quantified using a custom-built cytokine/chemokine panel (IP-10, Granzyme B, IFNγ, IL-2, IL-6, TNFα, IL-8, MIP-1a, MIP-1b, MCP-1, IL-10, MIG) from R&D systems on a Luminex reader. Flow panels: Day 0=Live/Dead, CD45, EpCAM, Nectin4, CD3, CD4, CD8, CD137; Day 2=Live/Dead, CD45, EpCAM, Nectin4, CD3, CD8, Ki67, and counting beads. Flow data is analysed with Flowjo software.

Figure 8:
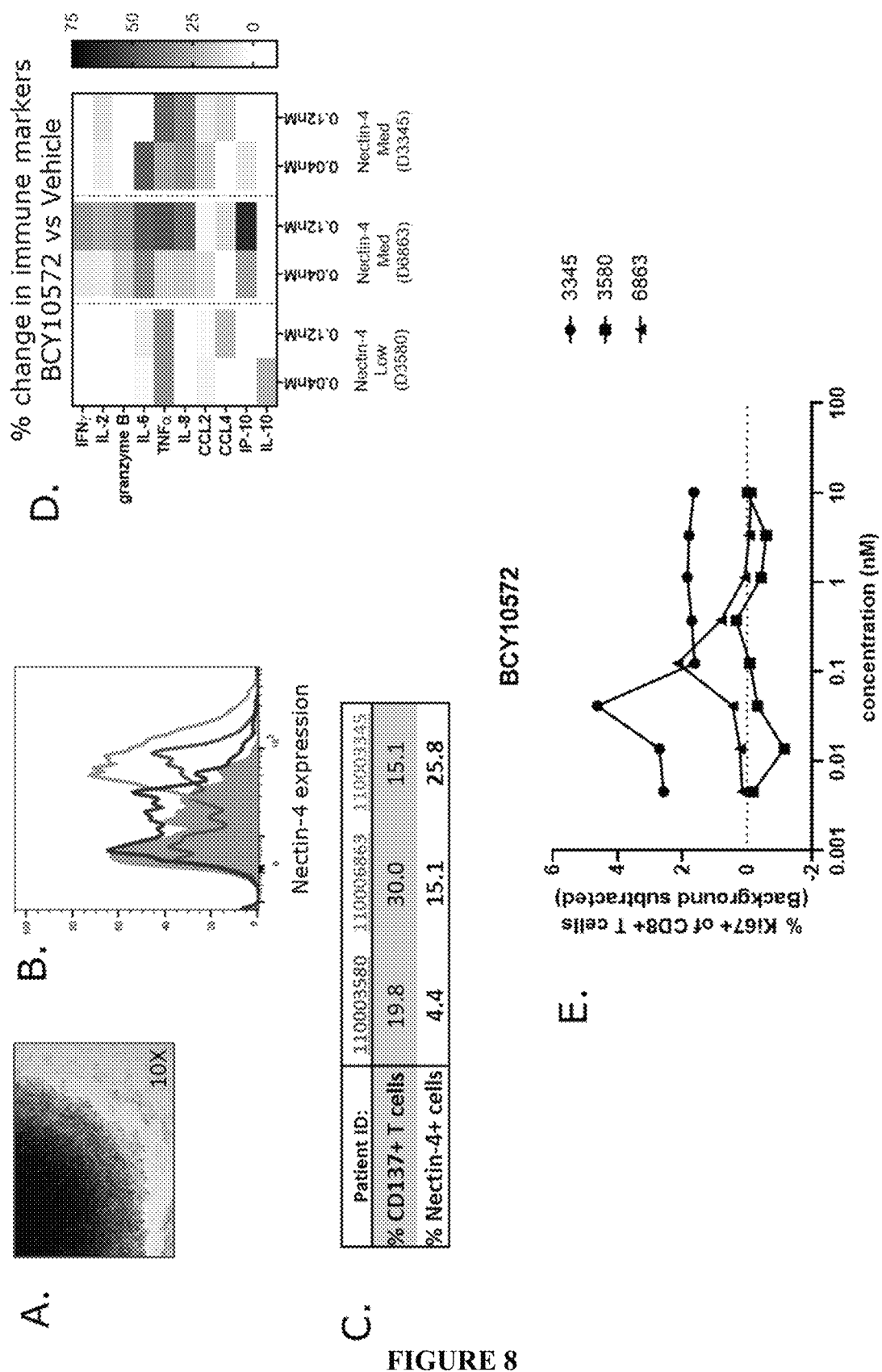
FIG. 8: Nectin-4/CD137 heterotandems induce target dependent cytokine release in ex-vivo cultures of primary patient-derived lung tumours. (A) Ex vivo patient derived tumour cells form 3D spheroids within 4 h in culture, 10× image under light microscope. (B) Flow analysis of Nectin-4 expression in patient derived tumour samples from 3 donors. (C) Table indicates % CD137$^+$ T cells and Nectin-4$^+$ cells in 3 donor samples. (D) Heatmap indicating % change in immune markers (normalized to vehicle) in response to treatment with control/test compounds. (E) % CD8$^+$ki67$^+$ T cells in response to treatment with control/test compounds (vehicle indicated with dotted line).

Data shown in FIG. 8 demonstrate that Nectin-4/CD137 heterotandems induce target dependent cytokine release in ex-vivo cultures of primary patient-derived lung tumours. Treatment of BCY10572 induced Nectin-4 dependent change in several immune markers (normalized to vehicle) and in % CD8 $^+$ki67$^+$ T cells in patient-derived samples.

8. Pharmacokinetics of CD137 Bispecifics in SD Rats

Male SD Rats were dosed with 2 mg/kg of each Bicycle multimer formulated in 25 mM Histidine HCl, 10% sucrose pH 7. Serial bleeding (about 80 µL blood/time point) was performed via submadibular or saphenous vein at each time point. All blood samples were immediately transferred into prechilled microcentrifuge tubes containing 2 µL K2-EDTA (0.5M) as anti-coagulant and placed on wet ice. Blood samples were immediately processed for plasma by centrifugation at approximately 4° C., 3000 g. The precipitant including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 µL of the supernatant samples were directly injected for LC-MS/MS analysis using an Orbitrap Q Exactive in positive ion mode to determine the concentrations of Bicycle multimer. Plasma concentration versus time data were analyzed by non-compartmental approaches using the Phoenix WinNonlin 6.3 software program. C0, Cl, Vdss, T½, AUC(0-last), AUC(0-inf), MRT (0-last), MRT(0-inf) and graphs of plasma concentration versus time profile were reported.

Figure 10:
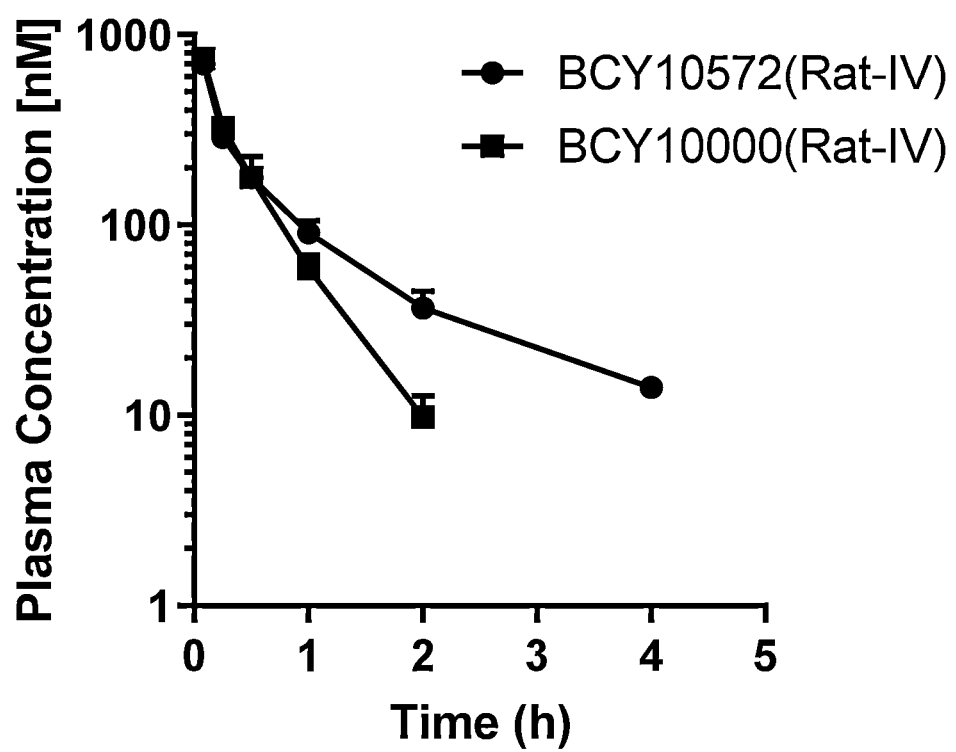
FIG. 10: Pharmacokinetics of heterotandems in SD Rats: BCY10572 and BCY10000 were dosed IV at 2 mg/kg (n=3).
Figure 11:
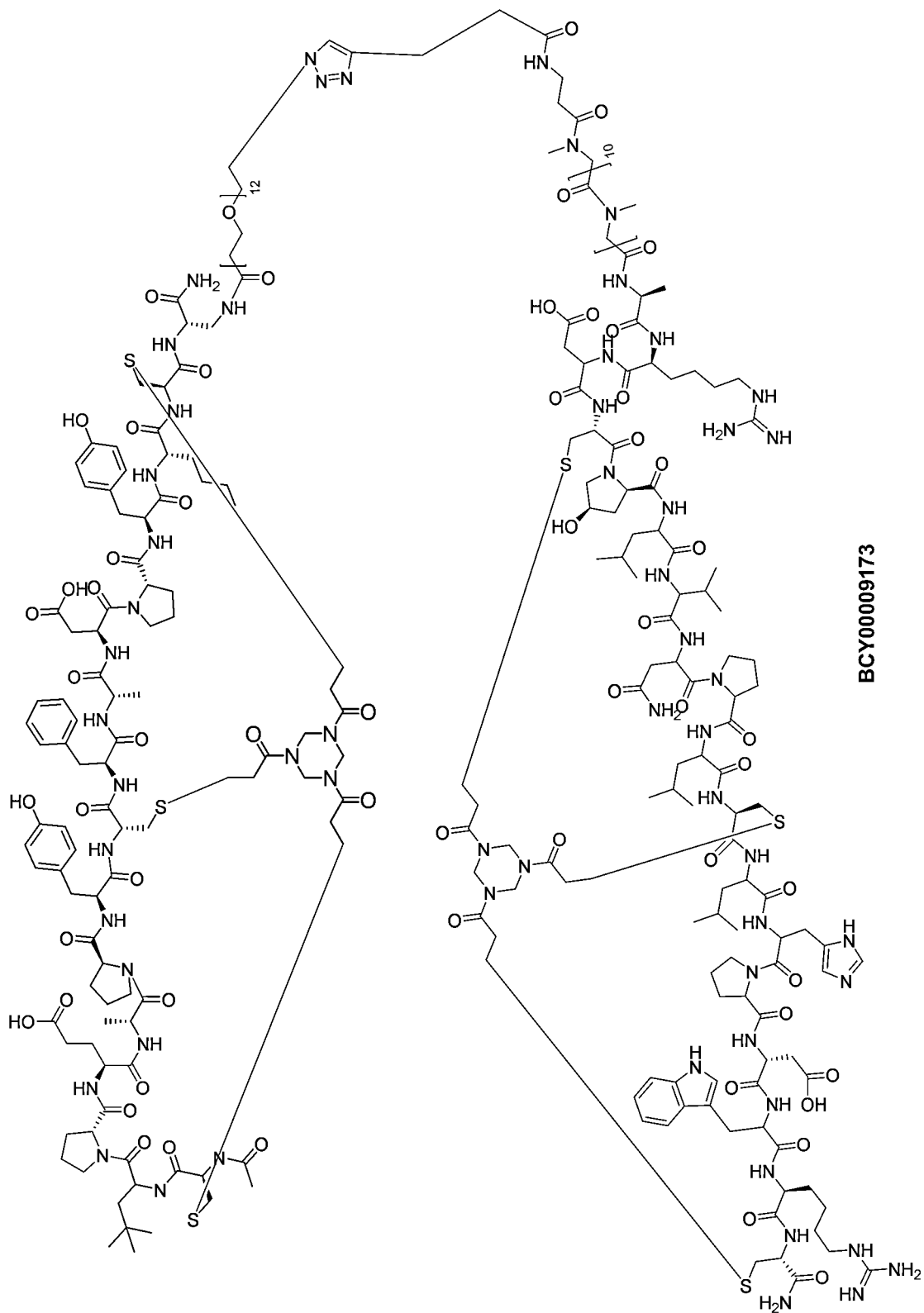
FIG. 11: Formula of BCY9173.
Figure 12:
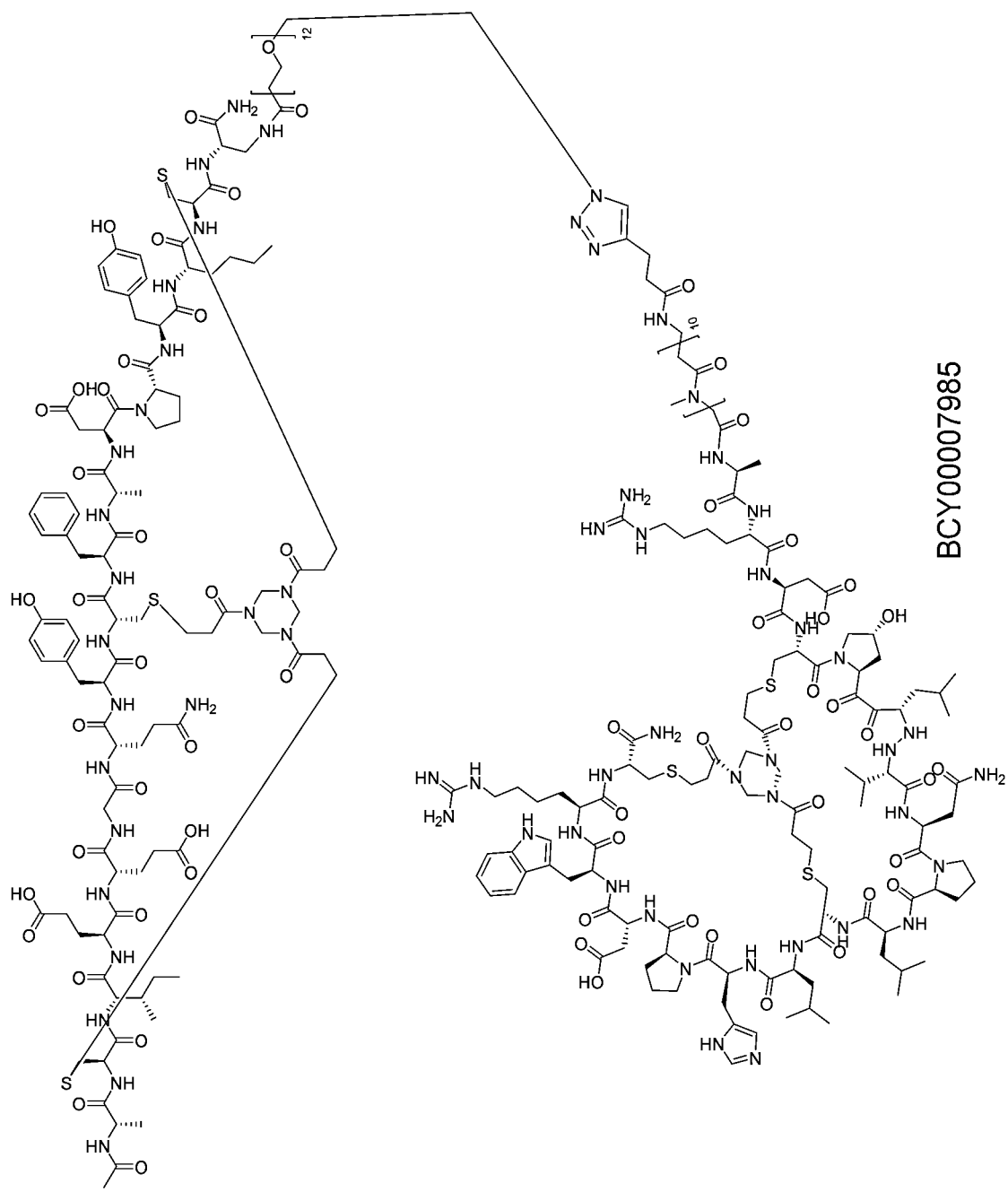
FIG. 12: Formula of BCY7985.
Figure 13:
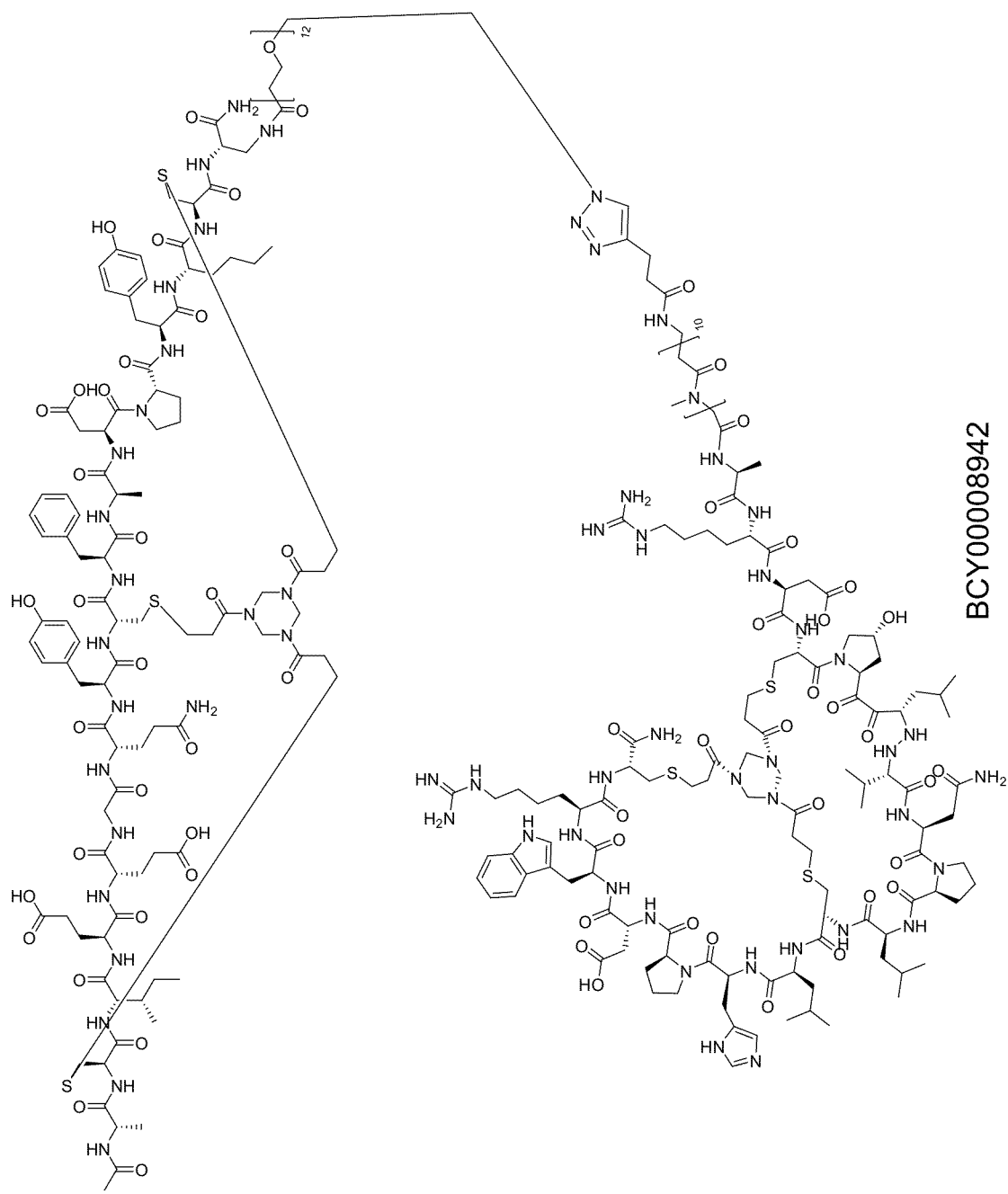
FIG. 13: Formula of BCY8942.
Figure 14:
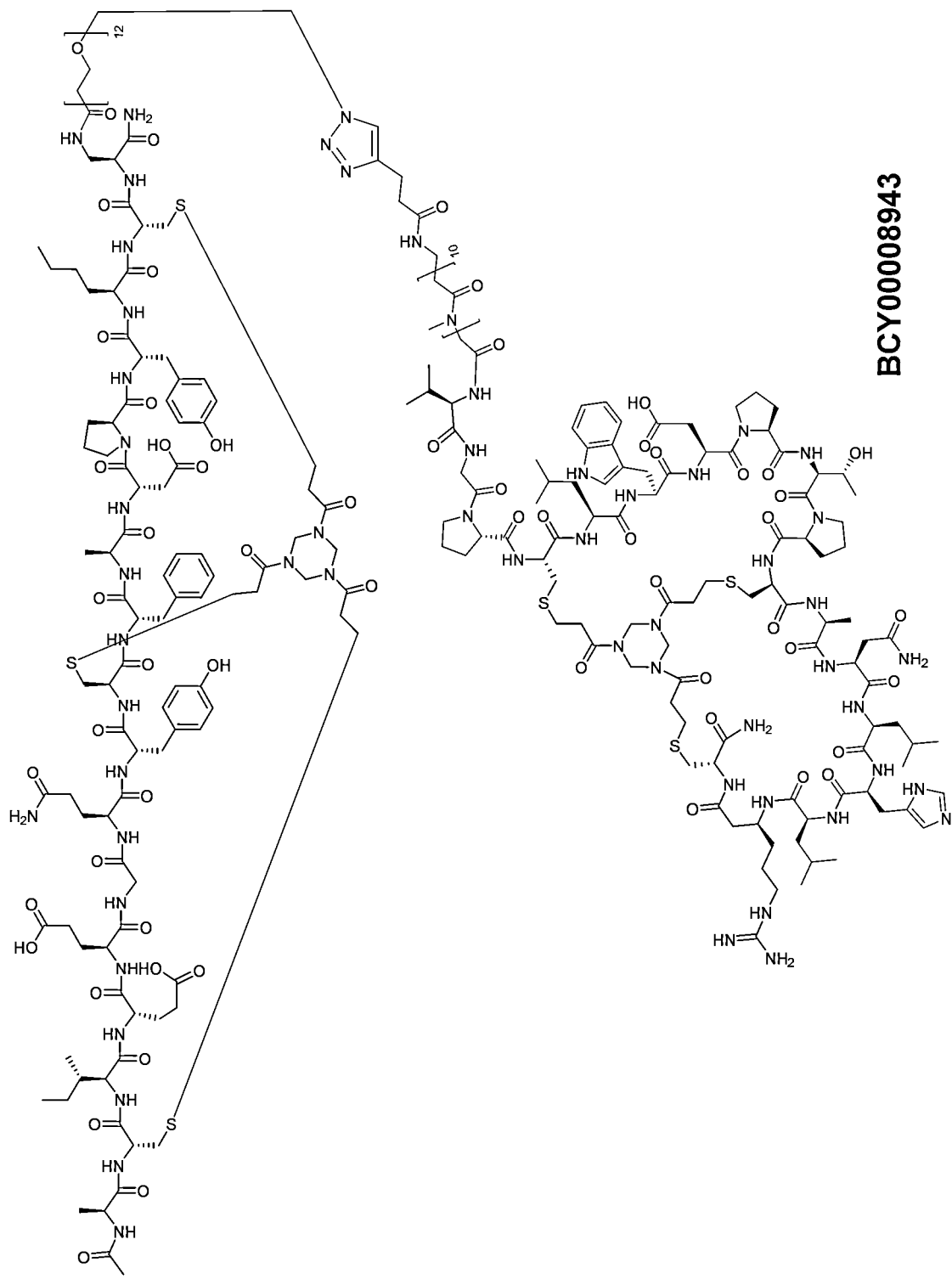
FIG. 14: Formula of BCY8943.
Figure 15:
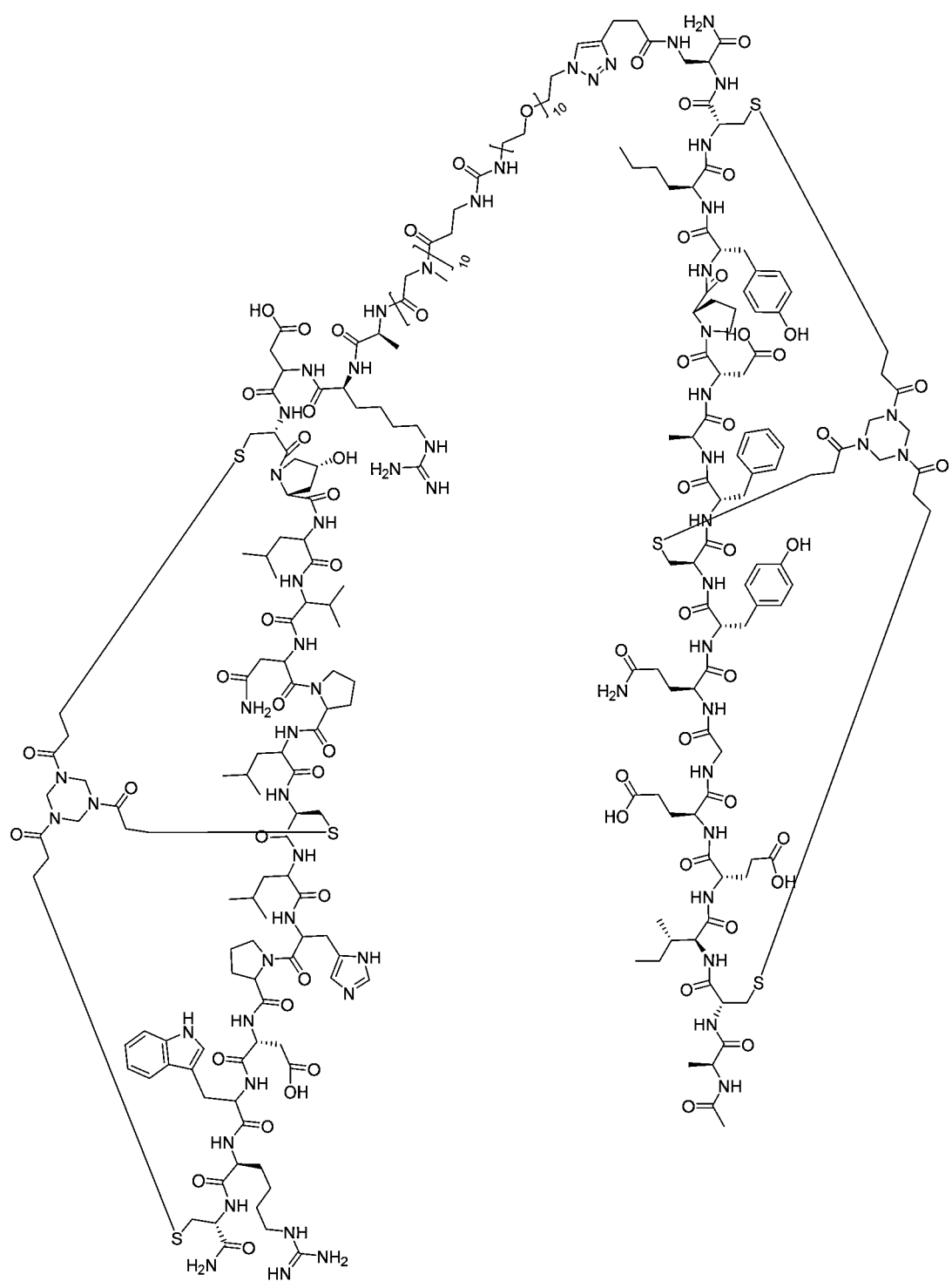
FIG. 15: Formula of BCY9647.
Figure 16:
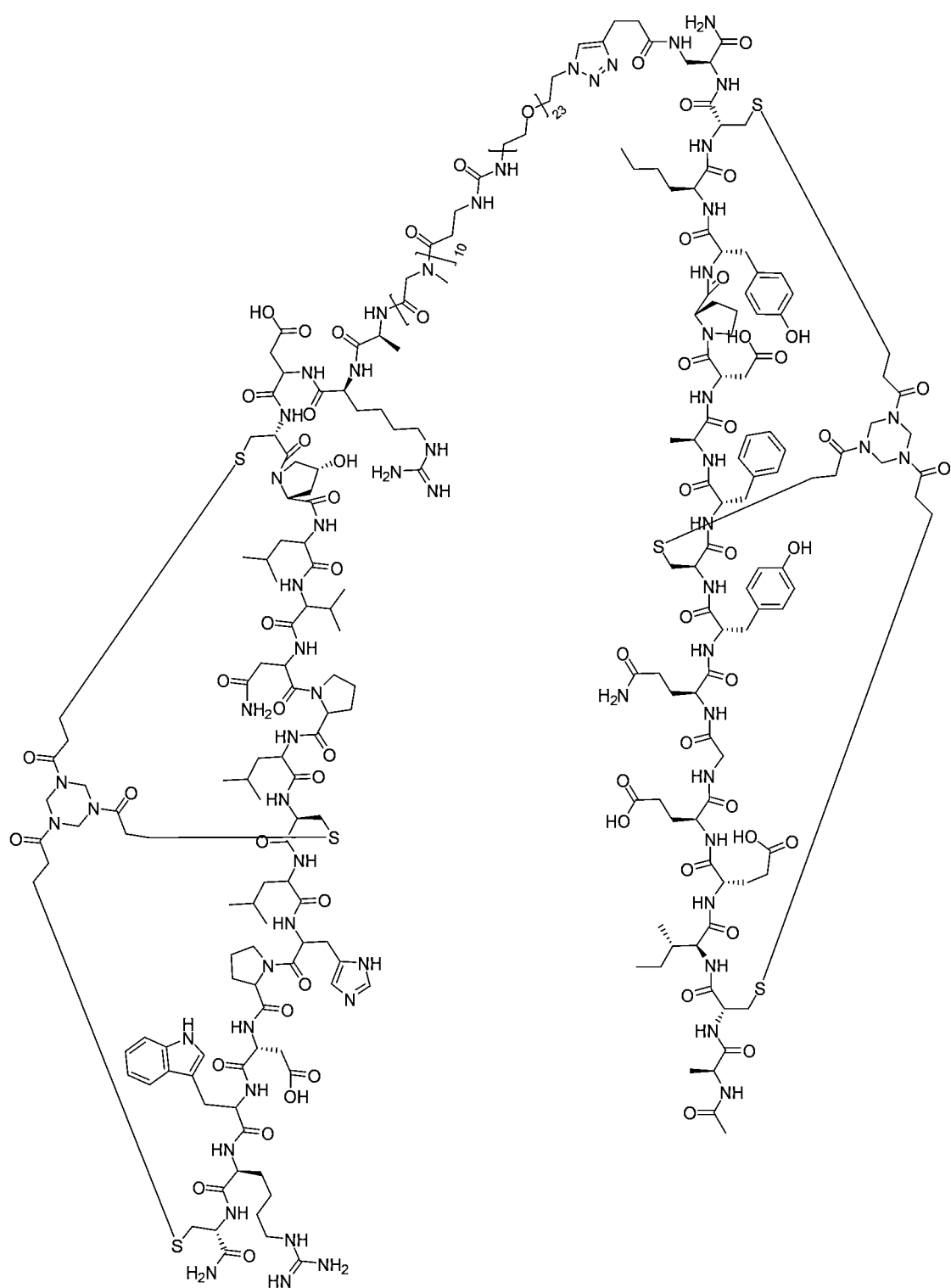
FIG. 16: Formula of BCY9648.
Figure 17:
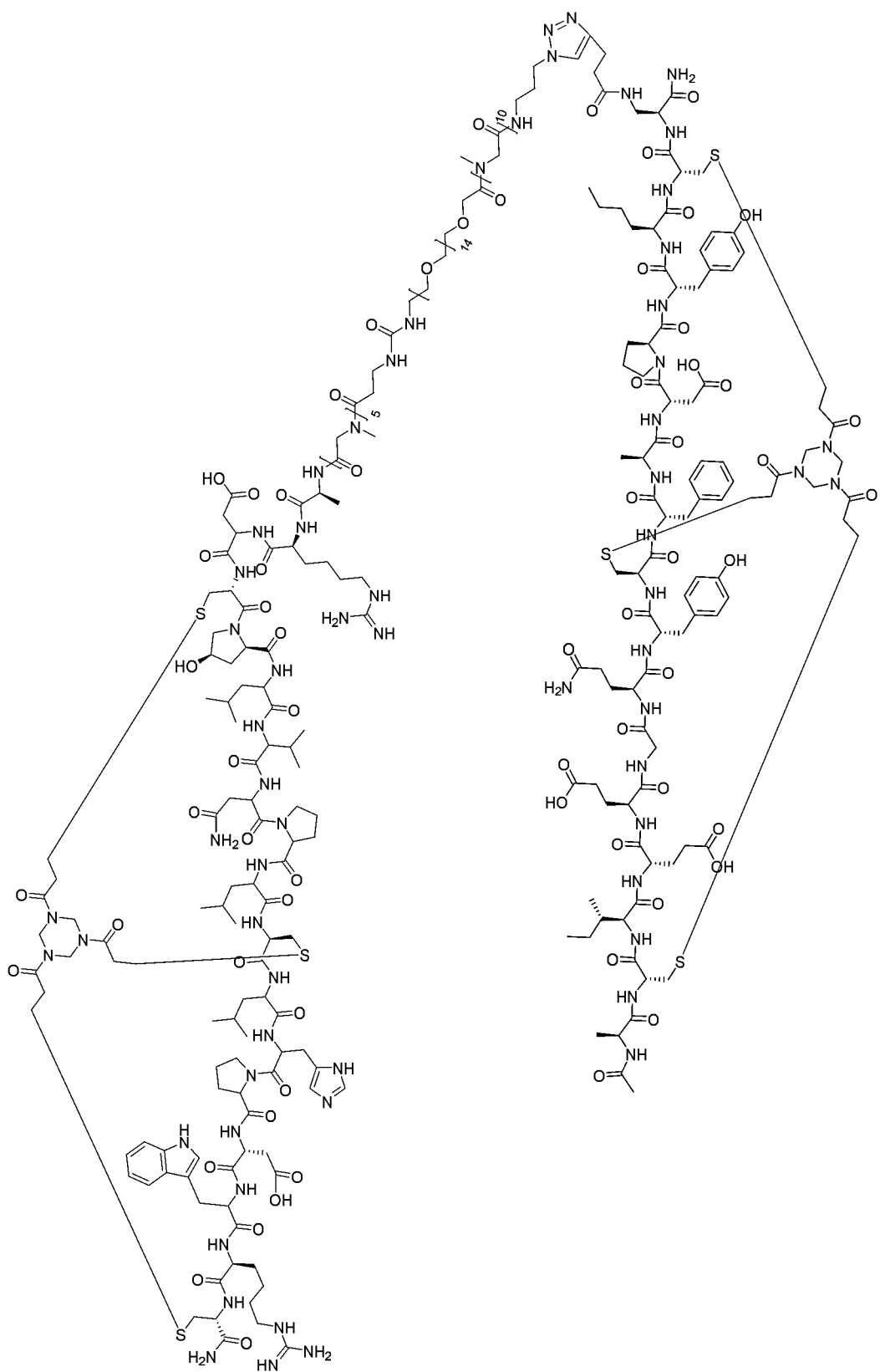
FIG. 17: Formula of BCY9655.
Figure 18:
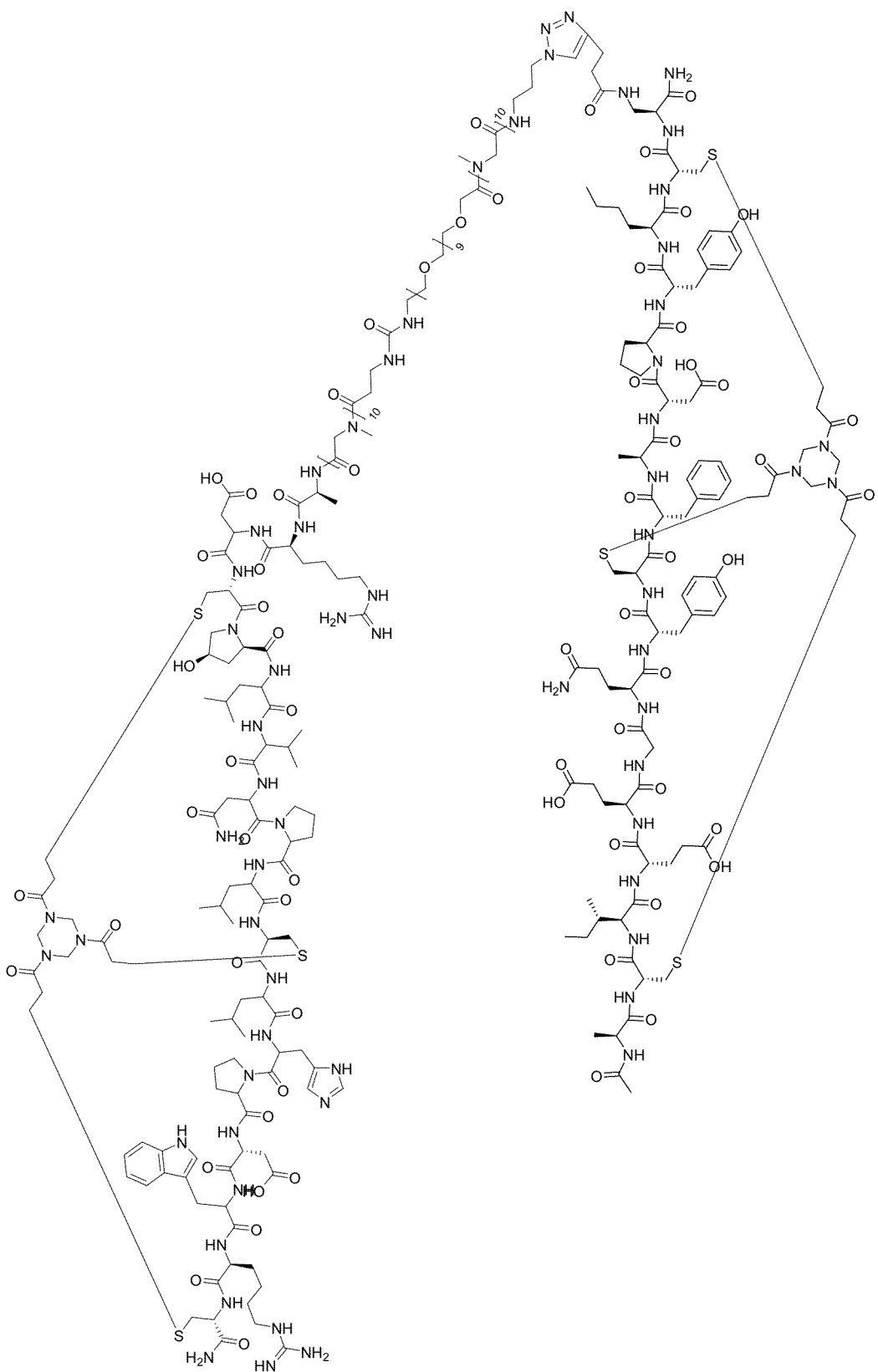
FIG. 18: Formula of BCY9656.
Figure 19:
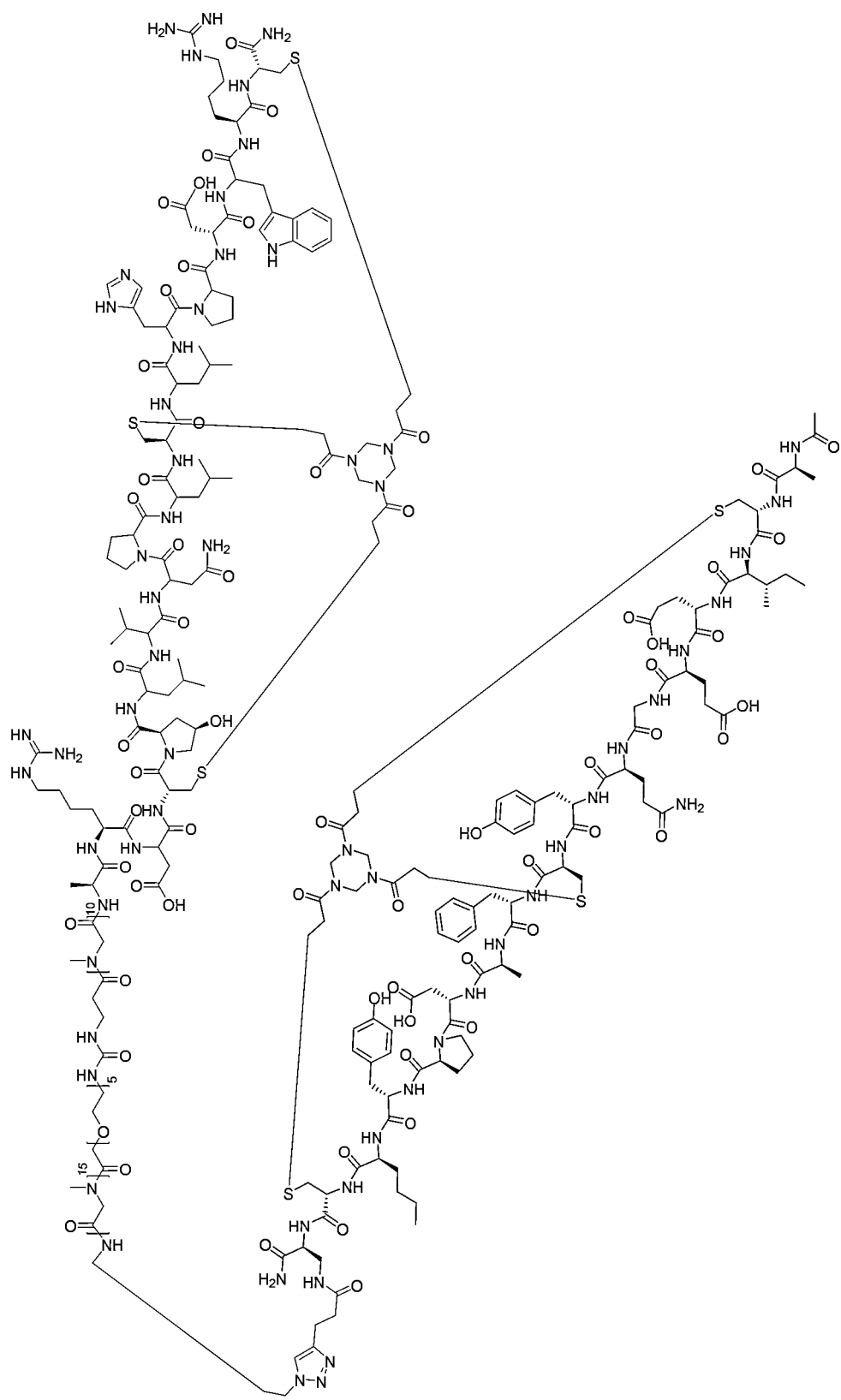
FIG. 19: Formula of BCY9657.
Figure 20:
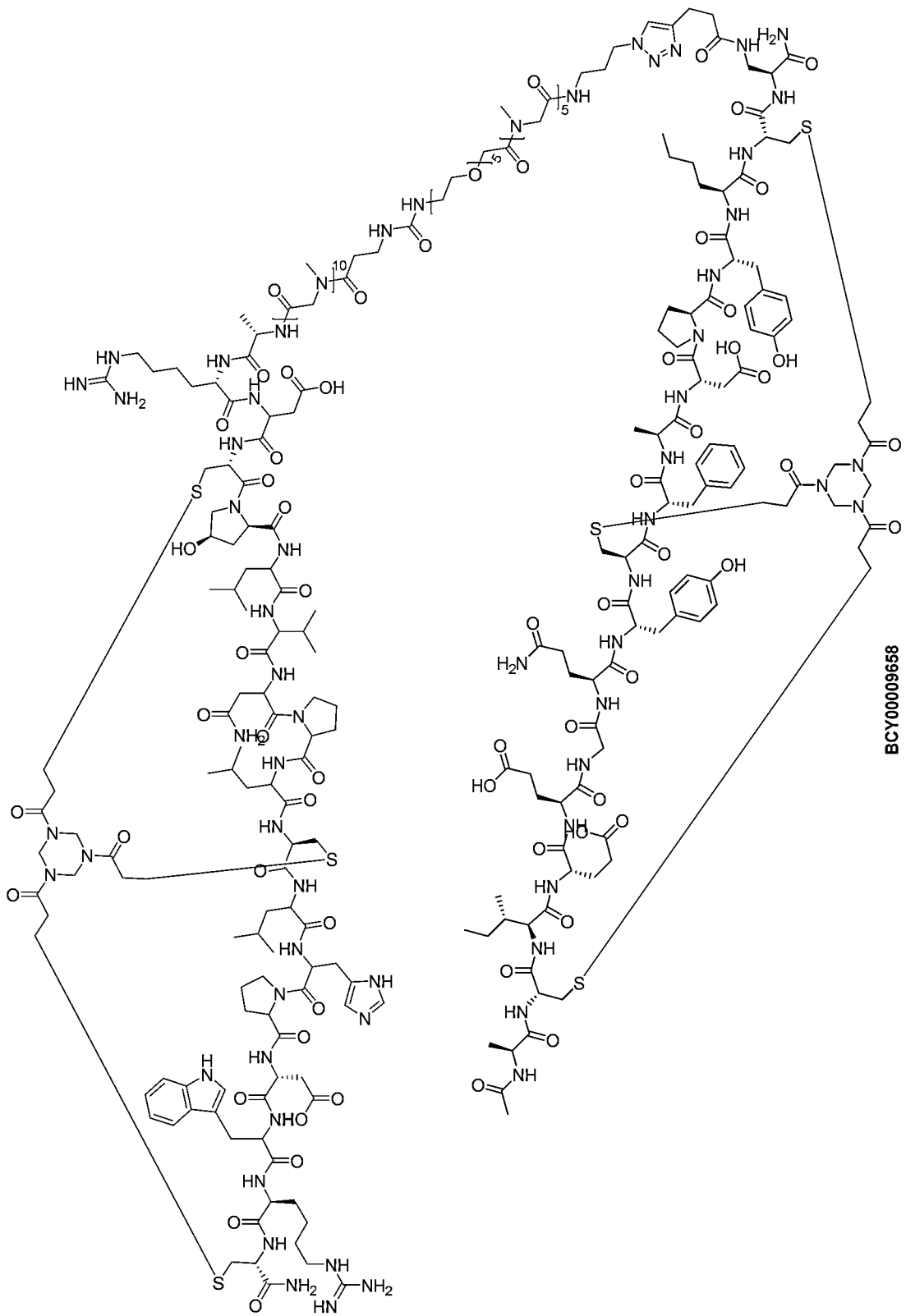
FIG. 20: Formula of BCY9658.
Figure 21:
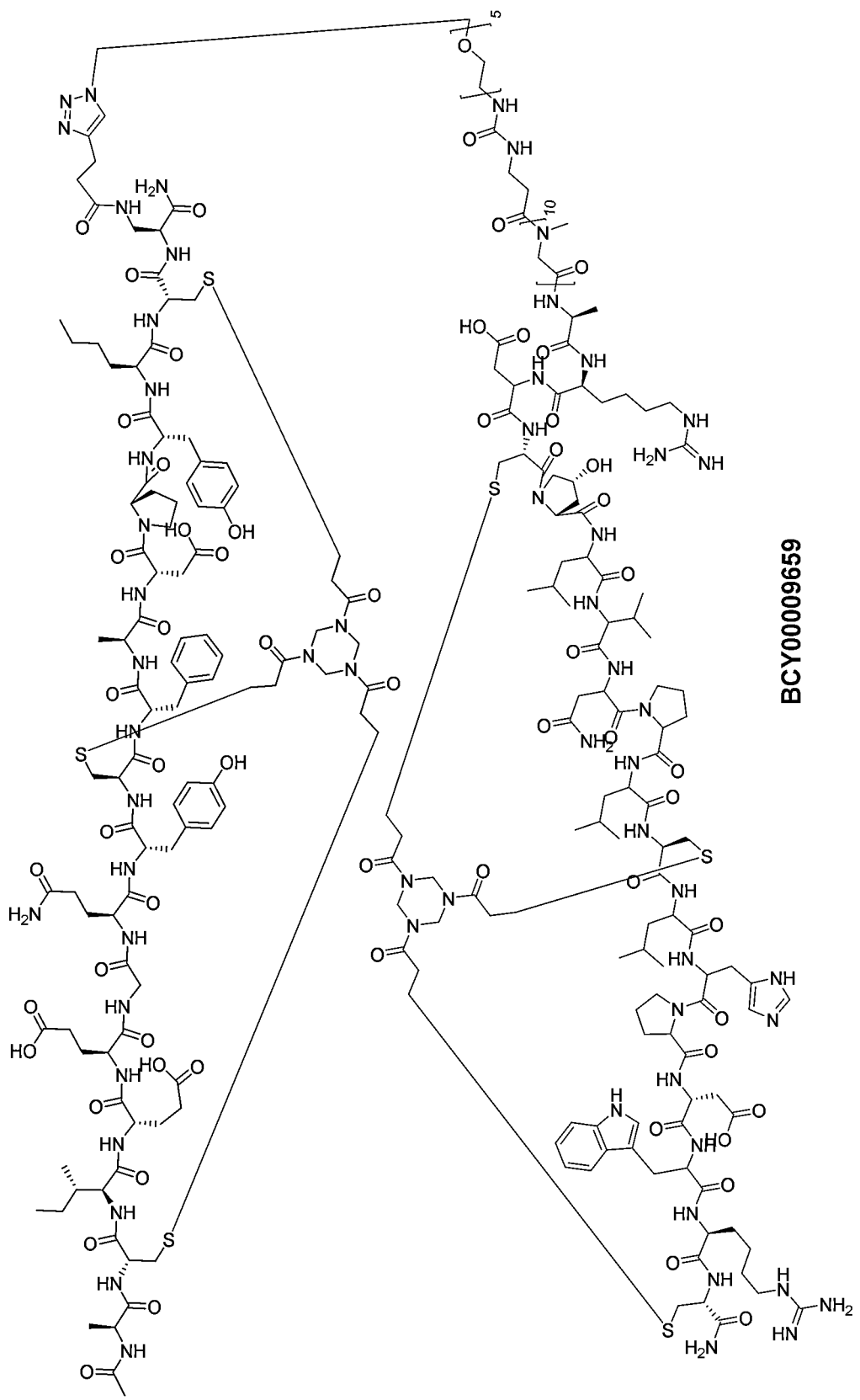
FIG. 21: Formula of BCY9659.
Figure 22:
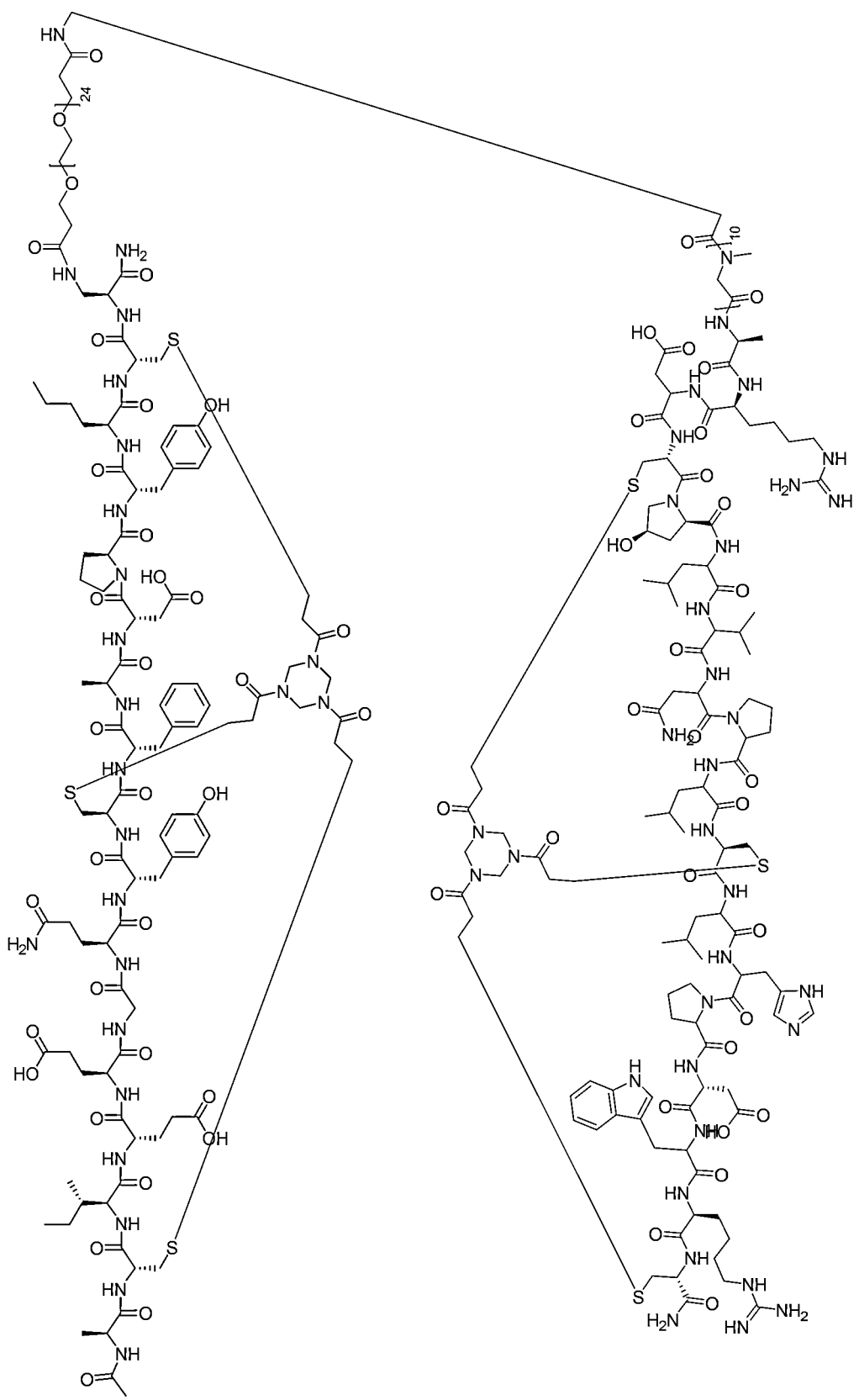
FIG. 22: Formula of BCY9758.
Figure 23:
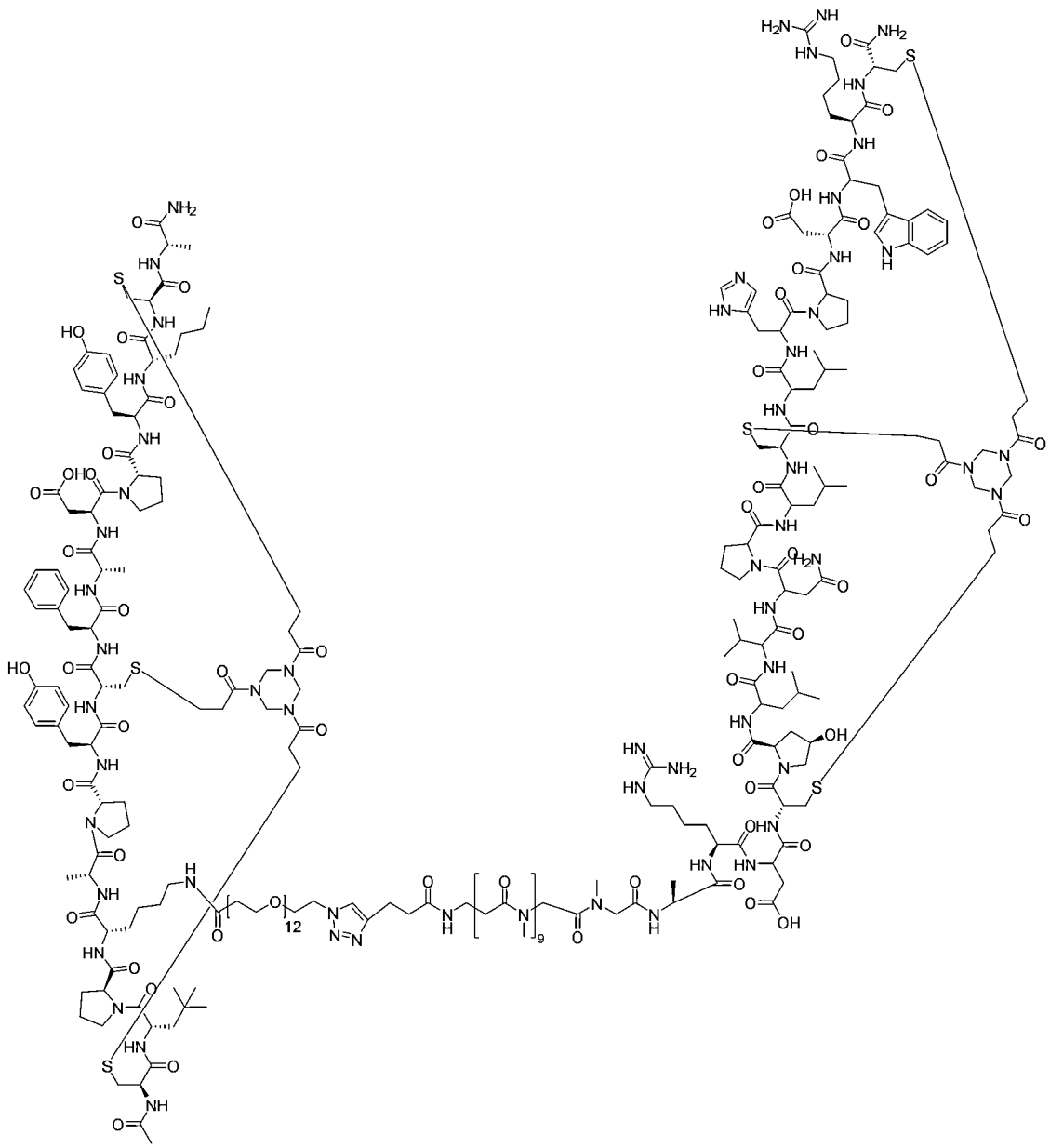
FIG. 23: Formula of BCY10568.
Figure 24:
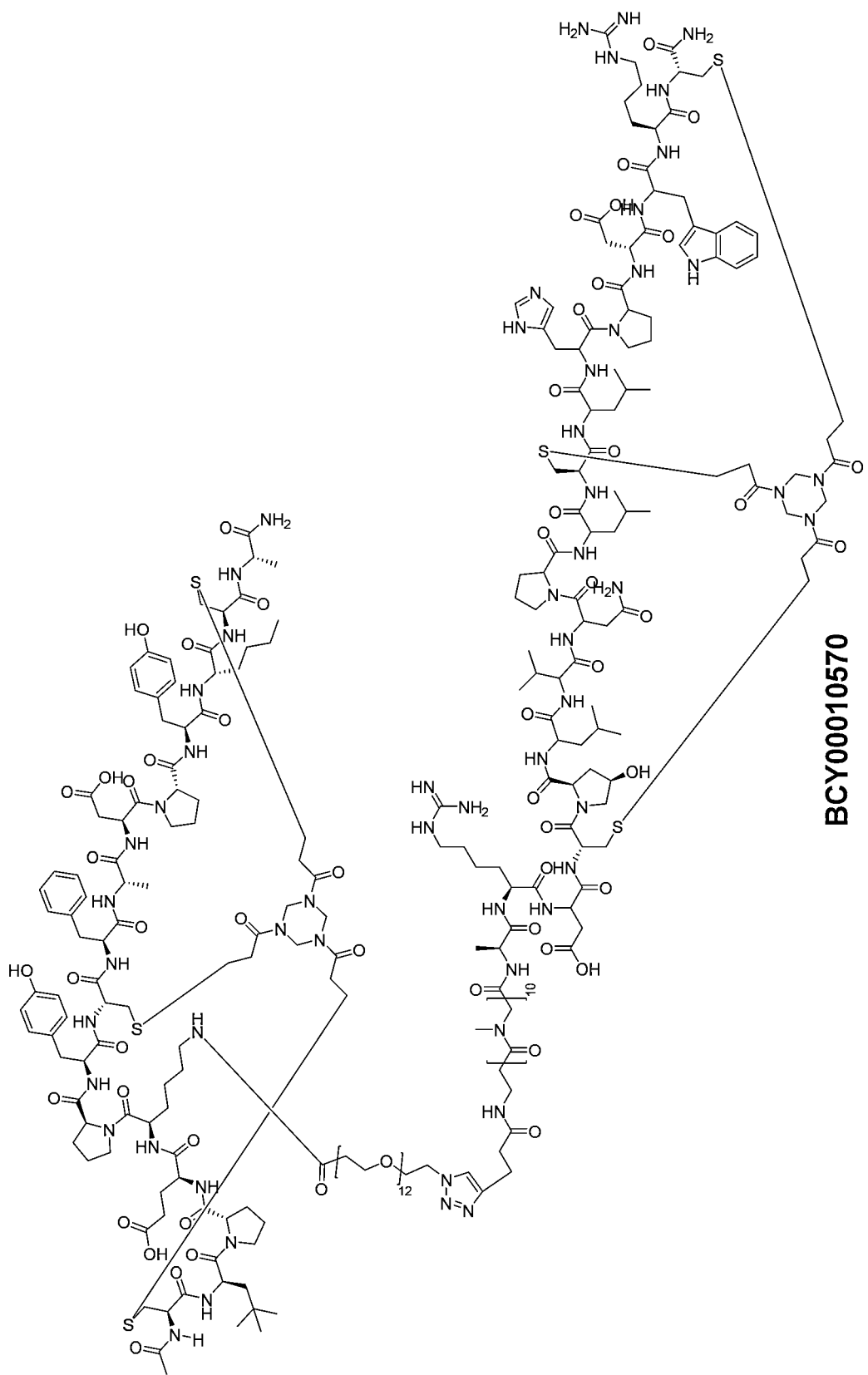
FIG. 24: Formula of BCY10570.
Figure 25:
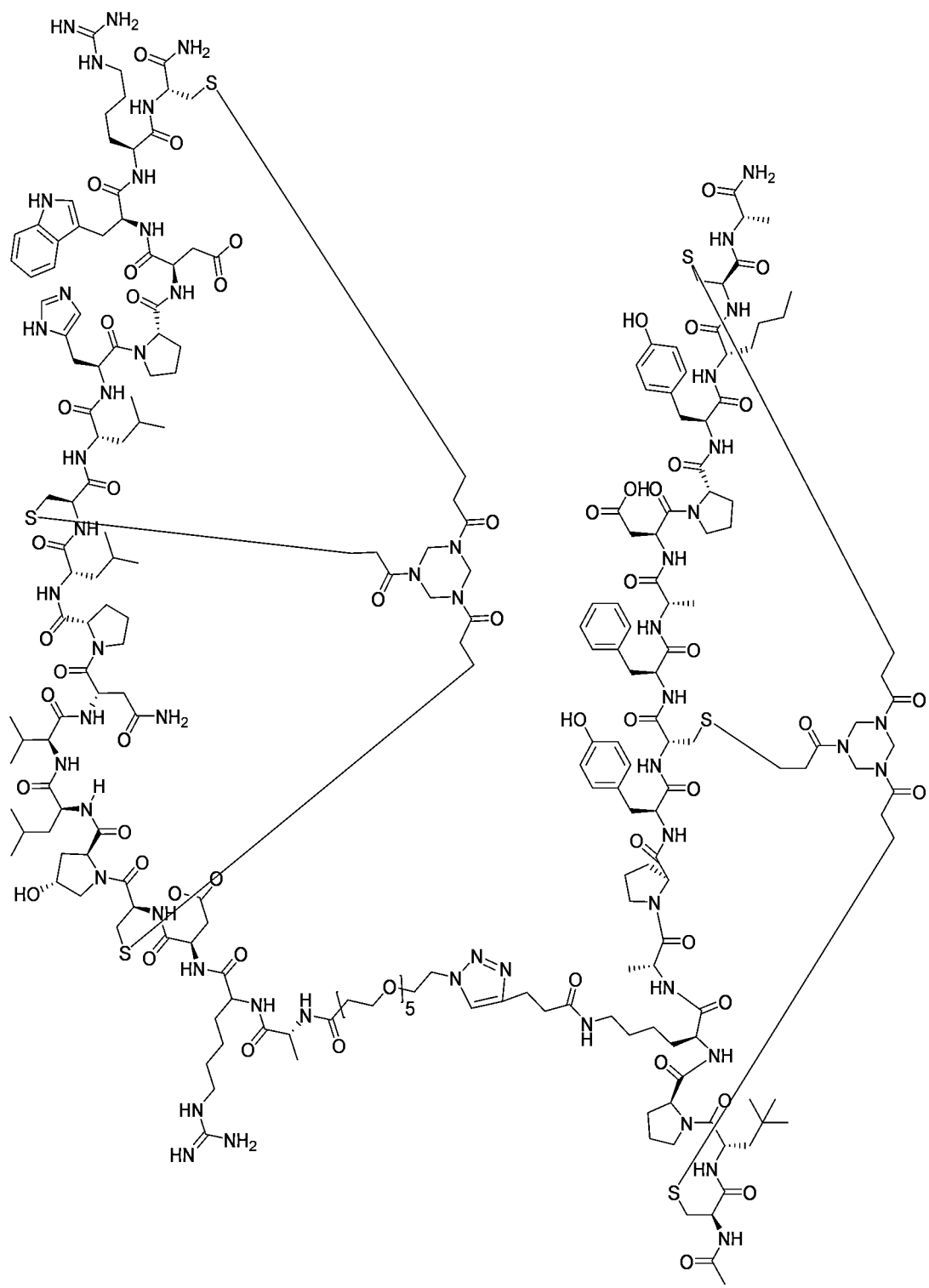
FIG. 25: Formula of BCY10574.
Figure 26:
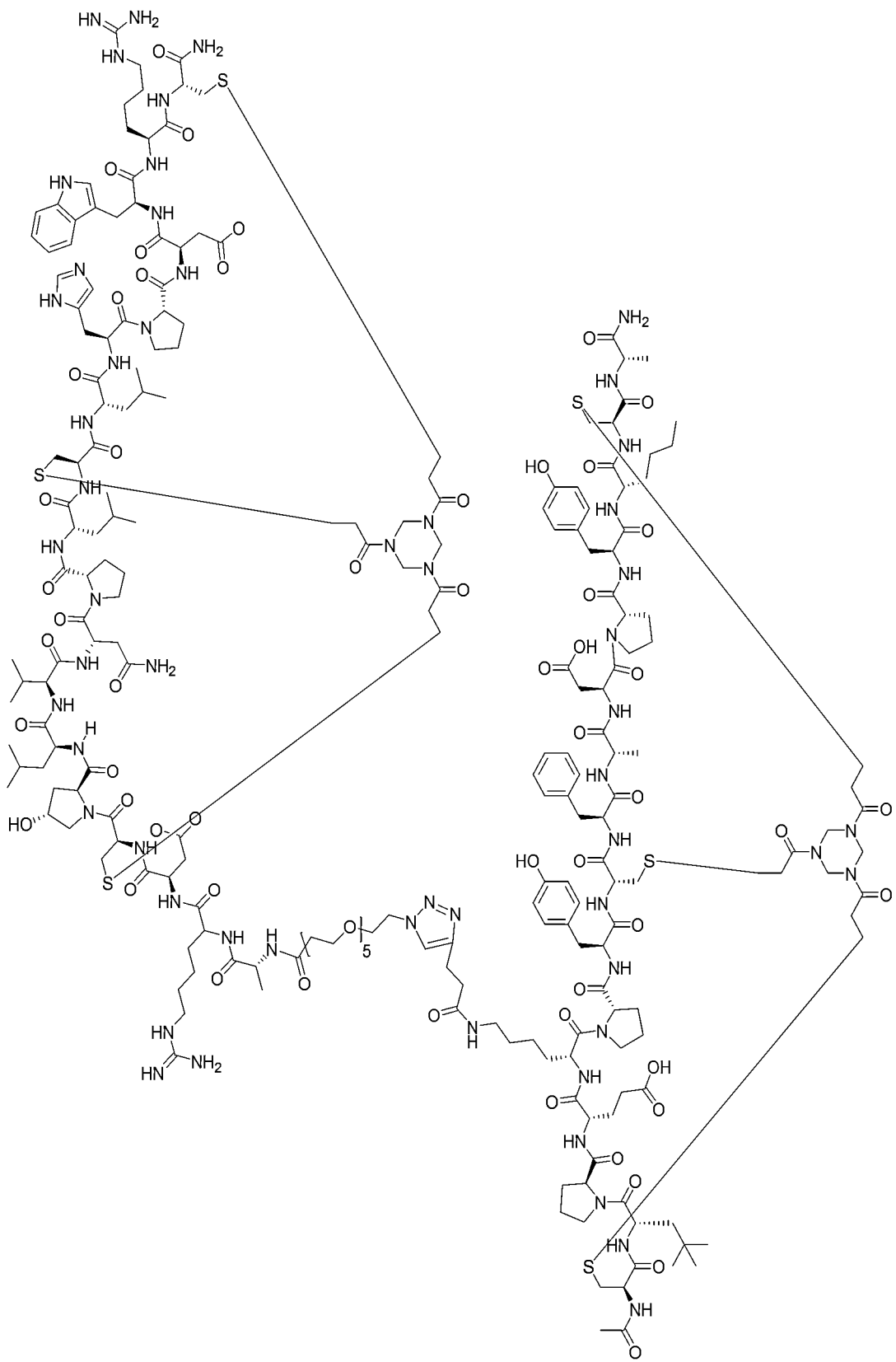
FIG. 26: Formula of BCY10575.
Figure 27:
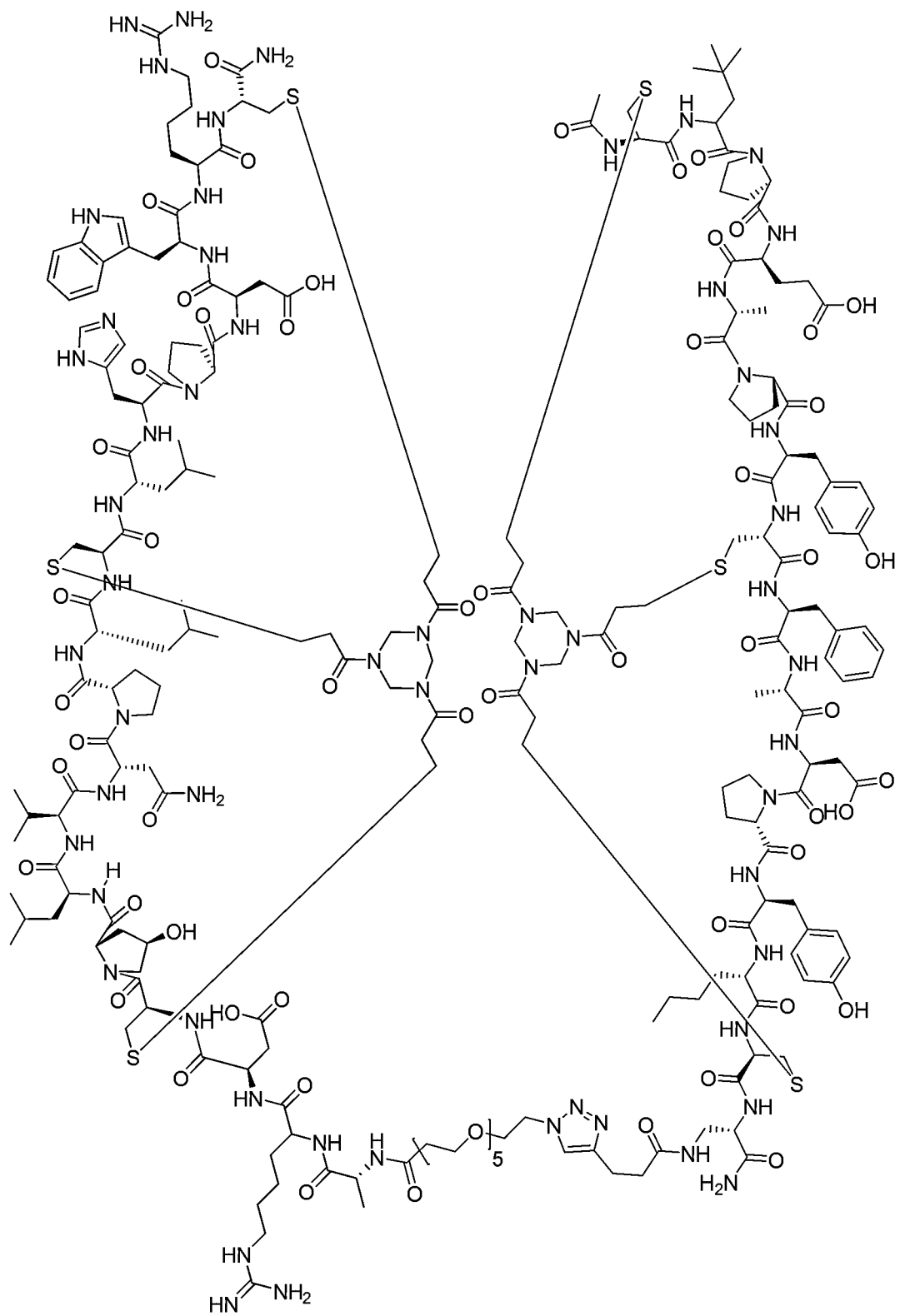
FIG. 27: Formula of BCY10576.
Figure 28:
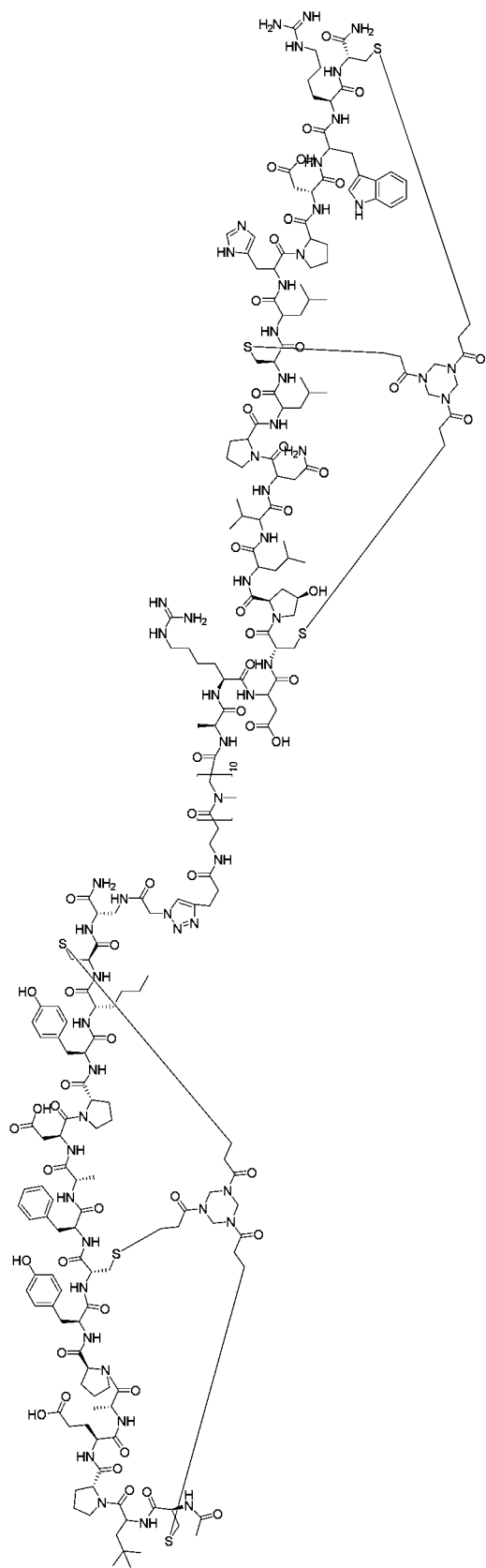
FIG. 28: Formula of BCY10577.
Figure 29:
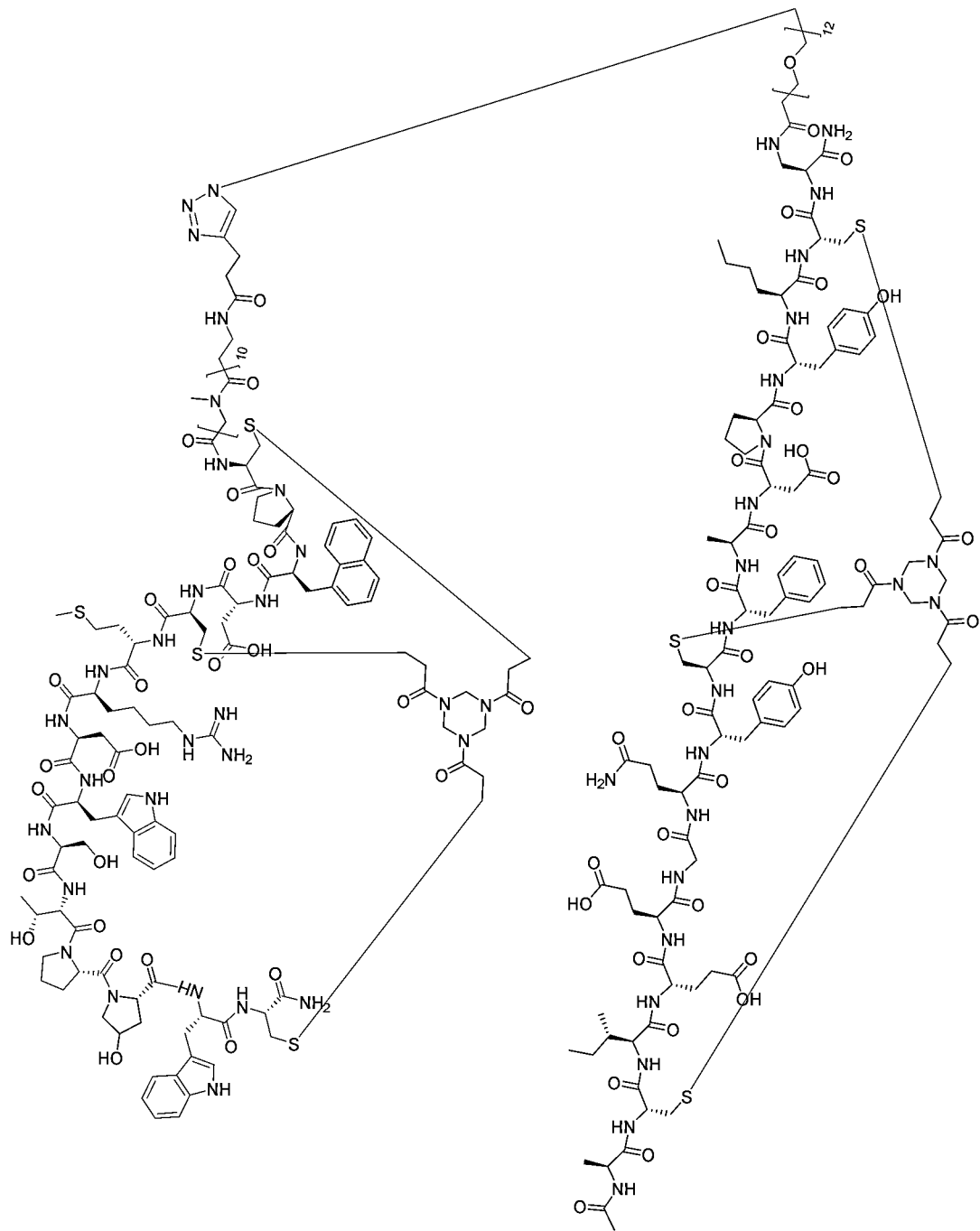
FIG. 29: Formula of BCY8854.
Figure 30:
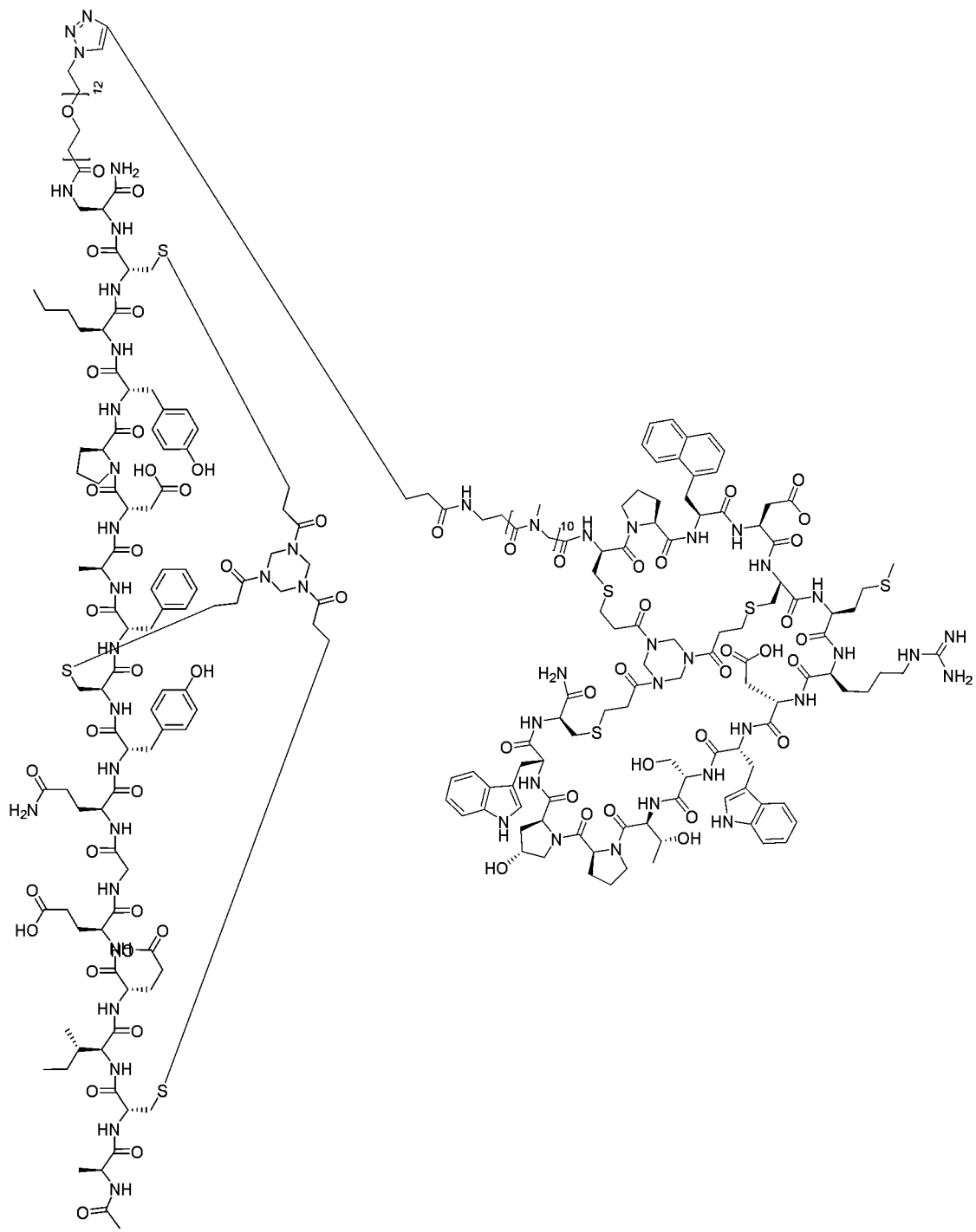
FIG. 30: Formula of BCY9350.
Figure 31:
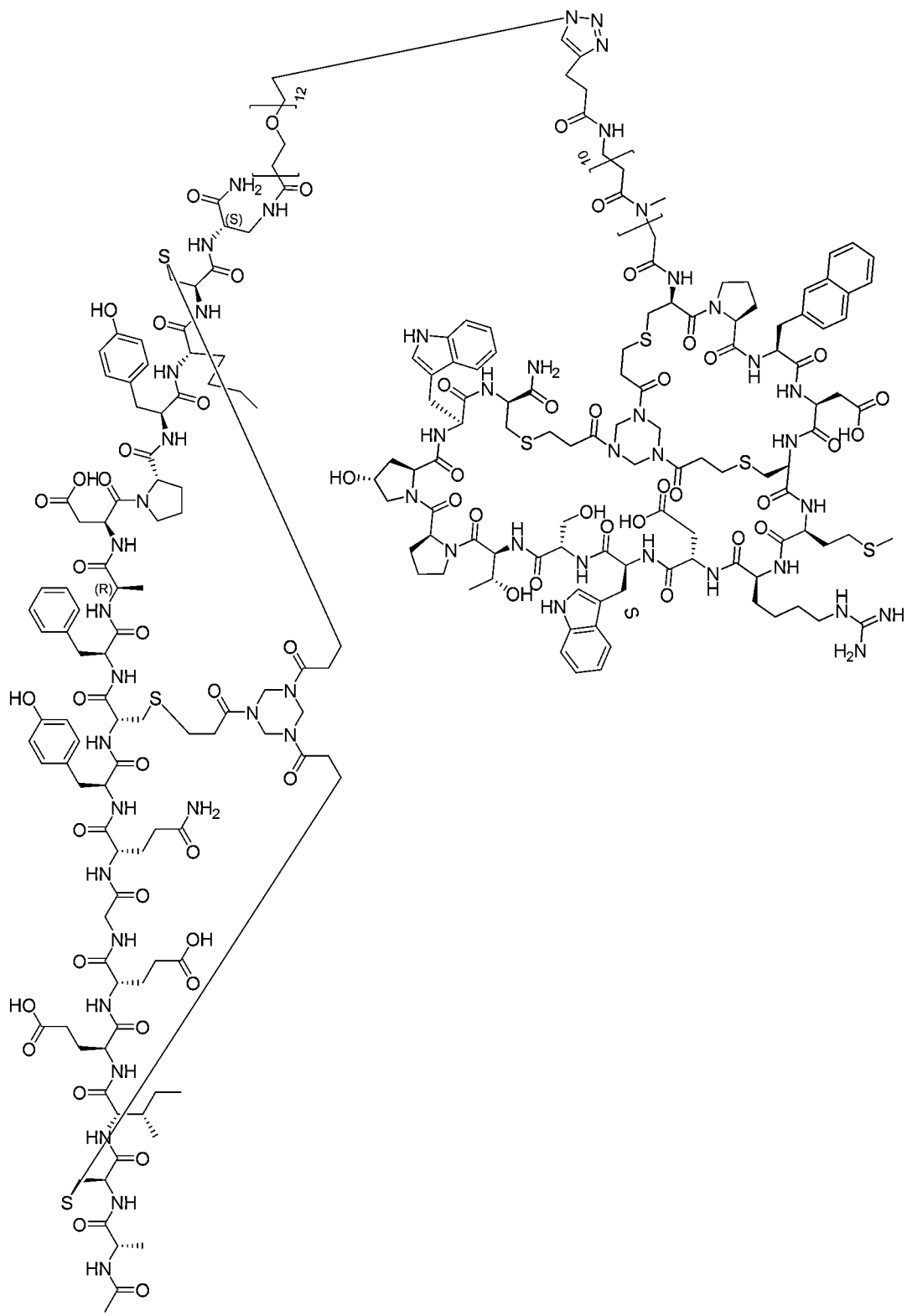
FIG. 31: Formula of BCY9351.
Figure 32:
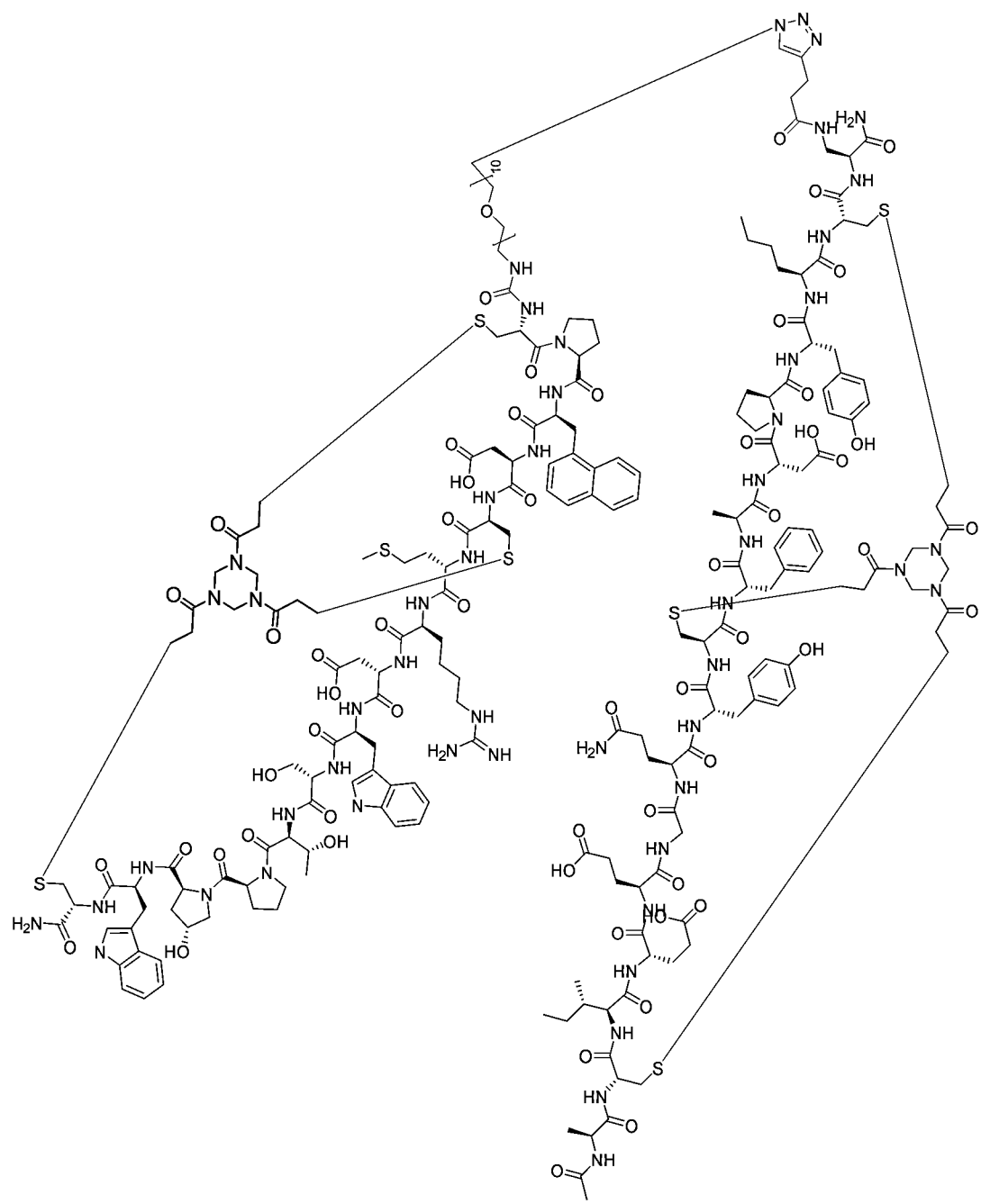
FIG. 32: Formula of BCY9399.
Figure 33:
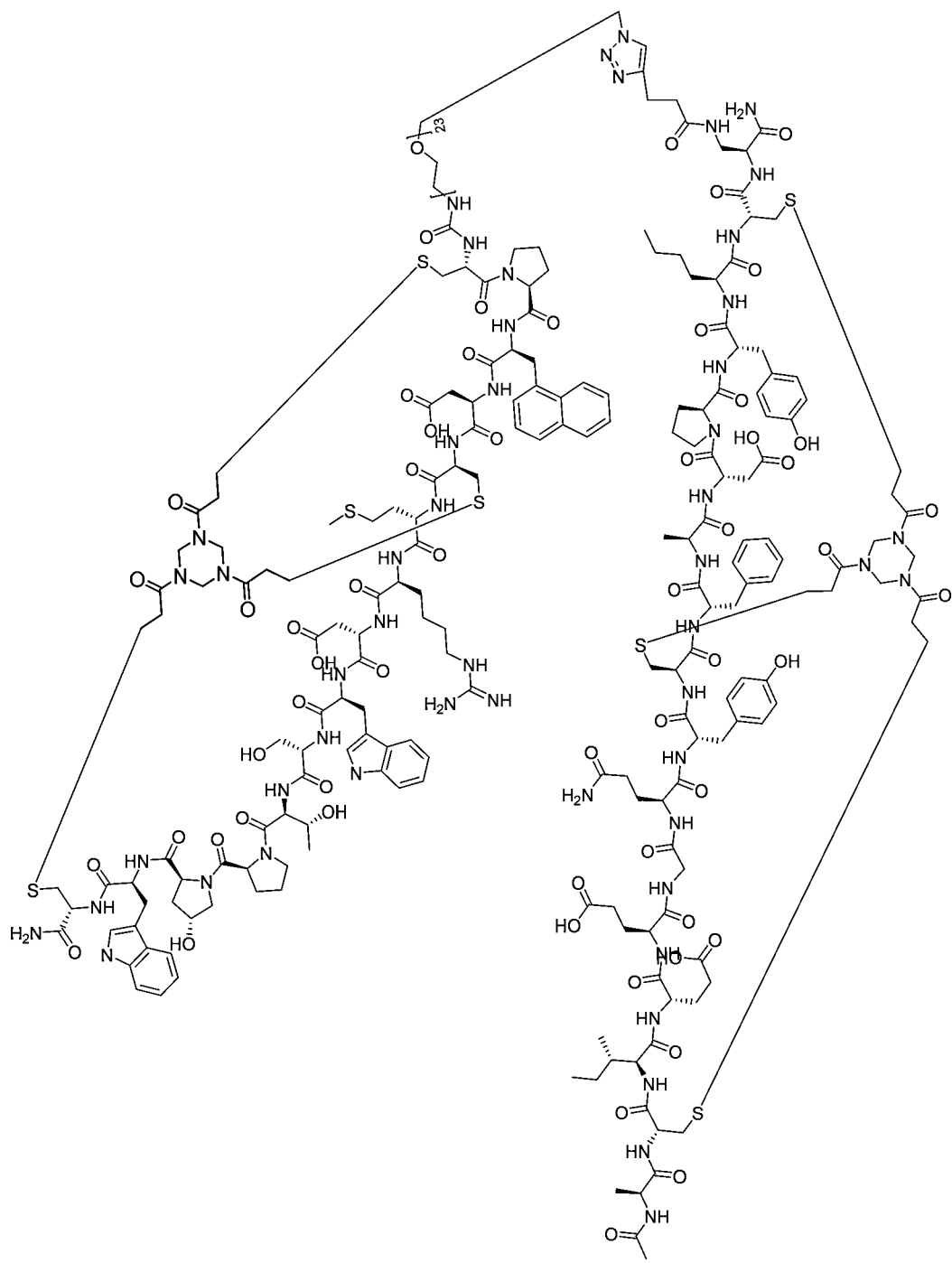
FIG. 33: Formula of BCY9400.
Figure 34:
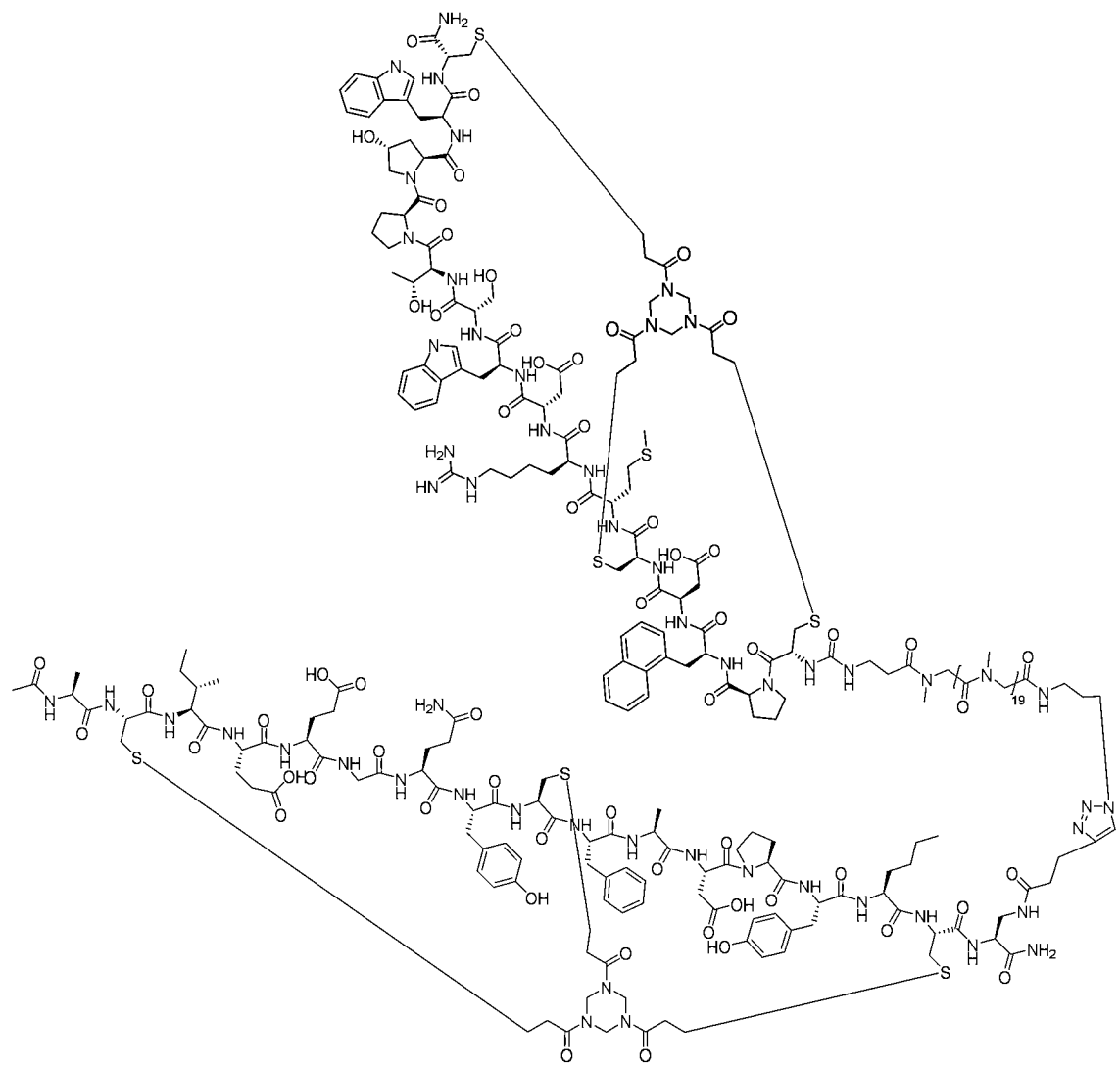
FIG. 34: Formula of BCY9401.
Figure 35:
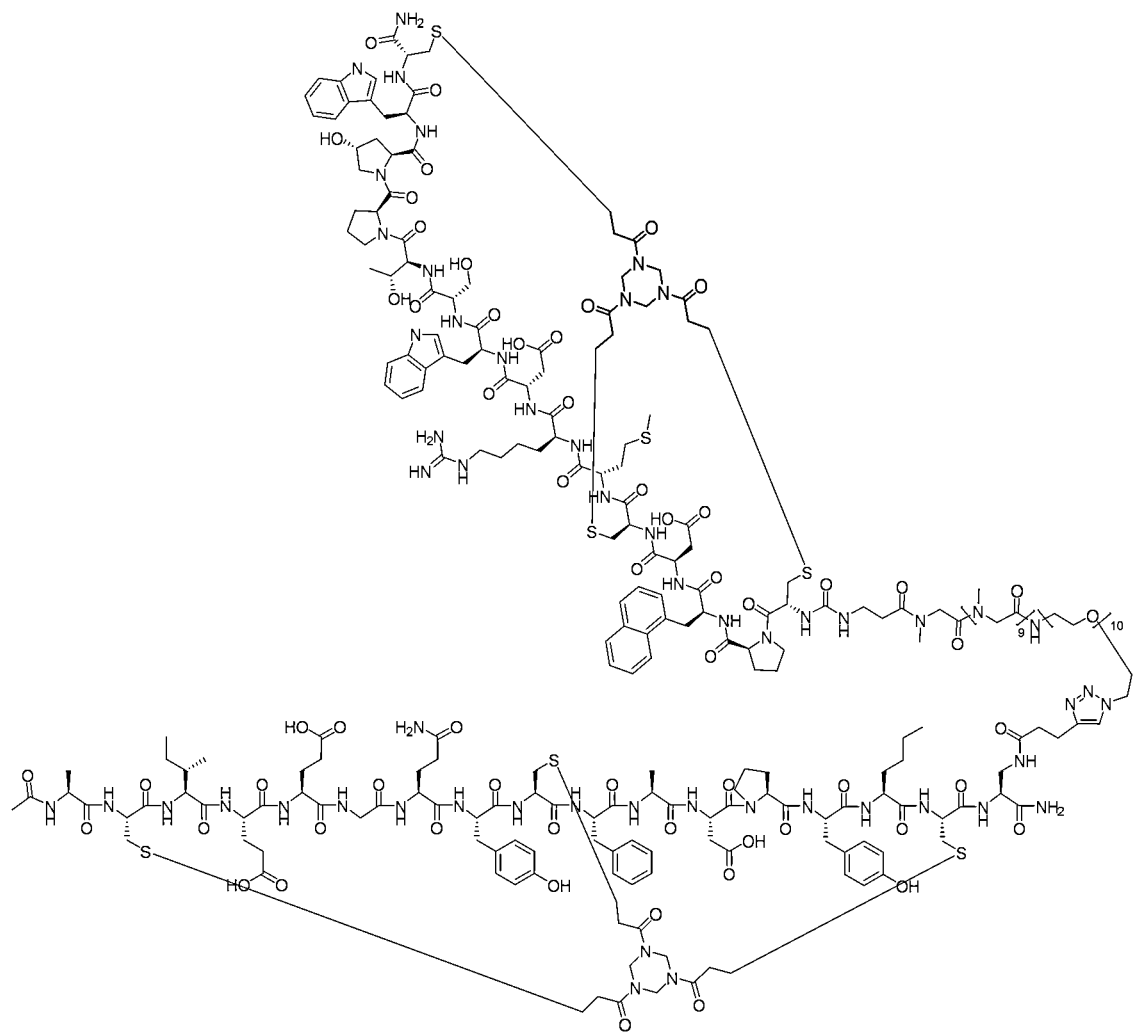
FIG. 35: Formula of BCY9403.
Figure 36:
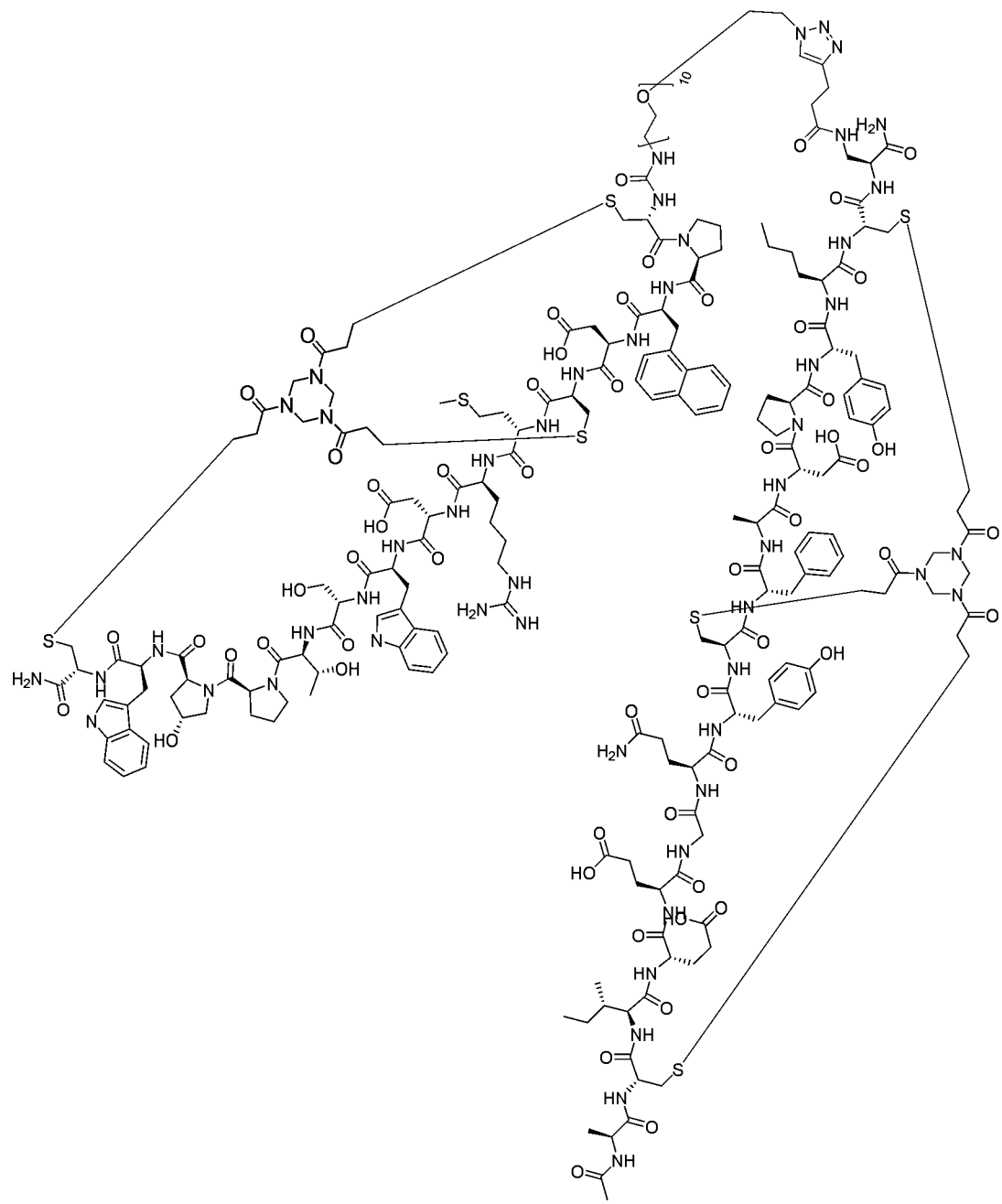
FIG. 36: Formula of BCY9405.
Figure 37:
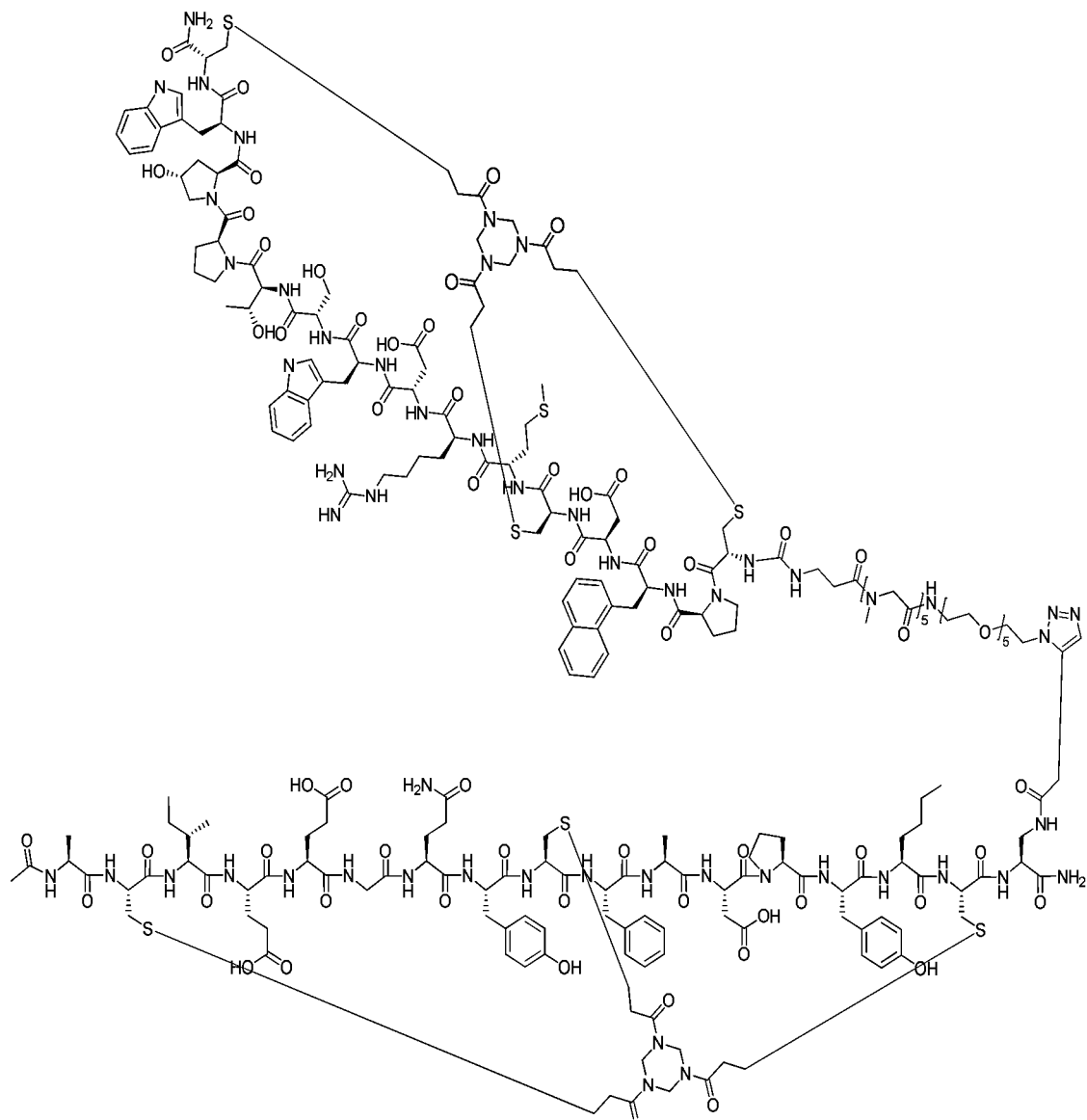
FIG. 37: Formula of BCY9406.
Figure 38:
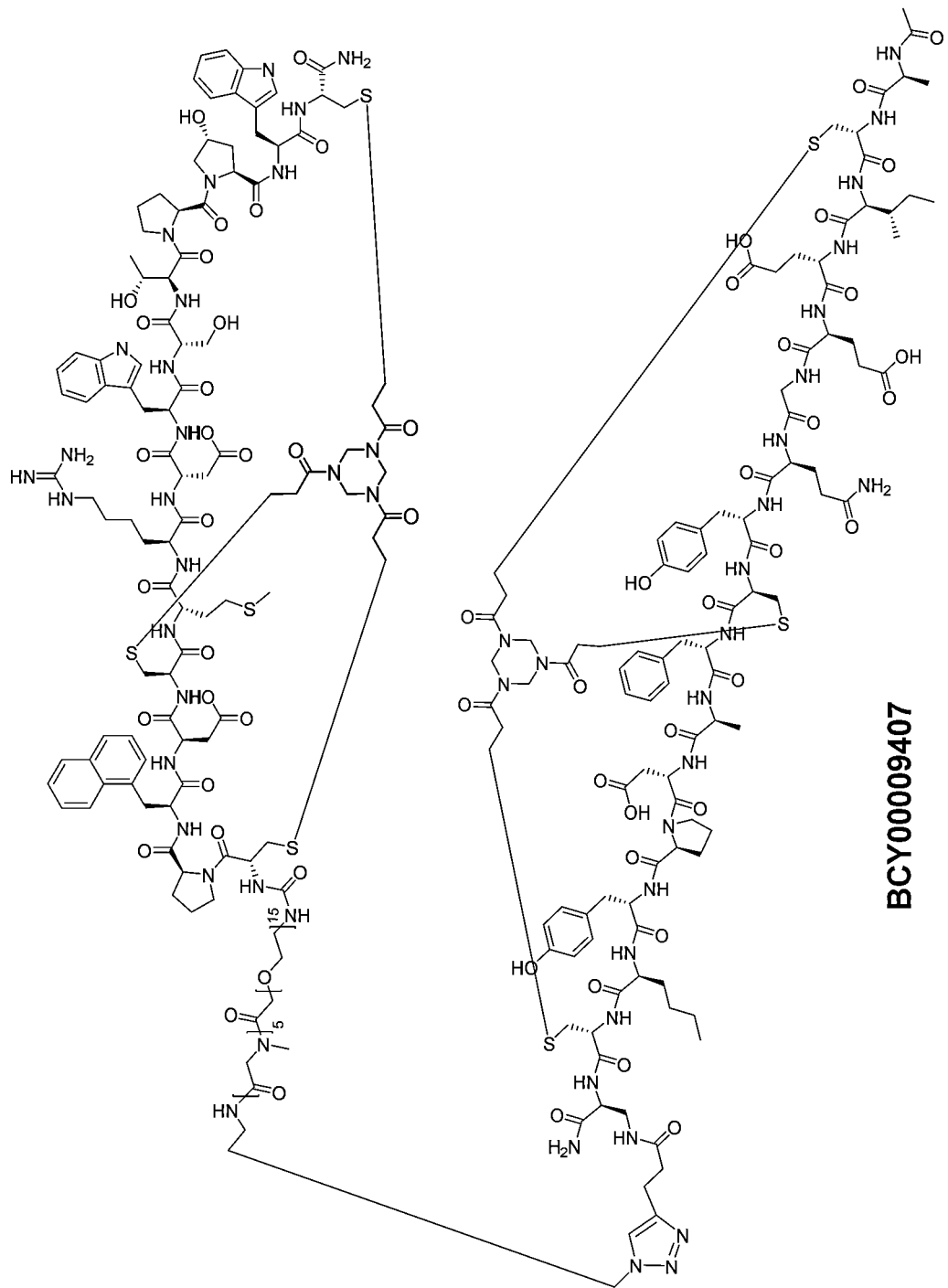
FIG. 38: Formula of BCY9407.
Figure 39:
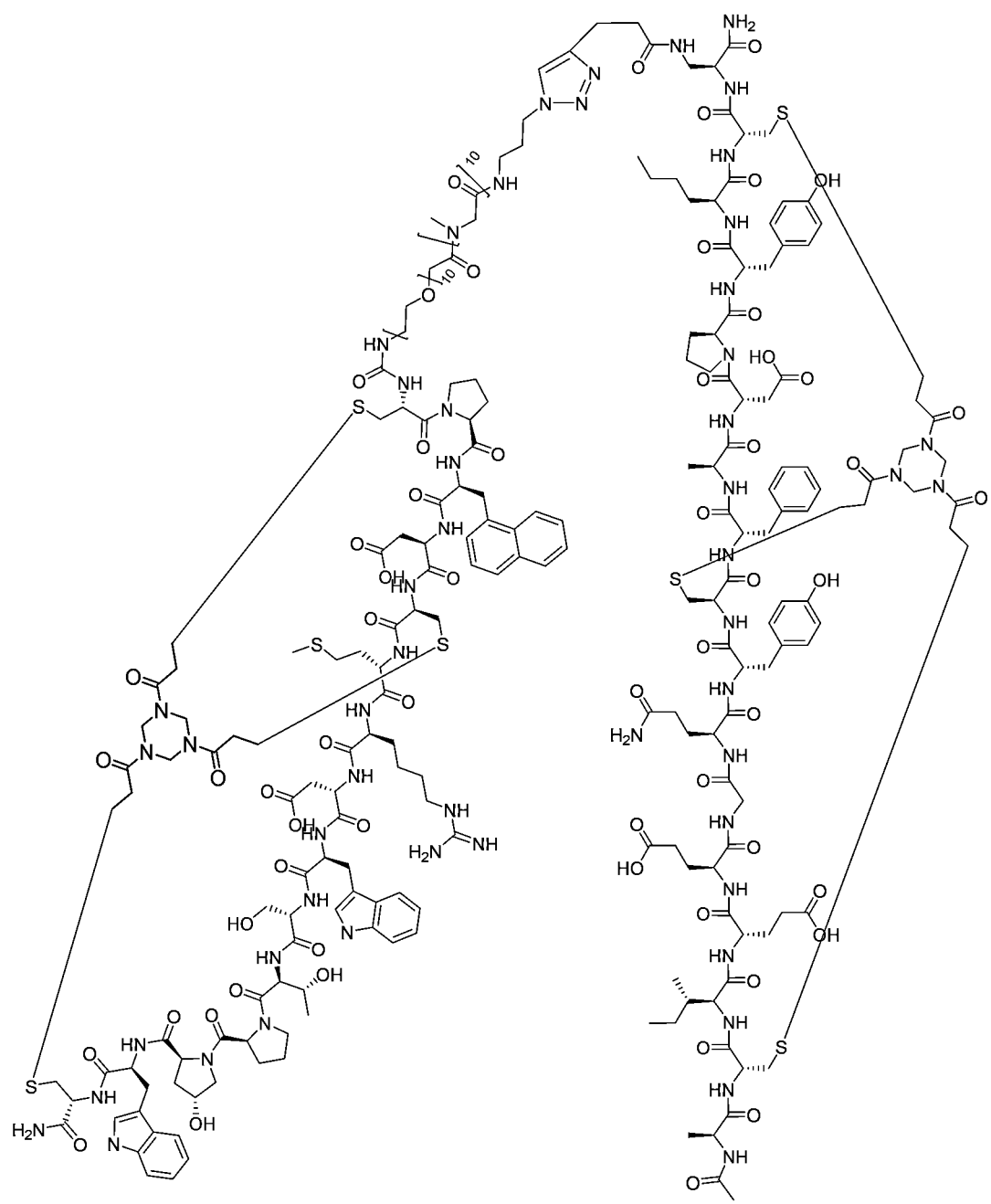
FIG. 39: Formula of BCY9408.
Figure 40:
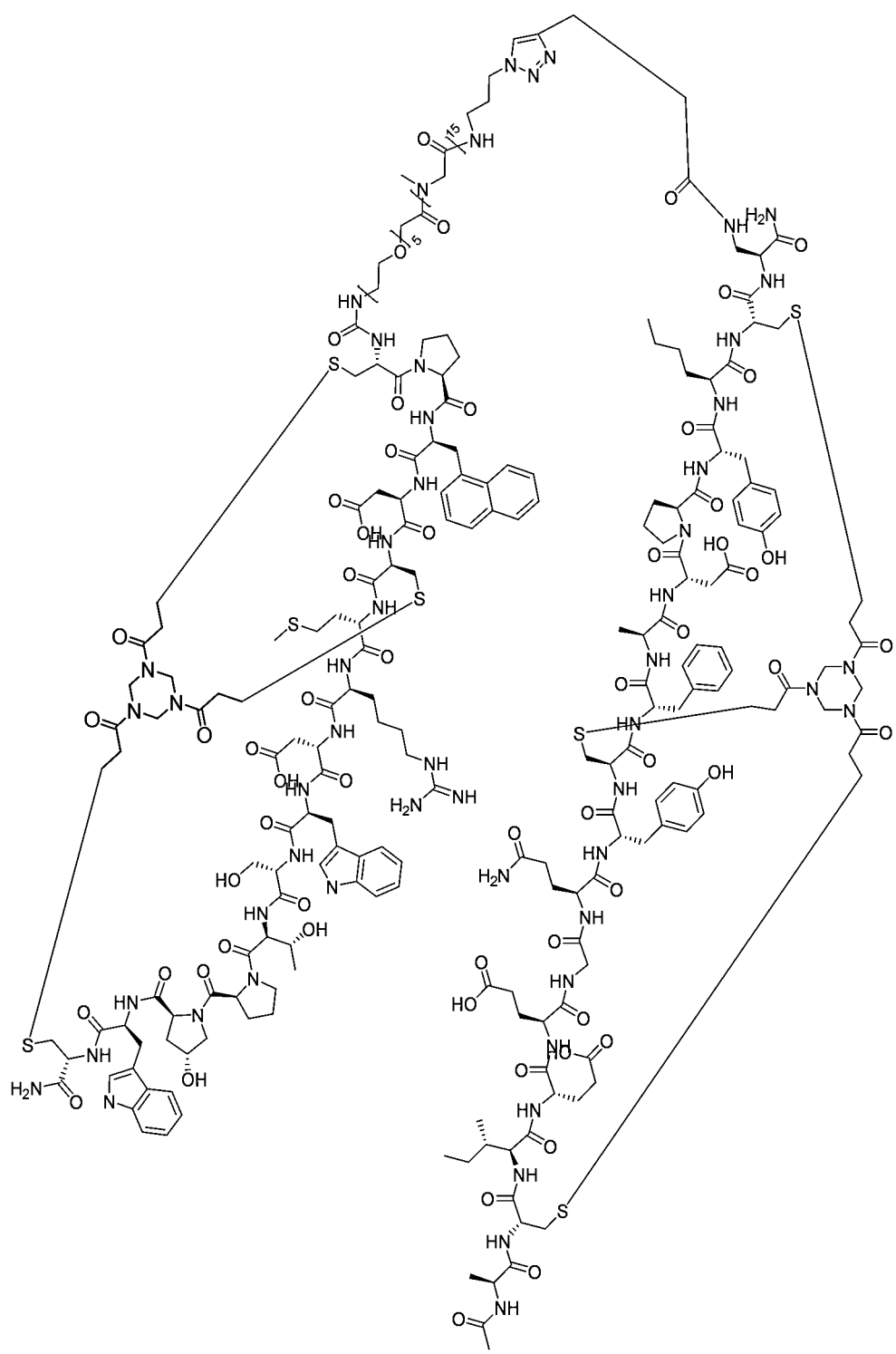
FIG. 40: Formula of BCY9409.
Figure 41:
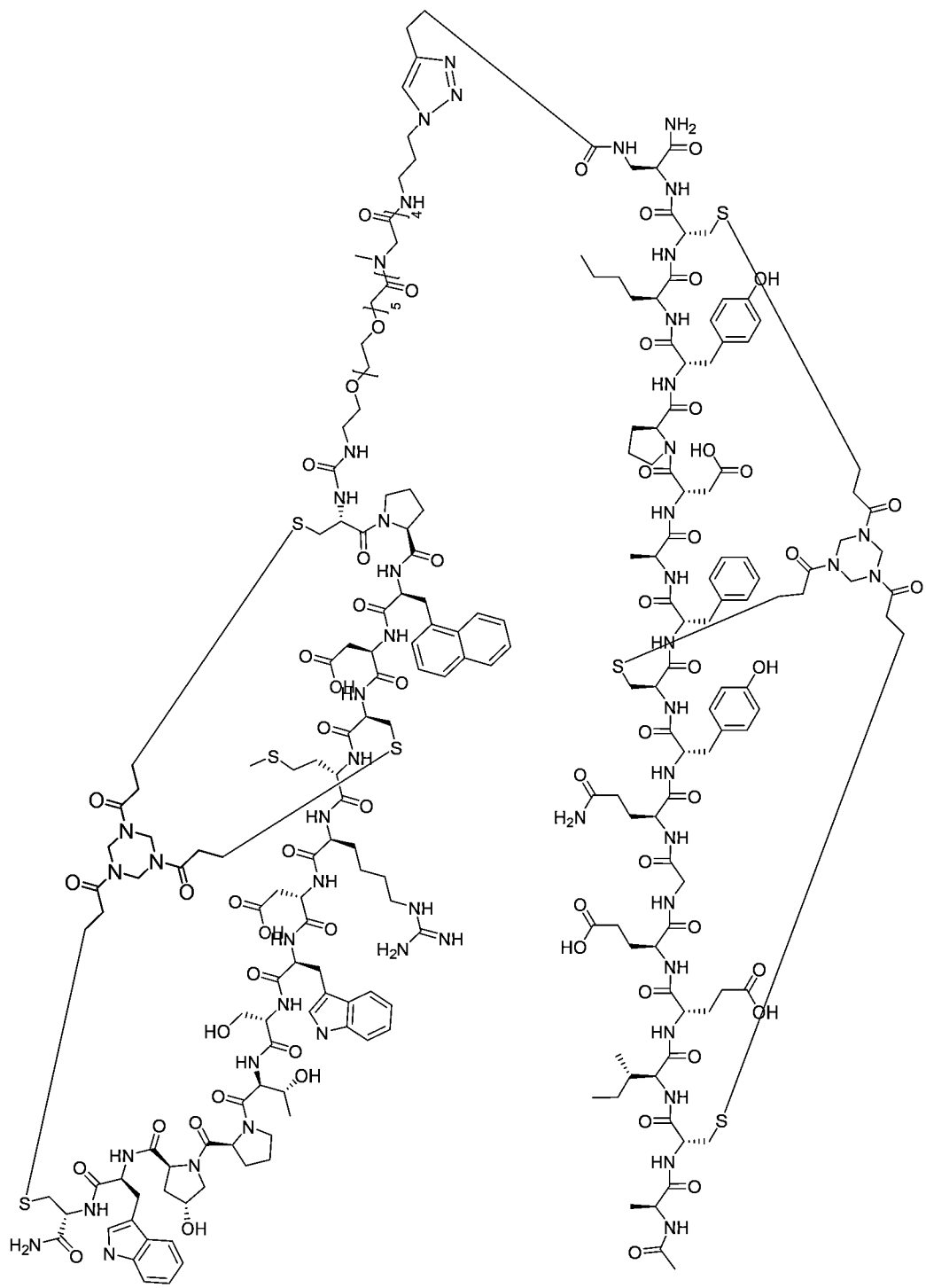
FIG. 41: Formula of BCY9410.
Figure 42:
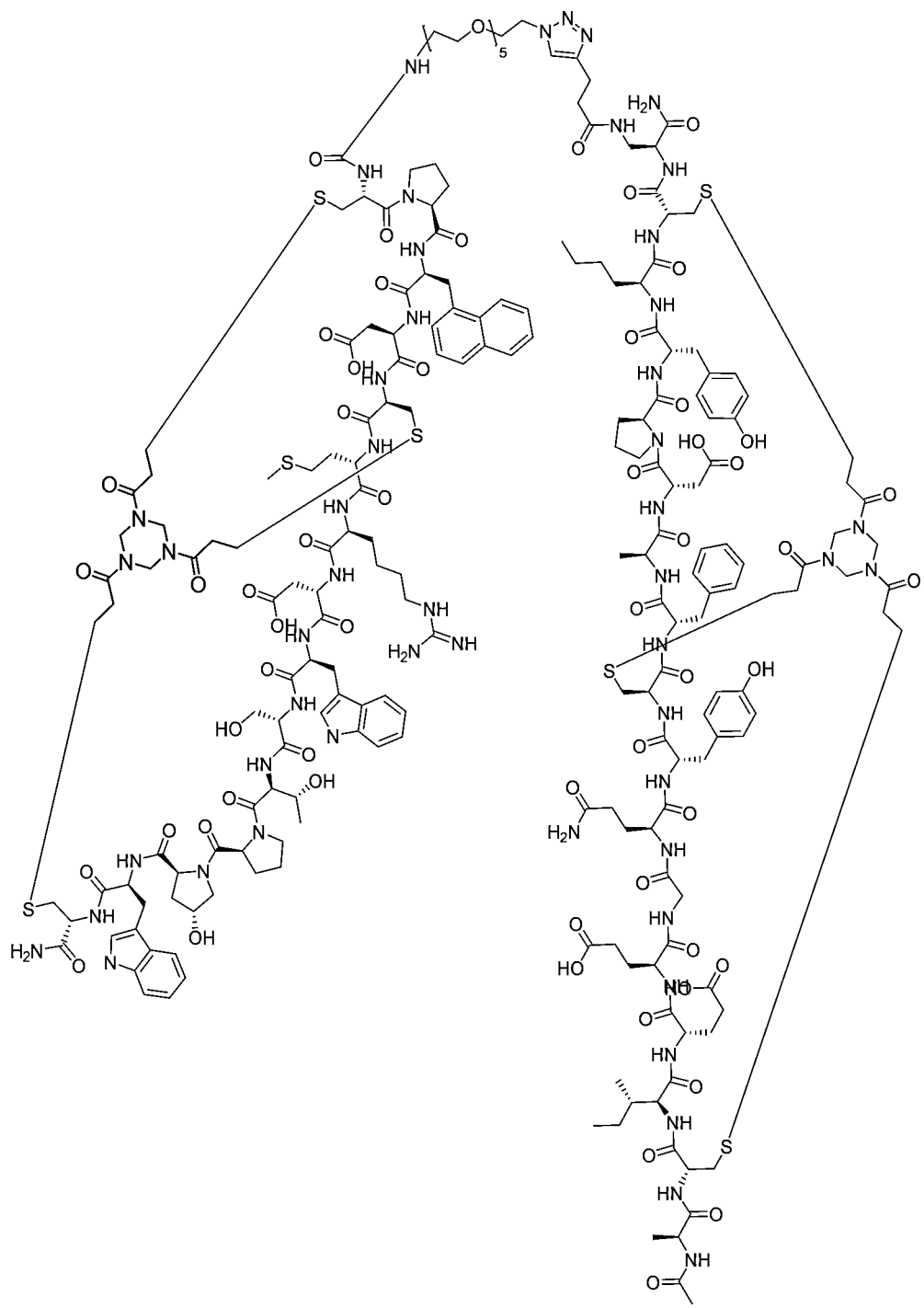
FIG. 42: Formula of BCY9411.
Figure 43:
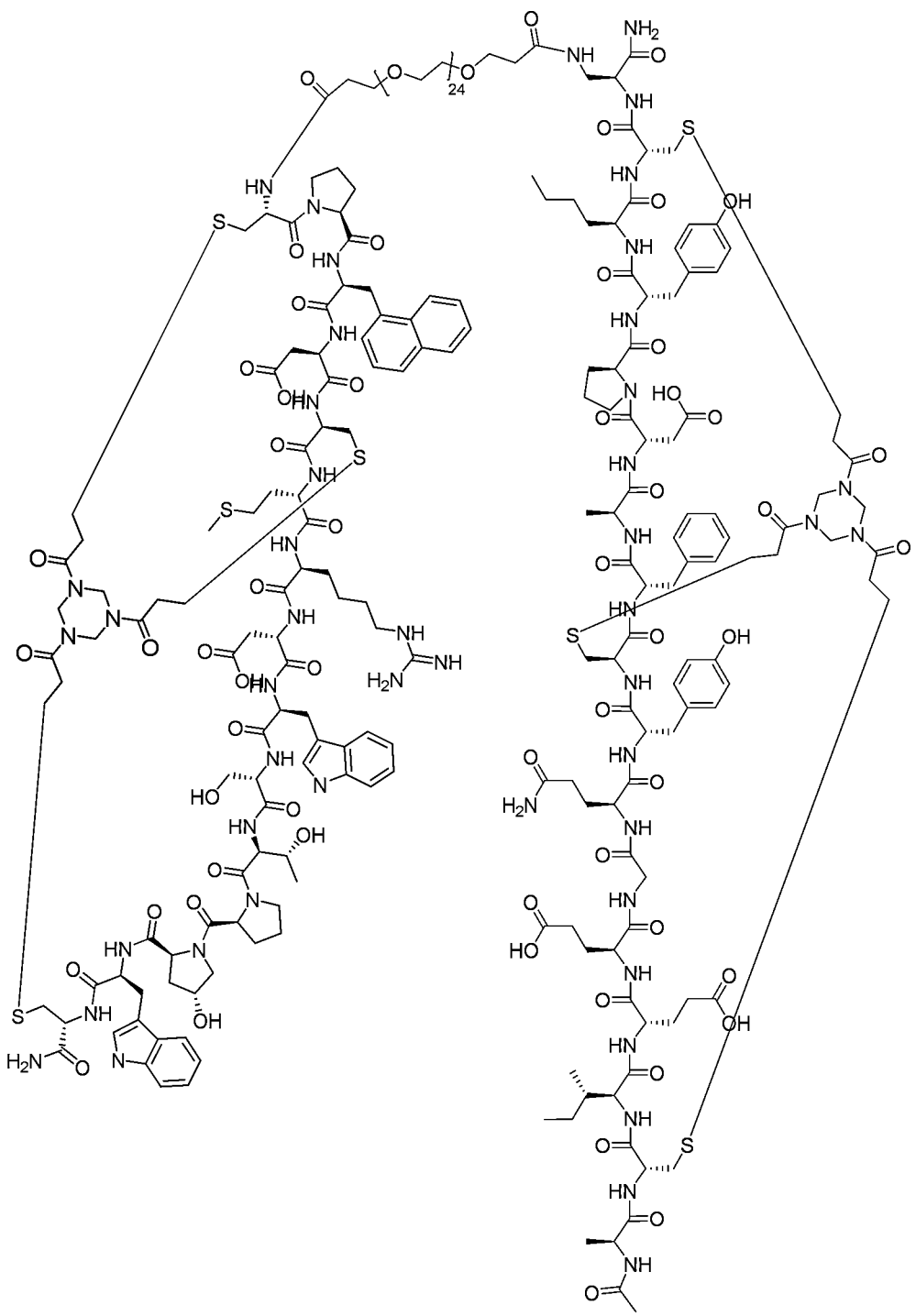
FIG. 43: Formula of BCY9759.
Figure 44:
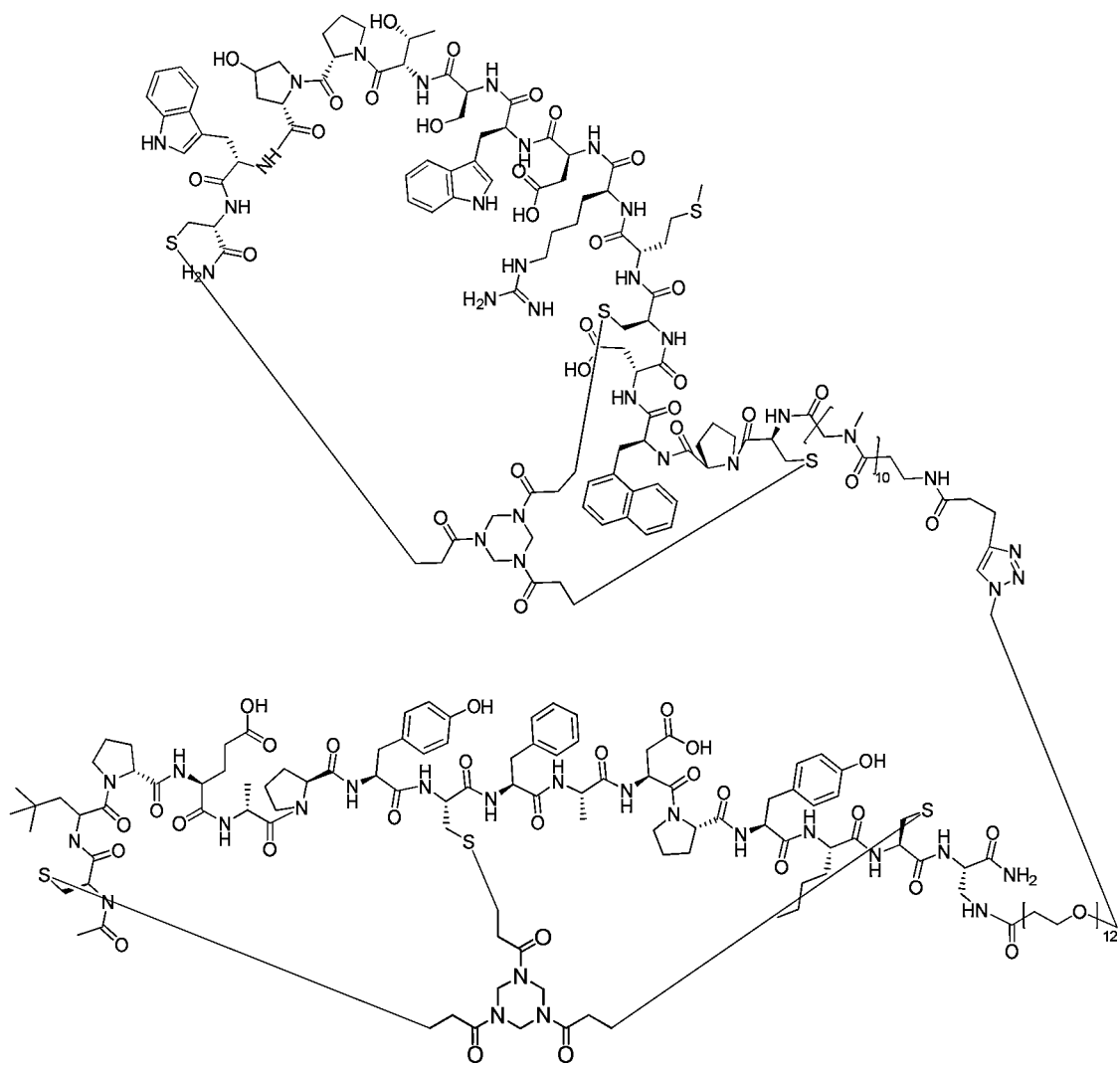
FIG. 44: Formula of BCY10000.
Figure 45:
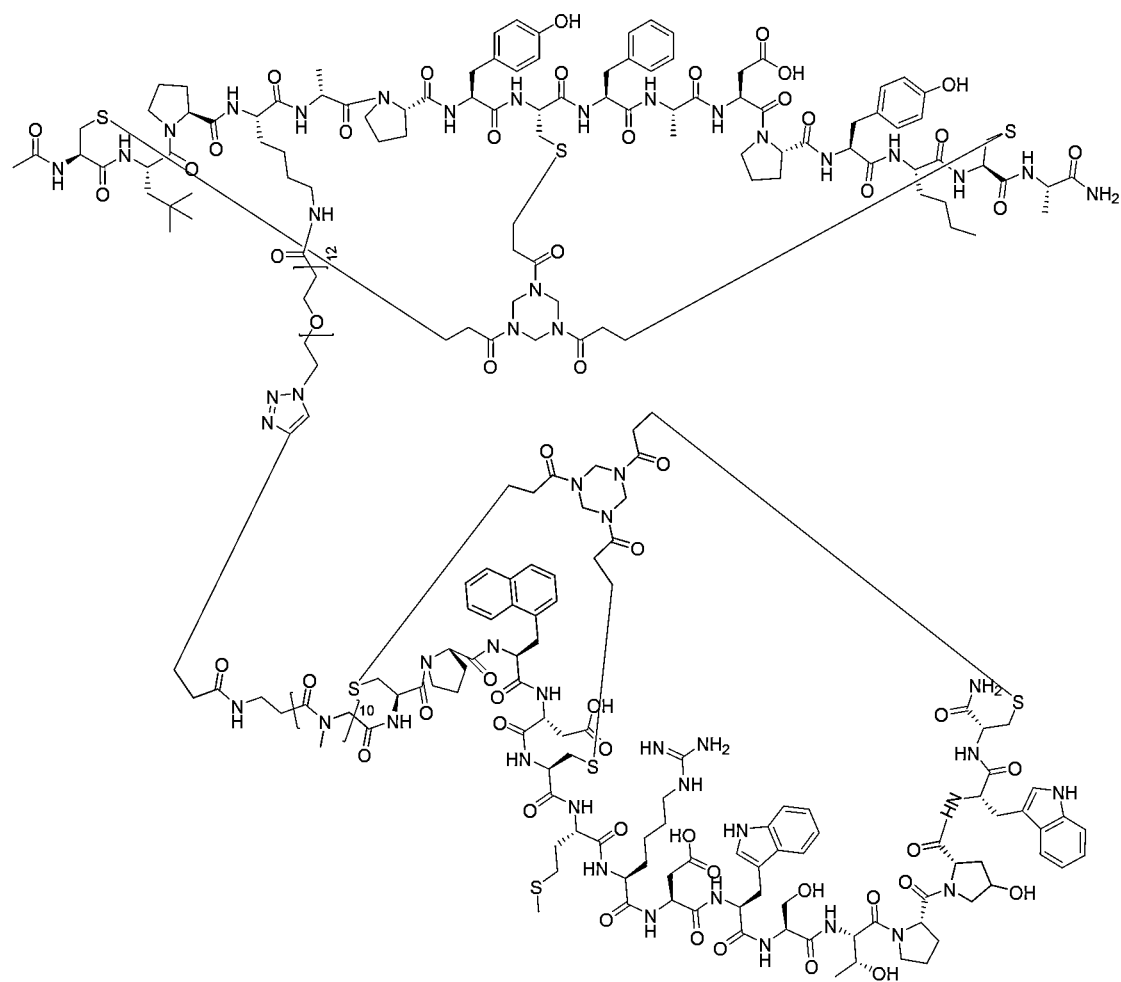
FIG. 45: Formula of BCY10567.
Figure 46:
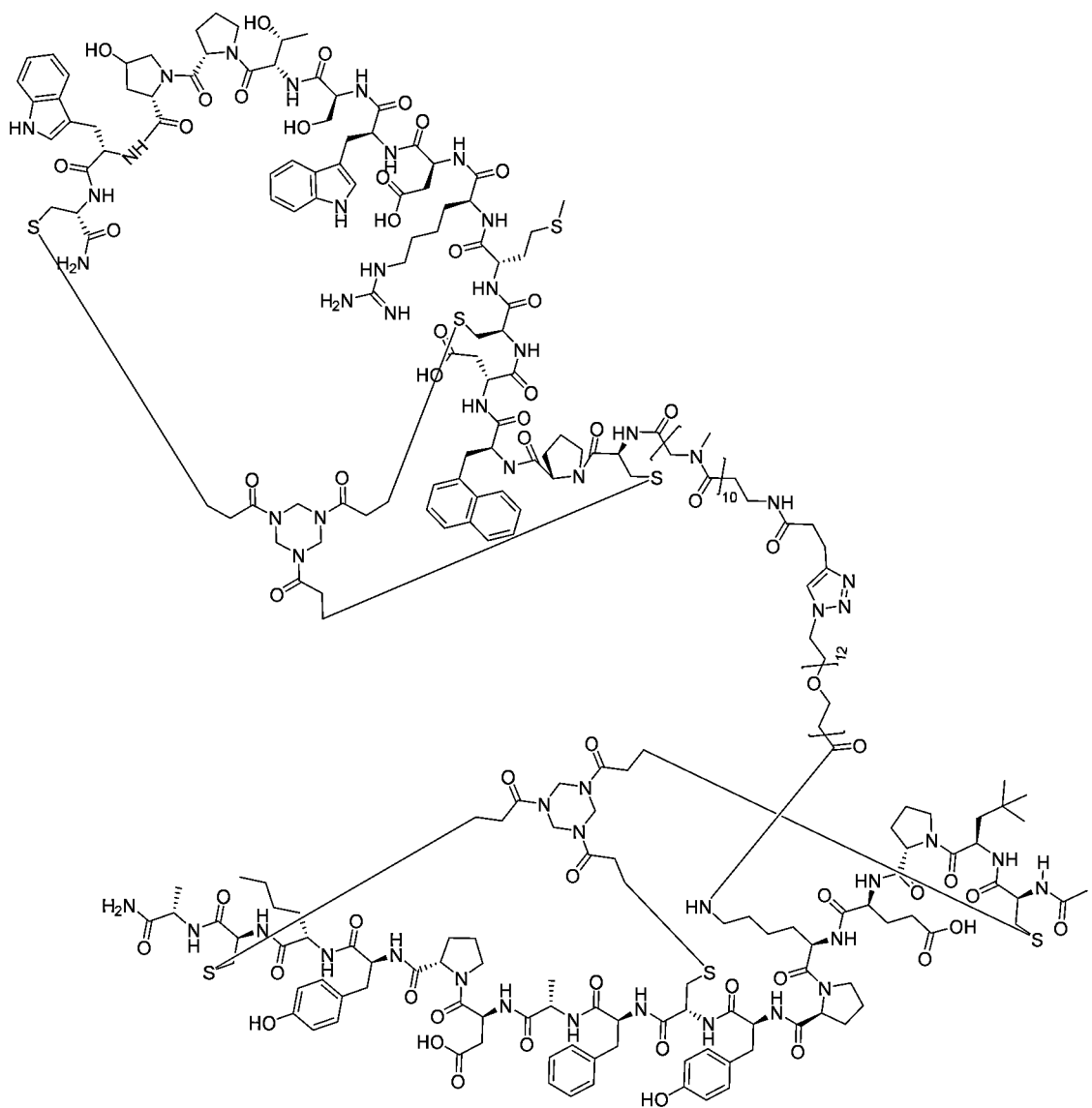
FIG. 46: Formula of BCY10569.
Figure 47:
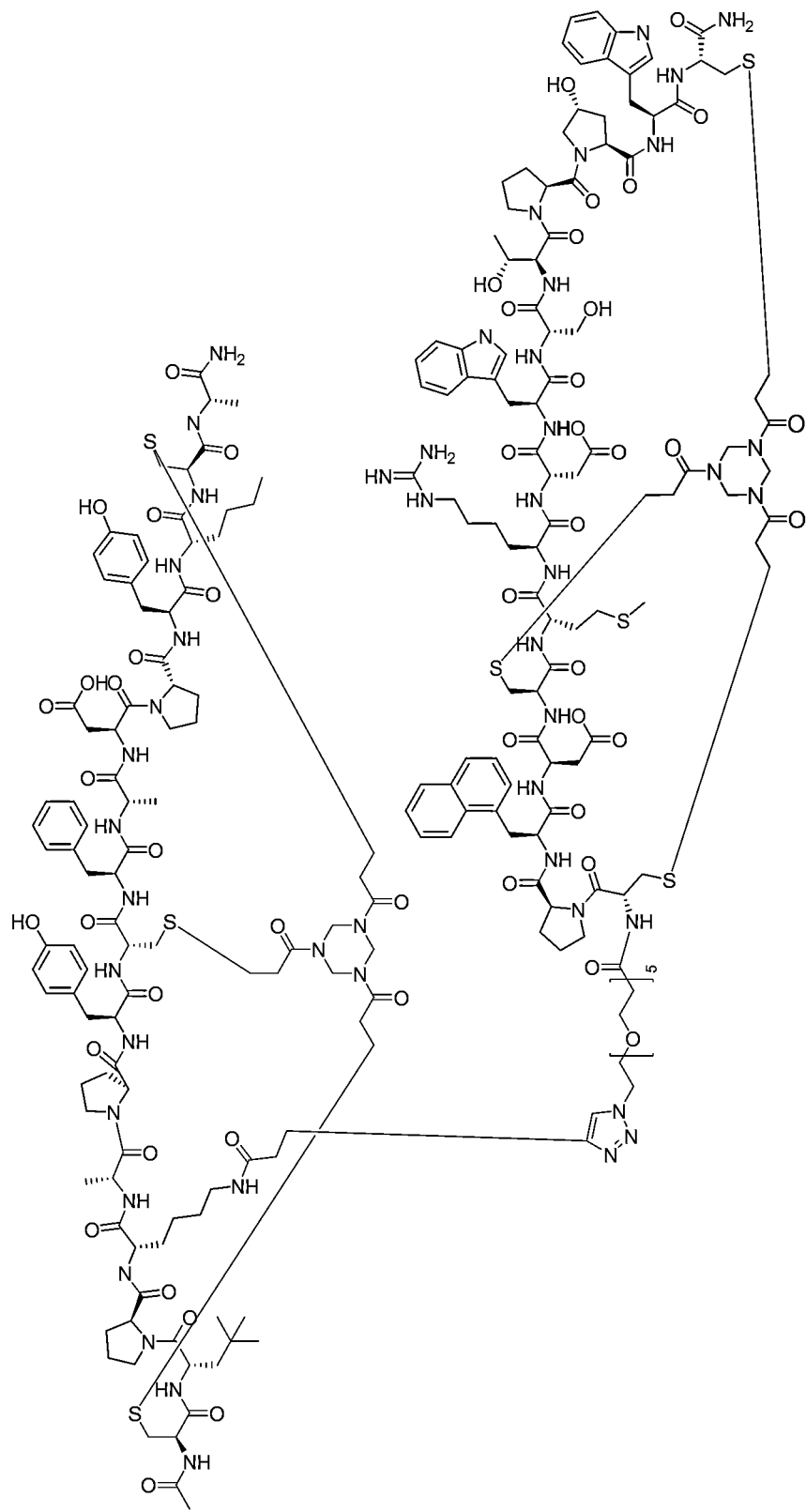
FIG. 47: Formula of BCY10571.
Figure 48:
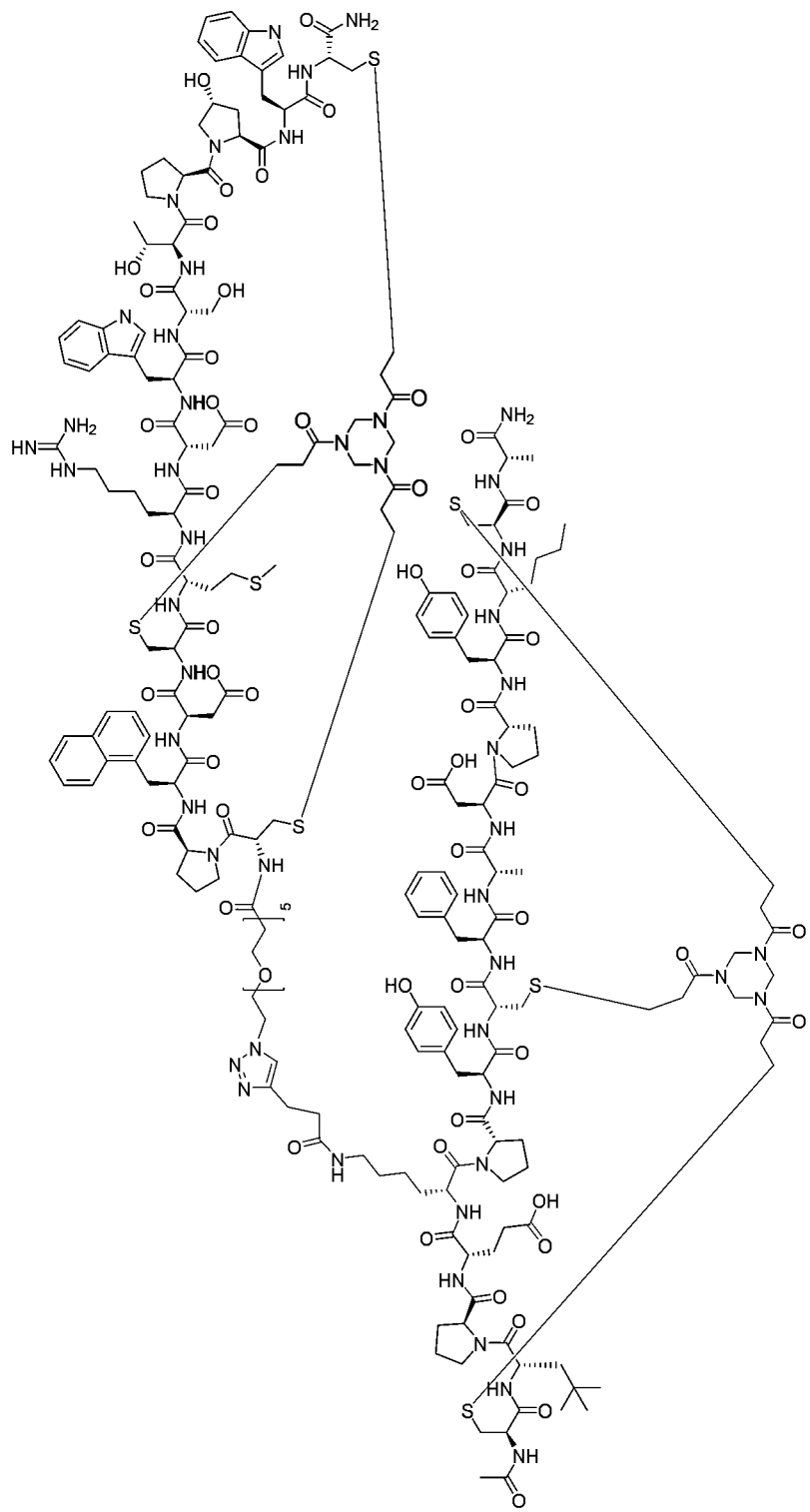
FIG. 48: Formula of BCY10572.
Figure 49:
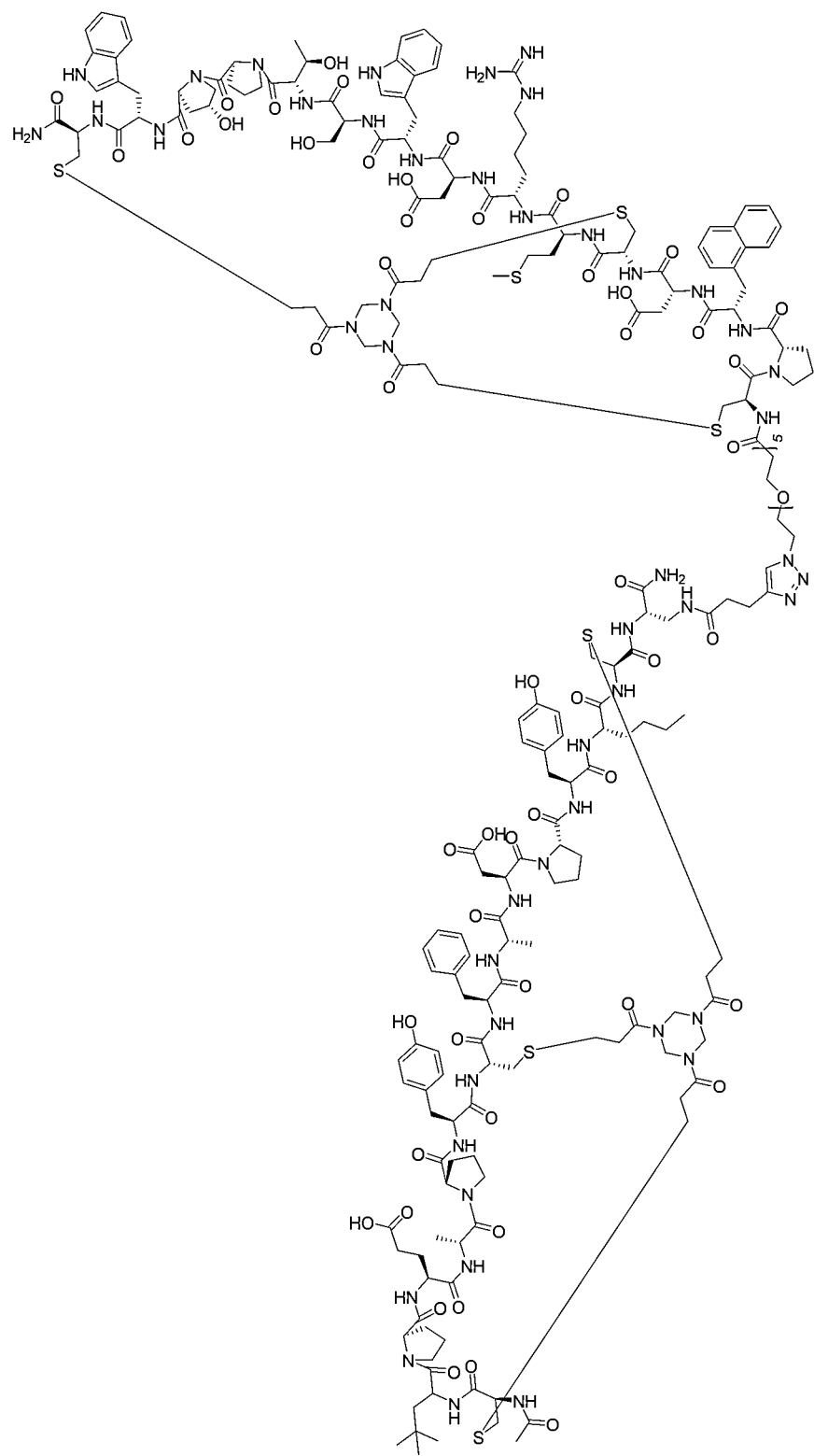
FIG. 49: Formula of BCY10573.
Figure 50:
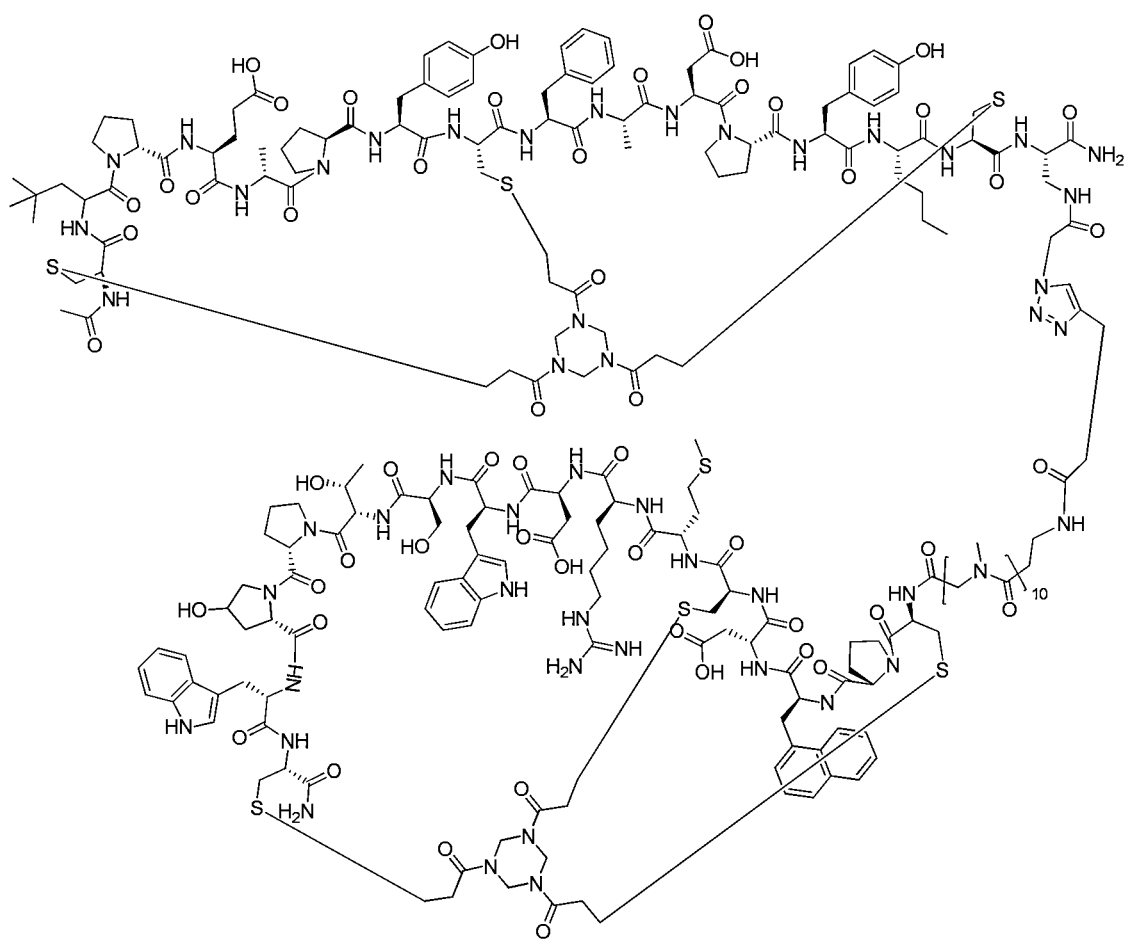
FIG. 50: Formula of BCY10578.
Figure 51:
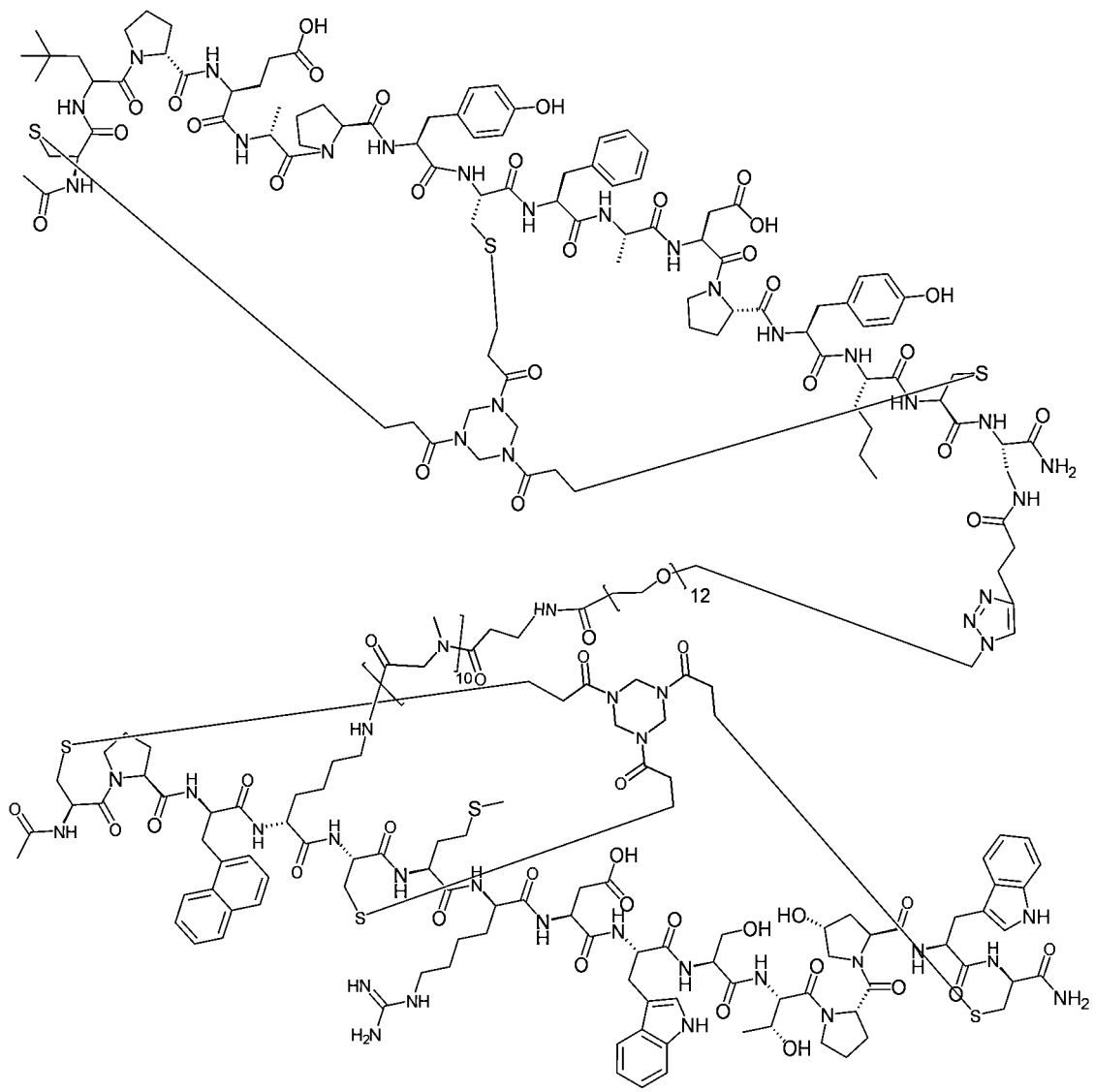
FIG. 51: Formula of BCY10917.
Figure 52:
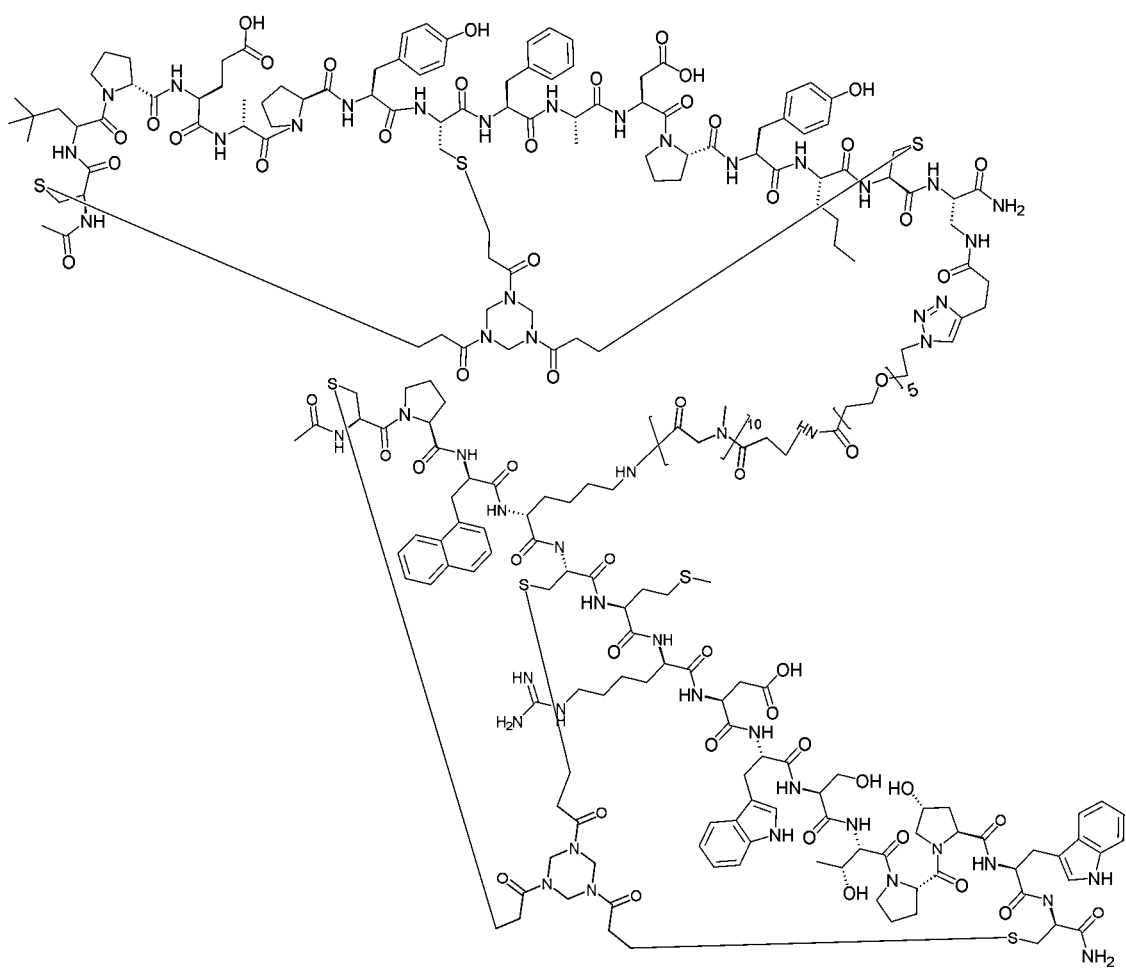
FIG. 52: Formula of BCY11020.
Figure 53:
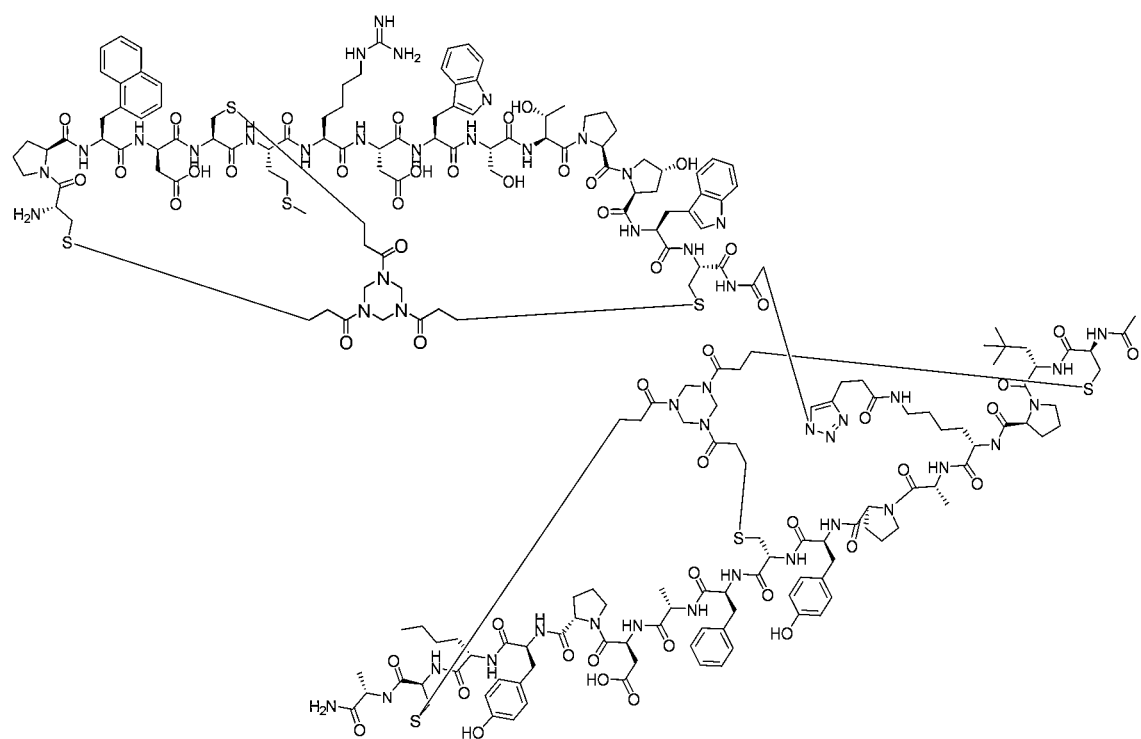
FIG. 53: Formula of BCY11373.
Figure 54:
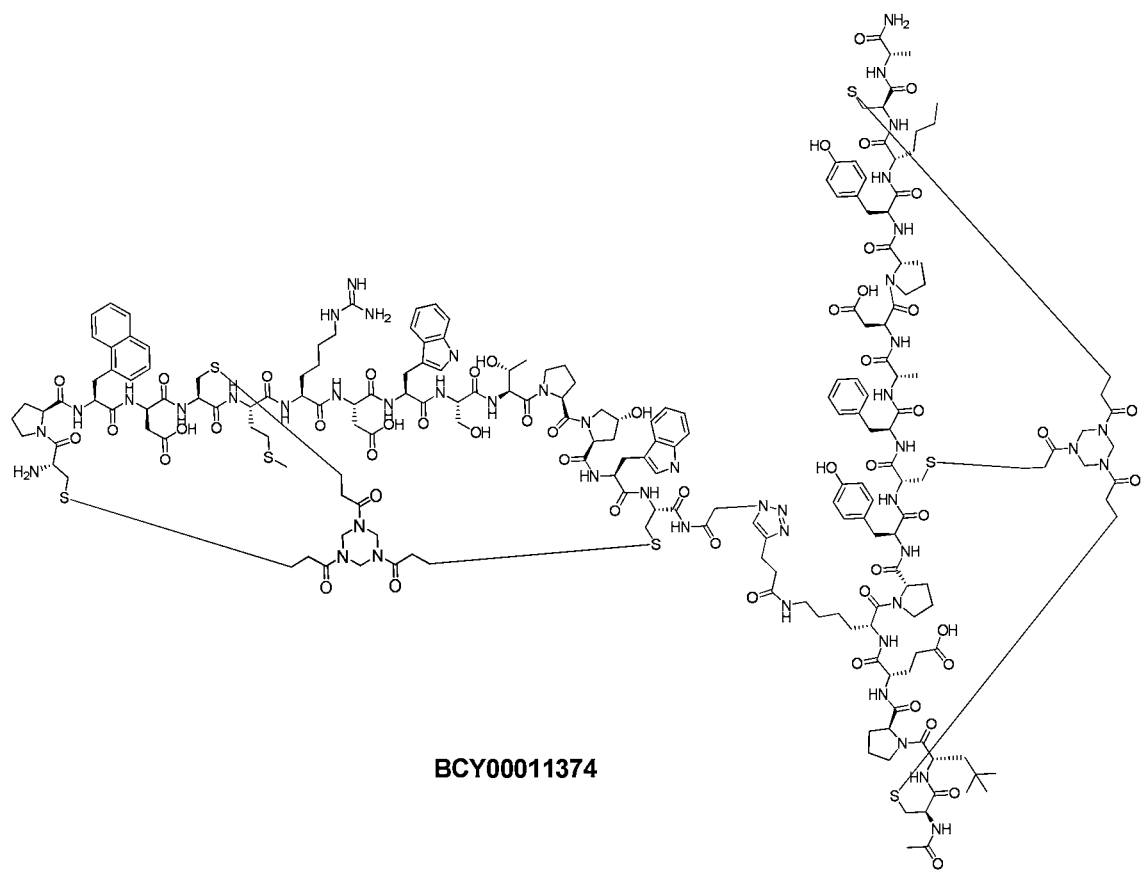
FIG. 54: Formula of BCY11374.
Figure 55:
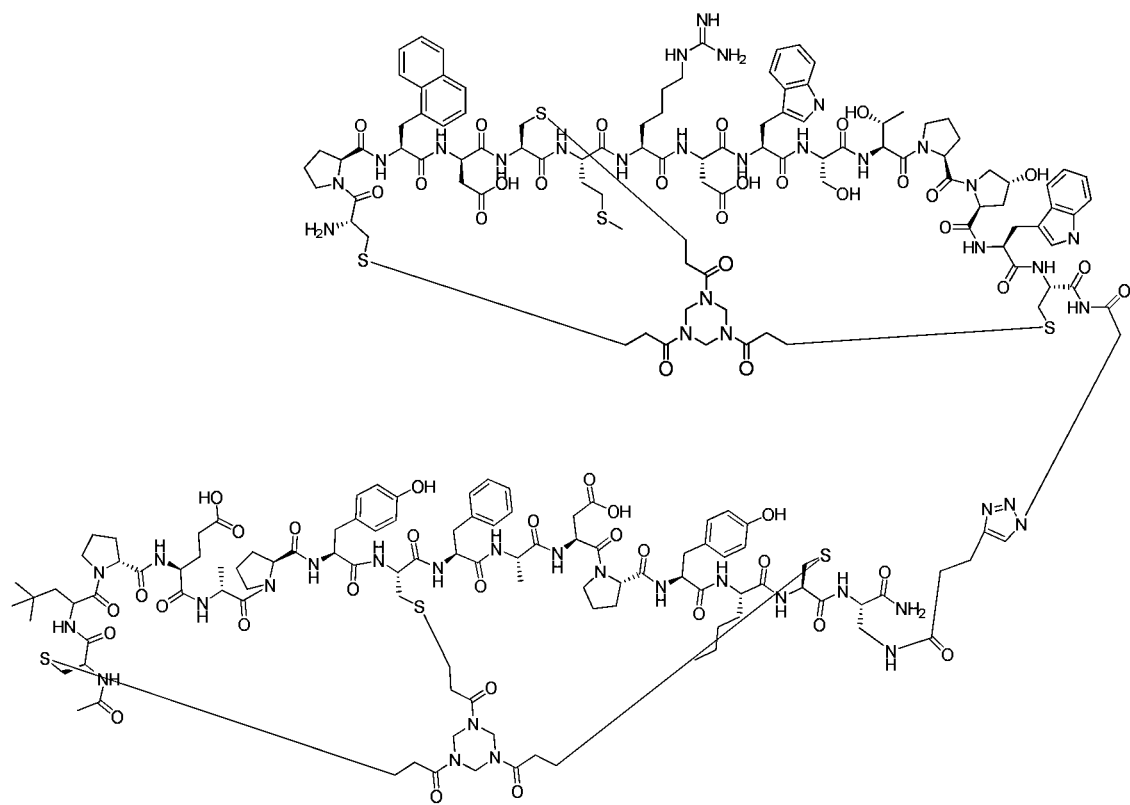
FIG. 55: Formula of BCY11375.
Figure 56:
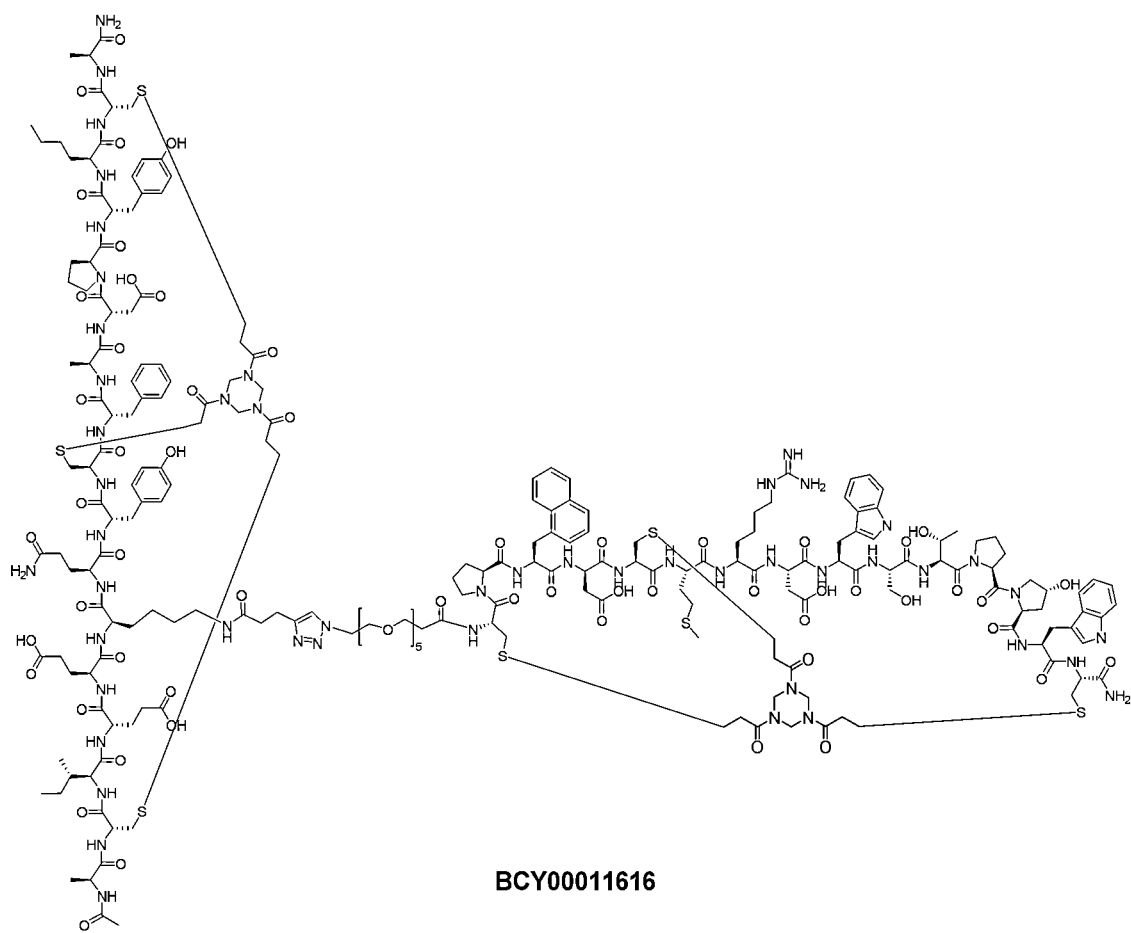
FIG. 56: Formula of BCY11616.
Figure 57:
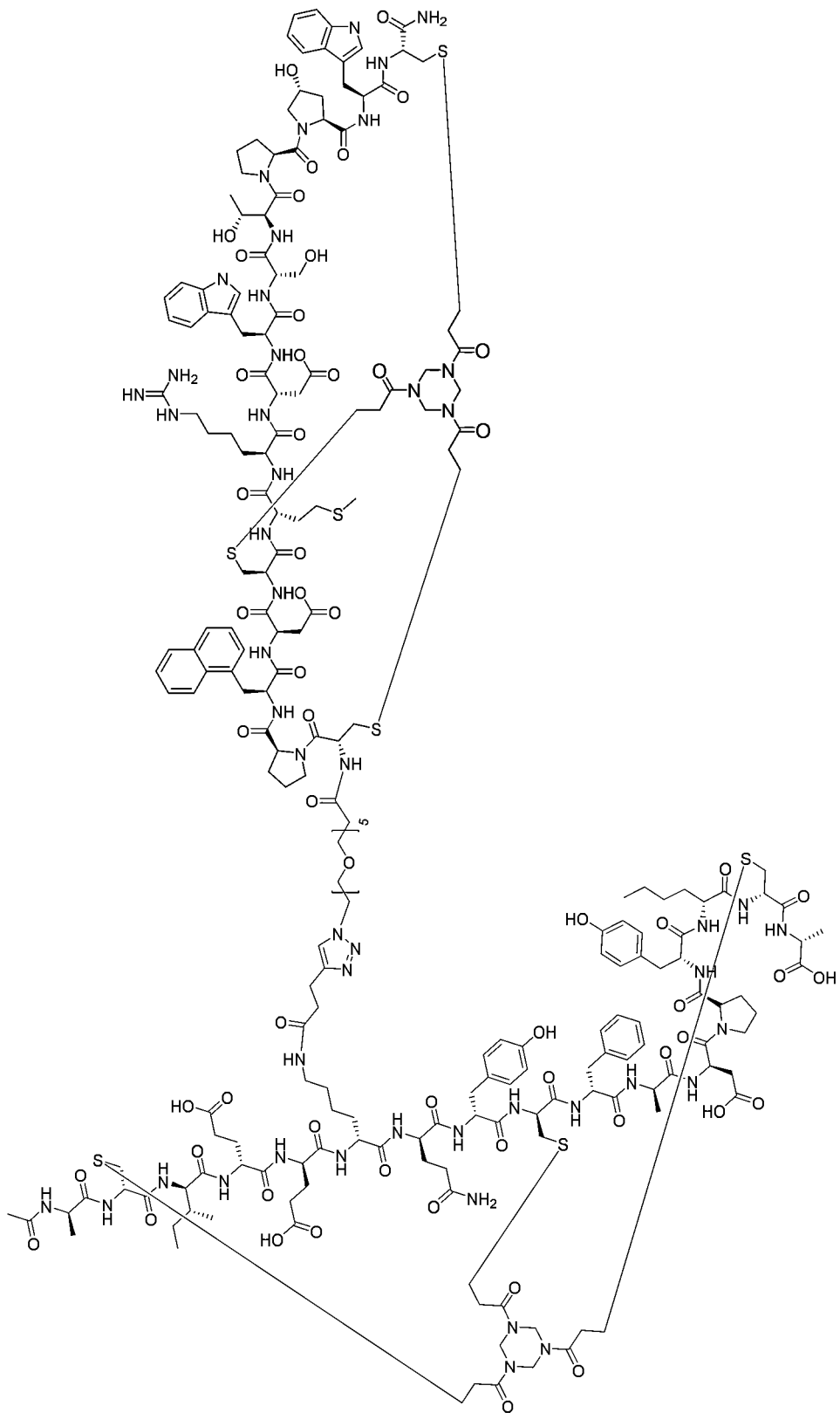
FIG. 57: Formula of BCY11617.
Figure 58:
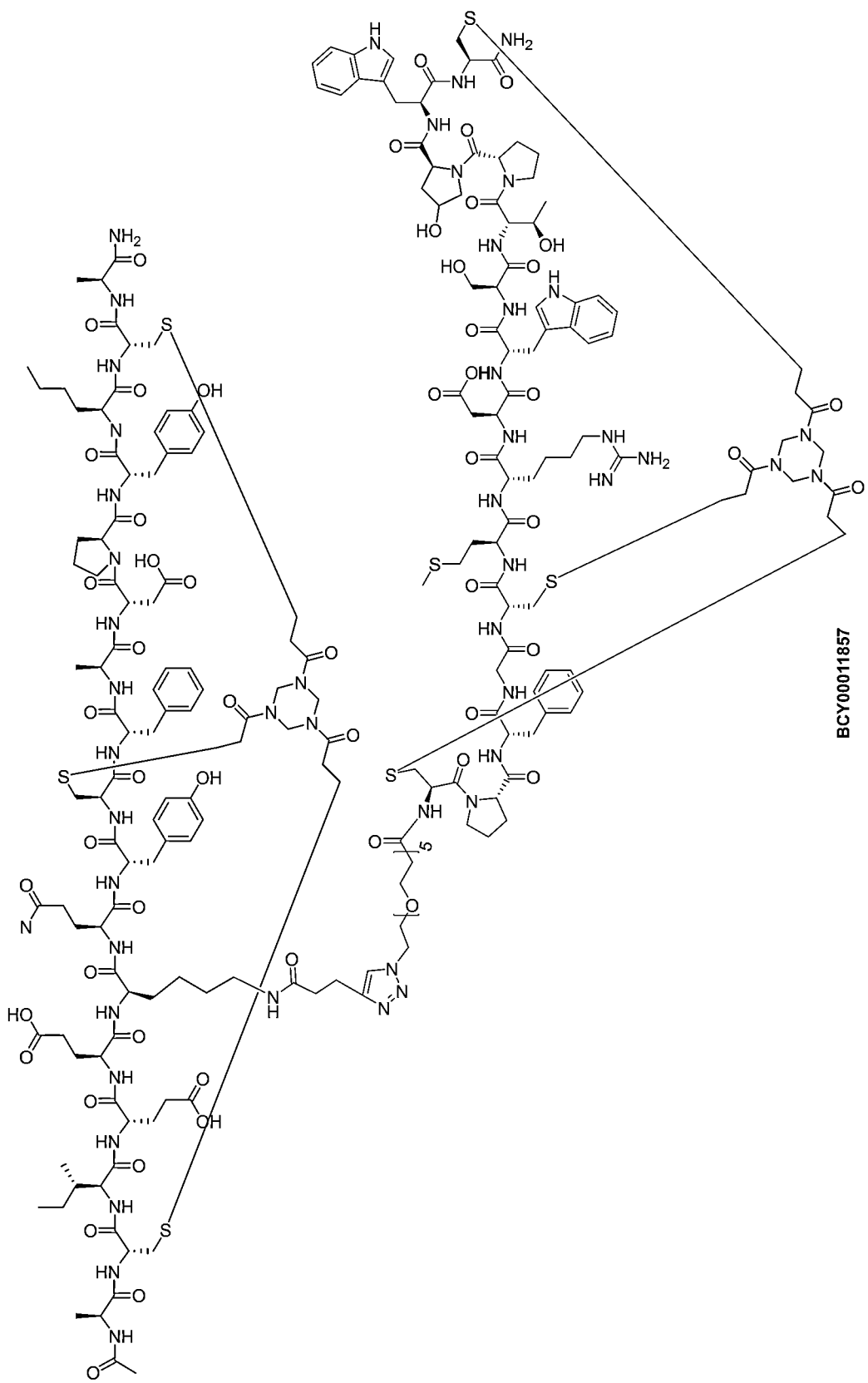
FIG. 58: Formula of BCY11857.
Figure 59:
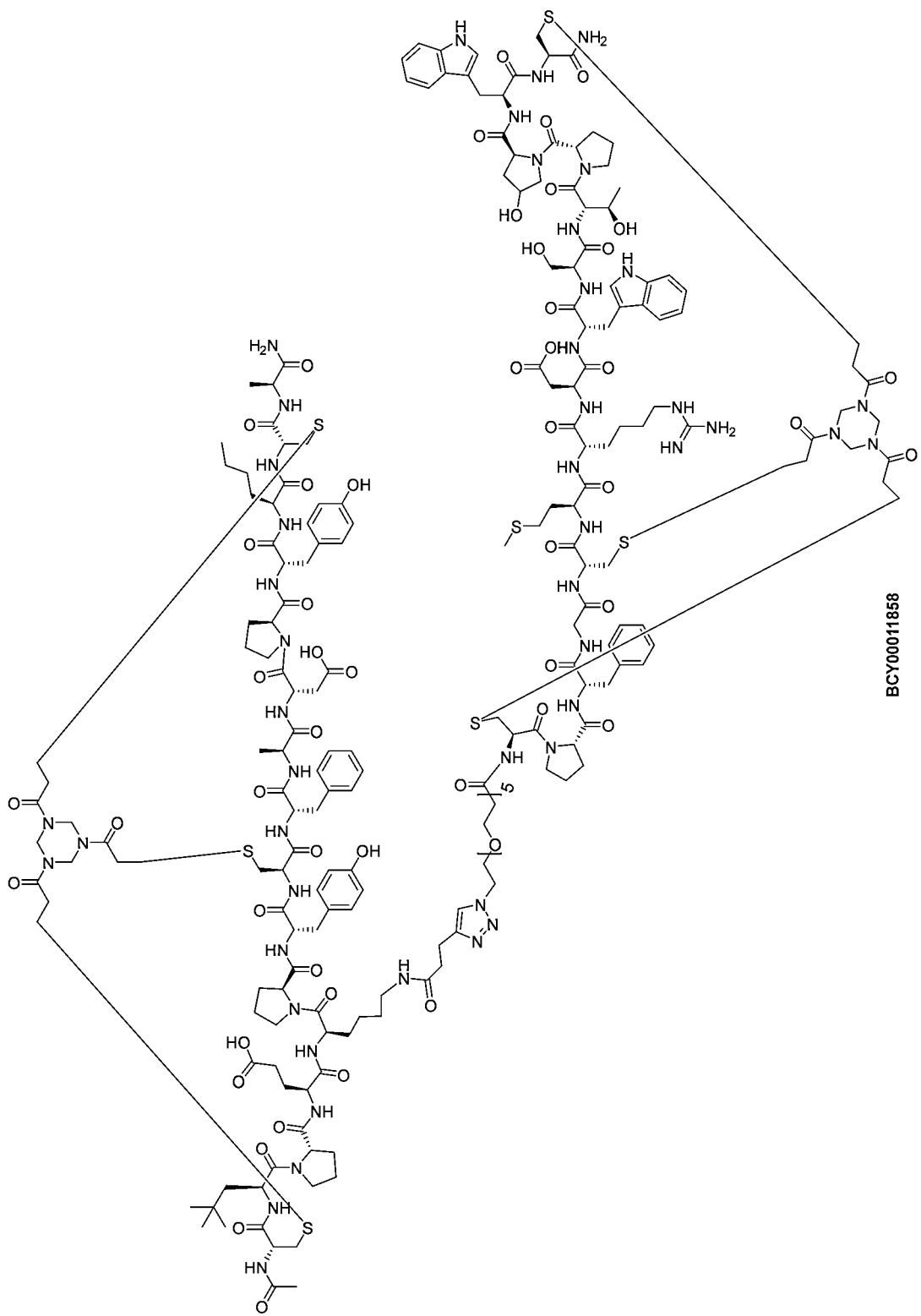
FIG. 59: Formula of BCY11858.
Figure 60:
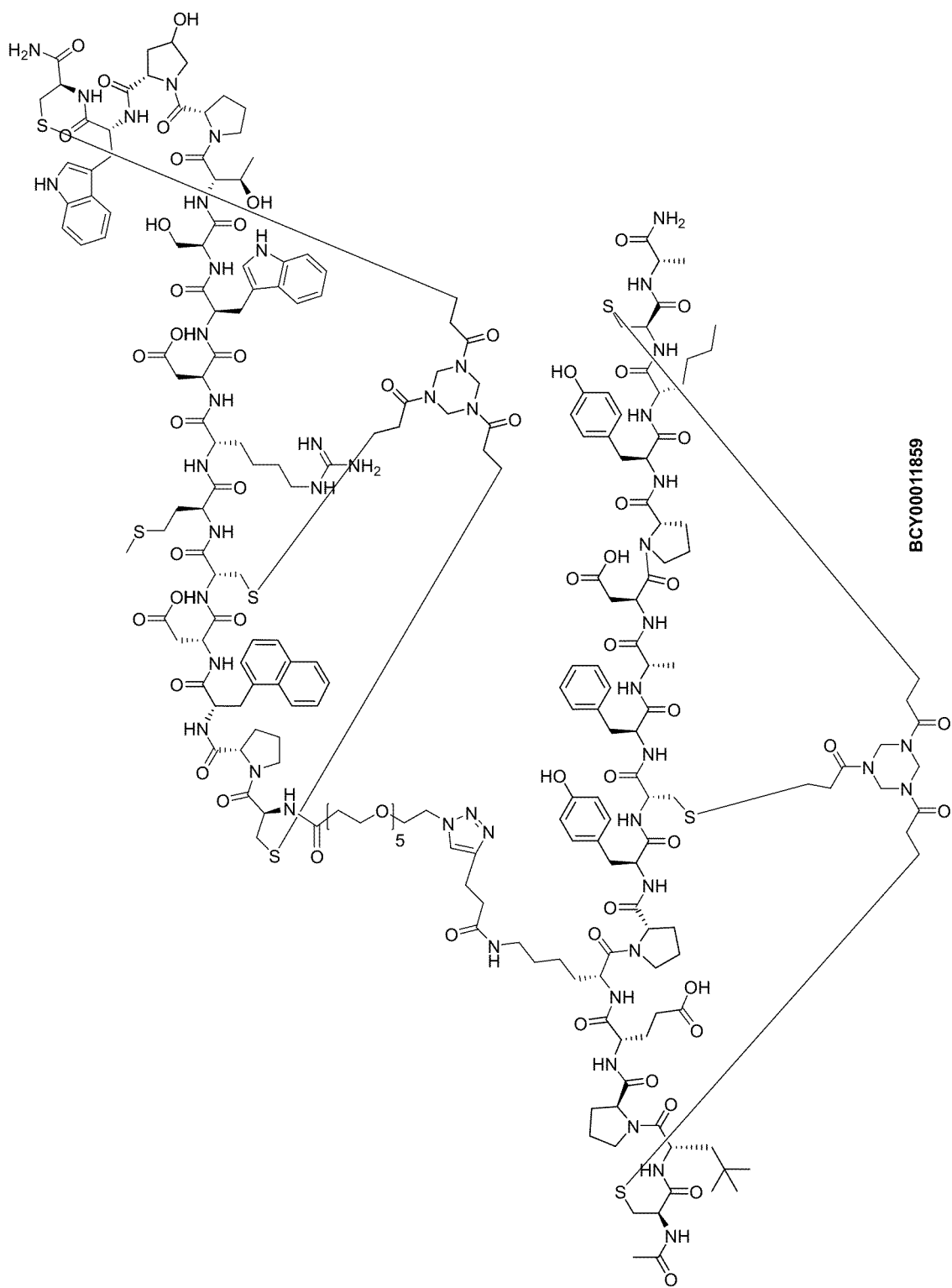
FIG. 60: Formula of BCY11859.
Figure 61:
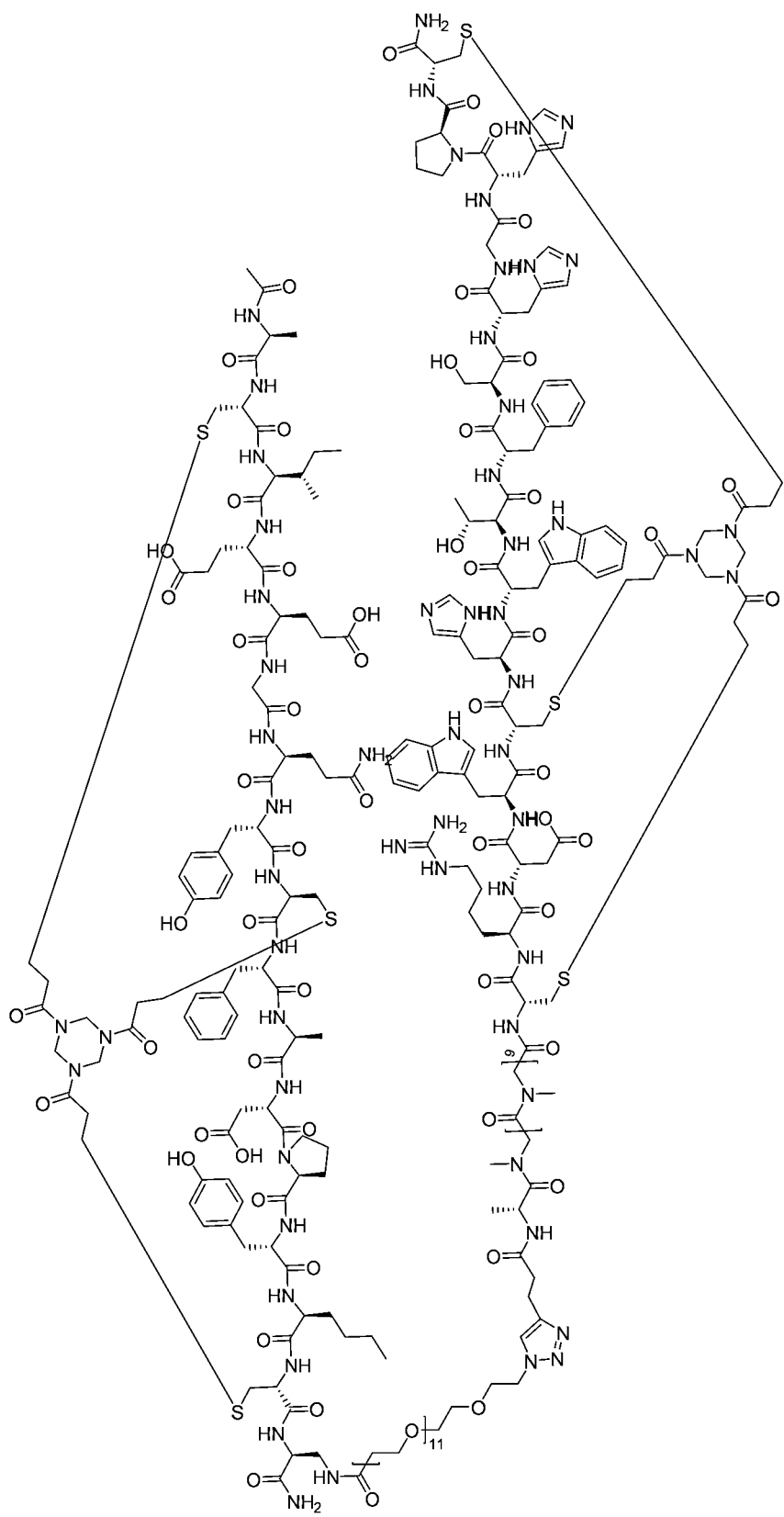
FIG. 61: Formula of BCY8939.
Figure 62:
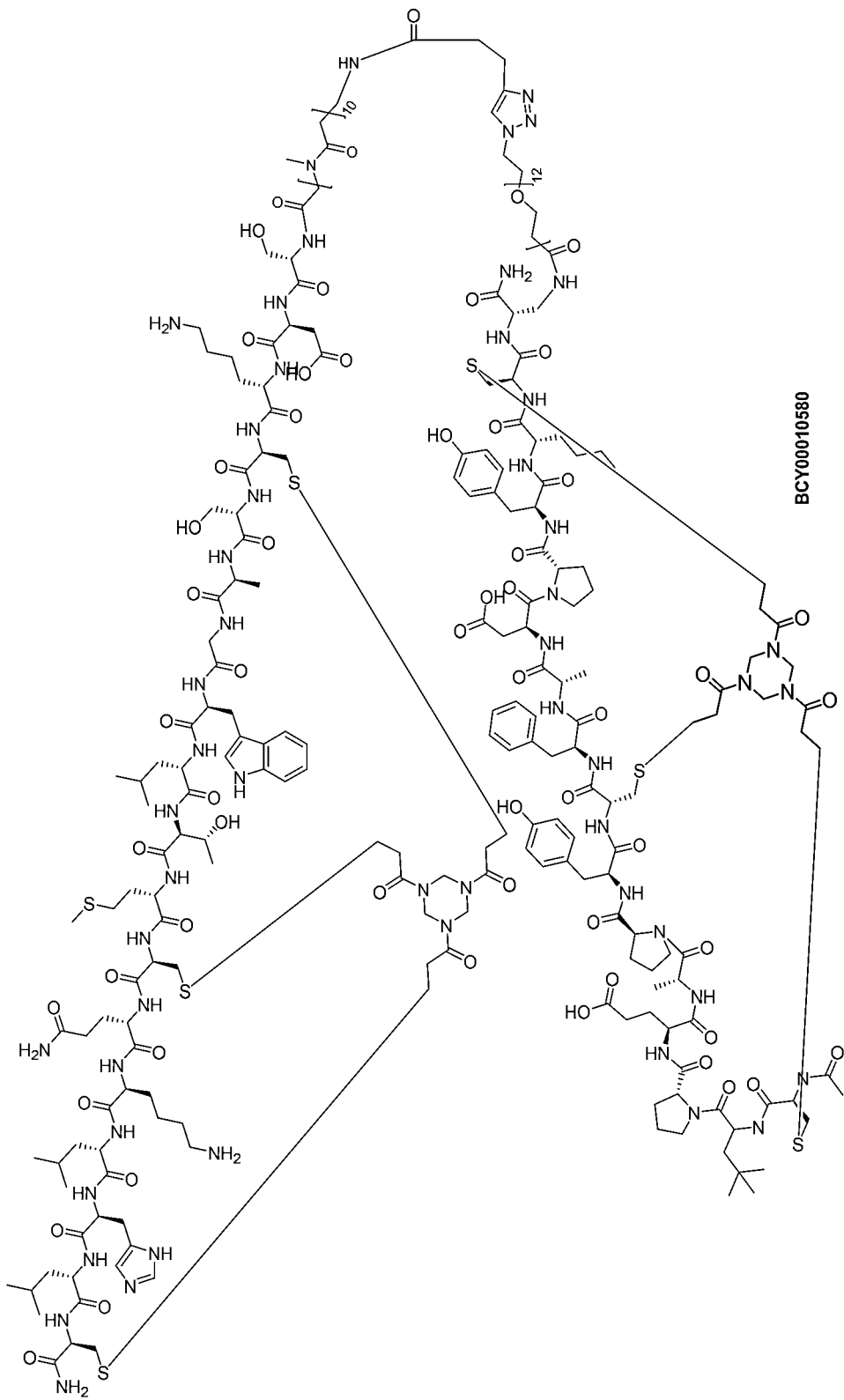
FIG. 62: Formula of BCY10580.
Figure 63:
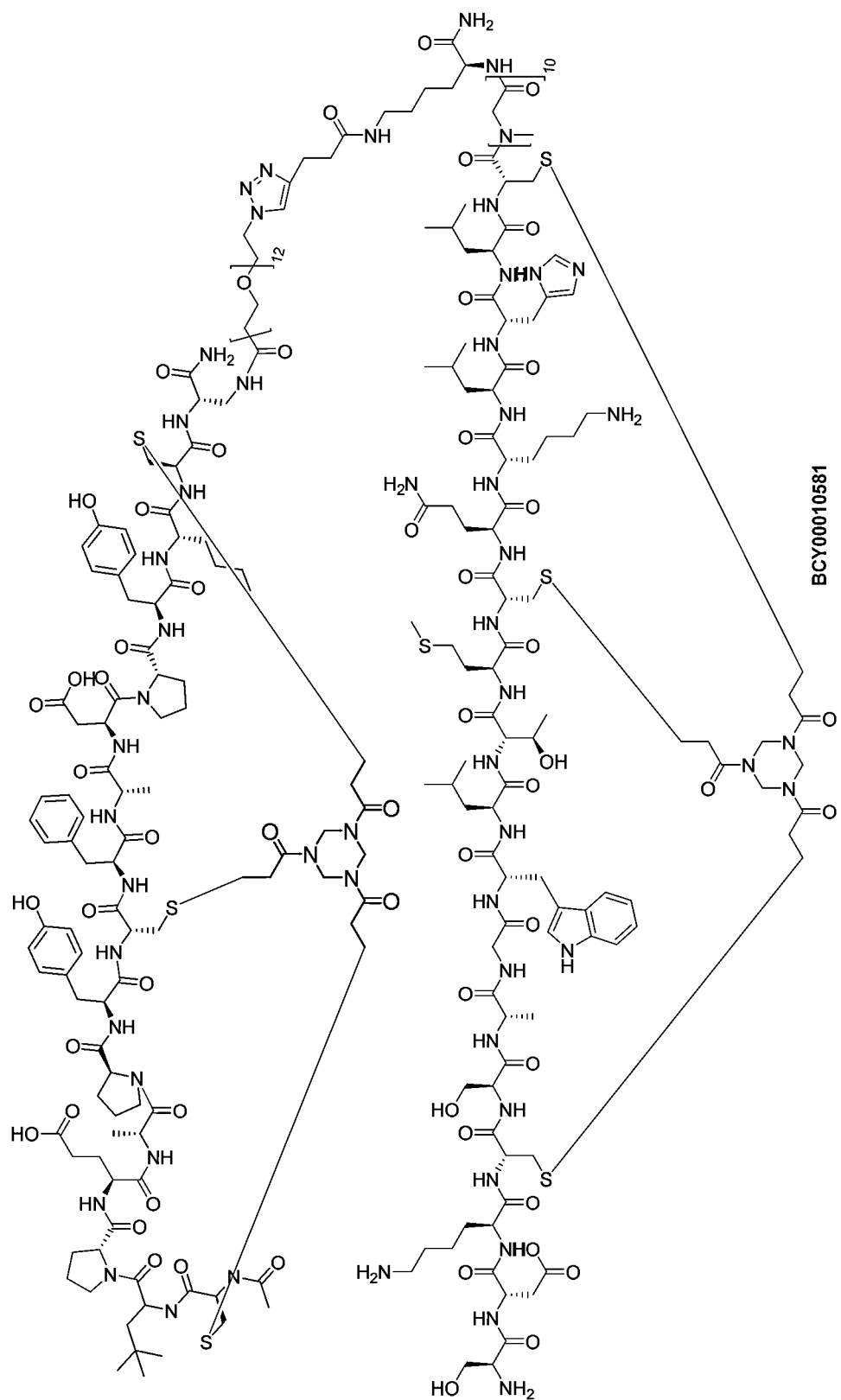
FIG. 63: Formula of BCY10581.
Figure 64:
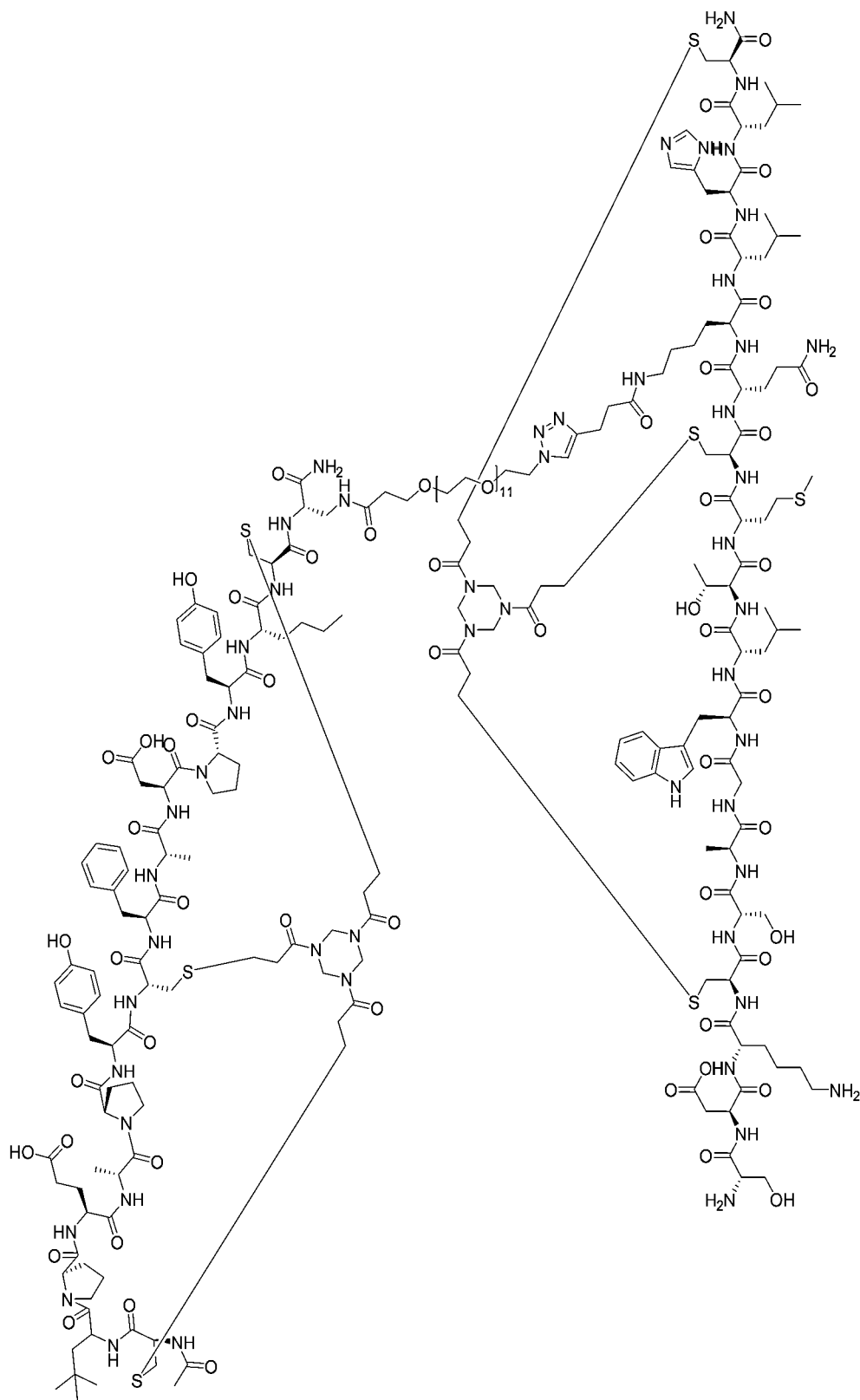
FIG. 64: Formula of BCY10582.
Figure 65:
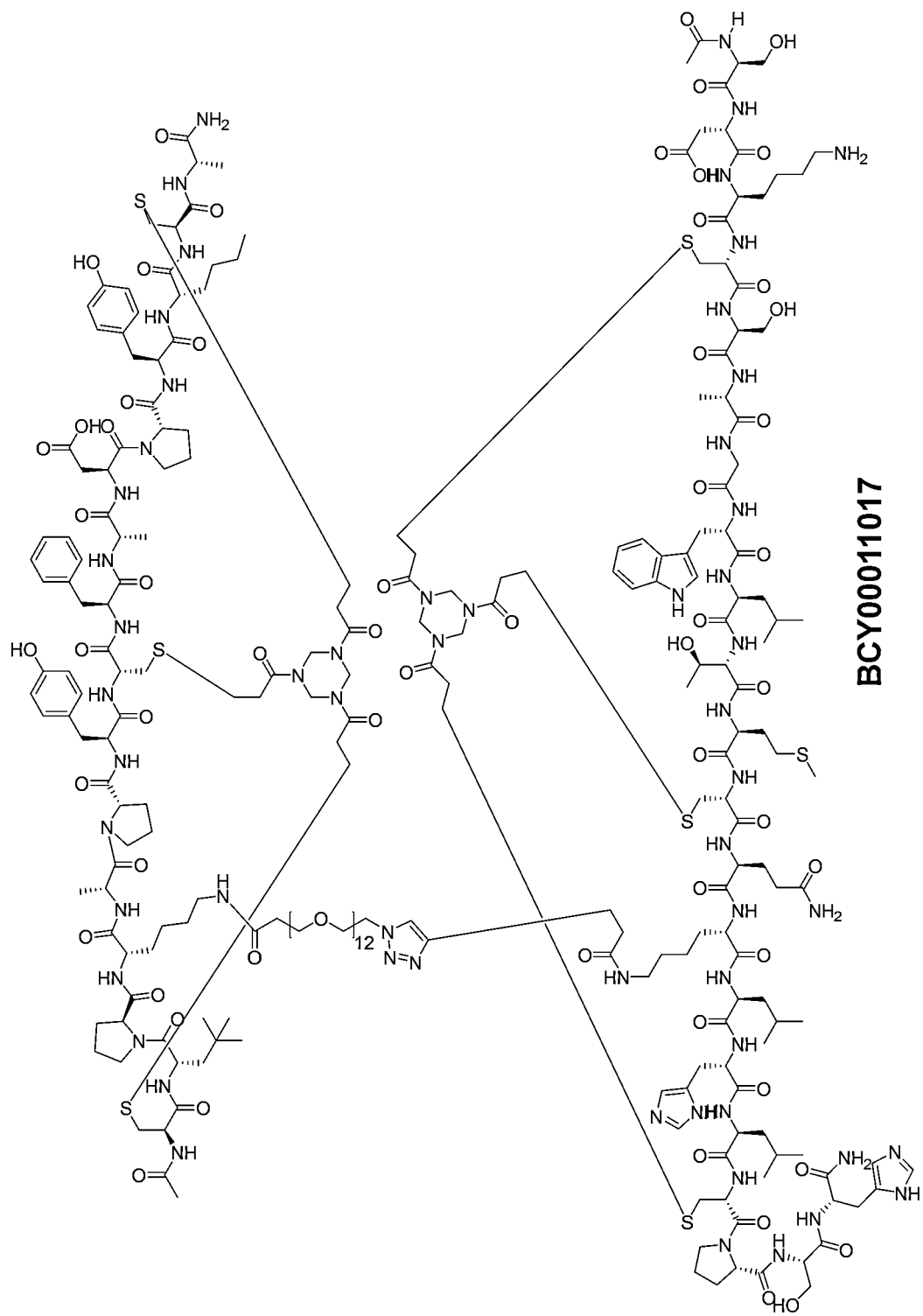
FIG. 65: Formula of BCY11017.
Figure 66:
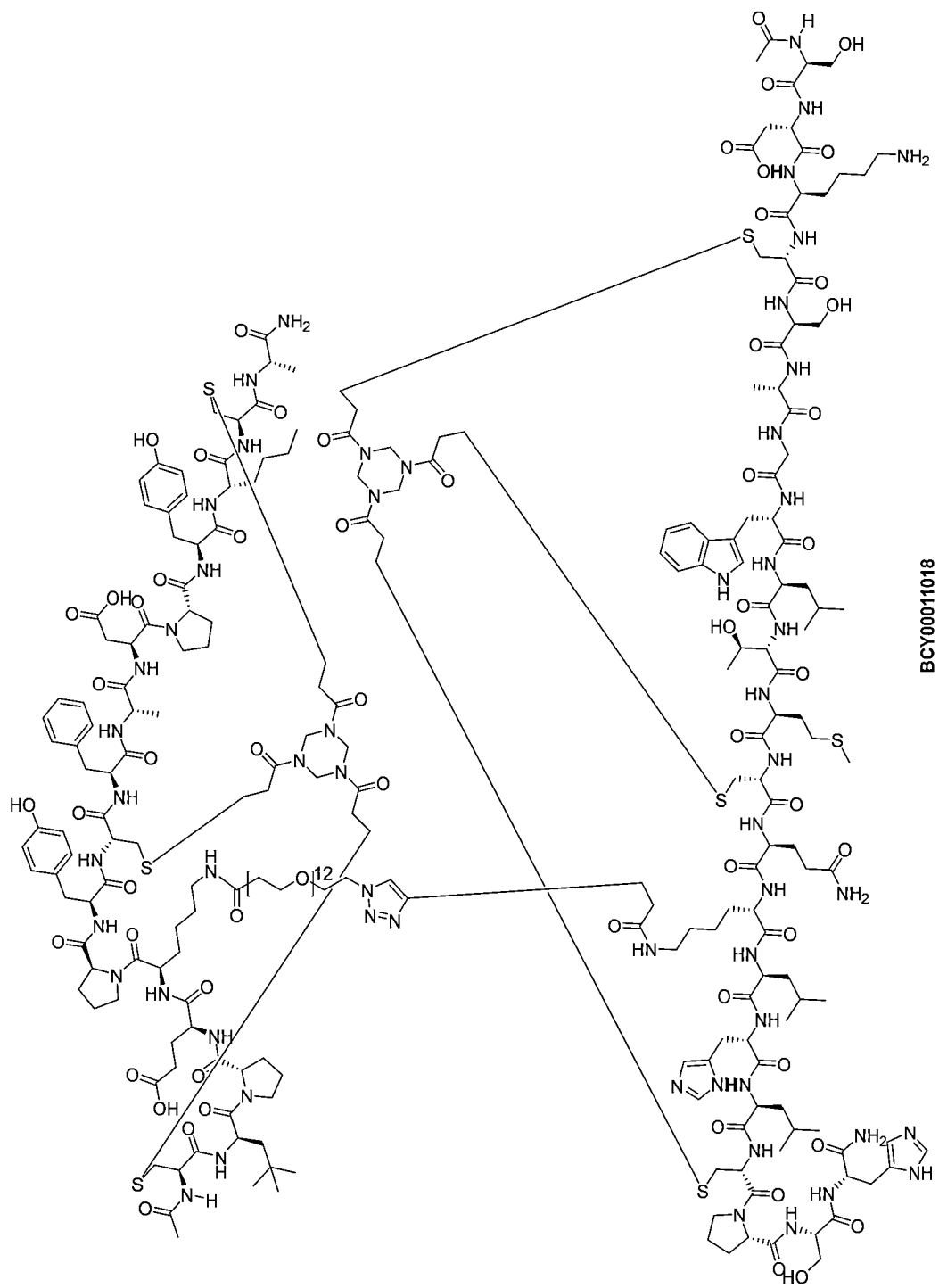
FIG. 66: Formula of BCY11018.
Figure 67:
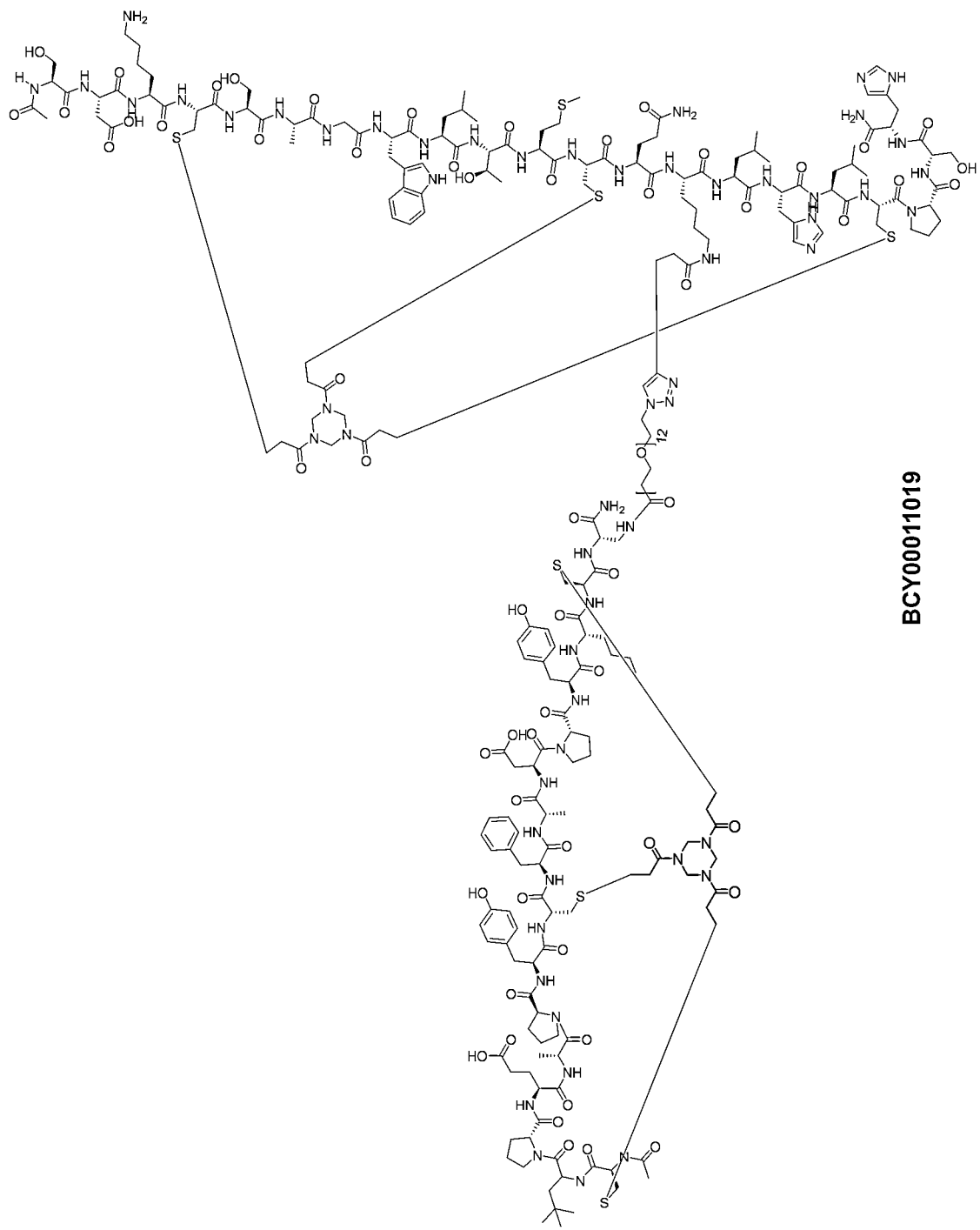
FIG. 67: Formula of BCY11019.
Figure 68:
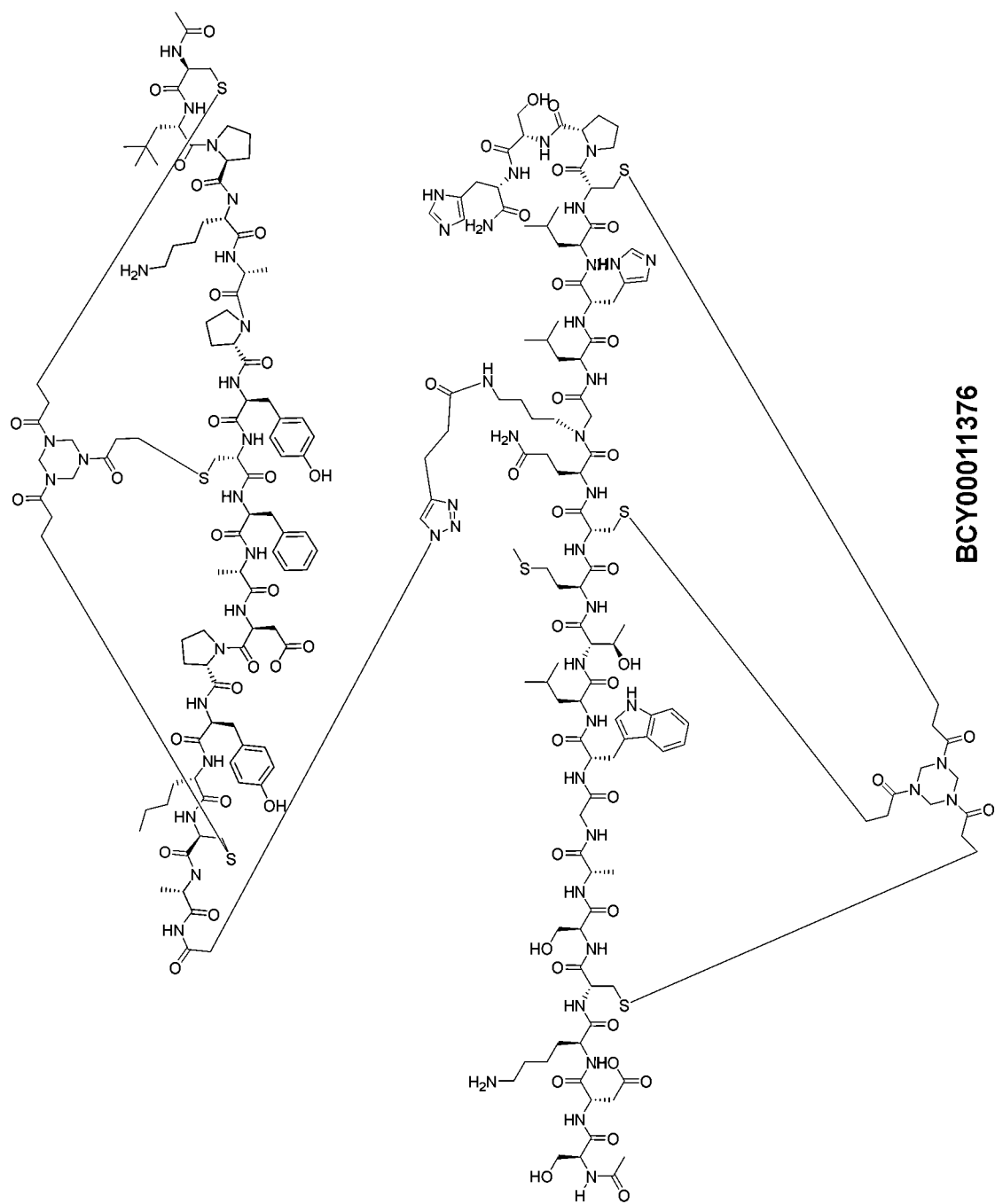
FIG. 68: Formula of BCY11376.
Figure 69:
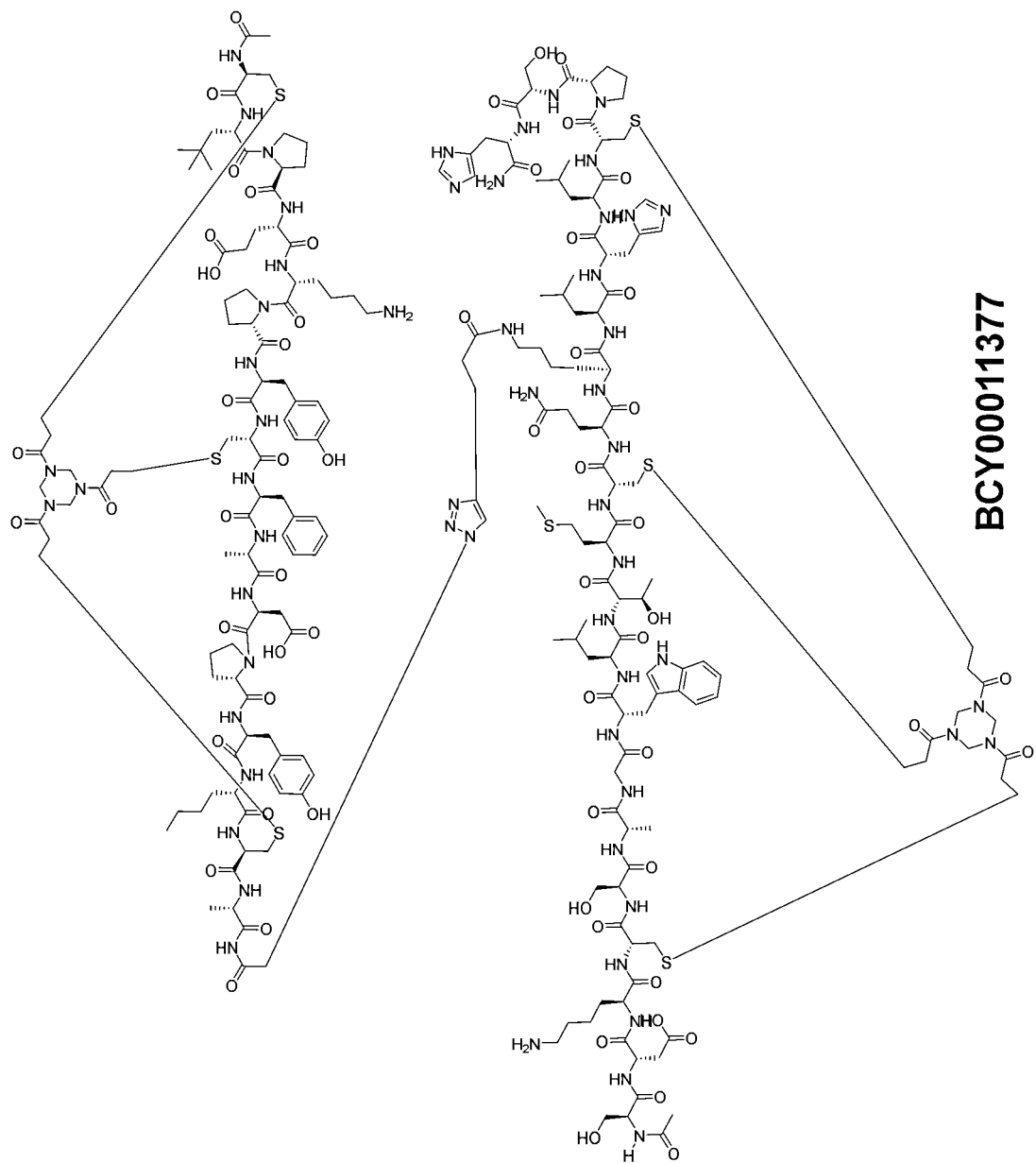
FIG. 69: Formula of BCY11377.
Figure 70:
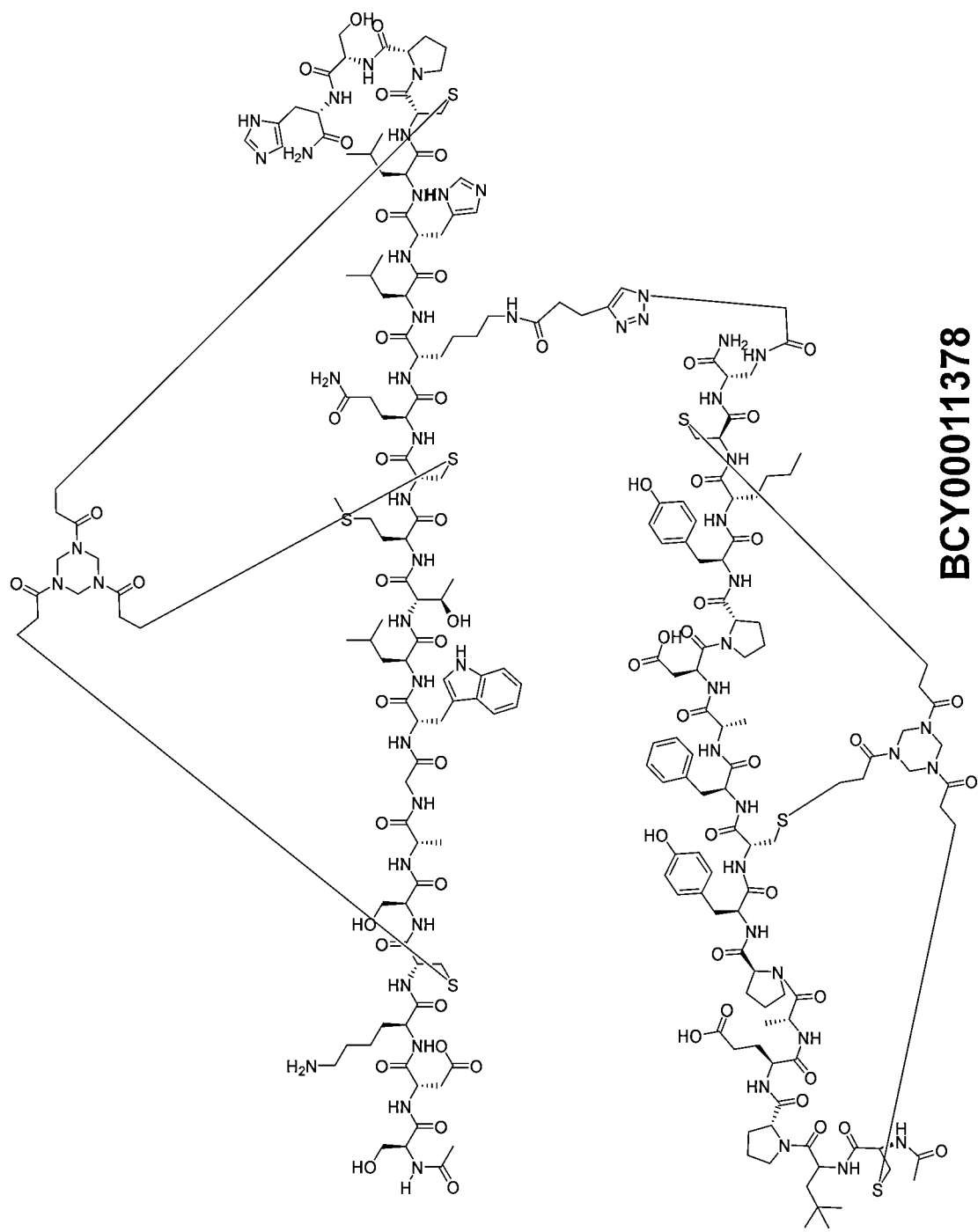
FIG. 70: Formula of BCY11378.
Figure 71:
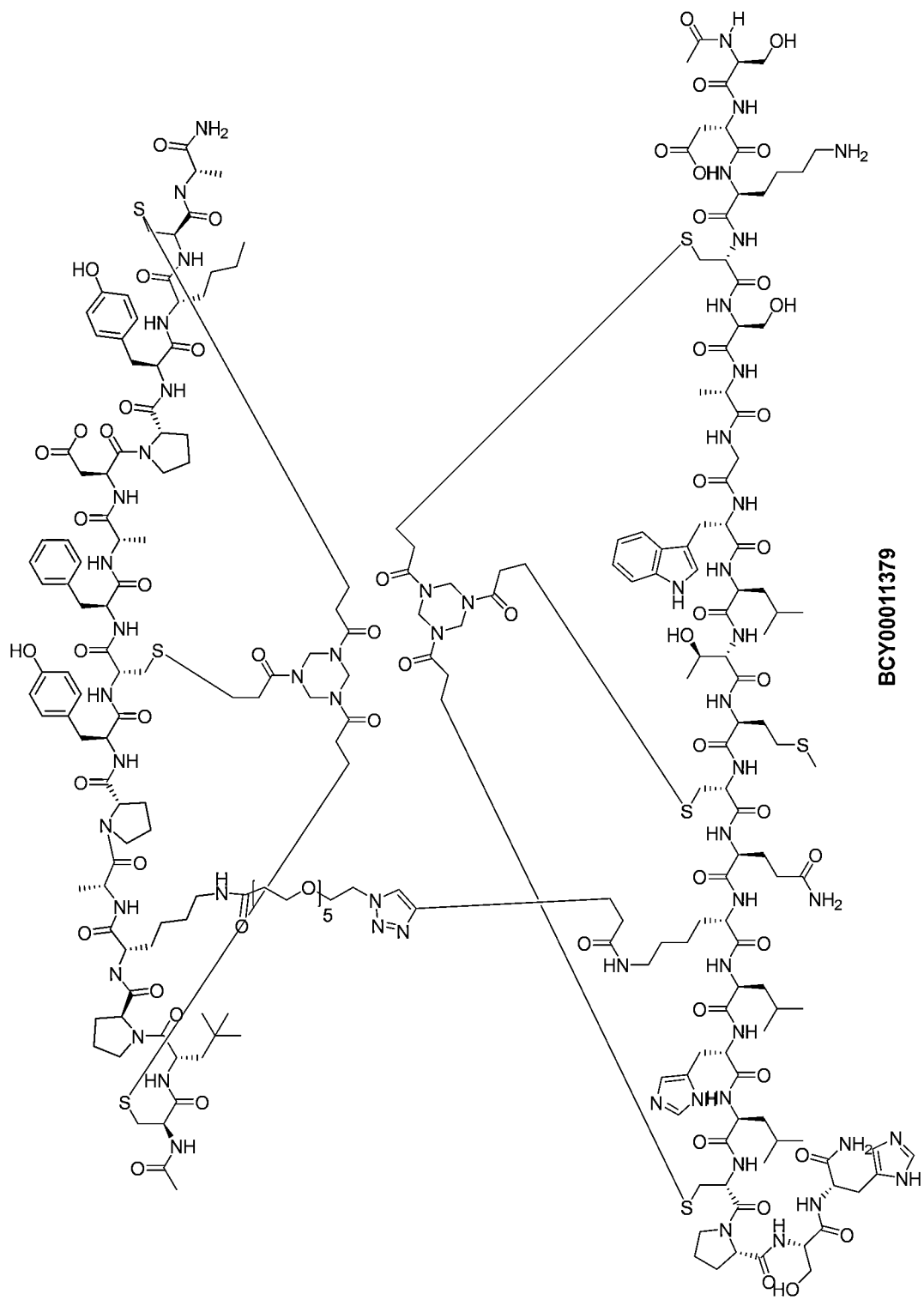
FIG. 71: Formula of BCY11379.
Figure 72:
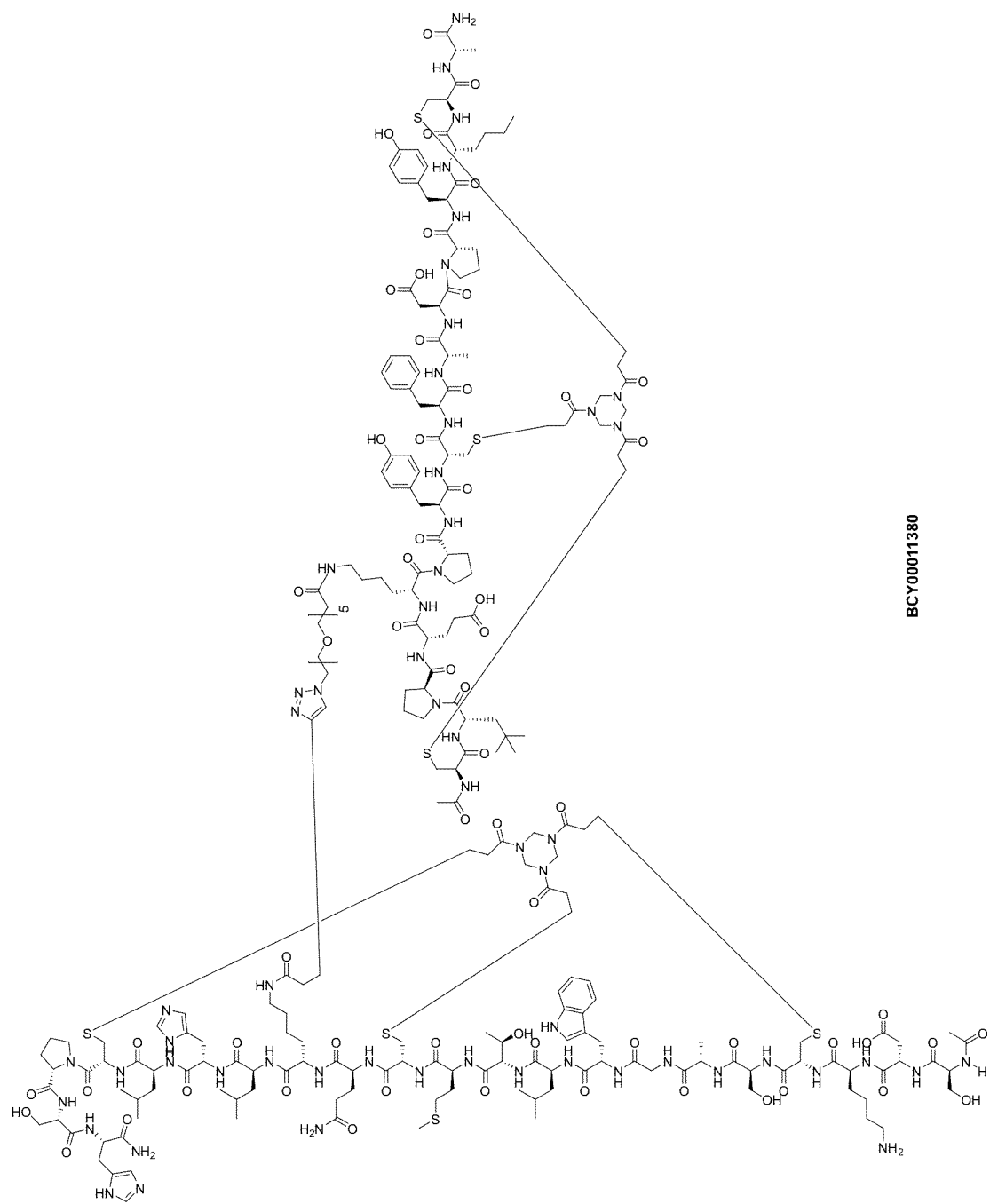
FIG. 72: Formula of BCY11380.
Figure 73:
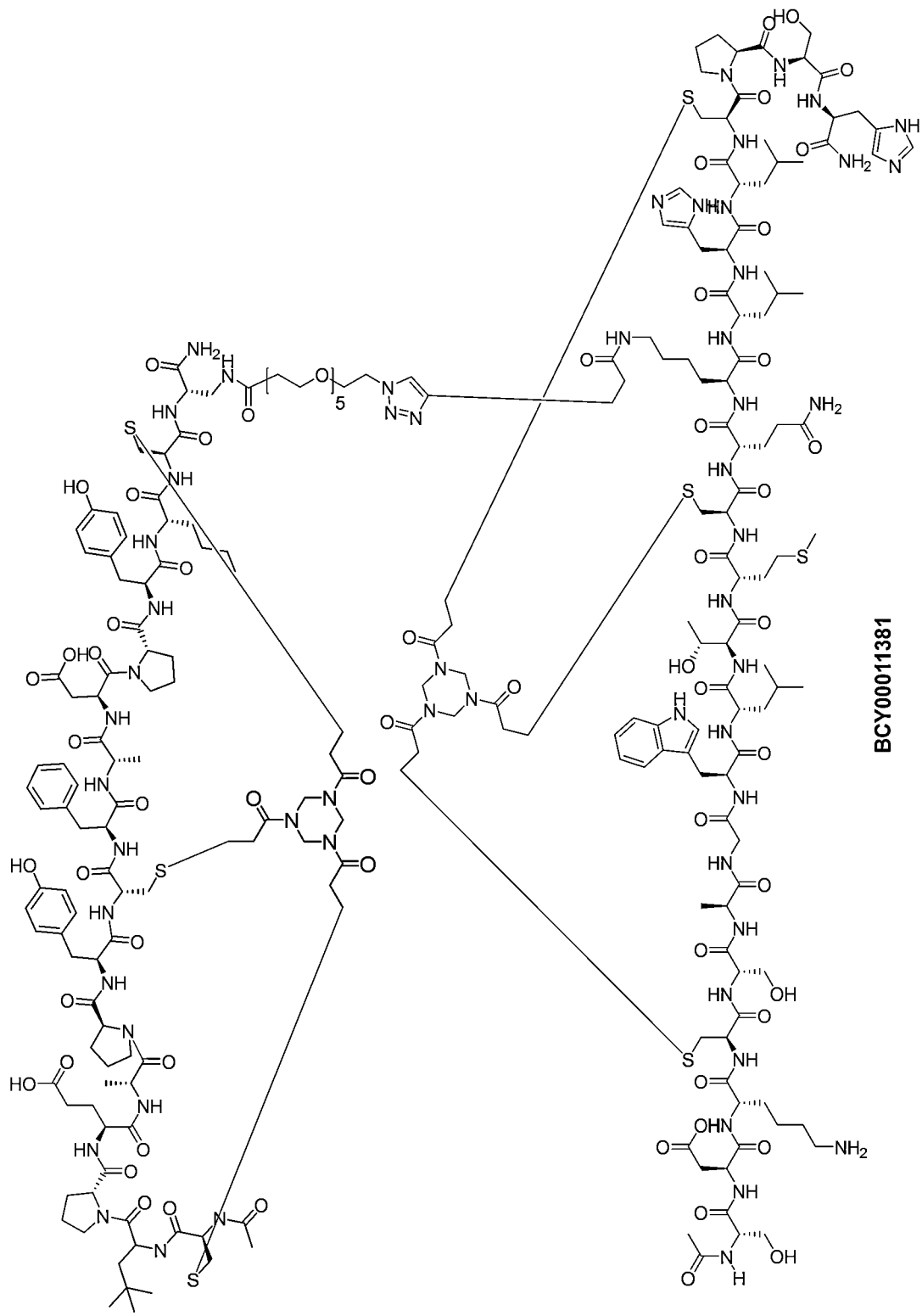
FIG. 73: Formula of BCY11381.

FIG. 10 shows the plasma concentration vs time curve of BCY10572 and BCY10000 from a 2 mg/kg IV dose in SD Rat (n=3). The pharmacokinetic parameters from the experiment are as shown in Table 7:

TABLE 7

Pharmacokinetic Parameters of plasma concentration vs time curve of BCY10572 and BCY10000

| Compound | T½ (h) | Clp (ml/min/kg) | Vdss (L/kg) |
| --- | --- | --- | --- |
| BCY10000 | 0.357 | 16.1 | 0.395 |
| BCY10572 | 0.926 | 15.6 | 0.882 |

---

The invention claimed is:

1. A heterotandem bicyclic peptide complex comprising:
   (a) a first peptide ligand which binds to CD137 on an immune cell;
   conjugated via a linker to
   (b) a second peptide ligand which binds to a component present on a cancer cell, wherein the component present on a cancer cell is EphA2; wherein each of said peptide ligands comprises a polypeptide comprising three cysteine residues, separated by two loop sequences, and a molecular scaffold which forms covalent bonds with the cysteine residues of the polypeptide such that two polypeptide loops are formed on the molecular scaffold,
wherein the first peptide ligand is a CD137 binding bicyclic peptide ligand comprising an amino acid sequence selected from:
   CiIEEGQYCiiFADPY[Nle]Ciii (SEQ ID NO: 1);
   Ci[tBuAla]PE[D-Ala]PYCiiFADPY[Nle]Ciii (SEQ ID NO: 3);
   CiIEEGQYCiiF[D-Ala]DPY[Nle]Ciii (SEQ ID NO: 4);
   Ci[tBuAla]PK[D-Ala]PYCiiFADPY[Nle]Ciii (SEQ ID NO: 5);
   Ci[tBuAla]PE[D-Lys]PYCiiFADPY[Nle]Ciii (SEQ ID NO: 6);
   Ci[tBuAla]P[K(PYA)][D-Ala]PYCiiFADPY[Nle]Ciii (SEQ ID NO: 7);
   Ci[tBuAla]PE[D-Lys(PYA)]PYCiiFADPY[Nle]Ciii (SEQ ID NO: 8);
   CiIEE[D-Lys(PYA)]QYCiiFADPY(Nle)Ciii (SEQ ID NO: 9); and
   [dCi][dI][dE][dE][K(PYA)][dQ][dY][dCii][dF][dA][dD][dP][dY][dNle][dCiii] (SEQ ID NO: 10); and
wherein the second peptide ligand is an EphA2 binding bicyclic peptide ligand comprising an amino acid sequence selected from:
   Ci[HyP]LVNPLCiiLHP[dD]W[HArg]Ciii (SEQ ID NO: 2); and
   CiLWDPTPCiiANLHL[HArg]Ciii (SEQ ID NO: 11);

wherein Ci, Cii and Ciii represent first, second and third cysteine residues, respectively, Nle represents norleucine, tBuAla represents t-butyl-alanine, PYA represents 4-pentynoic acid, HyP represents hydroxyproline, dD represents aspartic acid in D-configuration, and HArg represents homoarginine, or a pharmaceutically acceptable salt thereof.

2. The heterotandem bicyclic peptide complex as defined in claim 1, wherein the linker is selected from: —CH$_2$—, -PEG$_5$-, -PEG$_{10}$-, -PEG$_{12}$-, -PEG$_{23}$-, -PEG$_{24}$-, -PEG$_{15}$-Sar$_5$-, -PEG$_{10}$-Sar$_{10}$-, -PEG$_5$-Sar$_{15}$-, -PEG$_5$-Sar$_5$-, —B-Ala-Sar$_{20}$-, —B-Ala-Sar$_{10}$-PEG$_{10}$-, —B-Ala-Sar$_5$-PEG$_{15}$-, and —B-Ala-Sar$_5$-PEG$_5$-, wherein B-Ala represents beta-alanine.

3. The heterotandem bicyclic peptide complex as defined in claim 1, wherein the molecular scaffold is 1,1',1"-(1,3,5-triazinane-1,3,5-triyl)triprop-2-en-1-one (TATA), which forms covalent bonds with the cysteine residues of the polypeptide such that two polypeptide loops are formed on the molecular scaffold.

4. The heterotandem bicyclic peptide complex as defined in claim 1, wherein the heterotandem bicyclic peptide complex is a free acid, or a pharmaceutically acceptable salt selected from the sodium, potassium, calcium, and ammonium salt.

5. A pharmaceutical composition which comprises the heterotandem bicyclic peptide complex of claim 1 in combination with one or more pharmaceutically acceptable excipients.

6. The heterotandem bicyclic peptide complex as defined in claim 1, wherein the first peptide ligand is a CD137 binding bicyclic peptide ligand comprising an amino acid sequence with N- and C-terminal modifications selected from:
   Ac-A-(SEQ ID NO: 1)-Dap;
   Ac-A-(SEQ ID NO: 1)-Dap(PYA);
   Ac-(SEQ ID NO: 3)-Dap;
   Ac-(SEQ ID NO: 3)-Dap(PYA);
   Ac-A-(SEQ ID NO: 4)-Dap;
   Ac-(SEQ ID NO: 5)-A;

Ac-(SEQ ID NO: 6)-A;
Ac-(SEQ ID NO: 7)-A;
Ac-(SEQ ID NO: 8)-A;
Ac-A-(SEQ ID NO: 9)-A; and
Ac-[dA]-(SEQ ID NO: 10)-[dA]-NH2;
wherein Ac represents an acetyl group, Dap represents diaminopropionic acid and PYA represents 4-pentynoic acid, or a pharmaceutically acceptable salt thereof.

7. A pharmaceutical composition which comprises the heterotandem bicyclic peptide complex of claim 6 in combination with one or more pharmaceutically acceptable excipients.

8. The heterotandem bicyclic peptide complex as defined in claim 1, wherein the second peptide ligand is an EphA2 binding bicyclic peptide ligand comprising an amino acid sequence with N-terminal modifications selected from:

A-HArg-D-(SEQ ID NO: 2);
[B-Ala]-[Sar10]-A-[HArg]-D-(SEQ ID NO: 2);
[PYA]-[B-Ala]-[Sar10]-A-[HArg]-D-(SEQ ID NO: 2); and

```
A-HArg-D-(SEQ ID NO: 2) (hereinafter referred to
as BCY9594);

[B-Ala]-[Sar₁₀]-A-[HArg]-D-(SEQ ID NO: 2)

(hereinafter referred to as BCY6099);

[PYA][B-Ala]-[Sar₁₀]-A-[HArg]-D-(SEQ ID NO: 2)

(hereinafter referred to as BCY6169);
and

[PYA]-[B-Ala]-[Sar₁₀]-VGP-(SEQ ID NO: 11)

(hereinafter referred to as BCY8941);
``` wherein HArg represents homoarginine, PYA represents 4-pentynoic acid, $Sar_{10}$ represents 10 sarcosine units, B-Ala represents beta-alanine, or a pharmaceutically acceptable salt thereof.

9. A pharmaceutical composition which comprises the heterotandem bicyclic peptide complex of claim 8 in combination with one or more pharmaceutically acceptable excipients.

10. The heterotandem bicyclic peptide complex as defined in claim 1 which is a CD137/EphA2 complex selected from:

125 126
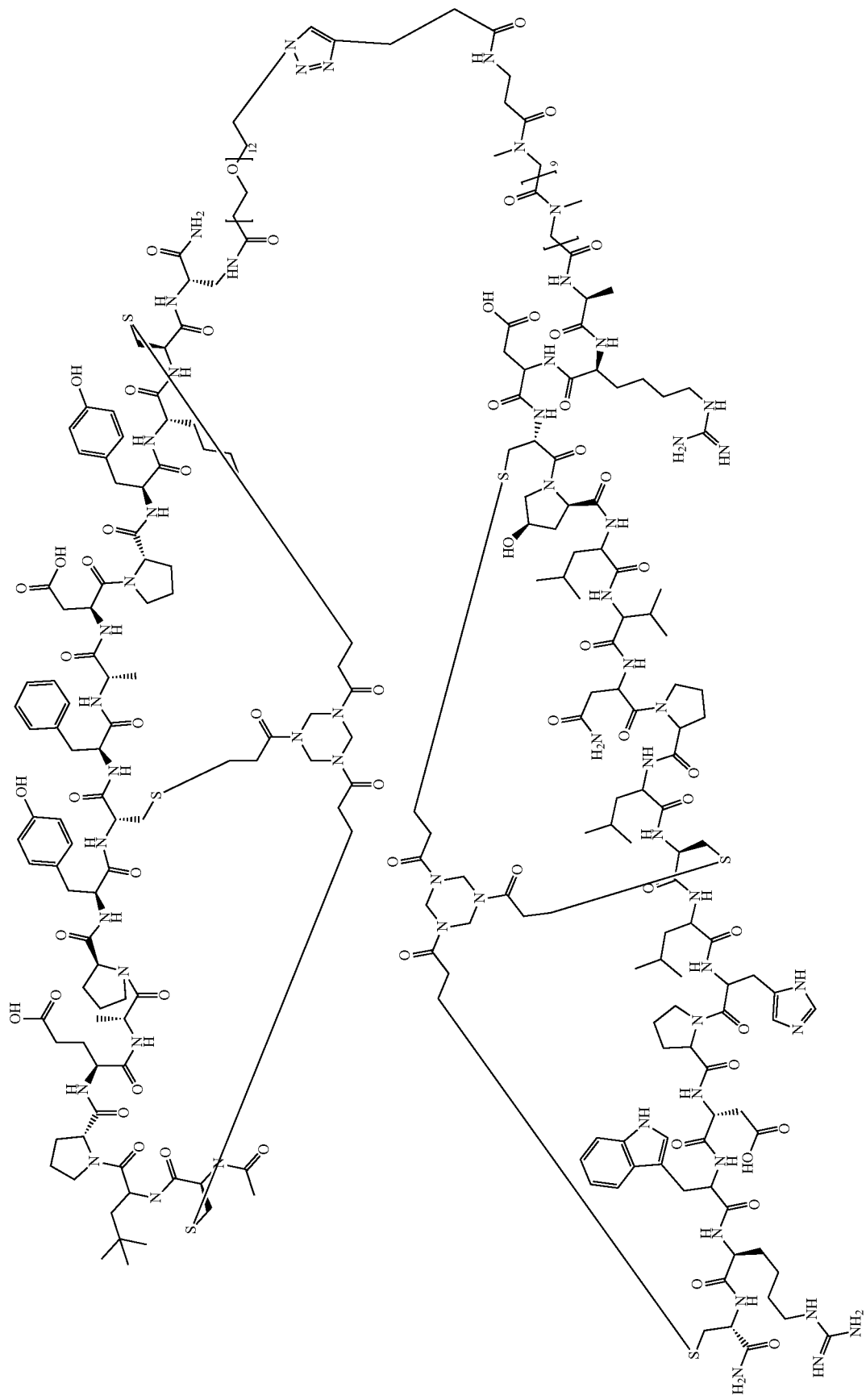

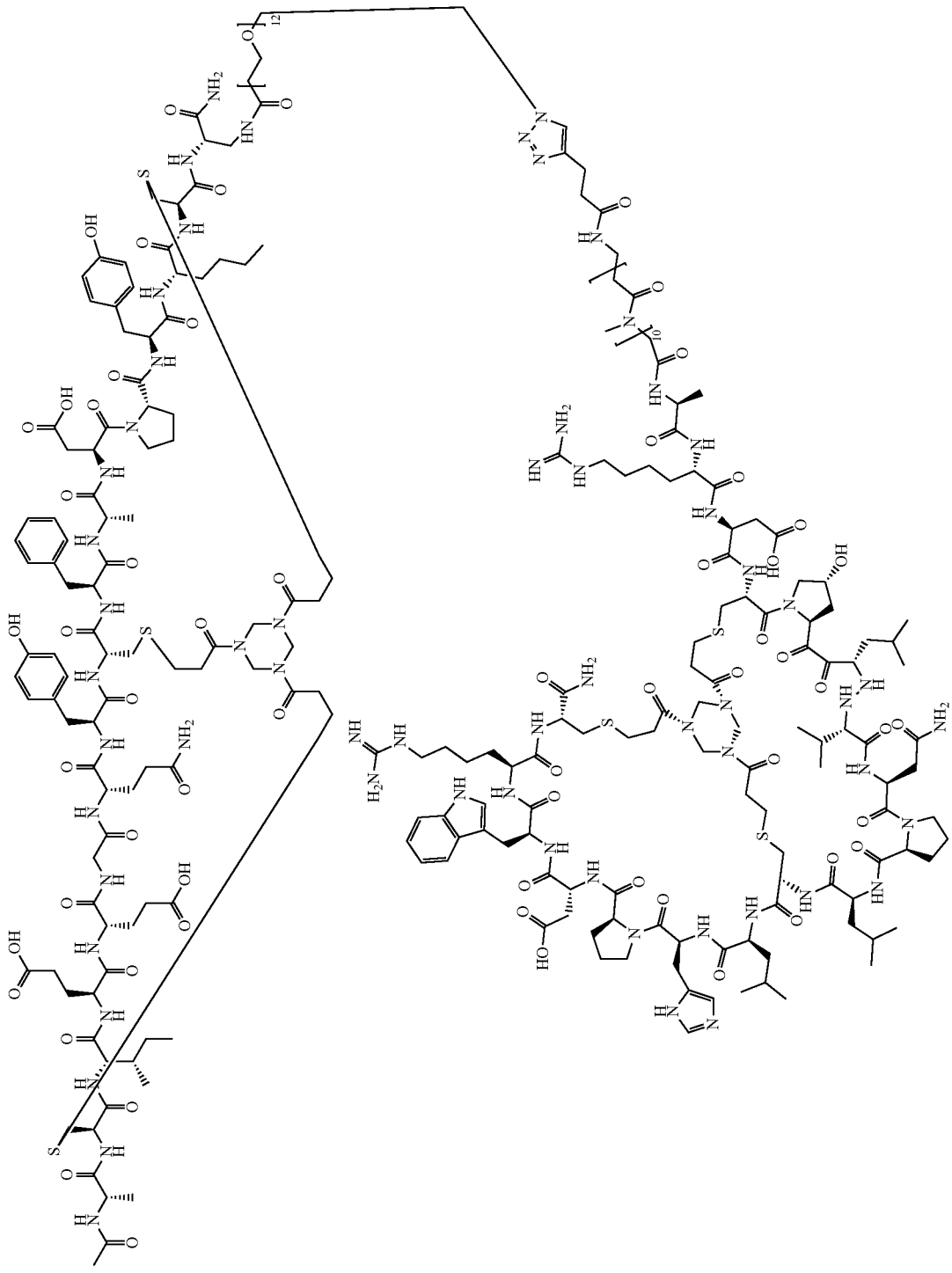
BCY7985

BCY8942
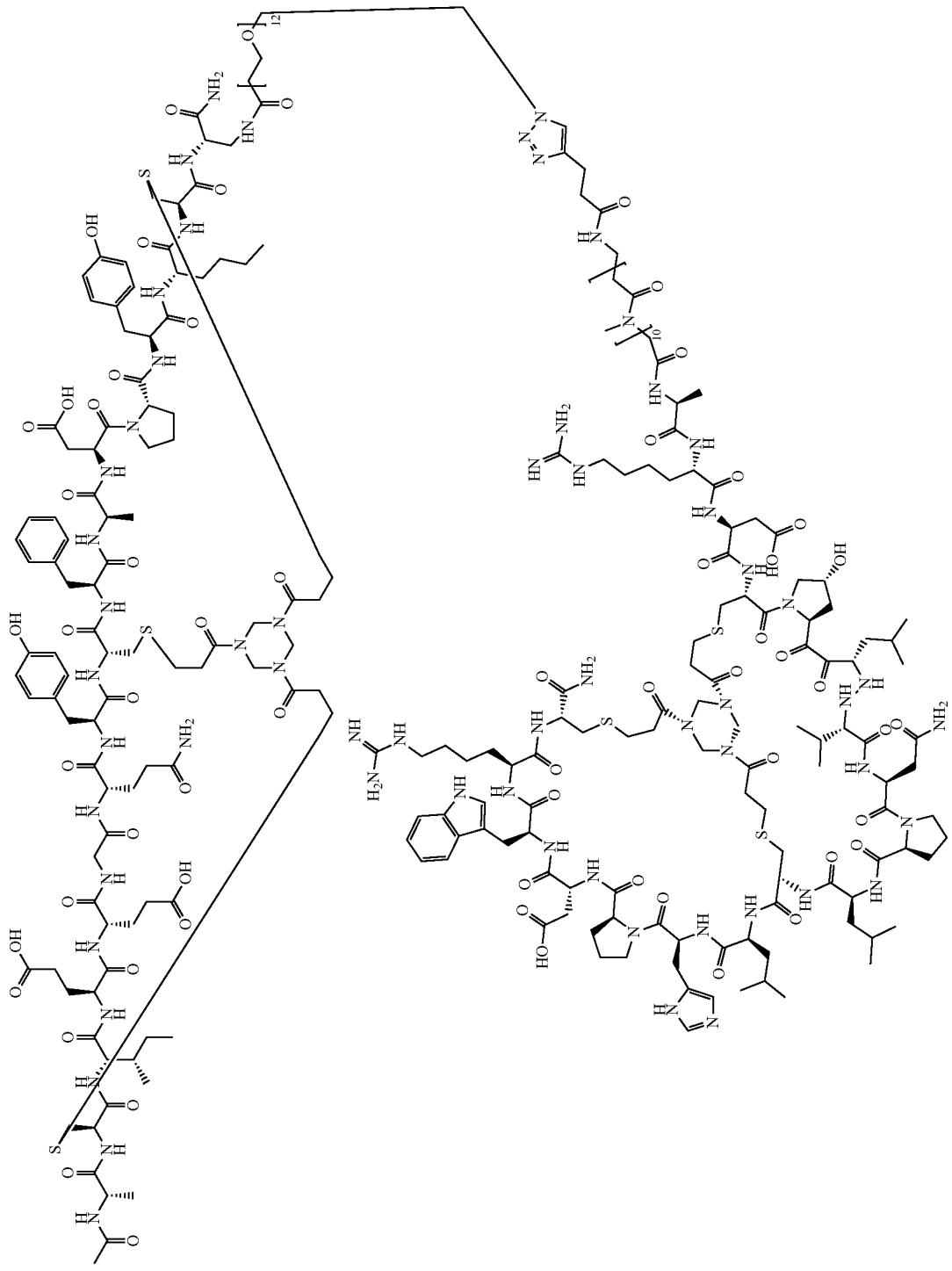

BCY8943
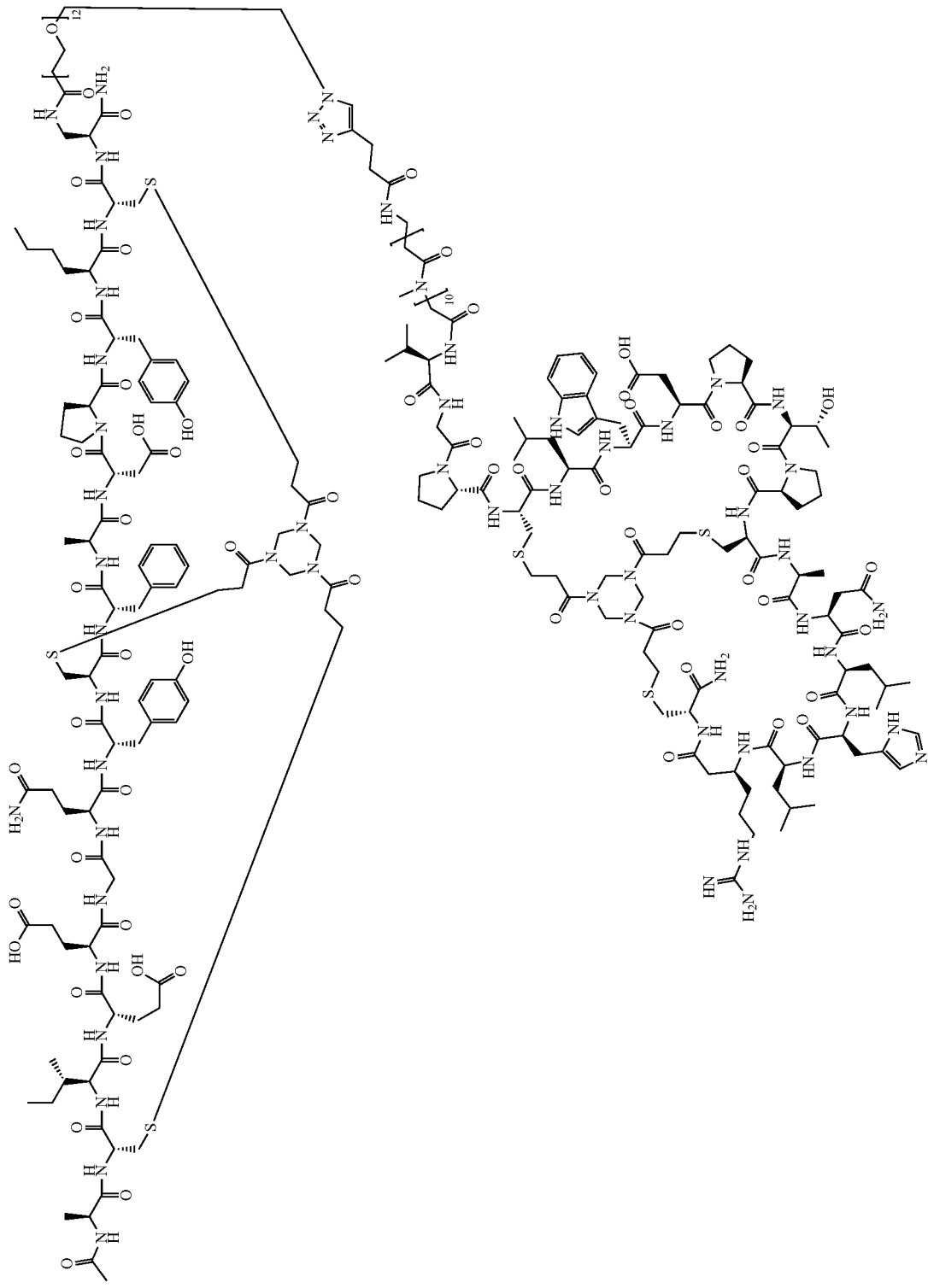

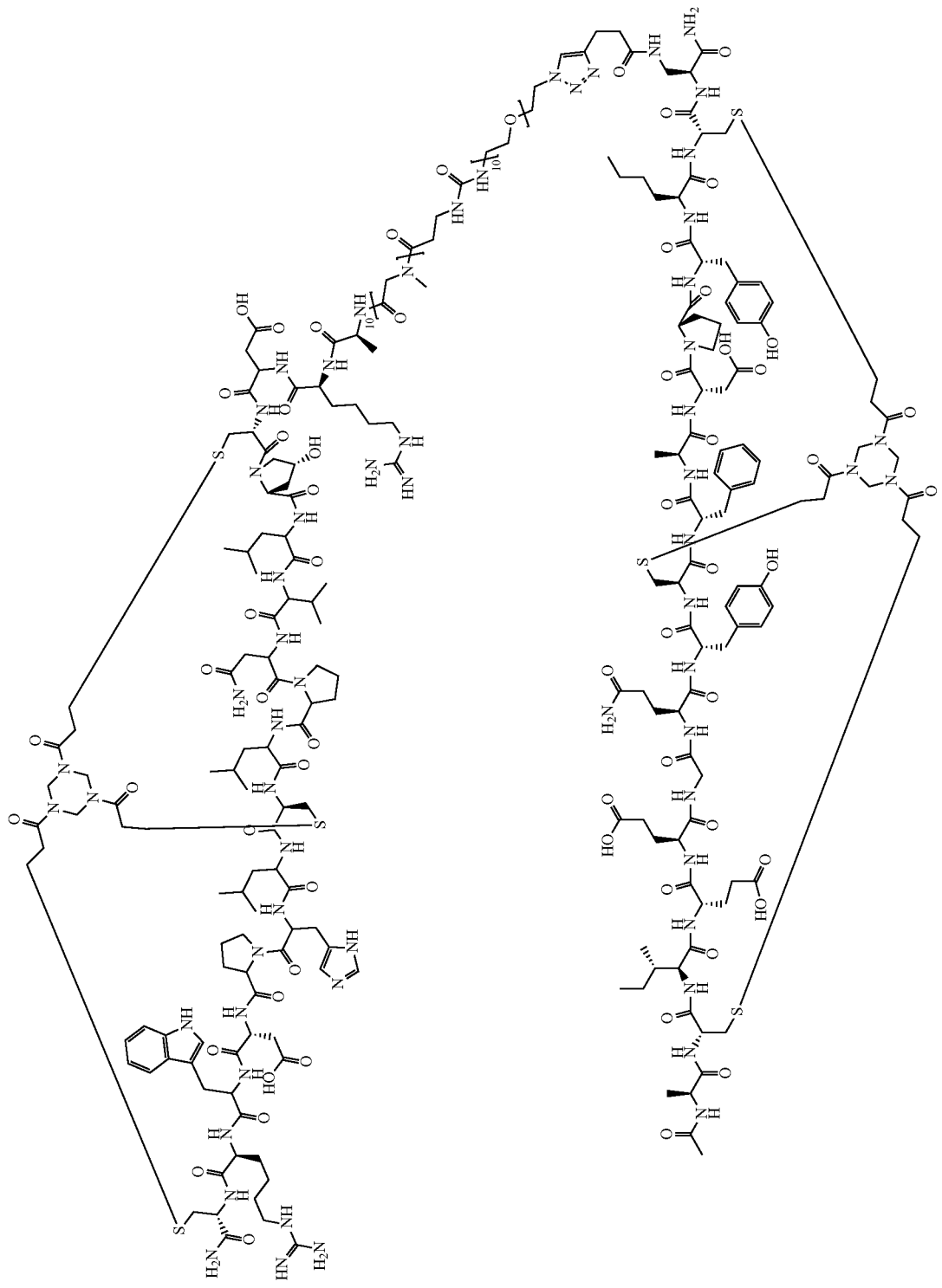

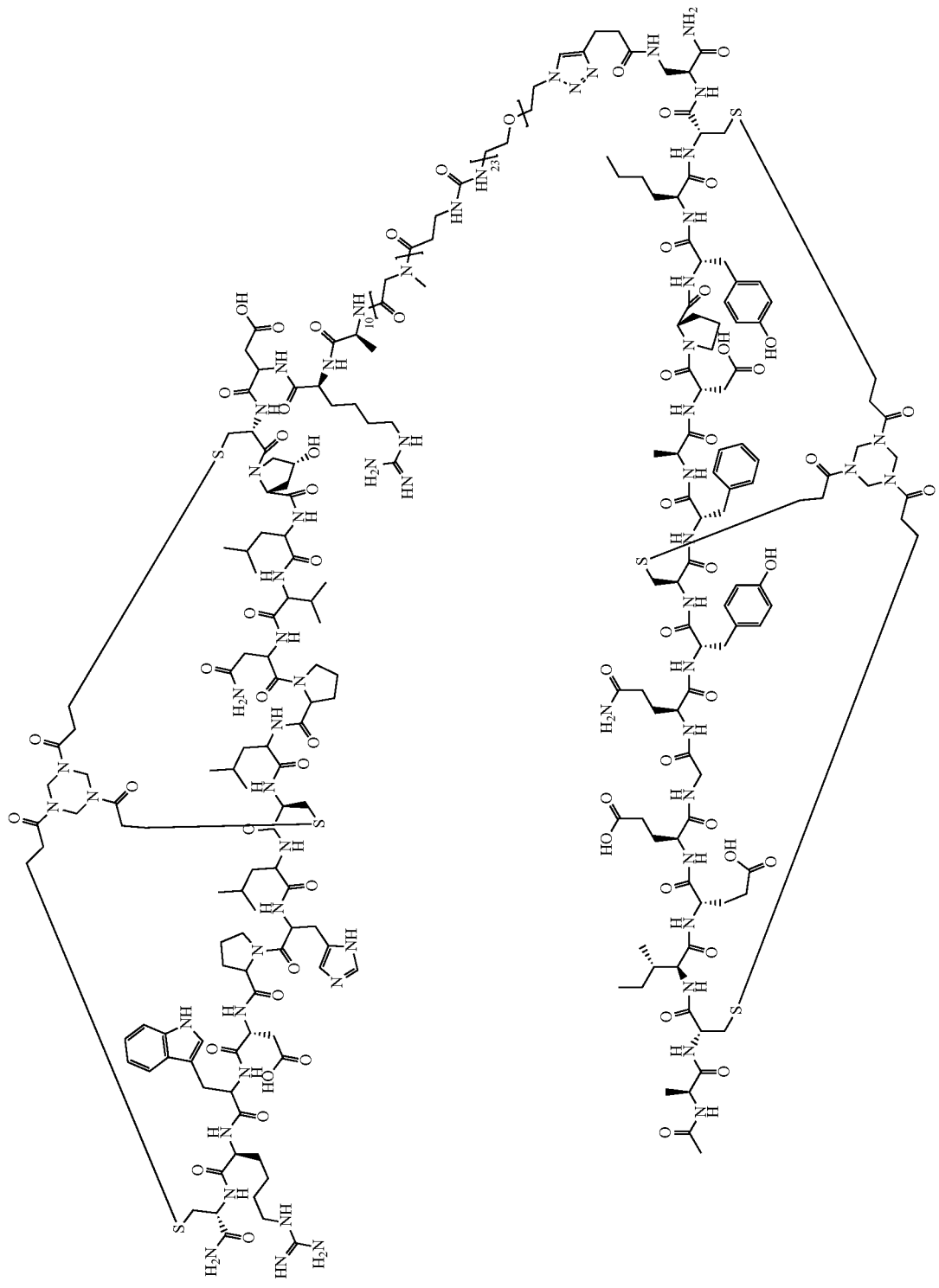

BCY9655
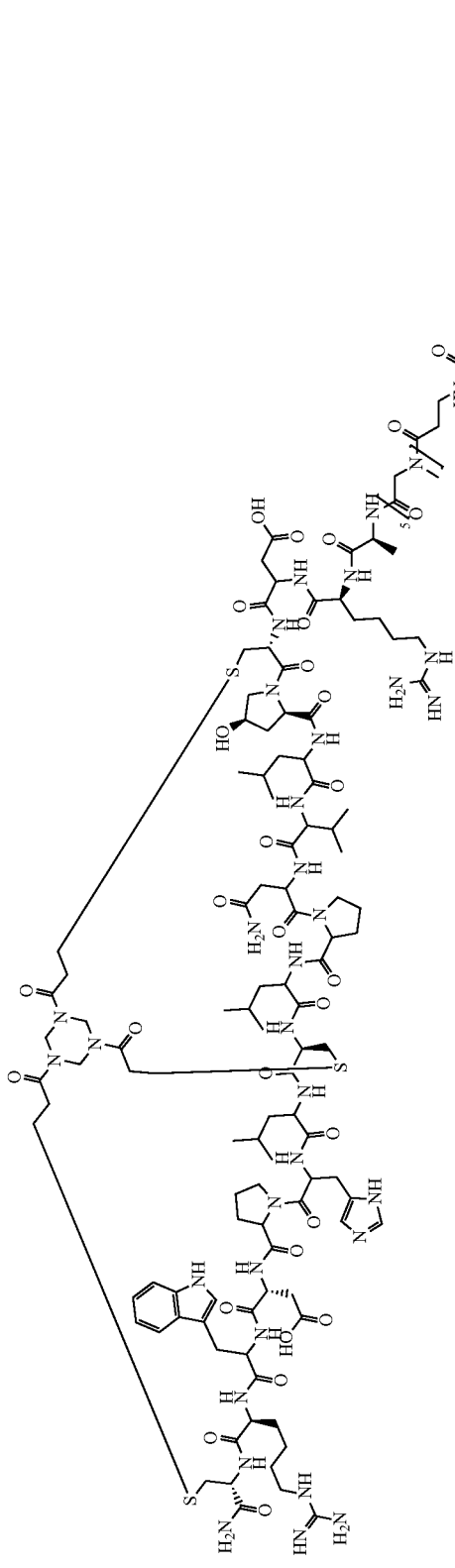
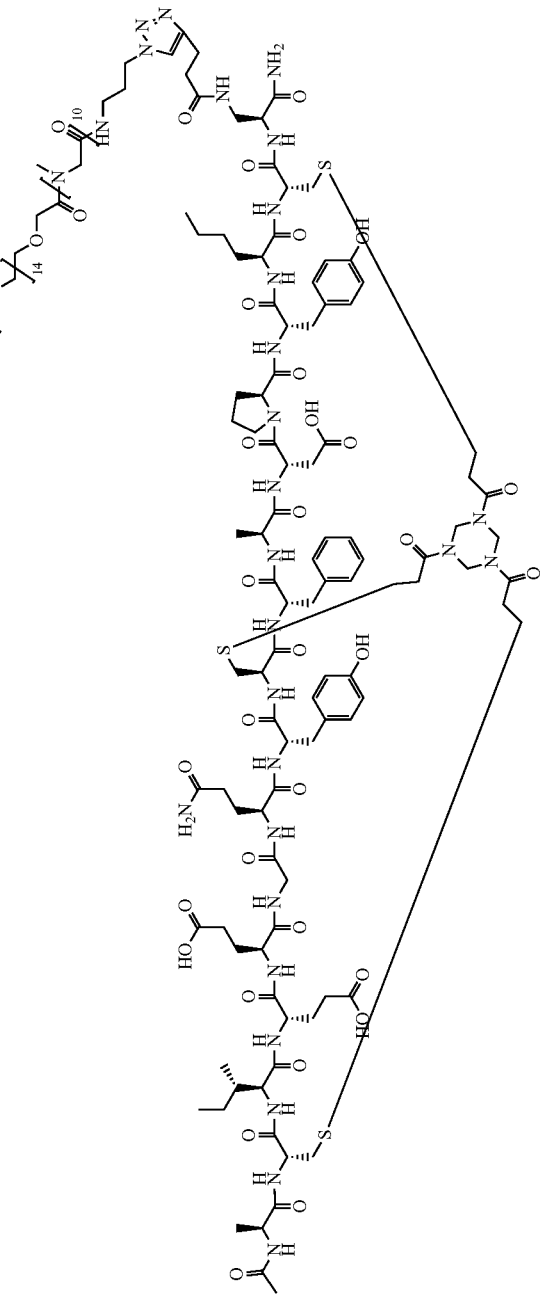

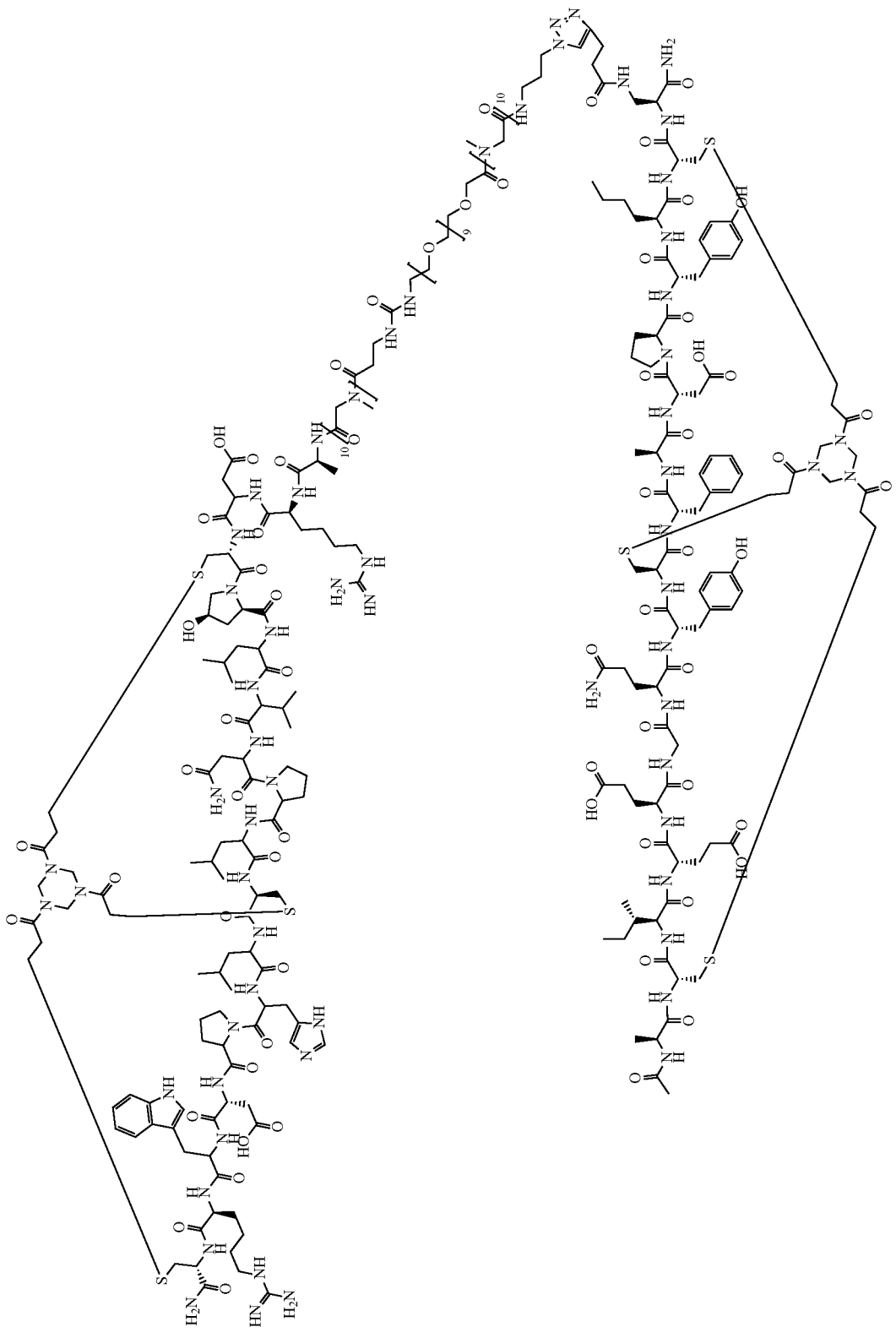

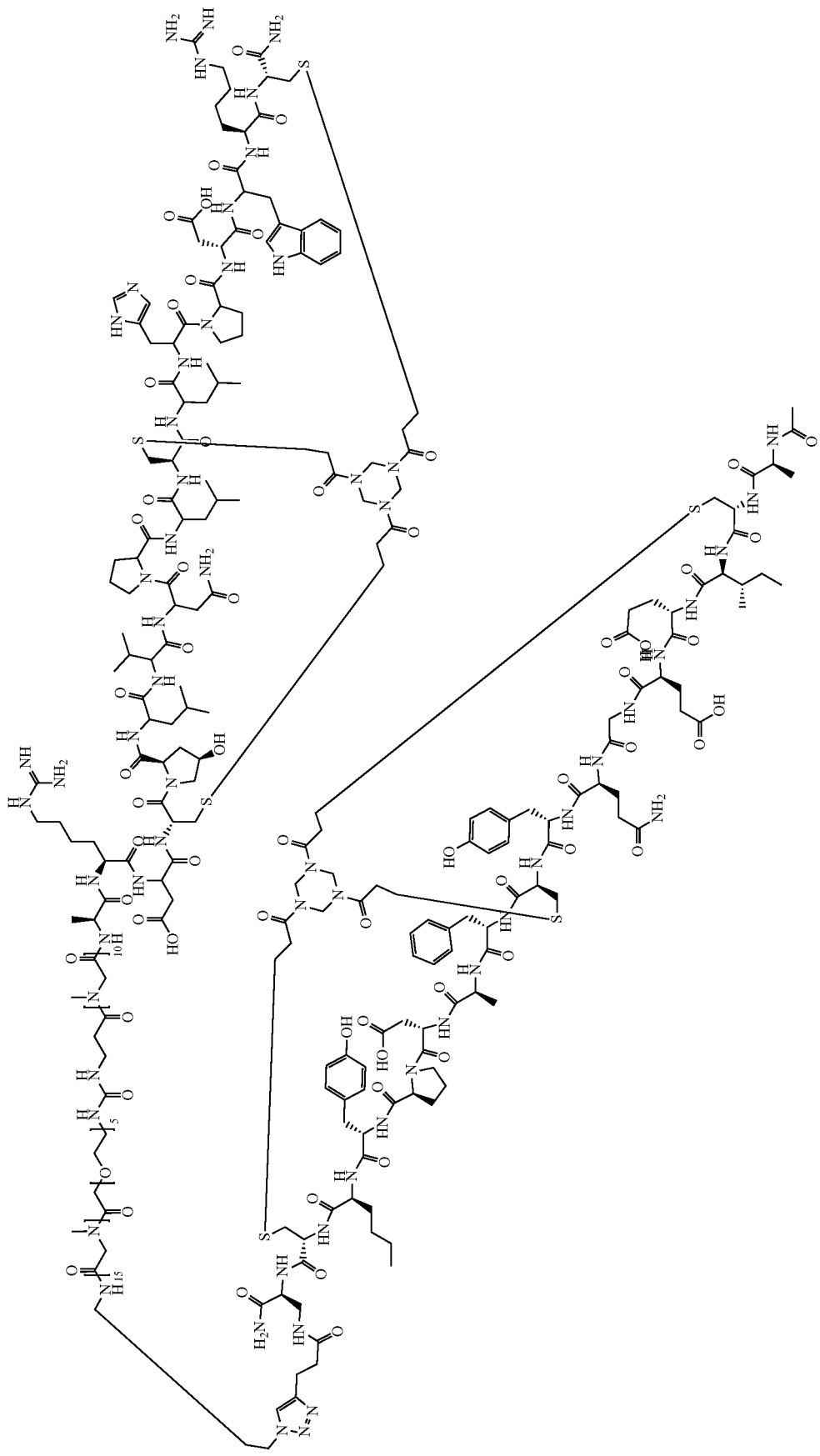

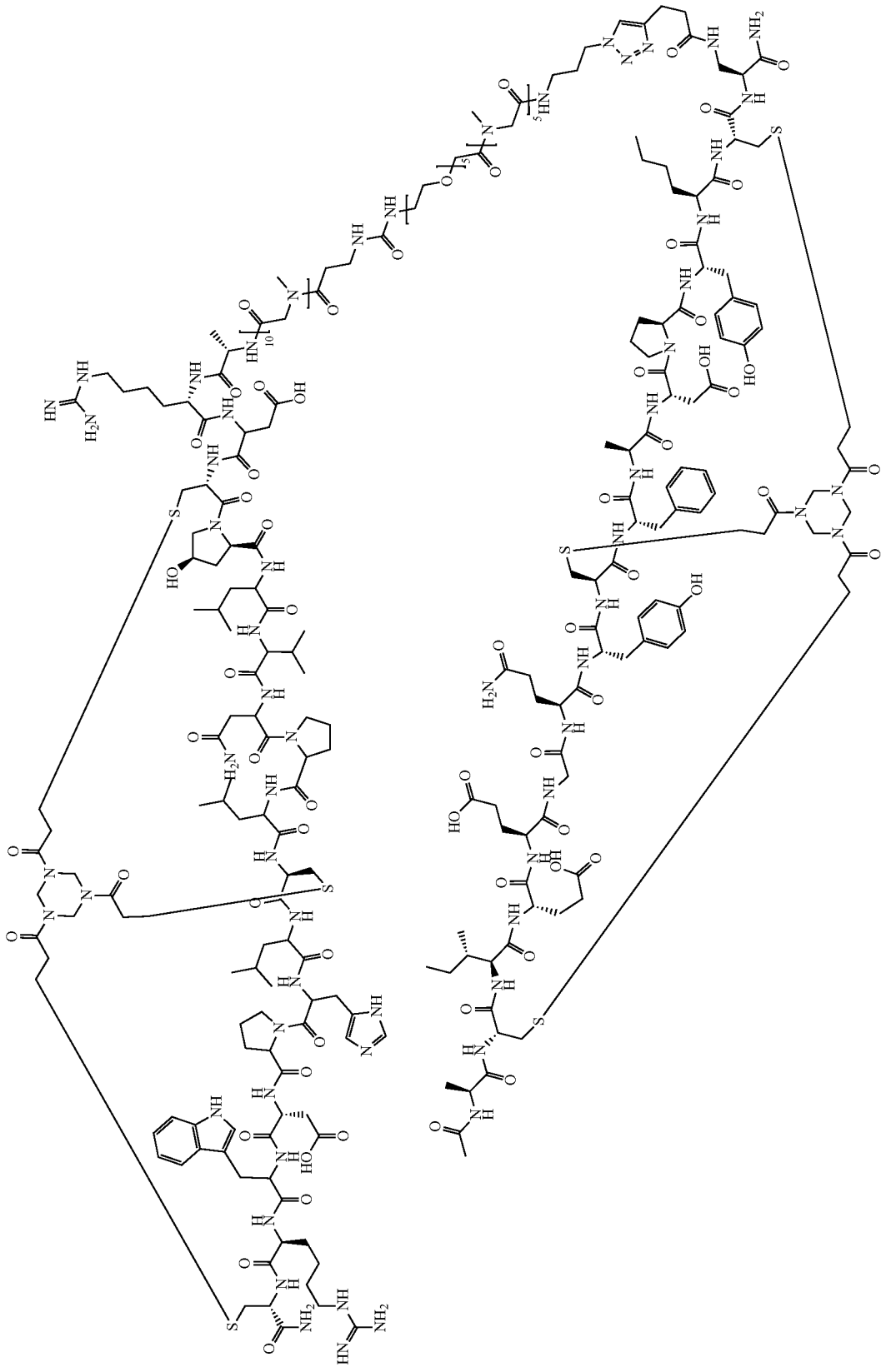
BCY9658
-continued

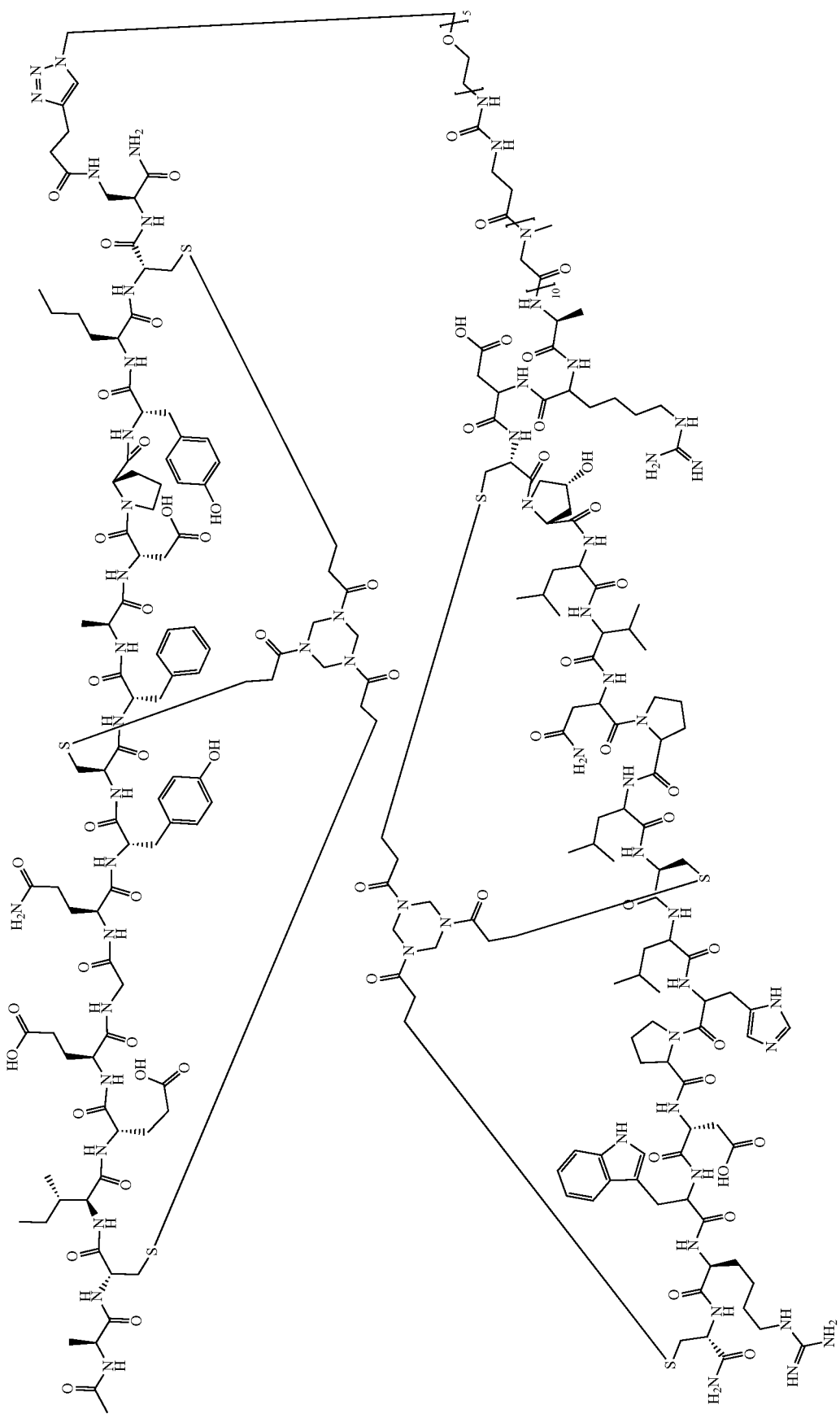

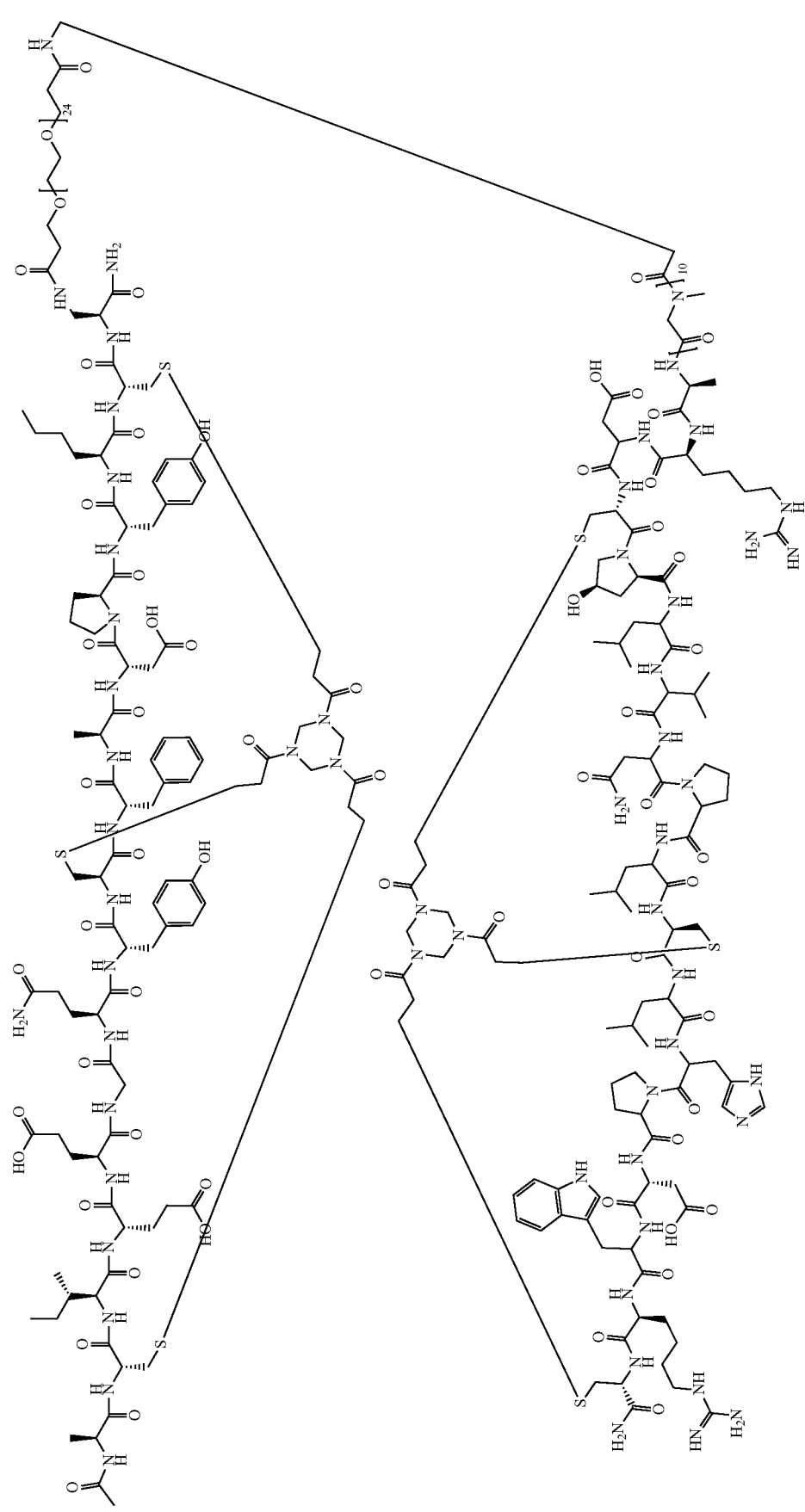

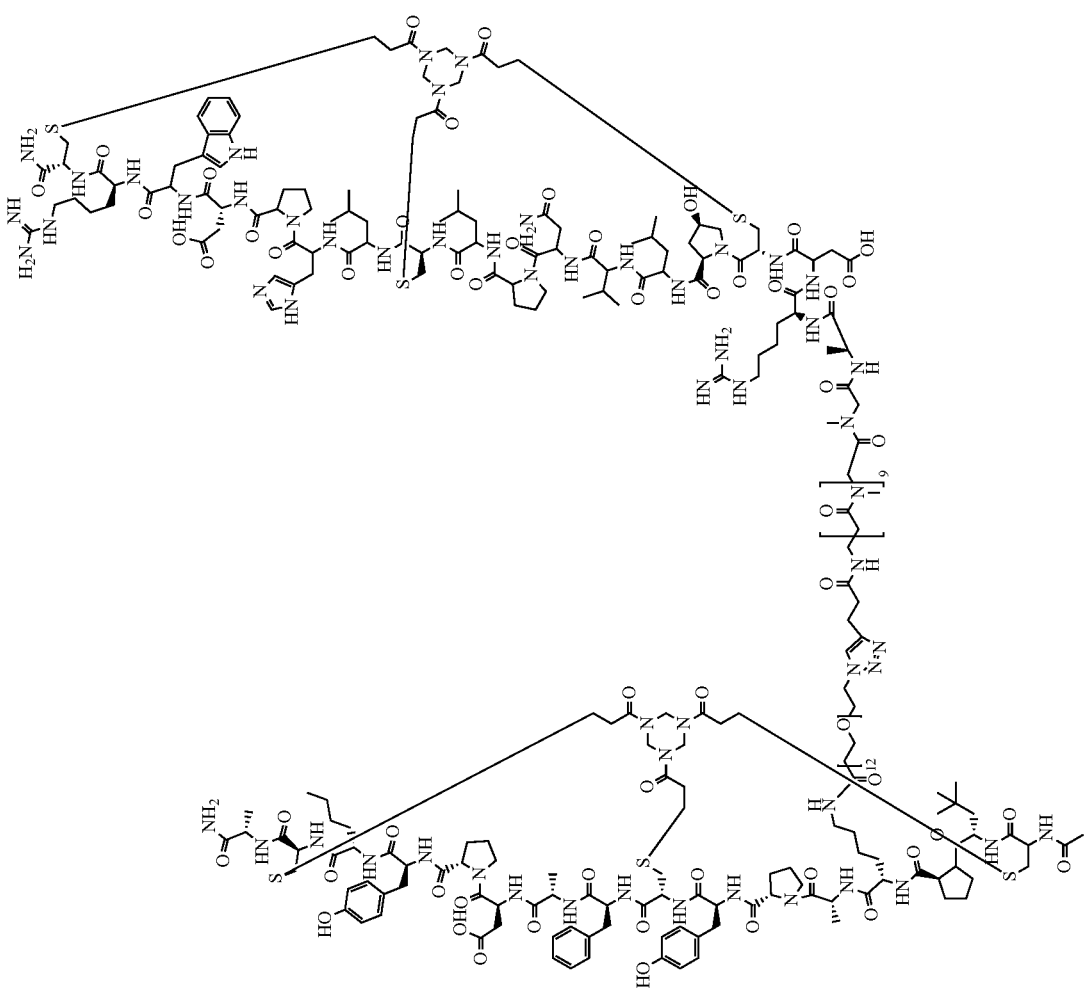

151
BCY10570
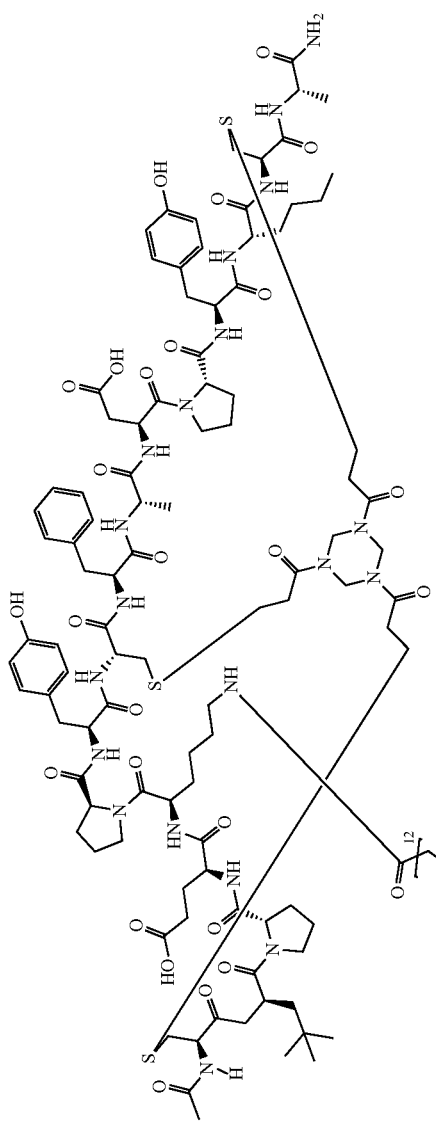
152
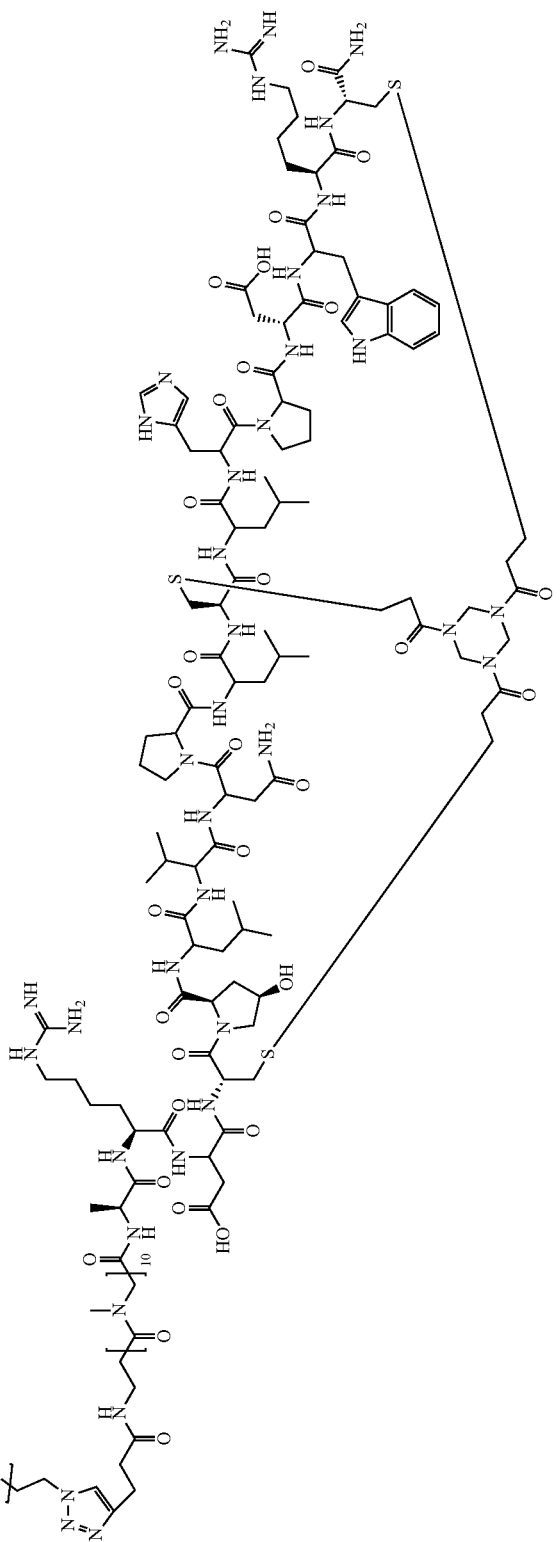

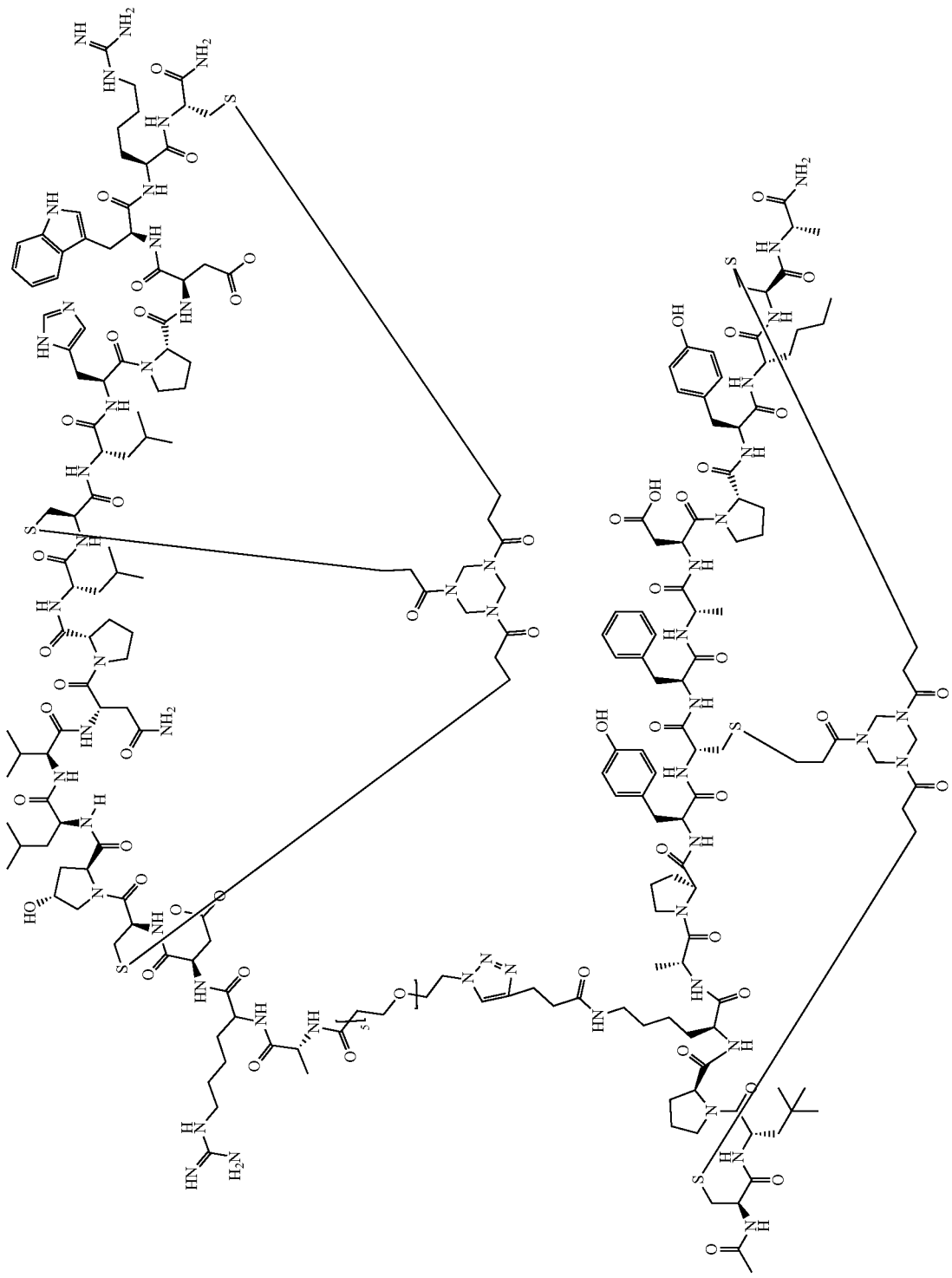

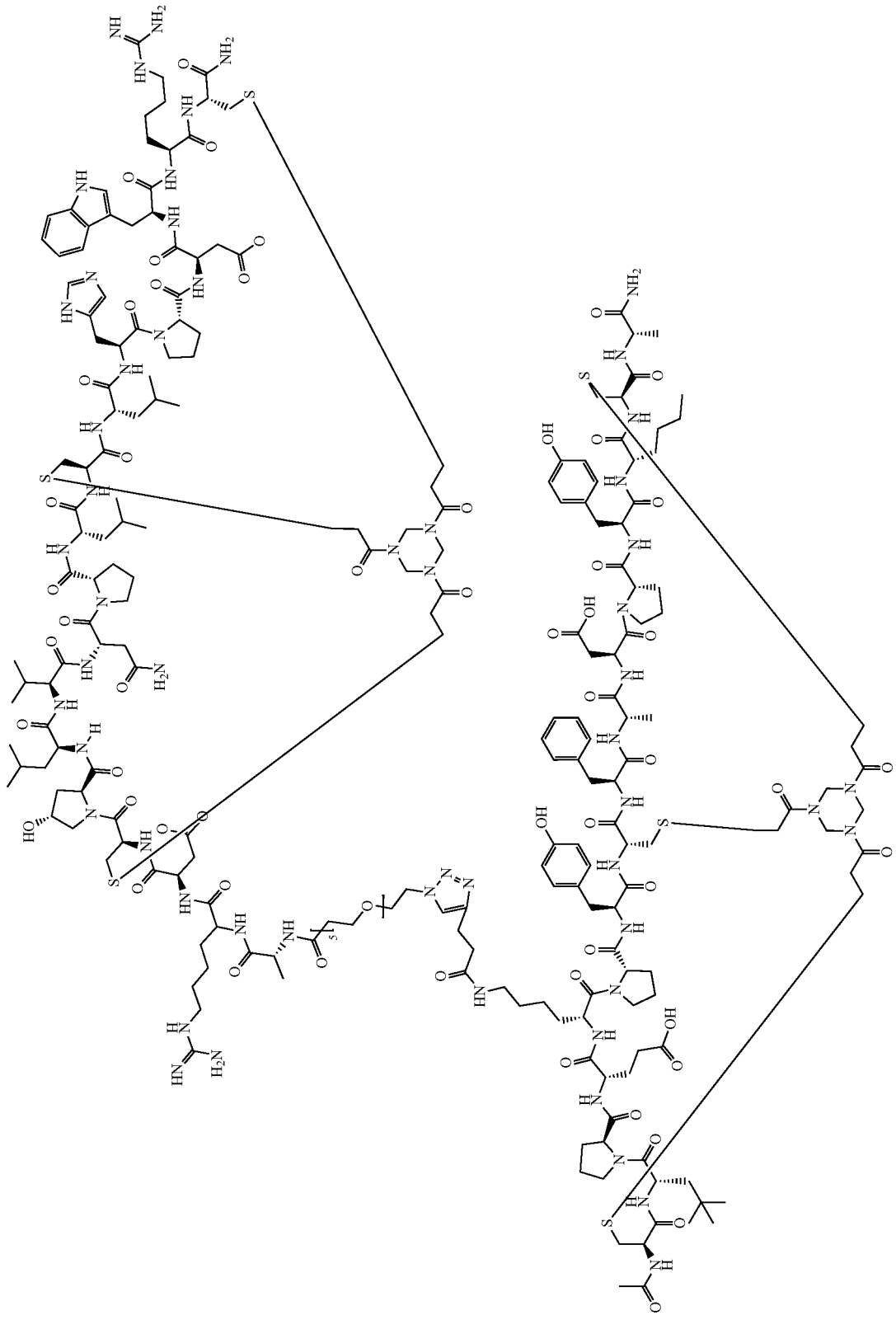

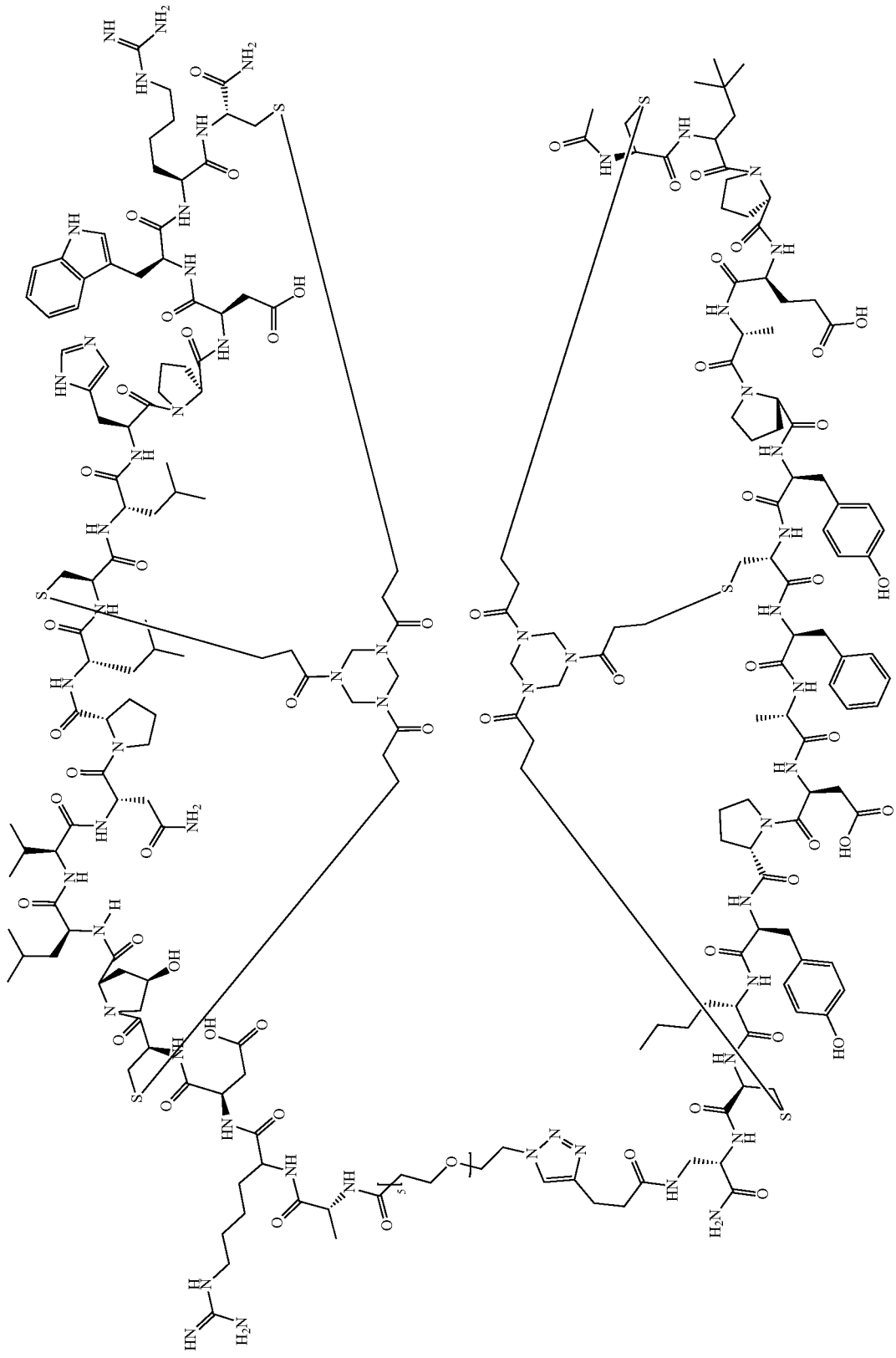

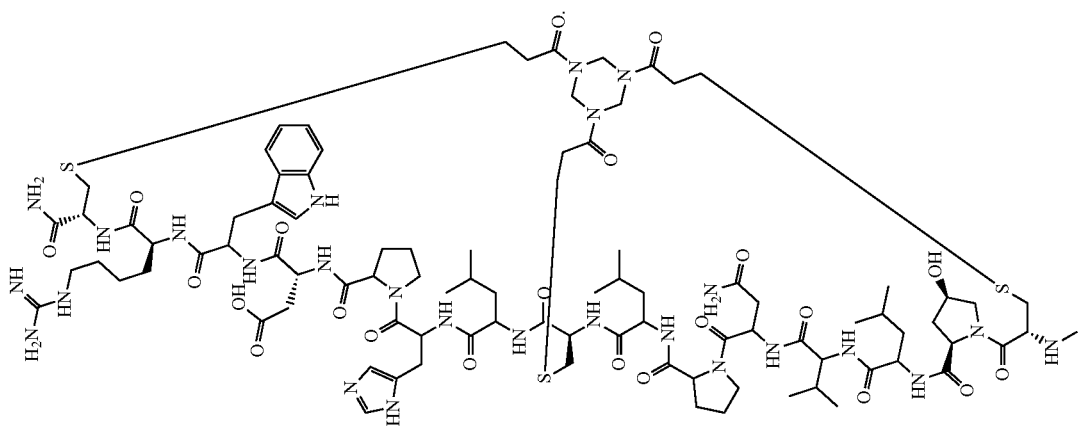
-continued
BCY10577

-continued
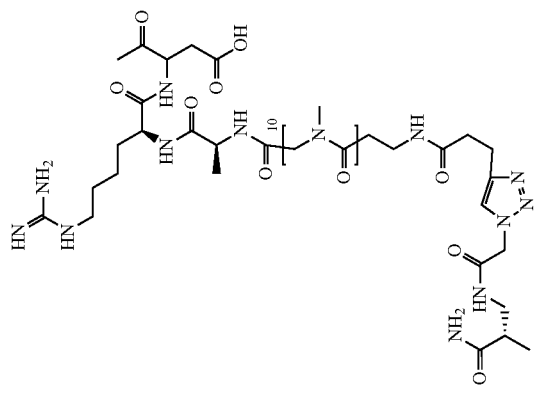

-continued
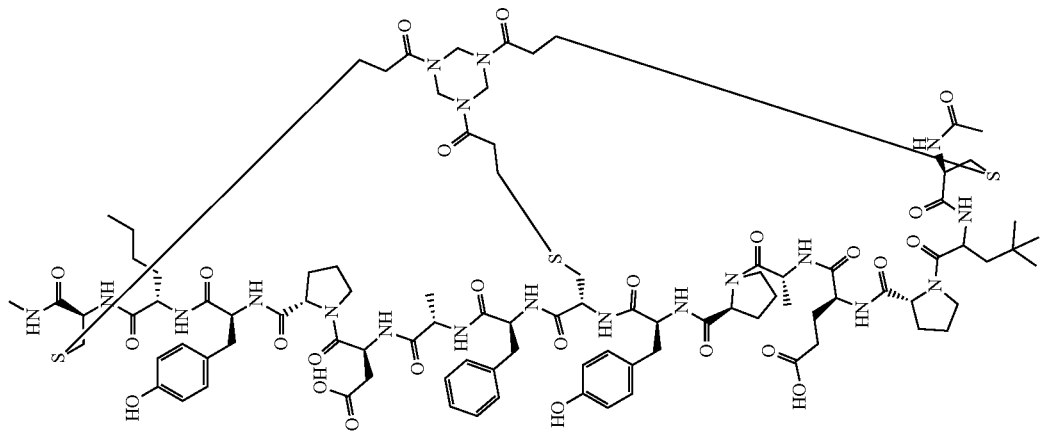

11. A pharmaceutical composition which comprises the heterotandem bicyclic peptide complex of claim 10 in combination with one or more pharmaceutically acceptable excipients.

12. A pharmaceutical composition which comprises the heterotandem bicyclic peptide complex of claim 3 in combination with one or more pharmaceutically acceptable excipients.

13. A method of treating cancer which comprising administering the heterotandem bicyclic peptide complex as defined in claim 1 to a subject in need thereof, wherein the cancer is breast cancer, lung cancer, gastric cancer, pancreatic cancer, prostate cancer, liver cancer, or glioblastoma.

14. The method of claim 13, wherein the first peptide ligand is a CD137 binding bicyclic peptide ligand comprising an amino acid sequence with N- and C-terminal modifications selected from:

Ac-A-(SEQ ID NO: 1)-Dap;
Ac-A-(SEQ ID NO: 1)-Dap(PYA);
Ac-(SEQ ID NO: 3)-Dap;
Ac-(SEQ ID NO: 3)-Dap(PYA);
Ac-A-(SEQ ID NO: 4)-Dap;
Ac-(SEQ ID NO: 5)-A;
Ac-(SEQ ID NO: 6)-A;
Ac-(SEQ ID NO: 7)-A;
Ac-(SEQ ID NO: 8)-A;
Ac-A-(SEQ ID NO: 9)-A; and
Ac-[dA]-(SEQ ID NO: 10)-[dA]-NH2;

wherein Ac represents an acetyl group, Dap represents diaminopropionic acid and PYA represents 4-pentynoic acid, or a pharmaceutically acceptable salt thereof.

15. The method of claim 13, wherein the second peptide ligand is an EphA2 binding bicyclic peptide ligand comprising an amino acid sequence with N-terminal modifications selected from:

A-HArg-D-(SEQ ID NO: 2)
[B-Ala]-[Sar10]-A-[HArg]-D-(SEQ ID NO: 2);
[PYA]-[B-Ala]-[Sar10]-A-[HArg]-D-(SEQ ID NO: 2); and
[PYA]-[B-Ala]-[Sar10]-VGP-(SEQ ID NO: 11);

wherein HArg represents homoarginine, PYA represents 4-pentynoic acid, Sar10 represents 10 sarcosine units, B-Ala represents beta-alanine, or a pharmaceutically acceptable salt thereof.

16. The method of claim 13, wherein the heterotandem bicyclic peptide complex is a CD137/EphA2 complex selected from:

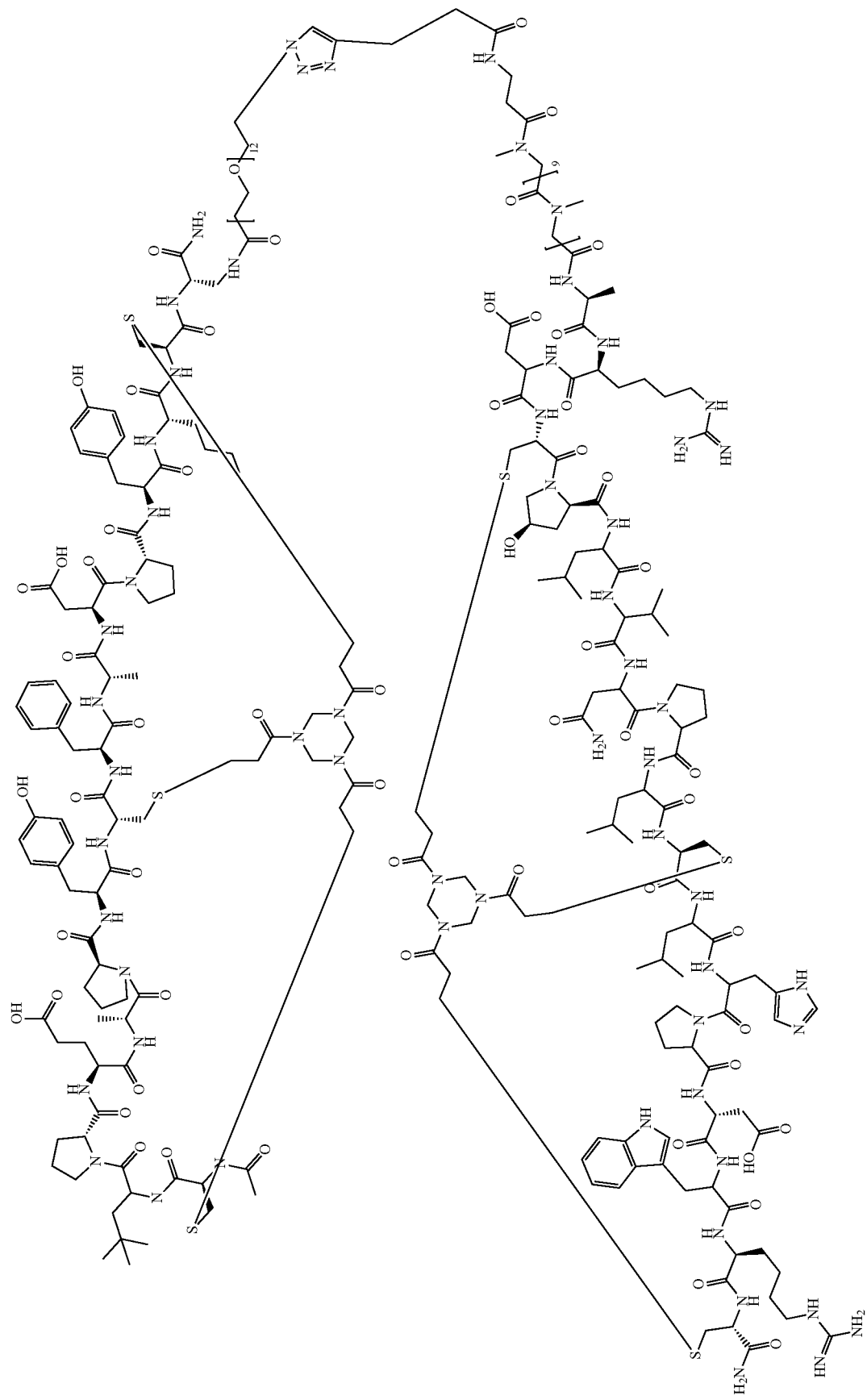

-continued
BCY7985
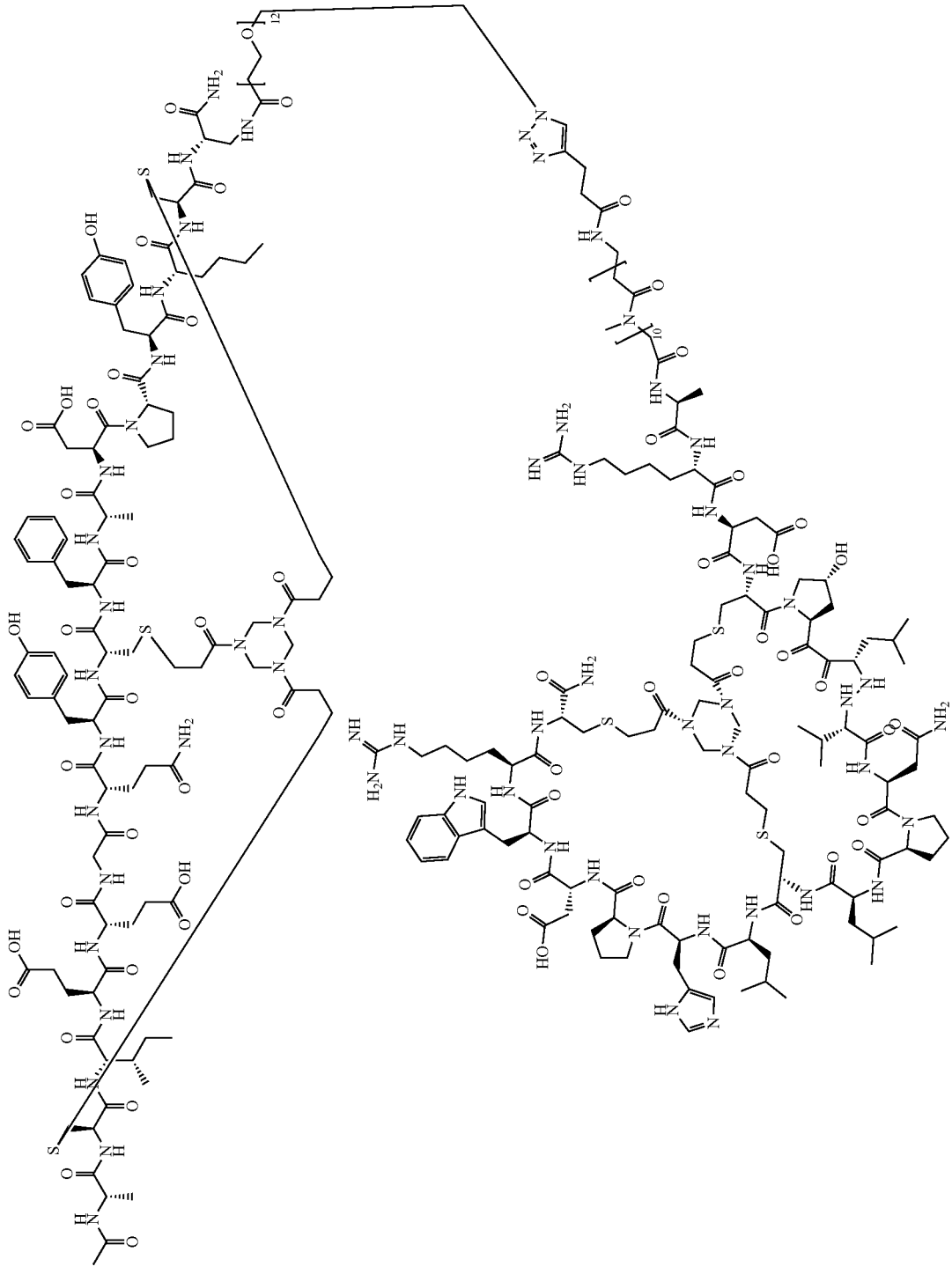

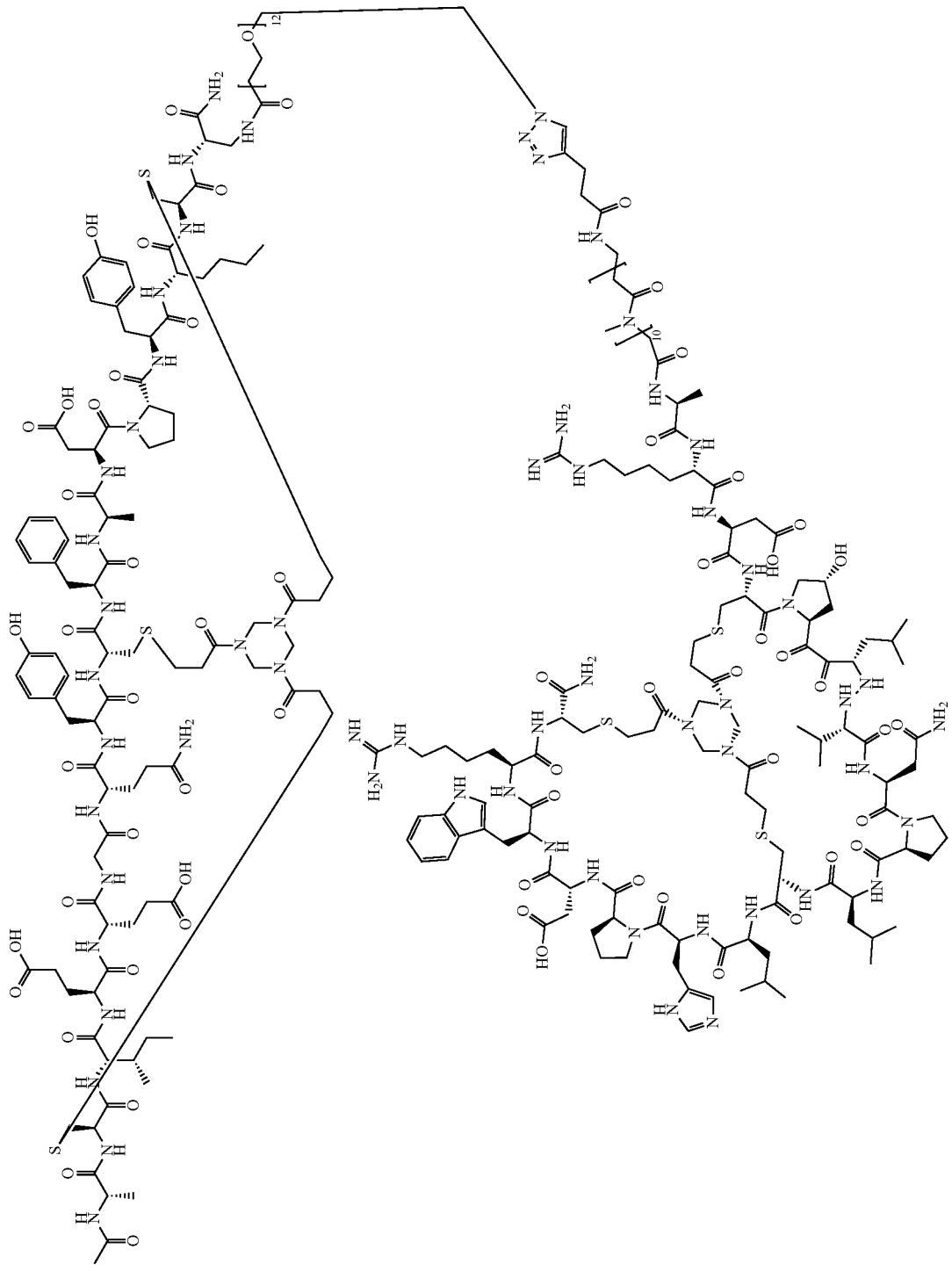

-continued
BCY8943
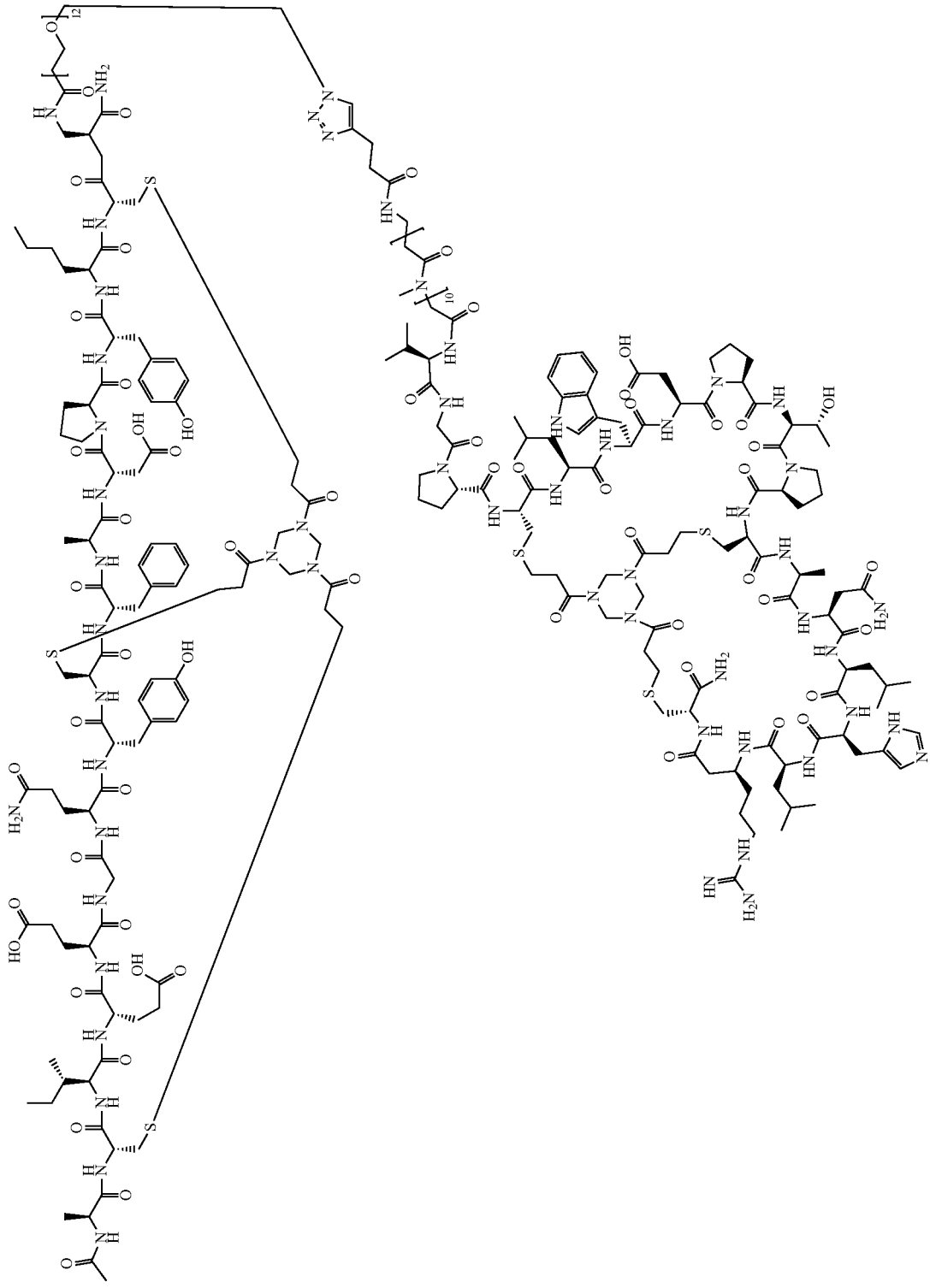

-continued
BCY9647
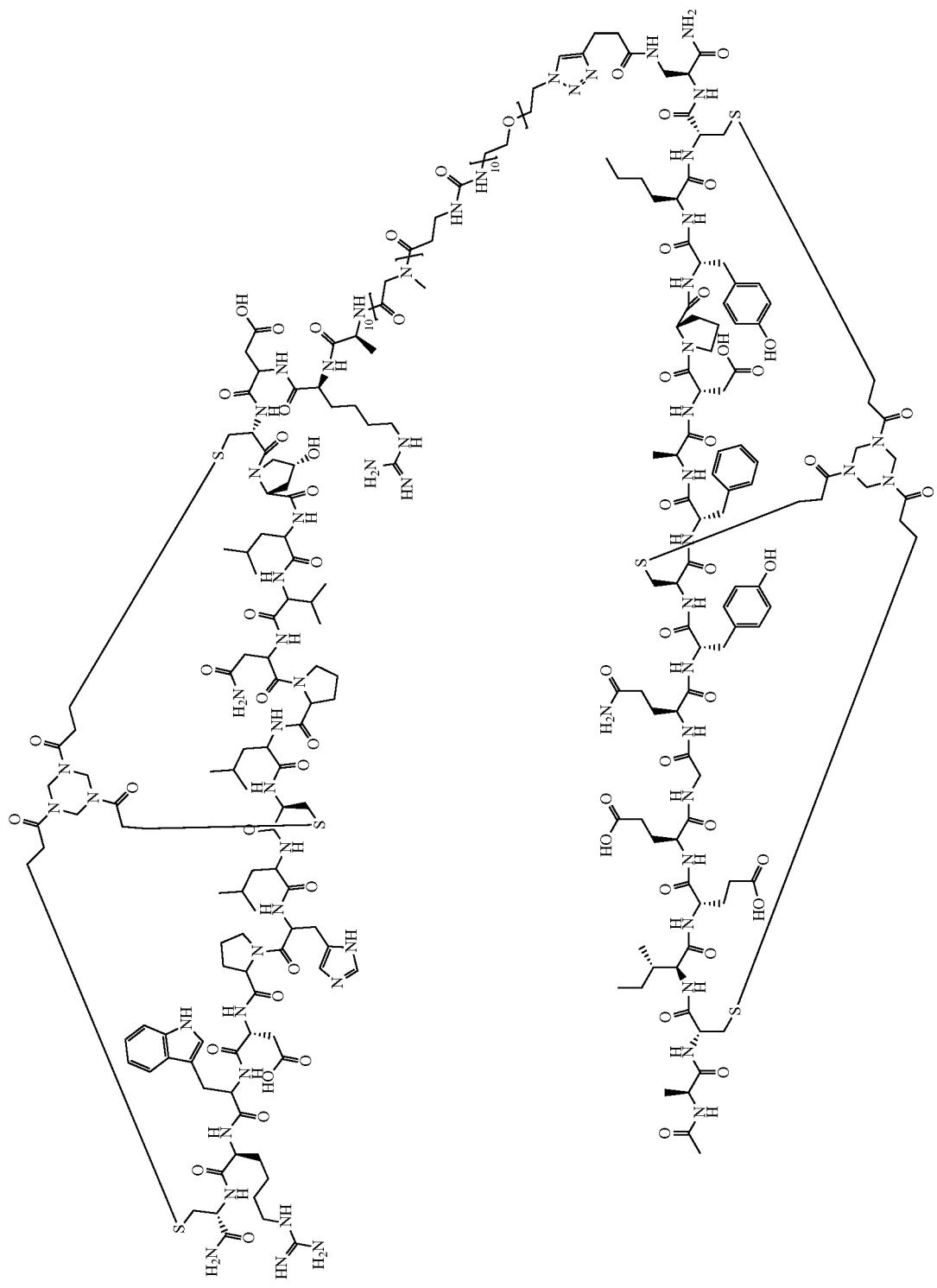

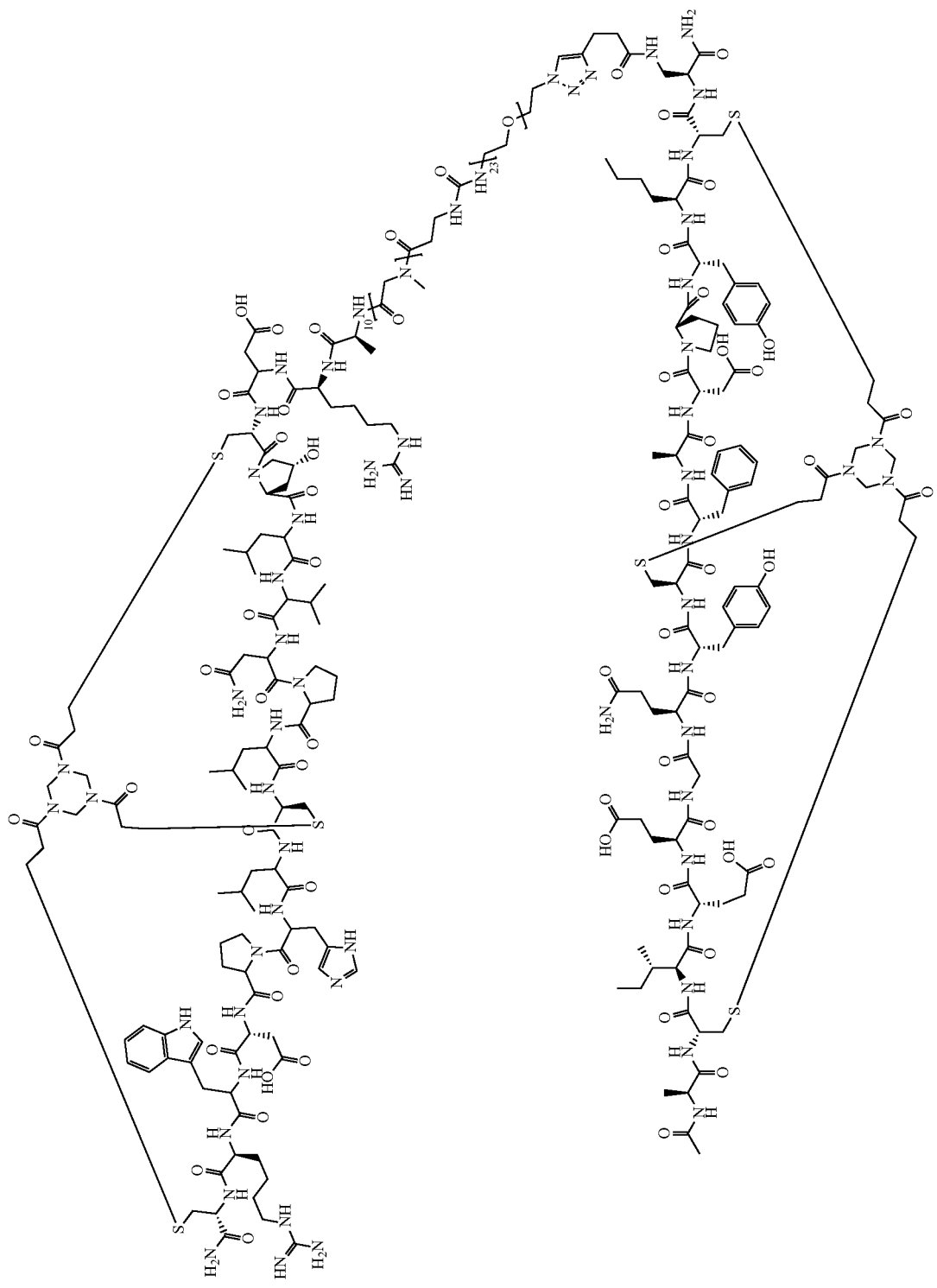

BCY9655
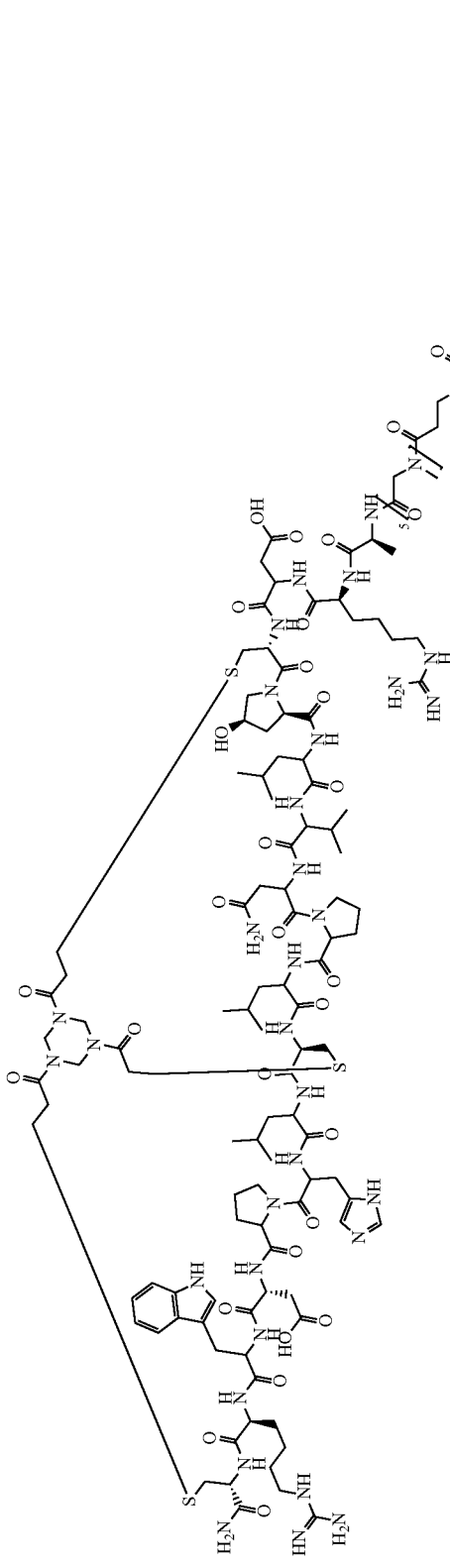
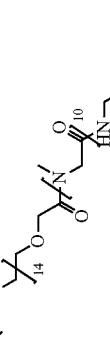
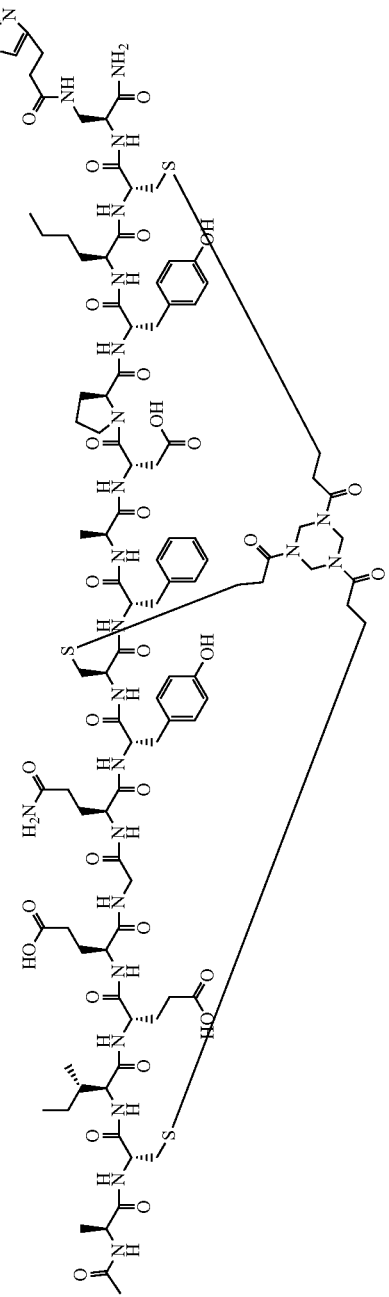

BCY9656
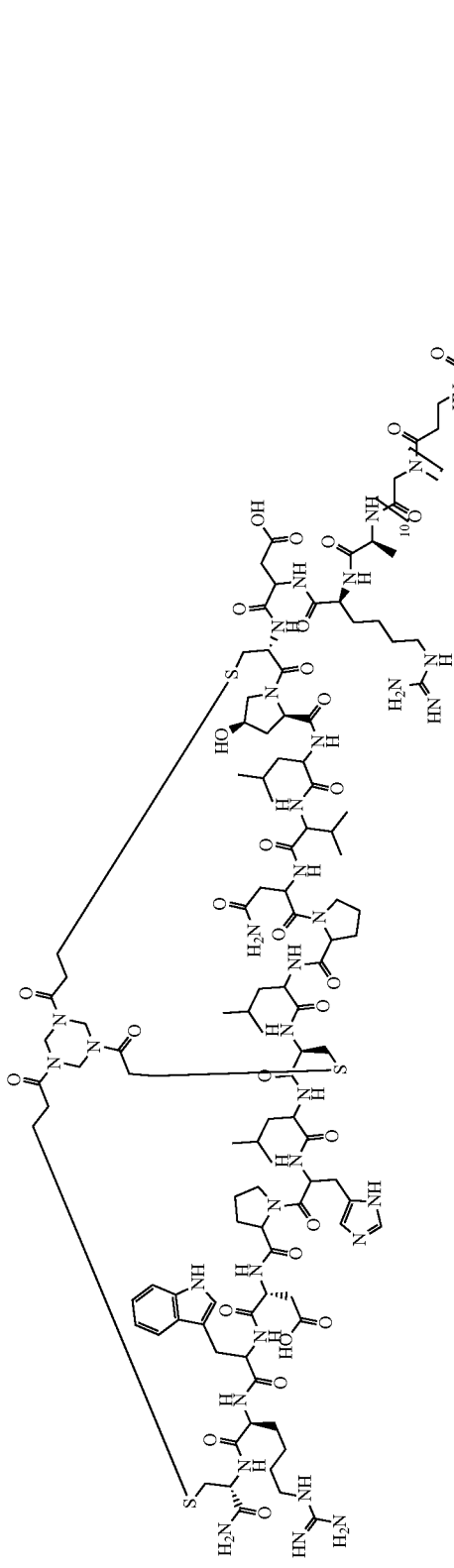
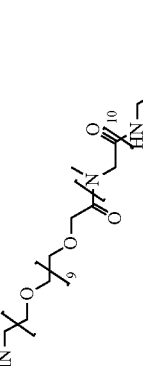
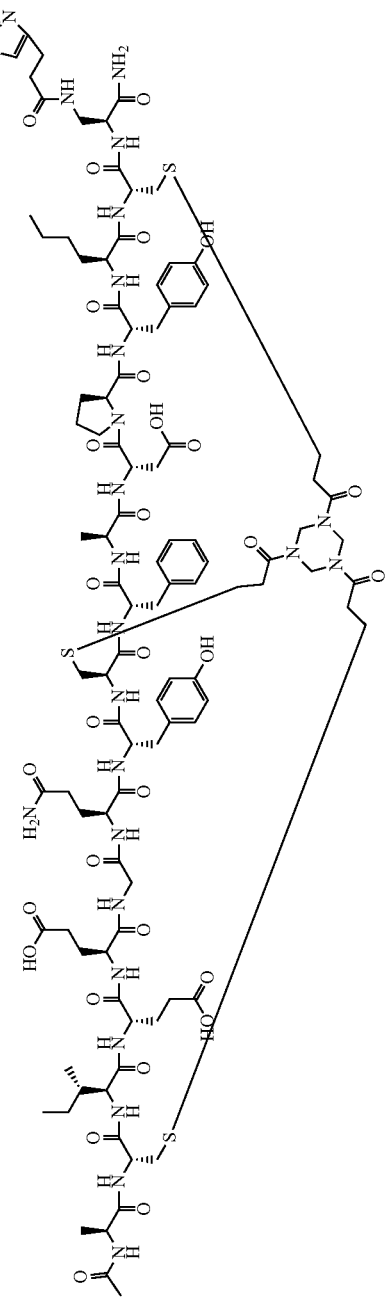

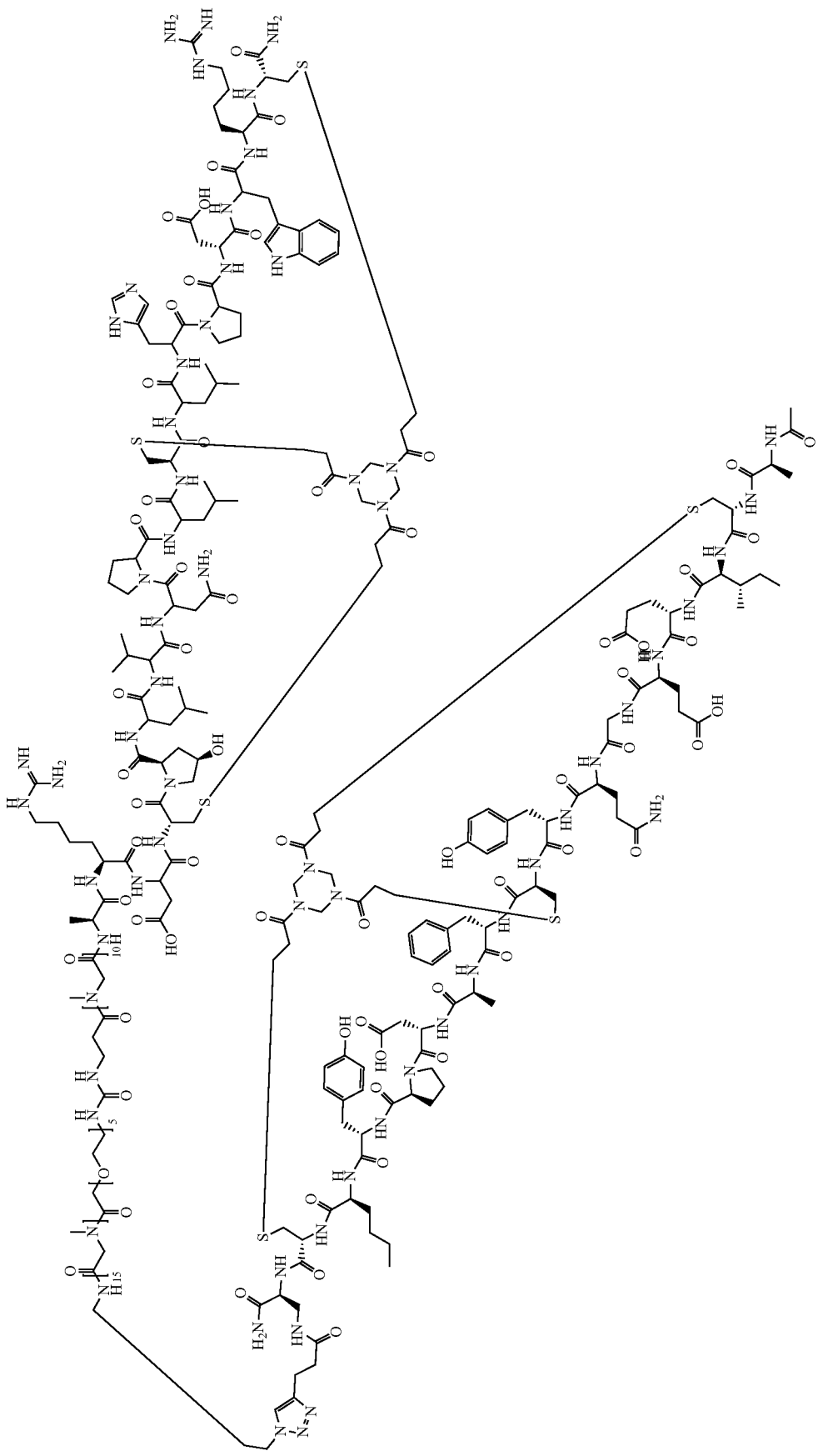

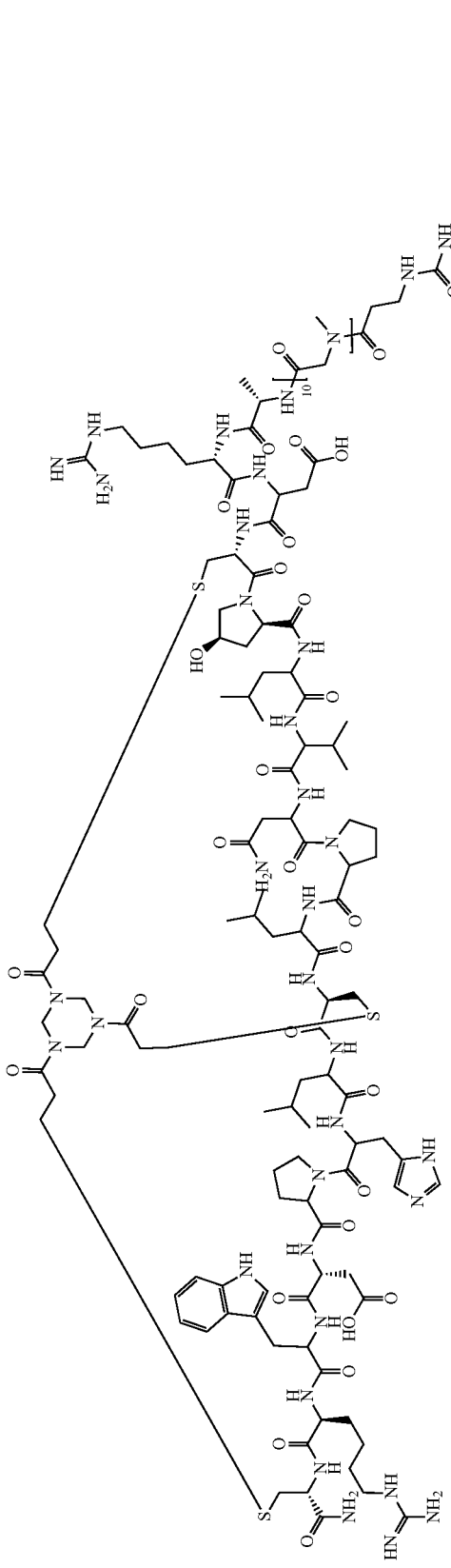
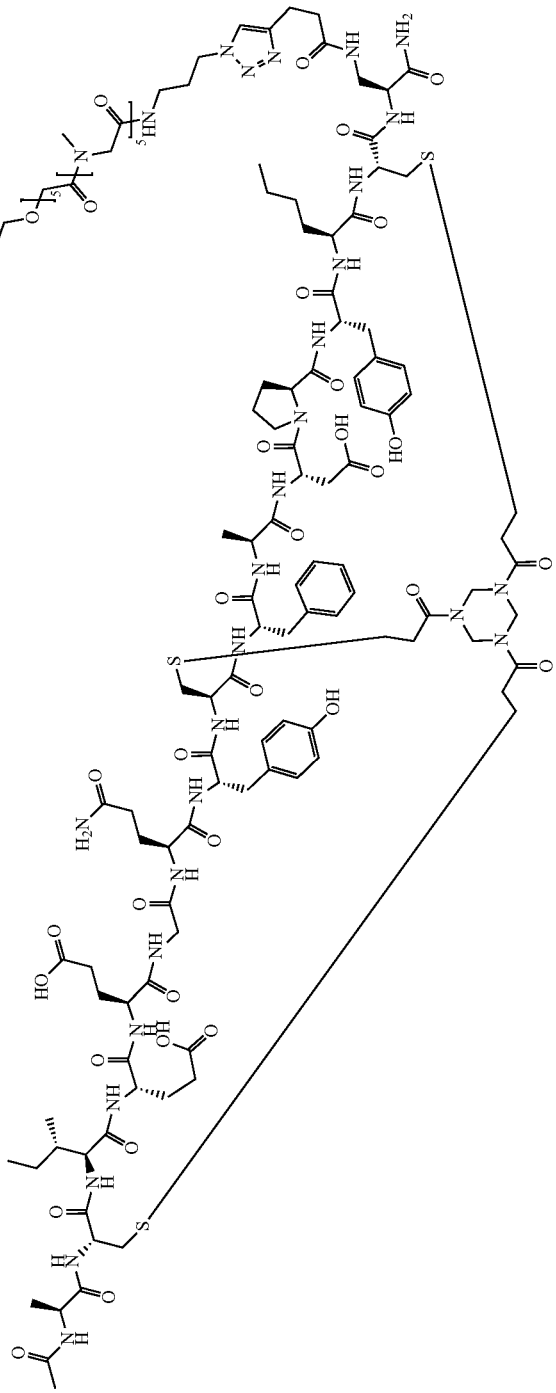

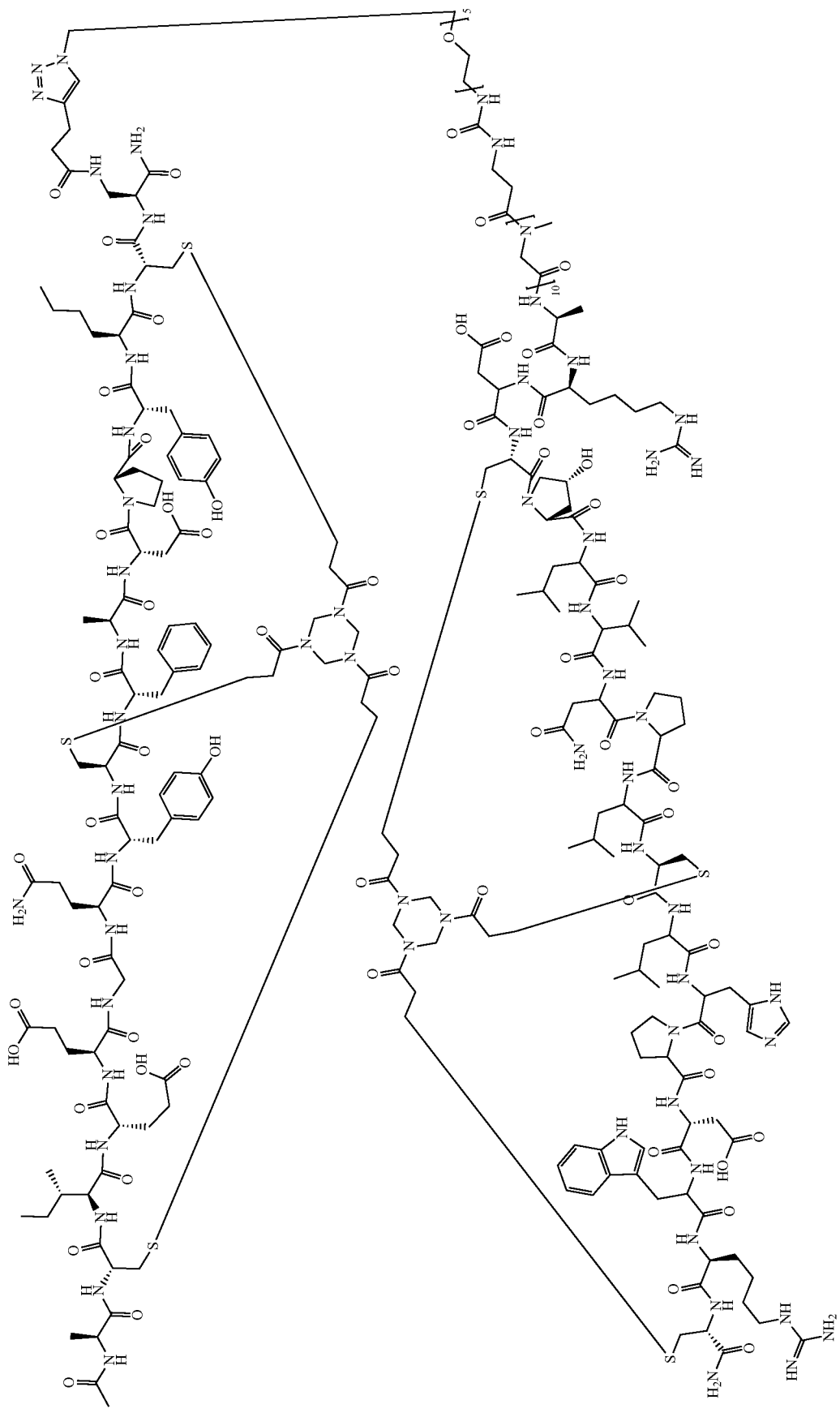

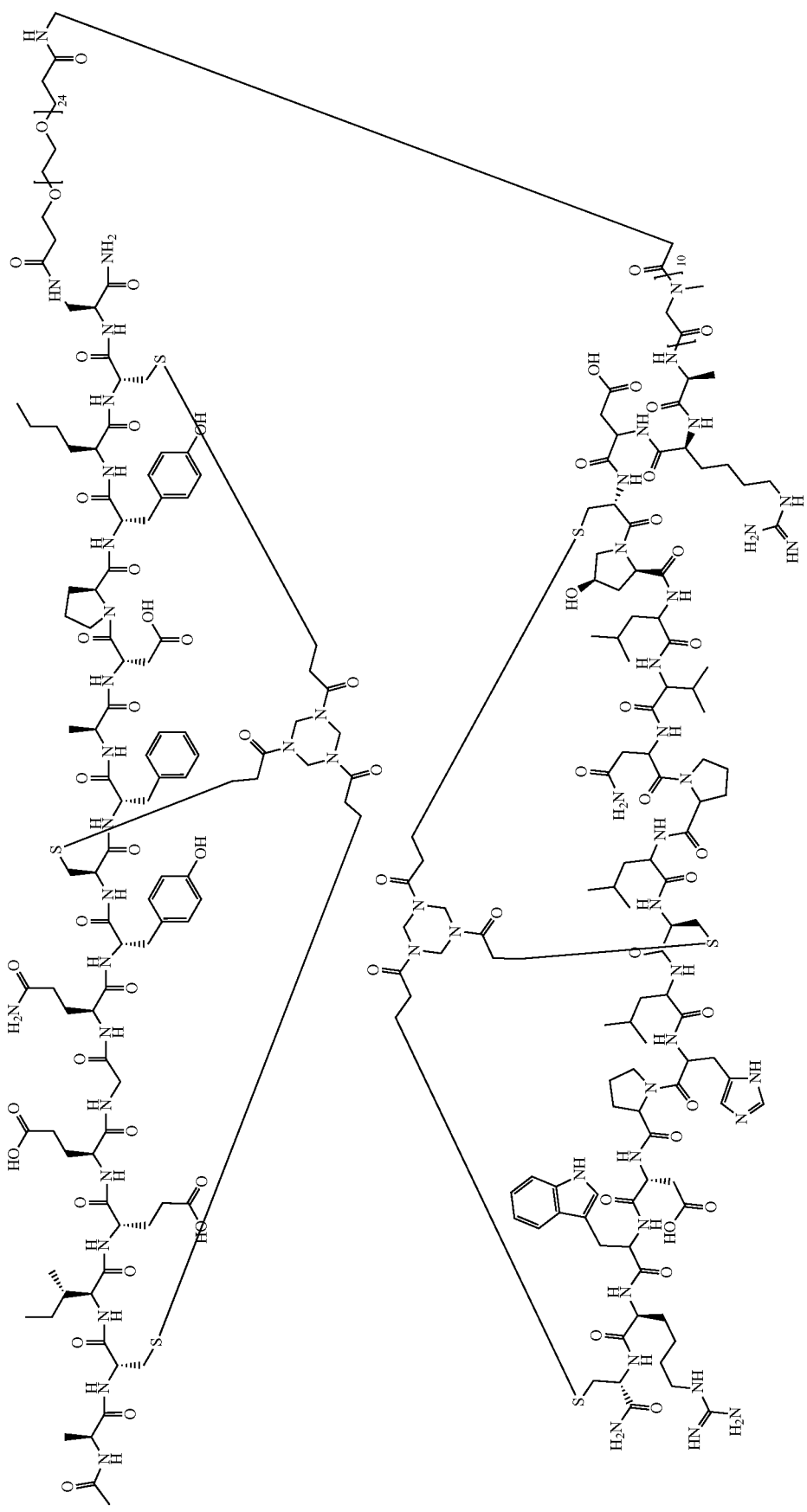

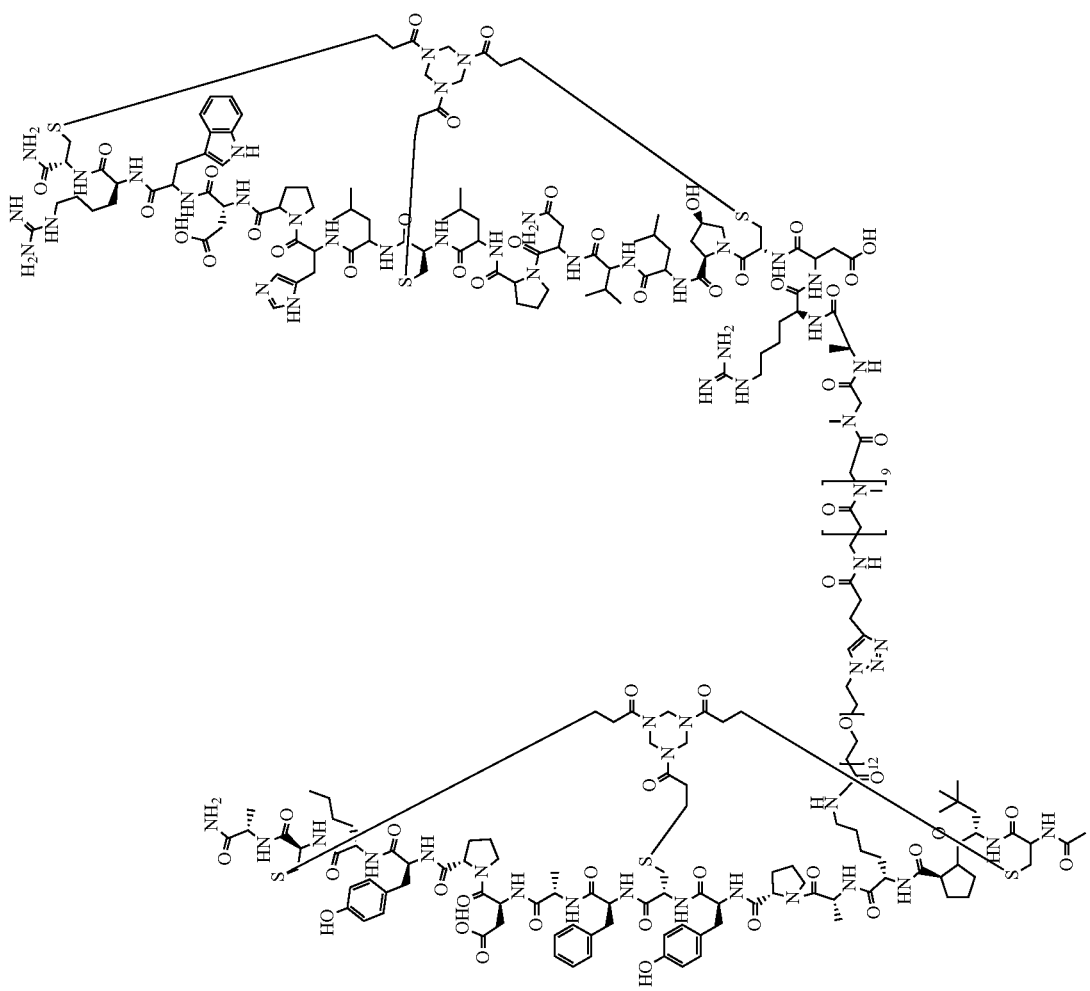

193 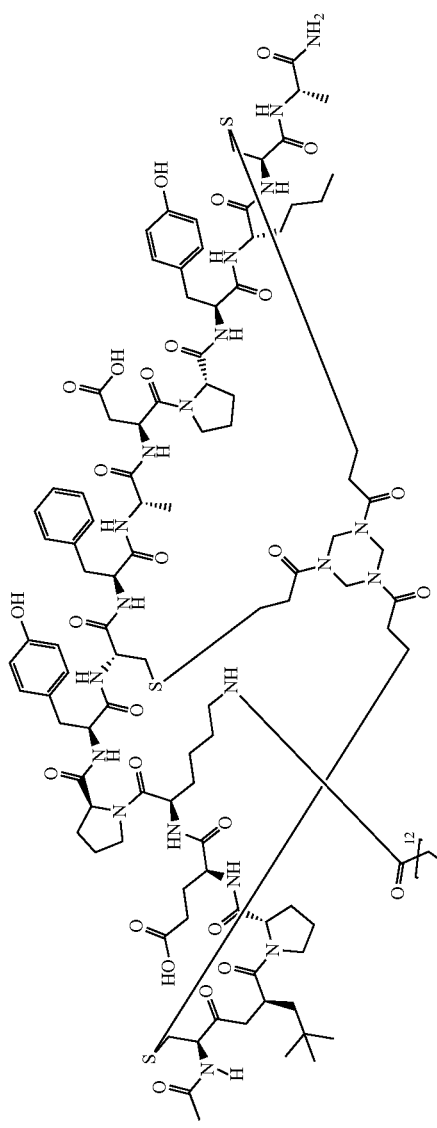
194 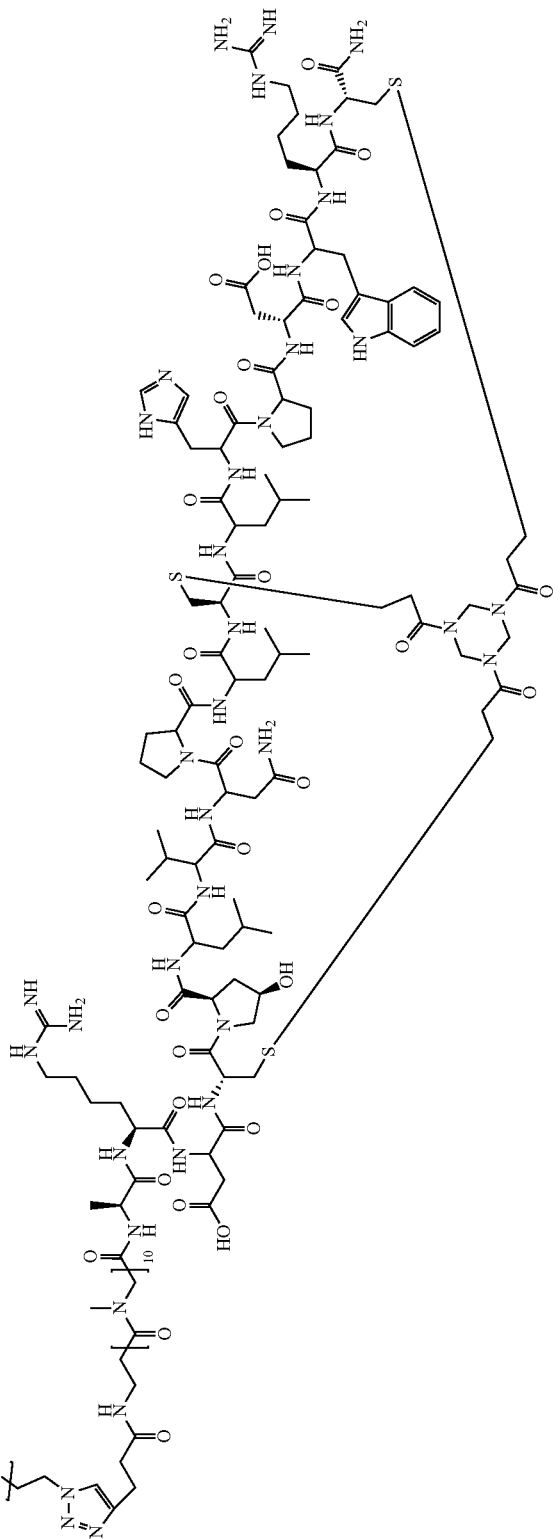

-continued
BCY10574
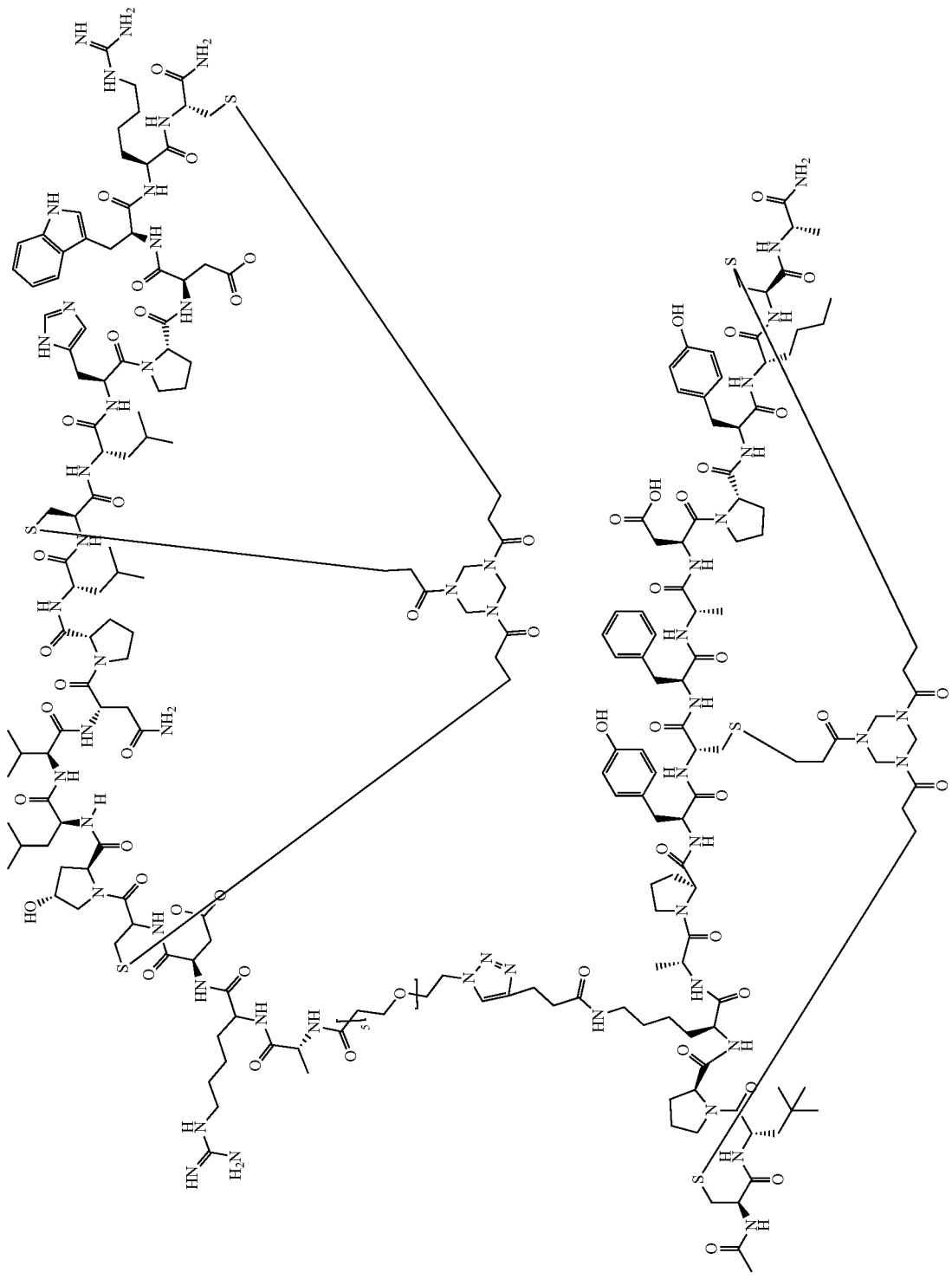

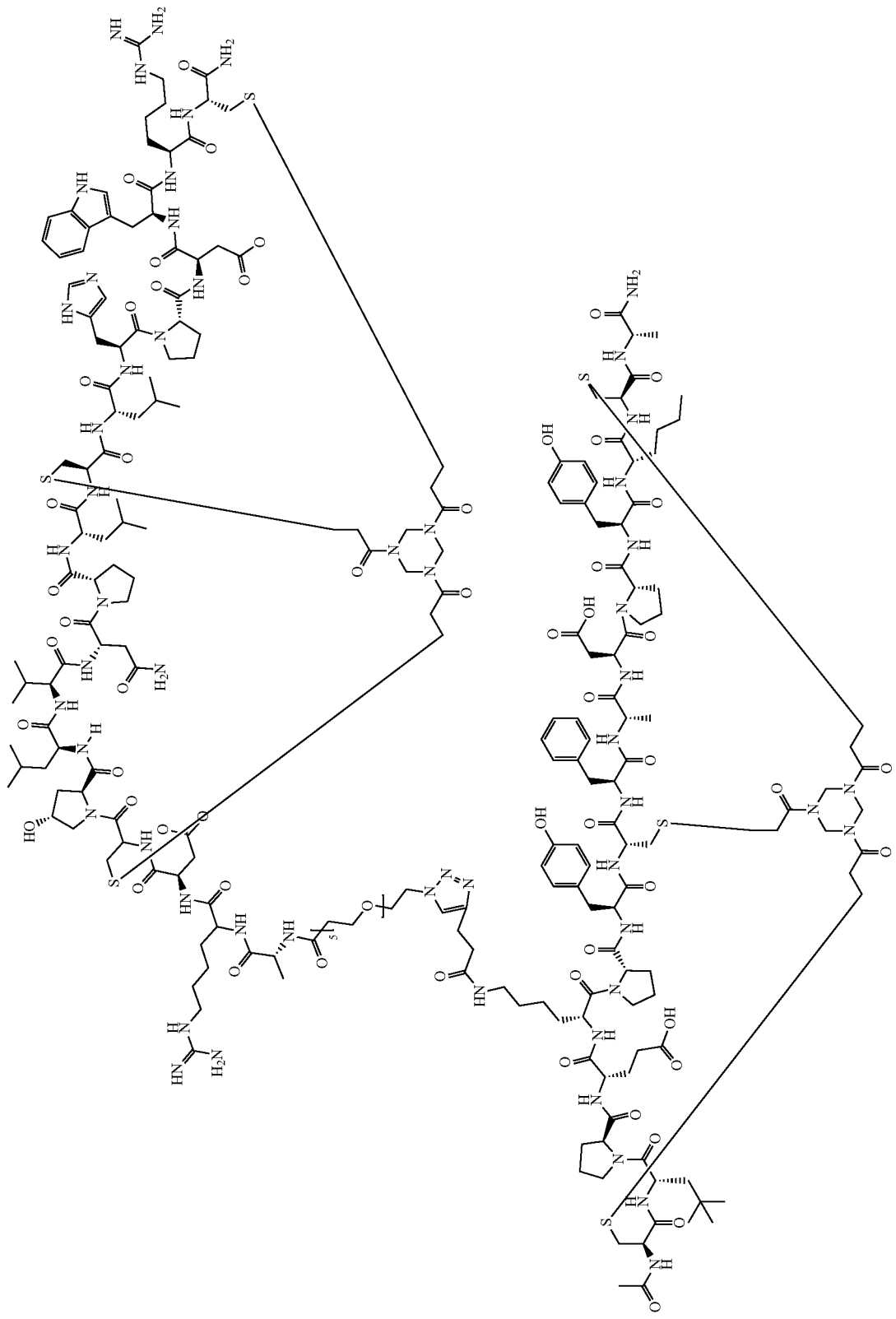

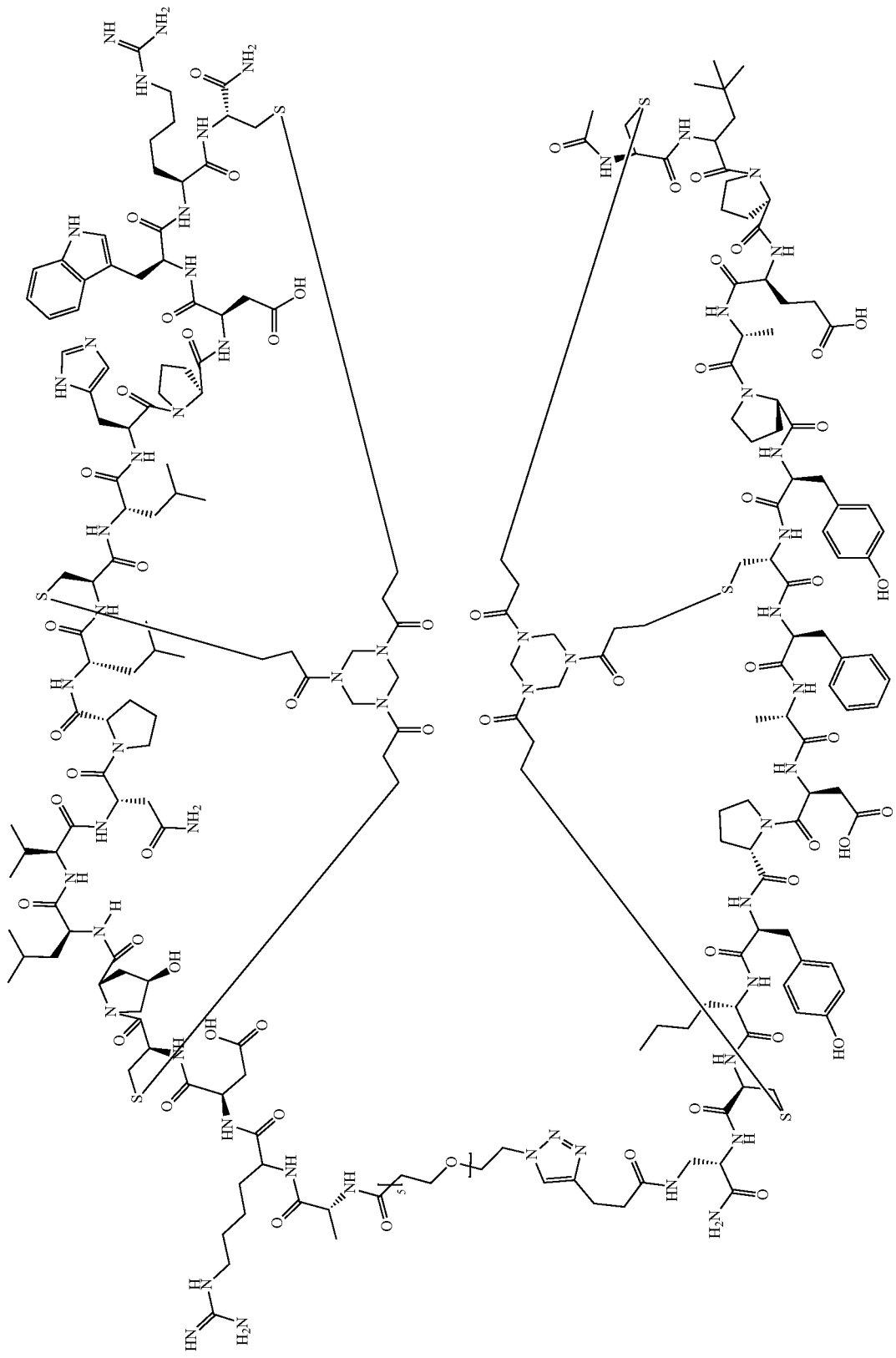

-continued
BCY10577
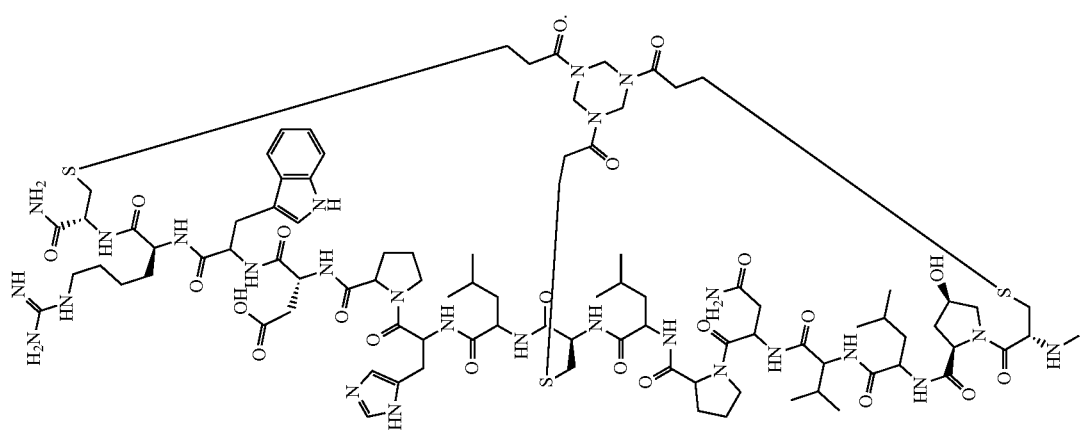

-continued
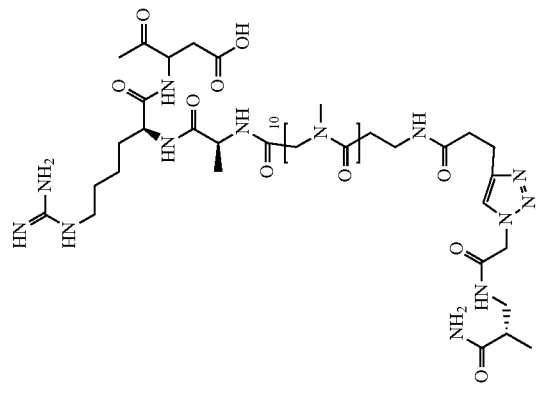

-continued
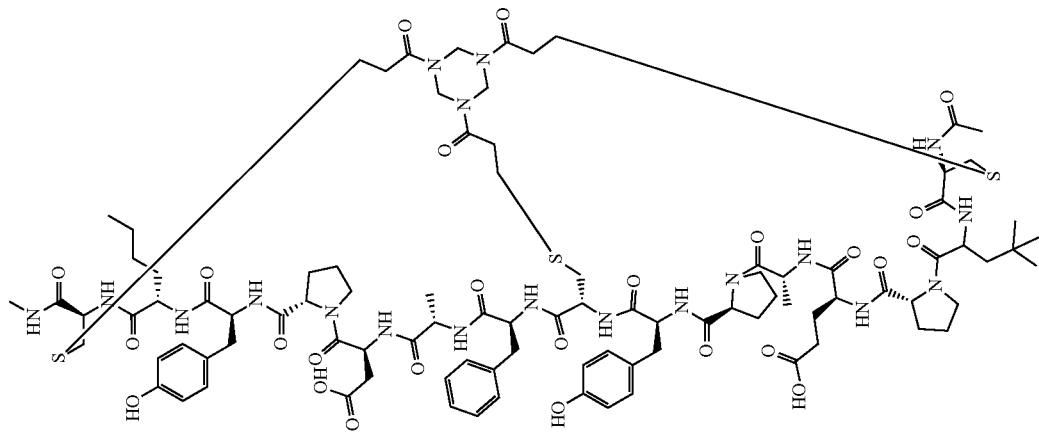

17. The method of claim 13, wherein the molecular scaffold in the heterotandem bicyclic peptide complex is 1,1',1"-(1,3,5-triazinane-1,3,5-triyl)triprop-2-en-1-one (TATA), which forms covalent bonds with the cysteine residues of the polypeptide such that two polypeptide loops are formed on the molecular scaffold.

* * * * *

SEQUENCE LISTING

```
<160> NUMBER OF SEQ ID NOS: 18

<210> SEQ ID NO 1
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Nle

<400> SEQUENCE: 1

Cys Ile Glu Glu Gly Gln Tyr Cys Phe Ala Asp Pro Tyr Xaa Cys
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HyP
```

```
<220> FEATURE:
<221> NAME/KEY: Xaa
<222> LOCATION: (14)..(14)
<223> OTHER INFORMATION: Xaa is HArg

<400> SEQUENCE: 2

Cys Xaa Leu Val Asn Pro Leu Cys Leu His Pro Asp Trp Xaa Cys
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 3

Cys Xaa Pro Glu Ala Pro Tyr Cys Phe Ala Asp Pro Tyr Xaa Cys
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Nle

<400> SEQUENCE: 4

Cys Ile Glu Glu Gly Gln Tyr Cys Phe Ala Asp Pro Tyr Xaa Cys
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 5

Cys Xaa Pro Lys Ala Pro Tyr Cys Phe Ala Asp Pro Tyr Xaa Cys
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
```

<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 6

Cys Xaa Pro Glu Lys Pro Tyr Cys Phe Ala Asp Pro Tyr Xaa Cys
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (4)..(4)
<223> OTHER INFORMATION: Xaa is K(PYA)
<220> FEATURE:
<221> NAME/KEY: Xaa
<222> LOCATION: (14)..(14)
<223> OTHER INFORMATION: Xaa is Nle

<400> SEQUENCE: 7

Cys Xaa Pro Xaa Ala Pro Tyr Cys Phe Ala Asp Pro Tyr Xaa Cys
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 8

Cys Xaa Pro Glu Xaa Pro Tyr Cys Phe Ala Asp Pro Tyr Xaa Cys
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 9

Cys Ile Glu Glu Xaa Gln Tyr Cys Phe Ala Asp Pro Tyr Xaa Cys
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is K(PYA)
<220> FEATURE:
<221> NAME/KEY: Xaa
<222> LOCATION: (14)..(14)
<223> OTHER INFORMATION: Xaa is dNle

<400> SEQUENCE: 10

Cys Ile Glu Glu Xaa Gln Tyr Cys Phe Ala Asp Pro Tyr Xaa Cys
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is HArg

<400> SEQUENCE: 11

Cys Leu Trp Asp Pro Thr Pro Cys Ala Asn Leu His Leu Xaa Cys
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HArg

<400> SEQUENCE: 12

Cys Xaa Asp Trp Cys His Trp Thr Phe Ser His Gly His Pro Cys
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Cys Ser Ala Gly Trp Leu Thr Met Cys Gln Lys Leu His Leu Cys
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic peptide
<220> FEATURE:

```
<221> NAME/KEY: Xaa
<222> LOCATION: (11)..(11)
<223> OTHER INFORMATION: Xaa is K(PYA)

<400> SEQUENCE: 14

Cys Ser Ala Gly Trp Leu Thr Met Cys Gln Xaa Leu His Leu Cys
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 15

Cys Pro Xaa Asp Cys Met Xaa Asp Trp Ser Thr Pro Xaa Trp Cys
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 16

Cys Pro Xaa Asp Cys Met Xaa Asp Trp Ser Thr Pro Xaa Trp Cys
1               5                   10                  15

<210> SEQ ID NO 17
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (5)..(5)
<223> OTHER INFORMATION: Xaa is (Sar10-(B-Ala))
<220> FEATURE:
<221> NAME/KEY: Xaa
<222> LOCATION: (8)..(8)
<223> OTHER INFORMATION: Xaa is HArg
<220> FEATURE:
```

```
<221> NAME/KEY: Xaa
<222> LOCATION: (14)..(14)
<223> OTHER INFORMATION: Xaa is HyP

<400> SEQUENCE: 17

Cys Pro Xaa Lys Xaa Cys Met Xaa Asp Trp Ser Thr Pro Xaa Trp Cys
1               5                   10                  15

<210> SEQ ID NO 18
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 18

Cys Pro Phe Gly Cys Met Xaa Asp Trp Ser Thr Pro Xaa Trp Cys
1               5                   10                  15
```